US008691187B2

(12) United States Patent
Szardenings et al.

(10) Patent No.: US 8,691,187 B2
(45) Date of Patent: Apr. 8, 2014

(54) IMAGING AGENTS FOR DETECTING NEUROLOGICAL DISORDERS

(75) Inventors: Anna Katrin Szardenings, Torrance, CA (US); Wei Zhang, Los Angeles, CA (US); Dhanalakshmi Kasi, Los Angeles, CA (US); Anjana Sinha, San Diego, CA (US); Umesh B. Gangadharmath, Los Angeles, CA (US); Joseph C. Walsh, Pacific Palisades, CA (US)

(73) Assignee: Eli Lilly and Company, Indianapolis, IN (US)

( * ) Notice: Subject to any disclaimer, the term of this patent is extended or adjusted under 35 U.S.C. 154(b) by 324 days.

(21) Appl. No.: 13/035,405

(22) Filed: Feb. 25, 2011

(65) Prior Publication Data

US 2011/0182812 A1  Jul. 28, 2011

Related U.S. Application Data

(63) Continuation-in-part of application No. 12/661,777, filed on Mar. 23, 2010, now Pat. No. 8,491,869.

(60) Provisional application No. 61/162,421, filed on Mar. 23, 2009.

(51) Int. Cl.
*A61K 49/00* (2006.01)

(52) U.S. Cl.
USPC ......... 424/9.1; 424/1.11; 424/1.65; 424/1.81; 424/1.85; 424/1.89; 544/245

(58) Field of Classification Search
USPC .............. 424/1.11, 1.65, 1.82, 185, 1.89, 9.1, 424/9.2, 9.3, 9.4, 9.5, 9.6, 9.7, 9.8, 1.81, 424/1.85; 544/1, 224, 242, 245; 548/100, 548/300.1; 546/1
See application file for complete search history.

(56) References Cited

U.S. PATENT DOCUMENTS

| 5,871,934 | A  | 2/1999  | Lee et al. |
| 6,562,319 | B2 | 5/2003  | Mishani et al. |
| 2003/0149250 | A1 | 8/2003 | Kung et al. |
| 2006/0110787 | A1 | 5/2006 | Walker |
| 2007/0060618 | A1 | 3/2007 | Cosford et al. |
| 2007/0258887 | A1 | 11/2007 | Tamagnan et al. |
| 2008/0166299 | A1 | 7/2008 | Kung et al. |

FOREIGN PATENT DOCUMENTS

| EP | 1655287 | 5/2006 |
| EP | 1 815 872 A | 8/2007 |
| EP | 1944281 | 7/2008 |
| EP | 2218464 | 8/2010 |
| JP | 9165378 A | 6/1997 |
| JP | 2001048786 | 2/2001 |
| JP | 2006100537 | 4/2006 |
| JP | 2007223952 | 9/2007 |
| WO | WO 94/14477 A | 7/1994 |
| WO | WO 97/14679 | 4/1997 |
| WO | 02085903 | 10/2002 |
| WO | WO 2004/043496 A | 5/2004 |
| WO | 2004056399 | 7/2004 |
| WO | 2004087139 | 10/2004 |
| WO | 2006116736 | 11/2006 |
| WO | WO 2007/014467 | 2/2007 |
| WO | WO 2007/057705 A | 5/2007 |
| WO | 2007063946 | 6/2007 |
| WO | WO 2007/094718 A | 8/2007 |
| WO | 2008027162 | 3/2008 |
| WO | 2008073350 | 6/2008 |
| WO | WO 2008/083454 A | 7/2008 |
| WO | 2008124812 | 10/2008 |
| WO | WO 2008/131148 A | 10/2008 |
| WO | 2008132454 | 11/2008 |
| WO | WO 2008/132454 A | 11/2008 |
| WO | 2009004914 | 1/2009 |
| WO | 2009045535 | 4/2009 |
| WO | 2009055401 | 4/2009 |
| WO | 2009102498 | 8/2009 |
| WO | 2010011964 | 1/2010 |
| WO | 2010073719 | 7/2010 |
| WO | 2010111303 | 9/2010 |

OTHER PUBLICATIONS

Aoyama, et al., "Polymethylated .gamma.-carbolines with potent anti-bovine viral diarrhea virus (BVDV) activity", Heterocycles (2009), 77(2), 779-785.

Sako, et al., "Gamma-carboline derivatives with anti-bovine viral diarrhea virus (BVDV) activity", Bioorg Med Chem Apr. 1, 2008 16(7), 3780-3790.

Chen, et al., "Microwave-enhanced Fischer reaction: an efficient one-pot synthesis of γ-carbolines", Synlett (2008), (1), 77-82.

Engler, et al., "Lewis Acid-Directed Cyclocondensation of Piperidone Enol Ethers with 2-Methoxy-4-(N-phenylsulfonyl)-1,4-benzoquinoneimine: A New Regioselective Synthesis of Oxygenated Carbolines", Journal of Organic Chemistry (2000), 65(8), 2444-2457.

Mehta, et al., "The elimination of an alkoxy group in the photo-Graebe-Ullmann conversion of 1-(2,5-dialkoxyphenyl)triazolopyridines into carbolines, and the preparation of α-, γ- and δ-carboline quinones", J. Chem. Soc., Perkin Trans. 1, 1993, 1261-1267.

Parrick, et al., "Some carbazole and carboline quinones and an unexpected demethoxylation reaction", Journal of Chemical Research, Synopses (1990), (1), 1.

(Continued)

*Primary Examiner* — D L Jones
(74) *Attorney, Agent, or Firm* — Manisha A Desai; Zhigang Rao; Kyle W. Grimshaw

(57) ABSTRACT

Imaging agents of formulas (I)-(V) and methods for detecting neurological disorders comprising administering to a patient in need compounds of formulas (I)-(V) capable of binding to tau proteins and β-amyloid peptides are presented herein. The invention also relates to methods of imaging Aβ and tau aggregates comprising introducing a detectable quantity of pharmaceutical formulation comprising a radiolabeled compound of formulas (I)-(V) and detecting the labeled compound associated with amyloid deposits and/or tau proteins in a patient. These methods and compositions enable preclinical diagnosis and monitoring progression of AD and other neurological disorders.

12 Claims, 42 Drawing Sheets

(56) References Cited

OTHER PUBLICATIONS

Molina, et al., "Novel DNA Intercalators Based on the Pyridazino [1',6':1,2]pyrido [4,3-b] indol-5-inium System", J. Org. Chem, 1999, 64, 3907-3915.

Molina, et al., "Synthesis and DNA Binding Properties of y-Carbolinium Derivatives and Benzologues", J. Org. Chem, 1996, 61, 5587-5599.

PCT/US2010/028360 Search Report issued Nov. 22, 2010.

Kruglenko, et al.; "Condensed Imidazo-1,2,4-azines. 31. Synthesis and Chemical Transformations of Substituted 1,2,4-Triazepino[2,3-a]benzimidaloses"; Chemistry of Heterocyclic Compounds, vol. 38, No. 5, 2002- pp. 598-606.

Tseng, et al., "A Simple Regioselective Synthesis of Pyrimido[1,2-a]benzimidazoles"; vol. 24, May 1, 1987; Jun. 1, 1987, pp. 837-843.

Yousefi, et al., "Synthesis and Evaluation of 11C-Labeled Imidazo [2,1-b] benzothiazoles (IBTs) as PET Tracers for Imaging β-Amyloid Plaques in Alzheimer's Disease", J. Med. Chem., Article ASAP, DOI: 10.1021/jm101129a Publication Date (Web): Jan. 28, 2011.

Search Report in PCT/US2011/029368 dated Jun. 10, 2011.

Sundberg, et al., Synthesis Of Pyrido not 1,2-Alpha 3/4 Benzimidazoles by Cyclizative Condensation of 2-Halopyridines and 1,2-Benzemediamines, Scope and Mechanism of The Reaction, In Journal of Heterocyclic Chemistry, vol. 19, May 1, 1982, pp. 585-588.

Zheng, et al., "Biological Characters of [18F]0-FEt-PIB In a Rat Model of Alzheimer's Disease Using Micro-PET Imaging", Published in Acta Pharmacologica Sinica, vol. 29, No. 5, May 1, 2008 (pp. 548-554).

Wang, et al., "PET Imaging and Optical Imaging With D-Luciferin [<11>C]methyl Ester and D-Luciferin [11C]methyl Ether of Luciferase Gene Expression in Tumor Xenografts of Living Mice", Published in Bioorganic & Medicinal Chemistry Letters, vol. 16, No. 2, Jan. 15, 2006 (pp. 331-337).

Solbach, et al., "Efficient Radiosynthesis of Carbon-11 Labelled Uncharged Thioflavin T Derivatives Using [11C] methyl Triflate for Beta-Amyloid Imaging in Alzheimer's Disease With PET", Published in Applied Radiation and Isotopes, vol. 62, No. 4, Apr. 1, 2005 (pp. 591-595).

Mathis, et al., "Synthesis and Evaluation of 11C-Labeled 6-Substituted 2-Arylbenzothiazoles as Amyloid Imaging Agents", Published in Journal of Medicinal Chemistry, American Chemical Society, vol. 46, Jun. 19, 2003 (pp. 2740-2754).

Serdons, et al., "Synthesis and Evaluation of 18F-Labeled 2-Phenylbenzothiazoles as Positron Emission Tomography Imaging Agents for Amyloid Plaques in Alzheimer's Disease", Published in Journal of Medicinal Chemistry, American Cancer Society, vol. 52, Feb. 13, 2009 (pp. 1428-1437).

Johnson, et al., "AZD2184: A Radioligand For Sensitive Detection of Beta-Amyloid Deposits", Published in Journal of Neurochemistry, vol. 108, Mar. 1, 2009 (pp. 1177-1186).

Seneca, et al., "Brain and Whole-Body Imaging in Nonhuman Primates With [11C]MeS-IMPY, a Candidate Radioligand for Beta-Amyloid Plaques", Published in Nuclear Medicine and Biology, vol. 34, Aug. 6, 2007 (pp. 681-689).

Vasdev, et al., "Synthesis and Ex Vivo Evaluation of Carbon-11 Labelled N-(4-methoxybenzyl)-N'-(5-nitro-1,3-thiazol-2-yl)urea([11C]AR-A014418): A Radiolabelled Glycogen Synthase Kinase-3beta Specific Inhibitor for PET Studies", Published in Bioorganic & Medicinal Chemistry Letters, vol. 15, No. 23, Dec. 1, 2005 (pp. 5270-5273).

Qu, et al., Radioiodinated Aza-Diphenylacetylenes as Potential SPECT Imaging Agents for Beta-Amyloid Plaque Detection, Published in Bioorganic & Medicinal Chemistry Letters, vol. 17, No. 13, Jul. 1, 2007 (pp. 3581-3584). Science Direct, Elsevier.

Invitation to Pay Additional Fees in PCT/US2010/028360, dated Jul. 21, 2010.

Nobuyuki Okamura, et al., Quinoline and Benzimidazole Derivatives: Candidate Probes for In Vivo Imaging of Tau Pathology in Alzheimer's Disease, Journal of Neuroscience, Nov. 23, 2005, 25(47); pp. 10857-10862.

Rex Boyd, "New reactor needed for medical imaging—why cyclotrons cannot do the job", Radiotopes in Medicine; Article from May 1999 edition Australasian Science Magazine; Jun. 1999, pp. 10-11.

Hank F. Kung, et al., "F Stilbenes and Styrylpyridines for PET Imaging of Aβ Plaques in Alzheimer's Disease: A Miniperspective", J. Med. Chem., 2010, vol. 53, pp. 933-941.

M.N. Sabbagh, "Drug Development for Alzheimer's Disease: Where are we now and where are we headed?", American Journal of Geriatric Phamacotherapy, vol. 7, No. 3, Jun. 2009, pp. 167-185.

Dr. Richard A. Houghten and Michael Lebl, "Peptides: The Wave of the Future", 2nd International Peptide Symposium in conjunction with the 17th American Peptide Symposium, Jun. 9-14, 2001, San Diego, California.

Nordberg, A., "PET imaging of amyloid in Alzheimer's disease", Lancet Neurology, Lancet Publ. Group, London, GB, vol. 3, No. 9, Sep. 1, 2004, pp. 519-527.

Brizel, et al., "Tumor oxygenation predicts the likelihood of distant metastases in human soft tissue sarcoma", Cancer Res. (1996) 56:941-943.

Kolb, et al., "Click Chemistry: Diverse Chemical Function from a Few Good Reactions", Angewandte Chemie, International Edition (2001), 40:2004-2021.

Kolb, et al., "The growing impact of click chemistry on drug discovery", Drug Discovery Today (2003), 8:1128-1137.

Mocharla, et al., "In Situ Click Chemistry: Enzyme-Generated Inhibitors of Carbonic Anhydrase II", Agnew Andte Chemie. Intl. Edition, VCH Verlag, Weinheim, DE, vol. 44, No. 1, Dec. 17, 2004, pp. 116-120.

Tornoe, et al., "Peptidotriazoles on Solid Phase: [1,2,3]-Triazoles by Regiospecific Copper(I)-Catalyzed 1,3-Dipolar Cycloadditions of Terminal Alkynes to Azides", Journal of Organic Chemistry (2002), 67:3057-3064.

Wang, et al., "Bioconjugation by Copper(I)-Catalyzed Azide-Alkyne [3+2] Cycloaddition", Journal of the American Cancer Society (2003), 125:3192-3193.

Wang, et al., "Positron Emission Tomography: Application in Drug Discovery and Drug Development", Curr. Top. Med. Chem. (2005), 5:1053-1075.

Bergstrom, Mats et al.: "Synthesis of some 11C-labeled MAO-A inhibitors and their in vivo uptake kinetics in rhesus monkey brain", Nuclear Medicine and Biology, 24(5), 381-388 Coden: Nimbieo; ISSN: 0883-2897, 1997.

Sintas, Jose A. et al.: "Iodination, radioiodination and spectroscopic identification of beta.-carboline derivatives", Journal of Labelled Compounds & Radiopharmaceuticals, 42(5), 409-413 Coden: JLCRD4; ISSN: 0362-4803, 1999.

Karimi, Farhad et al.: "Synthesis of 11c-labelled amides by palladium-mediated carboxamination using [11C]carbon monoxide, in situ activated amines and 1,2,2,6,6-pentamethylpiperidine", European Journal of Organic Chemistry, (11), 2132-2137 Coden: Ejocfk; ISSN: 1434-193X, 2003.

Baranowska-Kortylewicz J et al.: "Radioiodination of 7-Methoxy- and 6,7-Dimethoxy-4-Bromomethylcoumarins", Journal of Labelled Compounds and Radiopharmaceuticals, John Wiley, Chichester, DB, vol. 29, No. 12, Jan. 1, 1991, pp. 1301-1307, ISSN: 0362-4803.

Heike Radeke et al.: "Synthesis and biological evaluation of the mitochondrial complex 1 inhibitor 2-[4-(4-fluorobutyl) benzylsulfanyl]-3-meth ylchromene-4-one as a potential cardiac positron emission tomography tracer", J. Med. Chem., vol. 50, 2007, pp. 4304-4315.

Maria Graciela Barolli et al.: "Synthesis of [131I]-iodinated quercetin", J. Label. Compds. Radiopharm., vol. 32, No. 11, 1997, pp. 297-933.

Hollie I. Swanson et al.: "Use of [125I]4'-iodoflavone as a tool to characterize ligand-dependent differences in Ah receptor behavior", J. Biochem. Molecular Toxicology, vol. 16, No. 6, 2002, pp. 298-310.

(56) References Cited

OTHER PUBLICATIONS

Takahashi K et al.: "Imaging of aromatase distribution in rat and rhesus monkey brains with [<11>C]vorozole" Nuclear Medicine and Biology, Elsevier, NY, US, vol. 33, No. 5, Jul. 1, 2006, pp. 599-605, XP025103506 ISSN: 0969-8051.

Wenchao Qu et al.: "Quick Assembly of 1,4-diphenyltriazoles as probes targeting beta-amyloid aggregates in alzheimer's disease", J. Med. Chem., vol. 50, 2007, pp. 3380-3387.

Glaser M et al.: "Click Labeling with 2-[418F]Fluoroethylazide for Positron Emission Tomography" Bioconjugate Chemistry, ACS, Washington, DC, US, vol. 18, Apr. 13, 2007, pp. 989-993, ISSN: 1043-1802.

Sirion et al.: "An efficient F-18 labeling method for PET study: Huisgen 1,3-dipolar cycloaddition of bioactive substances and F-18-labeled compounds" Tetrahenron Letters, Elsevier, Amsterdam, vol. 48, No. 23, Jun. 4, 2007, pp. 3953-3957, ISSN: 0040-4039.

Mathias C. J. et al.: "Radiolebeled hypoxic cell sensitizers: Tracers for assessment of ischemia" Life Sciences, Pergamon Press, Oxford, GB, vol. 41, No. 2, Jul. 13, 1987, pp. 199-206, ISSN: 0024-3205.

Jerabek P.A. et al.: "Synthesis and biodistrubtion of <18>F-labeled fluoronitroimidazoles: Potential in vivo markers of hypoxic tissue", Applied Radiation and Isotopes, International Journal of Radiation Applications and Instrumentation, Part A, Pergamon Press, Ltd., GB, vol. 37, No. 7, Jan. 1, 1986, pp. 599-605, ISSN: 0883-2889.

Visser G.W. M. et al.: "THe preparation and stability of <211>At-astato-imidazoles" International Journal of Applied Radiation and Isotops, Pergamon Press, New York, NY, US, vol. 31, No. 5, May 1, 1980, pp. 275-278, ISSN: 0020-708X.

Miriko Tanaka et al.: "radiosynthesis and evaluation of 11C-labeled diaryl-substituted imidazole and indole derivatives for mapping cyclooxygenase-2" Biological & Pharmaceutical Bulletin (Of Japan)., vol. 29, No. 10, 2006, pp. 2087-2094, Pharmaceutical Society of Japan, Tokyo.

Gareth Getvoldsen et al.: Microwave-assisted cyclocondensation of 1,2-diaminobenzene with [4-18F] fluorobenzoic acid: microwave synthesis of 2-([4-18F]fluorophenyl) benzimidazole, Journal of Labelled Compounds and Radiopharmaceuticals, research article, J. Label Compd Radiopharm 2004; 47: 139-145.

Piotr Garnuszek et al.: "Synthesis and characterisation of platinum(II) complexes with histamine and iodohistamine", Inorganica Chimica Acta, vol. 338 (2002) 119-126.

Fumihiko Yamamoto et al.: "Synthesis and Evaluation of 4-Bromo-1-(3-[18F]fluoropropyl)-2-nitroimidazole with a Low Entergy LUMO Orbital Designed as Brain Hypoxia-Targeting Imaging Agent", Biol.Pharm. Bull. 25(5) 616-621 (2002), vol. 25, No. 5.

Fumihiko Yamamoto et al.: "Synthesis and Characterization of Lipohilic 1-[18F]Fluoralkyl-2Initroimidazoles for Imaging Hypoxia", Biol. Pharm. Bull. 22(6) 590-597 (1999), vol. 22, No. 6.

Blom, Elisabeth et al.: "Synthesis and in vitro evaluation of 18F-.beta.-carboline alkaloids as PET ligands" Journal of Labelled Compounds and Radiophaarmaceuticlas, 51(6), 277-282 Coden: JLCRD4, May 2008.

Dumont F. et al.: "Synthesis and In Vivo Evaluation of 7-chloro-5-[<123>I]iodo-4-oxo-1,4 dihydroquinoline-2-carboxylic Acid" Applied Radiation and Isotopes, Elsevier, Oxford, GB, vol. 48, No. 9, Sep. 1, 1997, pp. 1173-1177.

Livni E. et al.: "Synthesis and biodistribution of <18>F-labeled Fleroxacin" Nuclear Medicine and Biology, Elsevier, NY, US, vol. 20, No. 1, Jan. 1, 1993, pp. 81-87.

Zijlstra S et al.: "Synthesis and evaluation of fluorine-18 labelled compounds for imaging of bacterial infections with pet" Applied Radiation and Isotopes, Elsevier, Oxford, GB, vol. 64, No. 7, Jul. 1, 2006, pp. 802-807.

Choi, Osaku Wataru et al.: "Preparation of F-18 labeling benzyl N-containing heterocyclyl compounds as PET diagnostic remedies", Chemical Abstracts Service, Columbus, Ohio, US: Database accession No. 127:65770 abstract & JP 09 165378 A, Jun. 24, 1997.

DOUBLE LABELING OF COMPOUND T482 (100uM) AND TOTAL-tau IHC STAINING ON HUMAN BRAIN SECTION #0185(40x)

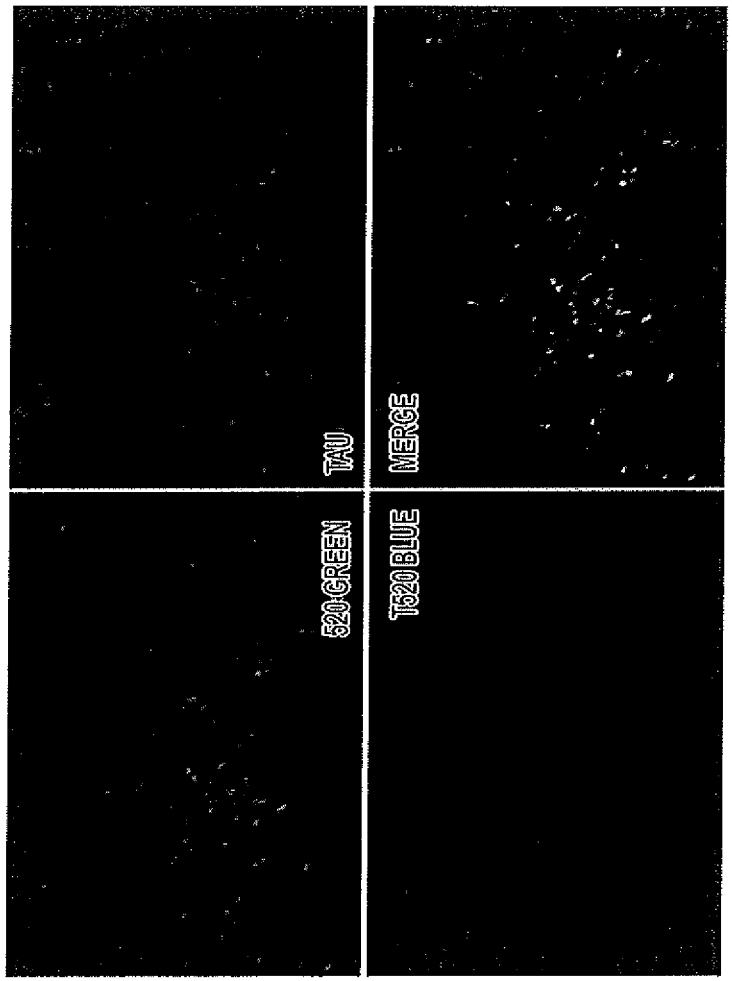
FIG. 8a
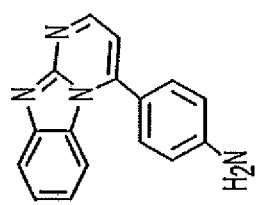

DOUBLE LABELING OF COMPOUND T522 (100uM) AND TOTAL-tau IHC STAINING ON HUMAN BRAIN SECTION #0185 (10x)

T522 IS A GOOD BINDER TO tau BUT NOT TO AMYLOID.

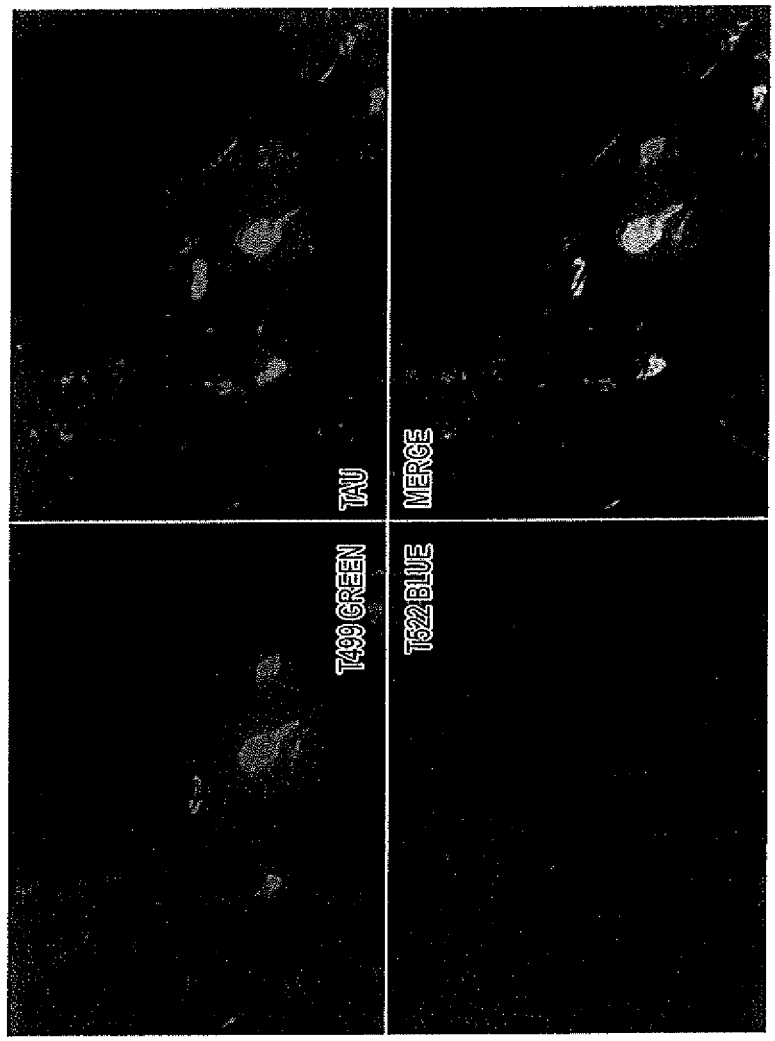
DOUBLE LABELING OF COMPOUND T522 (100uM) AND TOTAL-tau IHC STAINING ON HUMAN BRAIN SECTION #0185(60x)
T522 IS A GOOD BINDER TO tau BUT NOT TO AMYLOID.
FIG. 9b
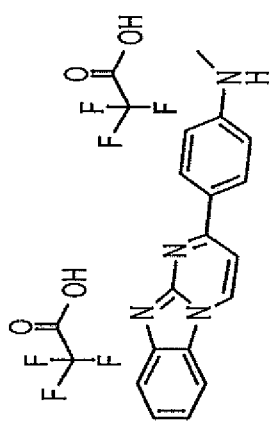

DOUBLE LABELING OF COMPOUND T539 (100uM) AND
TOTAL+AD-tau IHC STAINING ON HUMAN BRAIN SECTION #0185(60x)

DOUBLE LABELING OF COMPOUND T499 (100uM) AND
TOTAL-tau IHC STAINING ON HUMAN BRAIN SECTION #0185(10x)

DOUBLE LABELING OF COMPOUND T499 (100uM) AND
TOTAL-tau IHC STAINING ON HUMAN BRAIN SECTION #0185(40x)

IMAGING AGENTS FOR DETECTING NEUROLOGICAL DISORDERS

RELATED PATENT APPLICATIONS

The present application is a continuation-in-part of U.S. Ser. No. 12/661,777, filed Mar. 23, 2010, which is incorporated herein by reference, in its entirety. U.S. Ser. No. 12/661,777 is based on and claims a priority benefit of U.S. provisional application No. 61/162,421, filed Mar. 23, 2009, which is incorporated herein by reference in its entirety.

The foregoing application, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD

The present invention relates generally to imaging agents for detecting neurological disorders. More specifically, the present invention relates to the discovery of novel diagnostic imaging agents targeting senile plaques (SPs) and/or neurofibrillary tangles (NFTs) for detection, preclinical diagnosis and for tracking progression of Alzheimer's disease (AD).

BACKGROUND

Currently, Alzheimer's disease (AD), a leading cause of dementia, develops in one percent of the population between the ages 65 and 69, and increasing to 40-50% in those 95 years and older. AD patients exhibit telltale clinical symptoms that include cognitive impairment and deficits in memory function. In the current working model, there are three 'stages' that are associated with AD. First, neuronal cells become sick as a result of synaptic/metabolic malfunctioning that leads to neuronal deficiencies. Secondly, in the histological stage, an accumulation of neurofibrillary tangles and beta amyloid plaques begins, leading to the untimely aggregation of insoluble proteins in the brain. Finally, AD ultimately causes neuronal death and shrinkage in brain volume. AD patients typically have a heavy senile plaque (SP) burden found in the cerebral cortex which is verified by postmortem histopathological examination. SPs are extracellular deposits containing β-amyloid peptide cleaved from a longer amyloid precursor protein to produce a 40-43 amino acid peptide. Amyloid aggregates in brain play a key role in a cascade of events leading to AD. Interestingly, despite the development and presence of senile plaques in elderly persons with normal cognitive function, the severity of NFT and senile plaque deposition purportedly correlates with a loss of cognitive function and neuronal circuitry deterioration.

Major neuropathology observations of postmortem examination of AD brains confirm the presence of AD through the detection of extracellular β-amyloid peptides and intracellular neurofibrillary tangles (NFT). NFTs derive from filaments of hyperphosphorylated tau proteins. The presence and severity of NTFs correlate with severity of dementia and cognitive impairment (Dickinson, D. W., *Neurobiol. Aging* 1997, 18 [4 suppl]:521-526). The pathological process of AD must begin before the presentation of the clinical symptoms of dementia.

Despite Alzheimer's disease being the fourth leading cause of death in the United States, pharmaceutical intervention has yet to commercialize a curative therapy. Recently, Marwan N. Sabbagh published an overview of the current state of clinical development of AD pharmacotherapy (*The American Journal of Geriatric Pharmacotherapy*, 2009, 7(3), p. 167). Encouraging results from completed Phase II trials of dimebon, huperzine A, intravenous immunoglobulin, and methylthioninium chloride were reported at ICAD 2008. Nineteen compounds are currently in Phase II trials, and 3 compounds (AN1792, lecozotan SR, and SGS742) failed at this stage of development.

In addition to pharmaceutical approaches for curbing the effects of AD, researchers are attempting to detect AD by other means, including establishing technologies for early detection. Currently, there are many strategies that attempt to identify AD-associated pathologies by targeting either the cell sickness or histological stages of the disease. There is an array of AD imaging agents that potentially confirm the well-established manifestation of AD, however, this late stage diagnosis offers little defense against further disease progression past 36 months. Interestingly, the detection of senile plaques and tangles in the brain may not necessarily prove that a patient has developed AD.

As summarized from a recent discussion group on Dec. 5, 2006 (Biochemical Pharmacology Discussion Group, cosponsored by the American Chemical Society's New York section), researchers are now focusing on methods that target AD precursors by blocking either β-amyloid protein (BAP) production or by controlling mutant tau protein formation. Clearly, this focused research effort aims to control the formation of AD precursors that potentially lead to AD and this new strategy might delay full-onset AD more effectively that current therapeutics. In parallel, neurological imaging must mirror the therapeutic trend by identifying AD precursors in a duel effort to compliment both AD therapeutic development and, in addition, identify presymptomatic at-risk AD patients. Recent drug development has been aimed at preventing the accumulation of SPs and NFTs in presymptomatic AD patients. The ability to measure levels of these lesions in the living human brain is thus desirable for presymptomatic diagnosis of AD and also for monitoring the progression of the disease.

Unfortunately, since AD cannot be confirmed in the patients until a histological examination is performed, understanding the link between the uptake of these tracers and the relevant biochemical processes involved could remain unsolved for many years.

Thus, in vivo imaging of NFTs in conjunction with imaging SPs could prove useful for the early and accurate diagnosis of AD. Quantitative evaluation of tau pathology could also be helpful for tracking severity of dementia, because the formation of neuritic pathology correlates well with clinical severity of dementia (Dickson, 1997). NFT deposition in the entorhinal cortex is closely associated with neuronal loss in very early AD patients (Gomez-Isla et al., 1996). If novel treatments that prevent the pathological formation of neurofibrillary pathology could be turned into clinical applications, this imaging technique would be applicable for the evaluation of treatment efficacy.

Currently, neurological imaging of AD has seen the emergence of imaging tracers that appear to confirm the presence of AD based on plaque and fibril mediated tracer uptake and, subsequently, are currently undergoing extensive clinical examination. Many of these tracers contain chemotypes that are derived from fluorescent dyes.

Potential ligands for detecting Aβ aggregates in the living brain must cross the intact blood-brain barrier. Thus brain uptake can be improved by using ligands with relatively smaller molecular size and increased lipophilicity.

Previous neuropathological research suggests that the deposition of NFTs occurs before the presentation of clinical symptoms of AD. Even in the very early stages of AD, patients display considerable numbers of NFTs in the entorhinal cortex and hippocampus, sufficient for the neuropathological diagnosis of AD. Thus, in vivo imaging of NFTs in conjunction with imaging SPs could prove useful for the early and accurate diagnosis of AD, for motinoring the progression of the disease and for evaluation of treatment efficacy.

Optimization of current candidates and discovery of novel compounds that specifically bind tau or Aβ aggregates are of high interest for development of in vivo tau- and Aβ imaging agents for detection of neurological disorders, and in particular for imaging and detection of AD in patients.

SUMMARY

This invention discloses a series of compounds of formula (I) having enhanced binding properties to SPs and NFTs. The present invention also provides diagnostic pharmaceutical compositions comprising a radiolabeled compound of formula (I) and a pharmaceutically acceptable carrier or diluent. The present invention further relates to a method of imaging and detecting amyloid deposits and/or tau aggregates, the method comprising administering a detectable amount of a labeled compound of formula (I) or its pharmaceutically acceptable salt to a subject in need thereof and detecting the labeled compound associated with amyloid deposits or tau aggregates One embodiment of the present invention is directed to a biaryl or bis-aromatic compound of formula (I) or its pharmaceutically acceptable salt.

Another embodiment of the present invention is directed to the compound of formula (I) as described above, wherein at least one of the aryl components is substituted with a side chain having a radiolabel.

Another embodiment of the present invention is directed to the compound of formula (I) as described above, wherein the radiolabel is $^{18}$F.

Another embodiment of the present invention is directed to the compounds of formula (I) as described above, wherein at least one of the aryl components is unsubstituted or substituted phenyl, pyridine, pyrimidine or pyrazine.

Another embodiment of the present invention is directed to the compound of formula (I) as described above, wherein at least one of the aryl components is unsubstituted or substituted fused heteroaryl.

Yet another embodiment of the present invention is directed to the compound of formula (I) as described above, wherein at least one fused heteroaryl is a bicycle.

Yet another embodiment of the present invention is directed to the compound of formula (I) as described above, wherein at least one fused heteroaryl is a tricycle.

Yet another embodiment of the present invention is directed to diagnostic pharmaceutical compositions comprising a radiolabeled compound of formula (I) or its pharmaceutically acceptable salt as described above and, a pharmaceutically acceptable carrier or diluent.

Yet another embodiment of the present invention is directed to a method of imaging and detection of neurological disorders associated with amyloid plaque and/or tau protein aggregation comprising administering a detectable amount of a labeled compound of formula (I) as described above or its pharmaceutically acceptable salt to a subject in need thereof and detecting the labeled compound associated with amyloid deposits and/or tau aggregates.

Yet another embodiment of the present invention is directed to a method of imaging and detection of neurological disorders associated with amyloid plaque aggregation comprising administering a detectable amount of a labeled compound of formula (I) as described above or its pharmaceutically acceptable salt to a subject in need thereof and detecting the labeled compound associated with amyloid deposits.

Yet another embodiment of the present invention is directed to a method of imaging and detection of neurological disorders associated with tau protein aggregation comprising administering a detectable amount of a labeled compound of formula (I) as described above or its pharmaceutically acceptable salt to a subject in need thereof and detecting the labeled compound associated tau aggregates.

Yet another embodiment of the present invention is directed to a method of imaging and detection of Alzheimer's disease associated with amyloid plaque and/or tau protein aggregation comprising administering a detectable amount of a labeled compound of formula (I) as described above or its pharmaceutically acceptable salt to a subject in need thereof and detecting the labeled compound associated with amyloid deposits and/or tau aggregates.

Yet another embodiment of the present invention is directed to a method of imaging and detection of Alzheimer's disease associated with amyloid plaque aggregation comprising administering a detectable amount of a labeled compound of formula (I) as described above or its pharmaceutically acceptable salt to a subject in need thereof and detecting the labeled compound associated with amyloid deposits.

Yet another embodiment of the present invention is directed to a method of imaging and detection of Alzheimer's disease associated with tau protein aggregation comprising administering a detectable amount of a labeled compound of formula (I) as described above or its pharmaceutically acceptable salt to a subject in need thereof and detecting the labeled compound associated with tau aggregates.

Yet another embodiment of the present invention is directed to compounds of Formula (IV).

Yet another embodiment of the present invention is directed to compounds of Formula (V).

Yet another embodiment of the present invention is directed to methods of using compounds of Formula (IV).

Yet another embodiment of the present invention is directed to methods of using compounds of Formula (V).

Yet another embodiment of the present invention is directed to methods of synthesizing compounds of Formula (IV).

Yet another embodiment of the present invention is directed to methods of synthesizing compounds of Formula (V).

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments will become apparent from and encompassed by the following Detailed Description when taken in conjunction with the accompanying drawings.

The entire disclosures of all patents and references cited throughout this application are incorporated herein by reference in their entirety.

BRIEF DESCRIPTION OF THE DRAWINGS

The application file contains at least one image executed in color. Copies of this patent application publication with color images will be provided by the Office upon request and payment of the necessary fee.

The following detailed description, given by way of example, but not intended to limit the invention solely to the specific embodiments described, may best be understood in conjunction with the accompanying drawings, in which:

FIGS. 8a and 8b show binding of fluorescent compound T520 to AD brain sections confirmed by immunostaining with tau or Aβ antibodies.

FIGS. 9a and 9b show total binding of fluorescent compound T522 to AD brain sections confirmed by immunostaining with tau or Aβ antibodies.

DETAILED DESCRIPTION

Figure 1A:
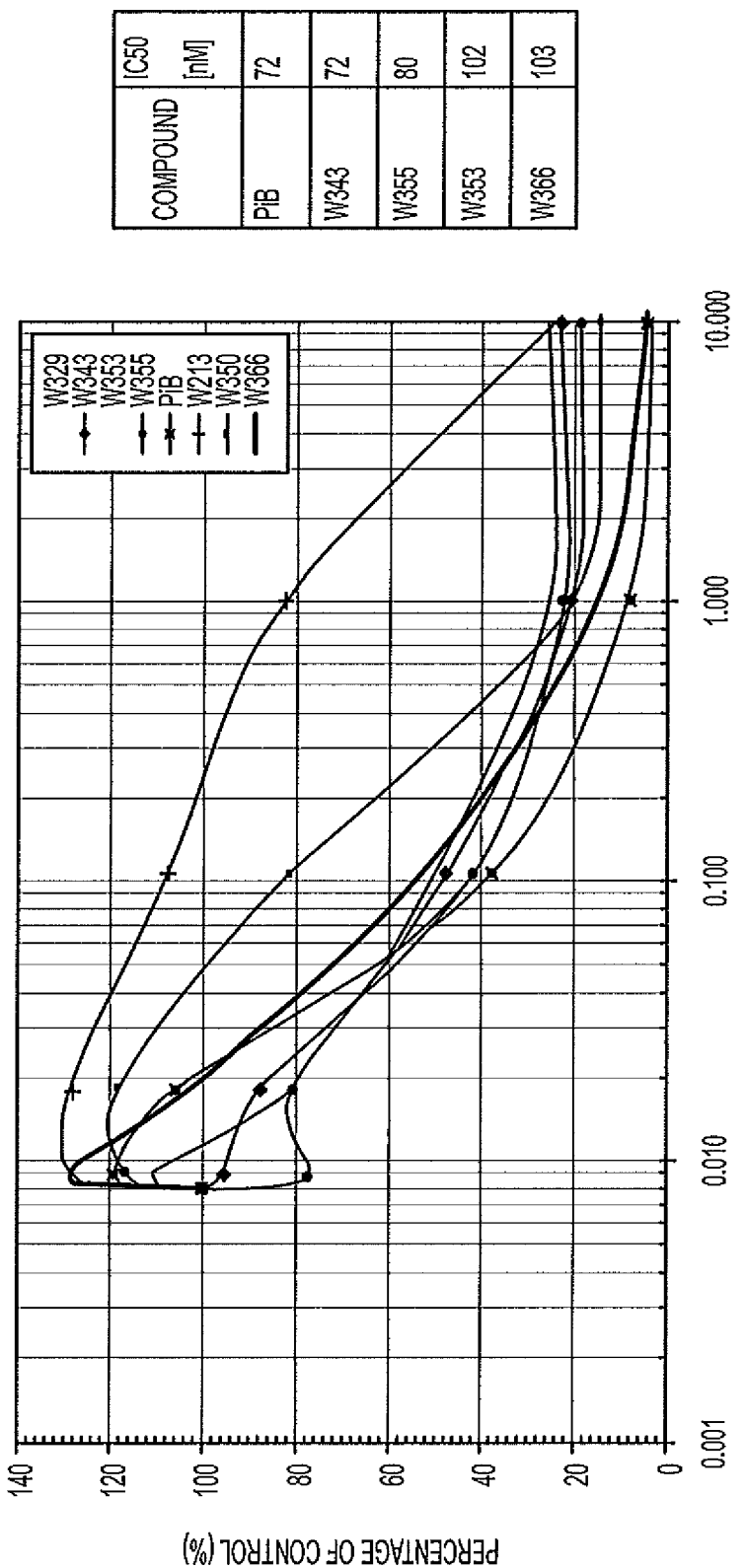
FIG. 1a shows an example of a brain slice assay used to determine the $IC_{50}$ values of W366 and related compounds.

The following description will describe the invention in relation to advantageous embodiments thereof. The invention is in no way limited to these advantageous embodiments as they are purely included to exemplify the invention and the invention is intended to include possible variations and modifications as would be readily apparent to a person skilled in the art without departing from the scope of the invention.

One of the embodiments of the present invention relates to a compound of general formula (I)

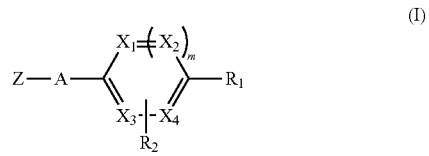

wherein
A is a bond, $(C_1-C_4)$alkyl, $(C_3-C_6)$cycloalkyl, $(C_2-C_4)$alkene, or $(C_1-C_4)$alkyne;
Z is aryl selected from the group consisting of:

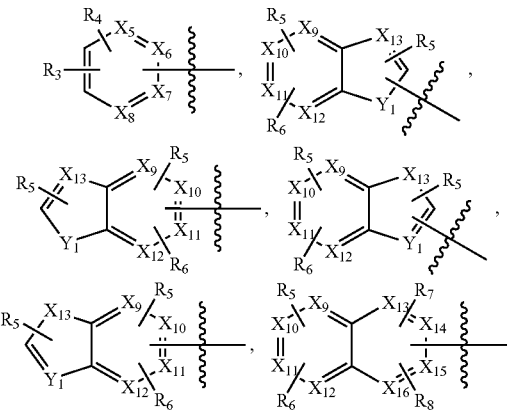

-continued

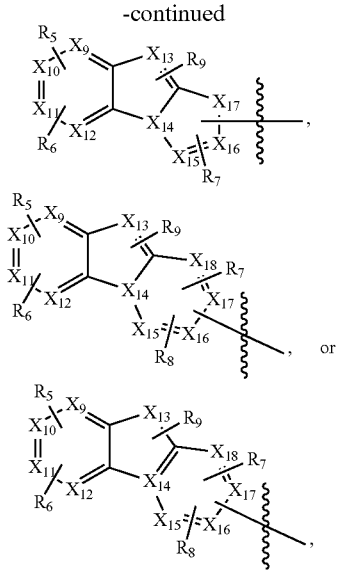

wherein
X₁ and X₁₃ are each independently C, CH, N, O, or S;
X₂-X₁₂ and X₁₄-X₁₈ are each independently C, CH or N;
Y₁ is N, O, or S;
R₁-R₂ are each independently H, halogen, hydroxy, nitro, cyano, amino, alkyl, alkoxy, —(O—CH₂—CH₂)ₙ—, monoalkylamino, dialkylamino, monoarylamino, diarylamino, primary amine, secondary amine, tertiary amine, NR₁₀COOalkyl, NR₁₀ COOaryl, NR₁₀ COalkyl, NR₁₀ CO aryl, COOalkyl, COOaryl, COalkyl, COaryl, aryl, saturated heterocyclyl,
wherein the last seventeen groups are unsubstituted or substituted by halogen, a leaving group or one or more radicals selected from the group consisting of halogen, alkyl, haloalkyl, cyano, hydroxyl, amino, monoalkylamino, dialkylamino, alkoxy, R₁₀, a radiolabel or alkyl substituted with a radiolabel; or
R₁ and R₂ together form a five- or six-membered saturated or unsaturated ring which optionally contains an additional heteroatom in the ring which is selected from N, O, and S, the ring being unsubstituted or substituted by a halogen or one or more radicals selected from the group consisting of halogen, alkyl, haloalkyl, cyano, hydroxyl, amino, monoalkylamino, dialkylamino, alkoxy, R₁₀, a radiolabel or alkyl substituted with radiolabel;
R₃-R₉ are each independently H, halogen, hydroxy, nitro, cyano, amino, alkyl, alkoxy, —(O—CH₂—CH₂)ₙ—, monoalkylamino, dialkylamino, monoarylamino, diarylamino, NR₁₀COOalkyl, NR₁₀ COOaryl, NR₁₀ COalkyl, NR₁₀ CO aryl, COOalkyl, COOaryl, COalkyl, COaryl, aryl, heterocyclyl,
wherein the last seventeen groups are unsubstituted or substituted by a halogen, leaving group or one or more radicals selected from the group consisting of halogen, alkyl, haloalkyl, cyano, hydroxyl, amino, monoalkylamino, dialkylamino, alkoxy, R₁₀, a radiolabel or alkyl substituted with a radiolabel;
R₁₀ is H, alkyl, alkene, aryl unsubstituted or substituted with halogen, hydroxyl, cyano, nitro, amino, —OSO₂alkyl, —OSO₂aryl, —OSi(alkyl)₃, —OTHP or a radiolabel;
n is 1, 2, or 3;
m is 0 or 1, and
a pharmaceutically acceptable salt thereof.

Another embodiment of the present invention is directed to the compound of formula (I) as described above wherein Z is

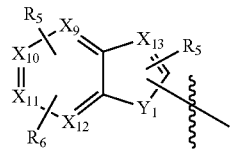

and at least one of $X_9$-$X_{13}$ is nitrogen and m is 1.

Another embodiment of the present invention is directed to the compound of formula (I) as described above, wherein at least one of $R_1$-$R_6$ is —(O—CH₂—CH₂)₂—.

Another embodiment of the present invention is directed to the compound of formula (I) as described above, wherein Z is

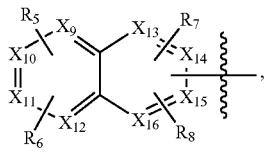

and at least one of $X_9$-$X_{16}$ is nitrogen and m is 1.

Another embodiment of the present invention is directed to the compound of formula (I) as described above, wherein Z is

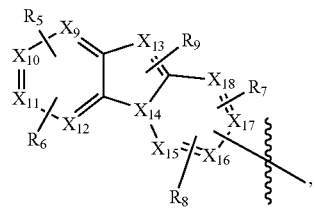

and at least one of $X_9$-$X_{18}$ is nitrogen and m is 1.

Another embodiment of the present invention is directed to the compound of formula (I) as described above, wherein Z is

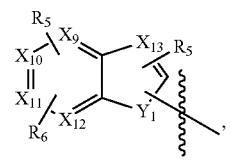

and
wherein at least one $X_9$-$X_{12}$ is nitrogen and m is 1.

Another embodiment of the present invention is directed to the compound of formula (I) as described above, wherein Z is

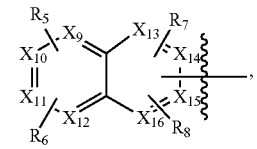

A is acetylene and at least one $X_9$-$X_{16}$ is nitrogen.

Another embodiment of the present invention is directed to the compound of formula (I) as described above, wherein A is a bond and Z is quinoline.

Another embodiment of the present invention is directed to the compound of formula (I) as described above, wherein at least one of $R_1$-$R_9$ is a saturated heterocycle.

Another embodiment of the present invention is directed to the compound of formula (I) as described above, wherein m is 1 and $R_1$ is saturated heterocycle.

Another embodiment of the present invention is directed to the compound of formula (I) as described above, wherein Z is

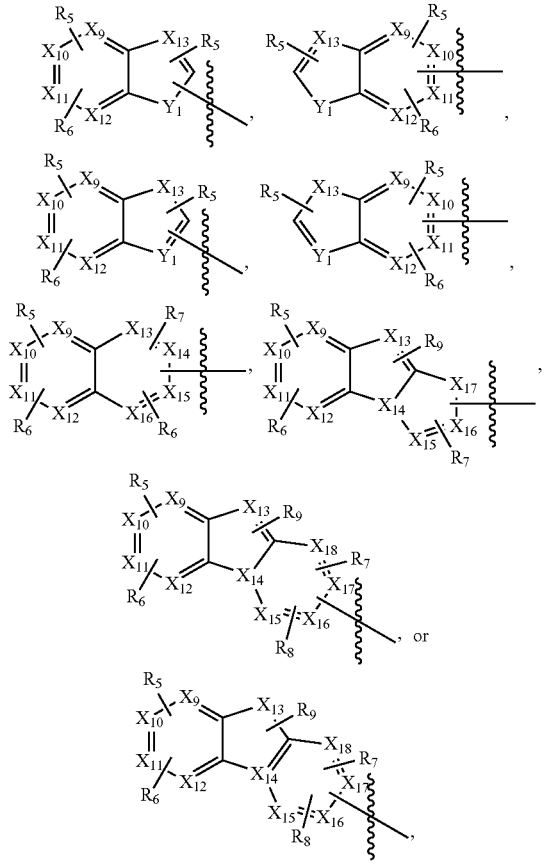

wherein at least two of $X_9$-$X_{16}$ are nitrogens.

Yet another embodiment of the present invention is directed to the compound of formula (I) as described above, wherein A is a bond and Z is

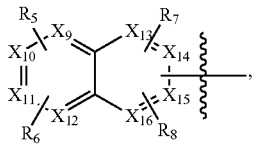

wherein at least three of $X_1$-$X_{16}$ are nitrogens.

Yet another embodiment of the present invention is directed to the compound of formula (I) as described above, wherein A is a bond and Z is

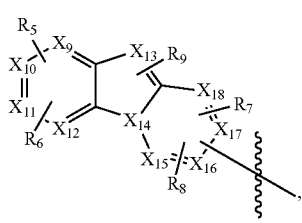

wherein at least two of $X_9$-$X_{18}$ are nitrogens.

Another embodiment of the present invention is directed to the compound of formula (I) as described above, wherein A is $C_2$ alkyne or acetylene and Z is

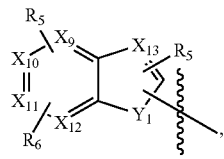

wherein at least two of $X_9$-$X_{13}$ or $Y_1$ are nitrogens.

Another embodiment of the present invention relates to the compound of formula (I) as described above, wherein at least one of $R_1$-$R_2$ comprises a heterocycle.

Another embodiment of the present invention relates to the compound of formula (I) as described above, wherein at least one of $R_1$-$R_2$ comprises a saturated heterocycle.

Another embodiment of the present invention relates to the compound of formula (I) as described above, wherein at least one of $R_1$-$R_9$ comprises —(O—CH$_2$—CH$_2$)$_2$— or —(O—CH$_2$—CH$_2$)$_3$—.

Another embodiment of the present invention relates to the compound of formula (I) as described above, wherein at least one of $R_1$-$R_9$ comprises a radiolabel selected from the group consisting of $^{11}C$, $^{13}N$, $^{15}O$, $^{18}F$, $^{123}I$, $^{124}I$, $^{125}I$, $^{131}I$, $^{76}Br$ and $^{77}Br$.

In another embodiment, the present invention provides the compound of formula (I) as described above, wherein the compound can be presented as formula (II). Formula (II) represents W366 and related compounds containing labeling elements on the left hand portion of the molecule:

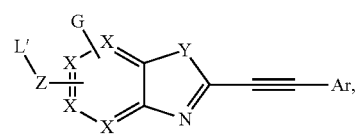

(II)

wherein
X is N or C;
Y is S or O;
Z is bond, S, O, alkyl, —(OCH$_2$CH$_2$)$_n$—, aryl or heteroaryl;
L* is radioactive label;
Ar is aryl, heteroaryl, optionally substituted with O, S, halogen, alkyl, or —(OCH$_2$CH$_2$)$_n$—;
G is H, S, O, halogen, alkyl, —(OCH$_2$CH$_2$)$_n$— or aryl; and
n is 1, 2, or 3.

In another embodiment, the present invention provides the compound of formula (I) as described above, wherein the compound can be presented as formula (III), which represents W366 and related compounds containing labeling elements on the right hand portion of the molecule:

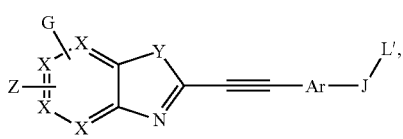

(III)

wherein
X is N or C;
Y is S or O;
Z is S, O, alkyl, —(OCH$_2$CH$_2$)$_n$—, aryl or heteroaryl optionally substituted with O, S, halogen, alkyl, aryl or —(OCH$_2$CH$_2$)$_n$—;

L* is radioactive label;

J is bond, S, O, alkyl, —(OCH$_2$CH$_2$)$_n$—, aryl or heteroaryl;

Ar is aryl, heteroaryl, optionally substituted with O, S, halogen, alkyl, or —(OCH$_2$CH$_2$)$_n$—;

G is H, S, O, halogen, alkyl, —(OCH$_2$CH$_2$)$_n$— or aryl; and n is 1, 2, or 3.

In another embodiment, the present invention provides W366 and related compounds containing labeling elements and substituted pyridyl moieties:

In another embodiment, the present invention provides the following compounds of formulas (II) and (III) containing labeling element (either $^{11}$C—NHMe or $^{18}$F):

Scheme 1. Representative examples of Aβ imaging agents of formula (II) and forumla (III).

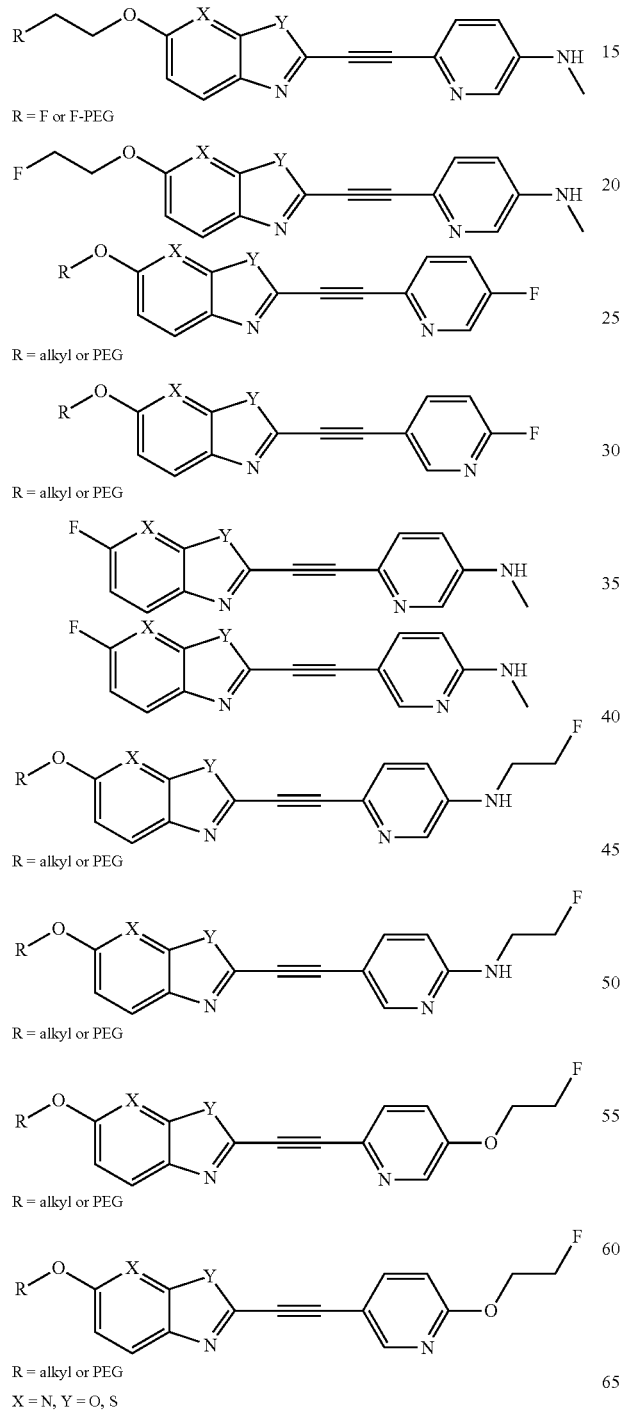

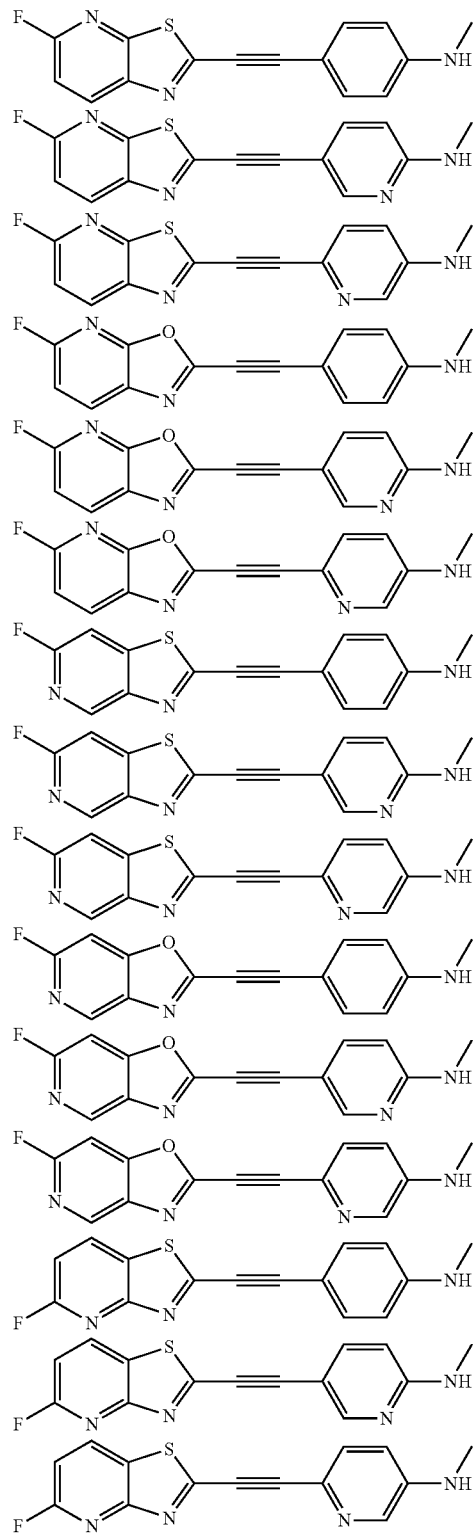

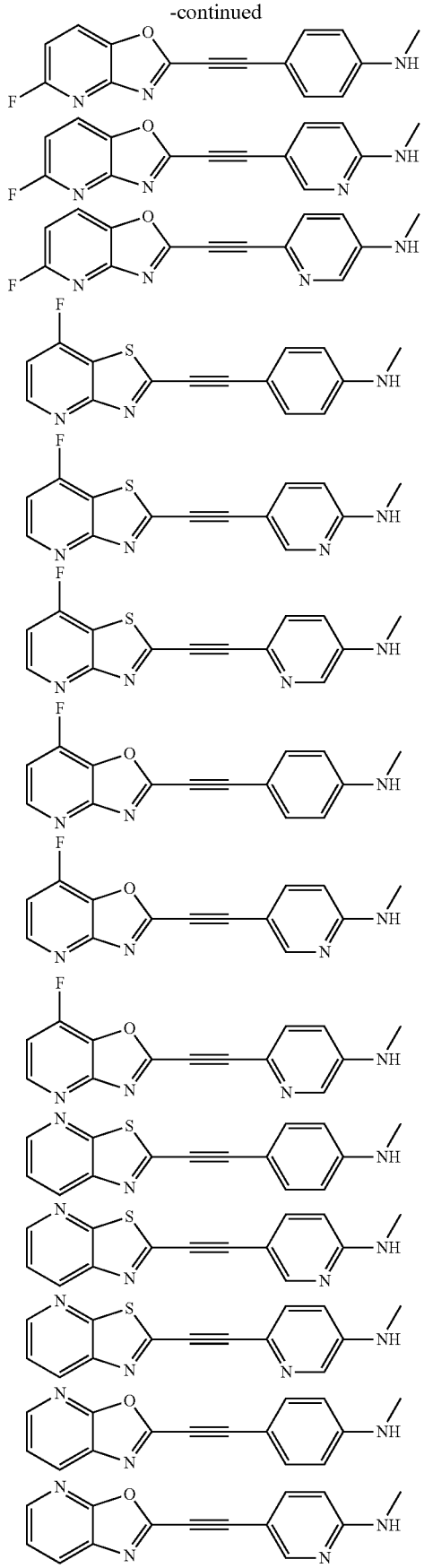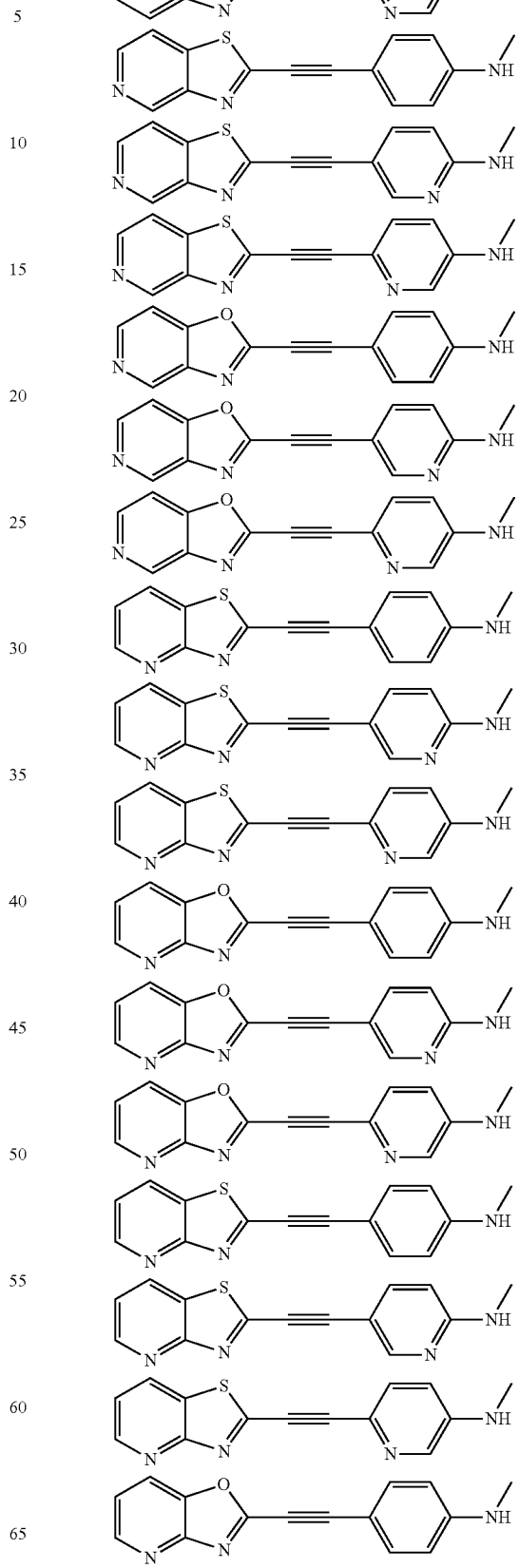

-continued

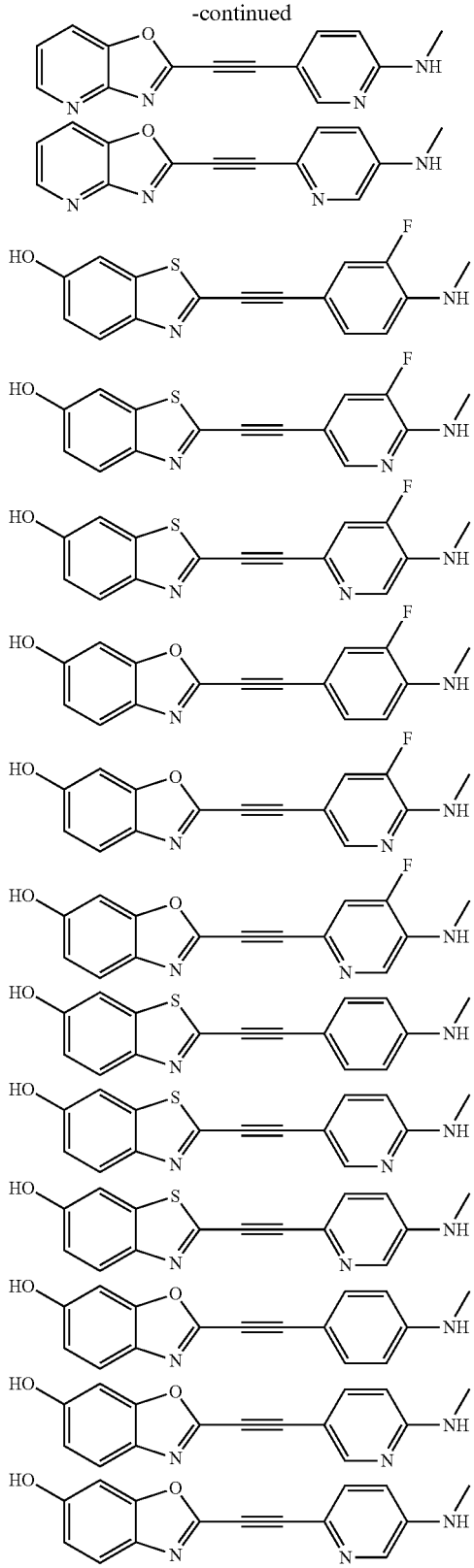

The present invention also includes stereoisomers of compounds of formula (I). Such stereoisomers include, but are not limited to mixtures of enantiomers and diastereomers as well as individual enantiomers and diastereomers.

When any variable occurs more than one time in any constituent of formula (I), its definition in each instance is independent of its definition at any other instance. Also, combinations of substituents and/or variables are permissible only if such combinations result in stable compounds.

The compounds of formula (I) may also be solvated, especially hydrated. Hydration may occur during preparation of the compounds or compositions comprising the compounds of formula (I), or hydration may occur over time due to hydroscopic nature of the compounds.

The compounds of formula (I) can be prepared by the application or adaptation of known methods (i.e. methods heretofore used (methods A-S, as presented in detail in EXPERIMENTAL EXAMPLES section) or described in the chemical literature.

Another embodiment of the present invention relates to a method of imaging amyloid deposits and/or tau aggregates. When the compounds of formula (I) are used as imaging agents, they are labeled with suitable radioactive isotopes, for example radioactive halogens, such as $^{18}F$, radioactive metals and other detectable radioactive atoms such as $^{11}C$.

In another embodiment, the present invention relates to radiolabeled compounds of formulas (II) and (III) as imaging agents. These imaging agents are unique as they contain new binding moieties of tightly tethered through the alkyne linker. These binding motifs may interact simultaneously with orthogonal binding sites providing a more complete overview of the biochemical phenomena associated with AD patients.

Figure 1B:
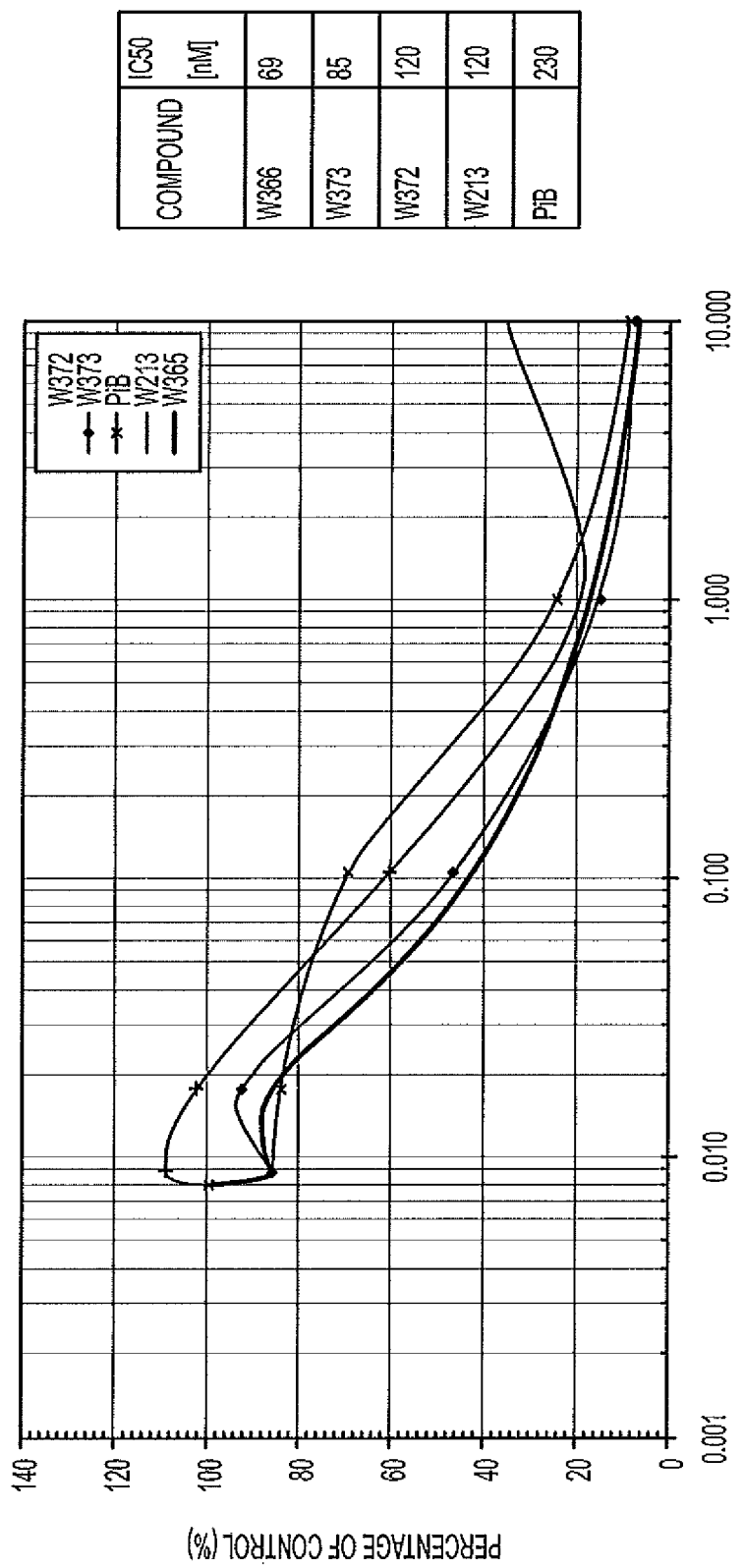
FIG. 1b shows an example of a brain slice assay used to determine the $IC_{50}$ values of W366 and related compounds.

Another embodiment of the present invention is directed to compounds containing both benzothiazole and acetylene binding motifs, such as W366 and related compounds, which are designed to interact with the orthogonal binding sites of senile plaques, and potentially NFTs. In this regard, these imaging agents offer the potential to provide a more complete dataset of biochemical information. FIGS. 1a and 1b show examples of brain slice assay used to determine the $IC_{50}$ values of W366 and related compounds.

Another embodiment of the present invention is directed to compounds of formula (I) as imaging agents for tau aggregates.

It has been shown that solutions of the compounds of the present invention when injected intravenously into normal mice, exhibit excellent brain uptake. These compounds also display high binding affinity to tau fibrils. Autoradiography using the present compounds demonstrated labeling of NFTs in AD brain sections. Fluorescence assay data shows the binding ability of these agents to tau aggregates and Aβ fibrils. In neuropathological staining, compounds of the present invention stained amyloid plaques and/or tau aggregates.

The results presented herein are based on the brain section staining studies and autoradiography of tracers in brain sections of three different types (Tau+/Aβ+, Tau−/Aβ+, and Tau−/Aβ−). These results are shown in FIGS. 2-16 and Tables 1-3.

Another embodiment of the present invention is directed to quinoline compounds of formula (I), having extended side chains containing radiolabel as illustrated in Scheme 2. As shown in Scheme 2 and in Table 1, compounds of this class bind to tau proteins. These compounds incorporate extended side chains, especially containing piperidine or morpholine and/or polyethers such as polyethylene glycols (PEG or —(OCH$_2$CH$_2$)$_n$—, wherein n can be 1-10, preferably 1-3). These structural features may play a role in binding affinity of these compounds to tau aggregates. Fluorescence assay data show the binding ability of these agents to tau aggregates.

Figure 15:
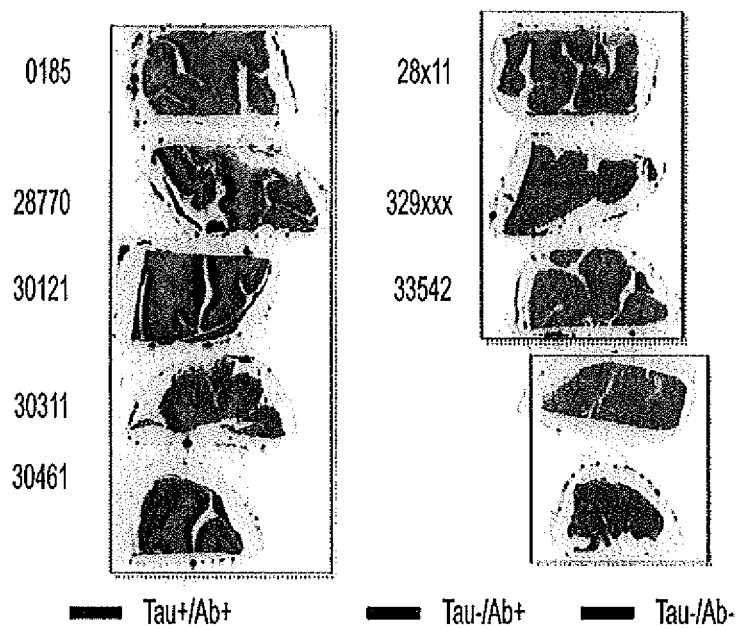
FIG. 15 shows ex vivo autoradiograph images of a preferred compound, T525.
Figure 16:
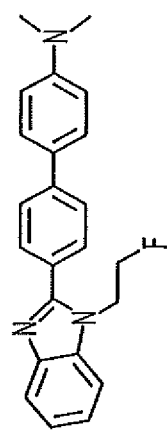
FIG. 16 shows binding of fluorescent compound T543 to AD brain sections confirmed by immunostaining with tau or Aβ antibodies.
Figure 16:
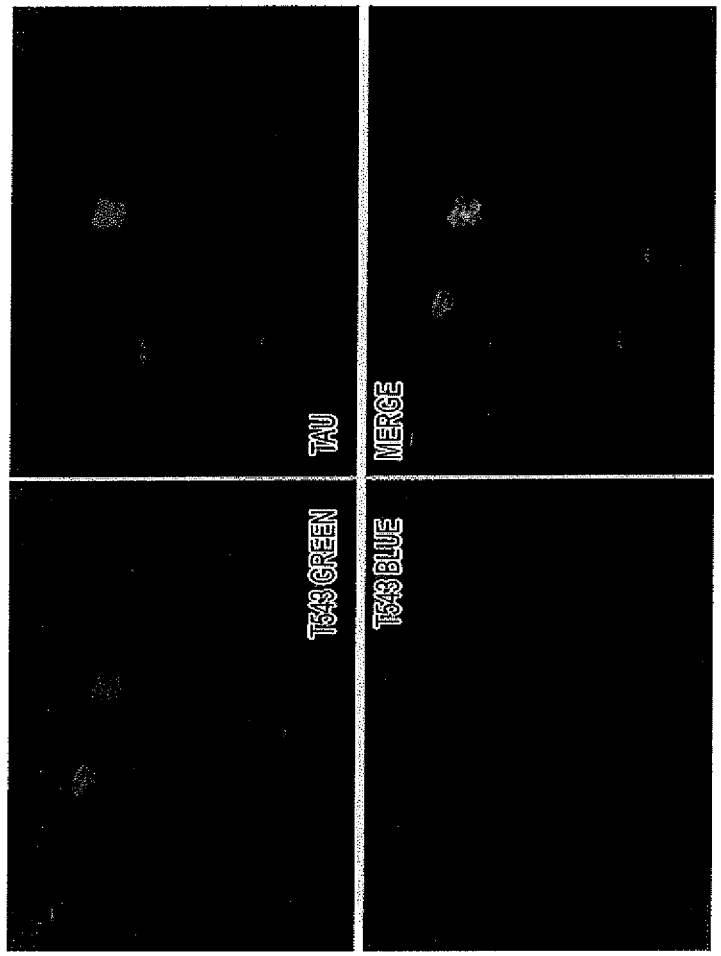
Figure 17:
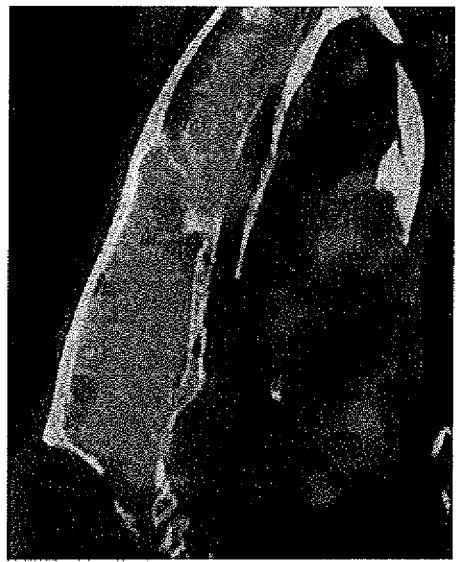
FIG. 17 shows brain images (brain uptake) for tracer T114.
Figure 17:
Figure 18:
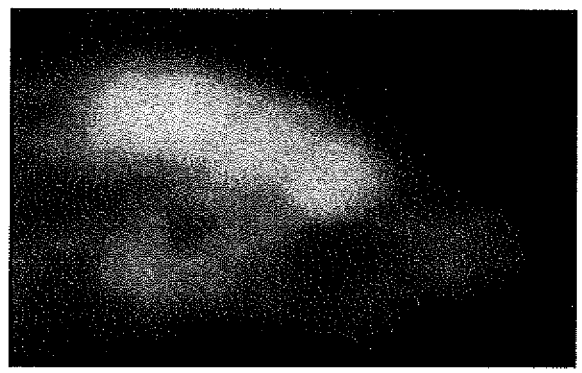
FIG. 18 shows brain images (brain uptake) for tracer T442.
Figure 19:
FIG. 19 shows brain images (brain uptake) for tracer T549.
Figure 19:
Figure 19:
Figure 20:
FIG. 20 shows brain images (brain uptake) for tracer T525.
Figure 20:
Figure 21:
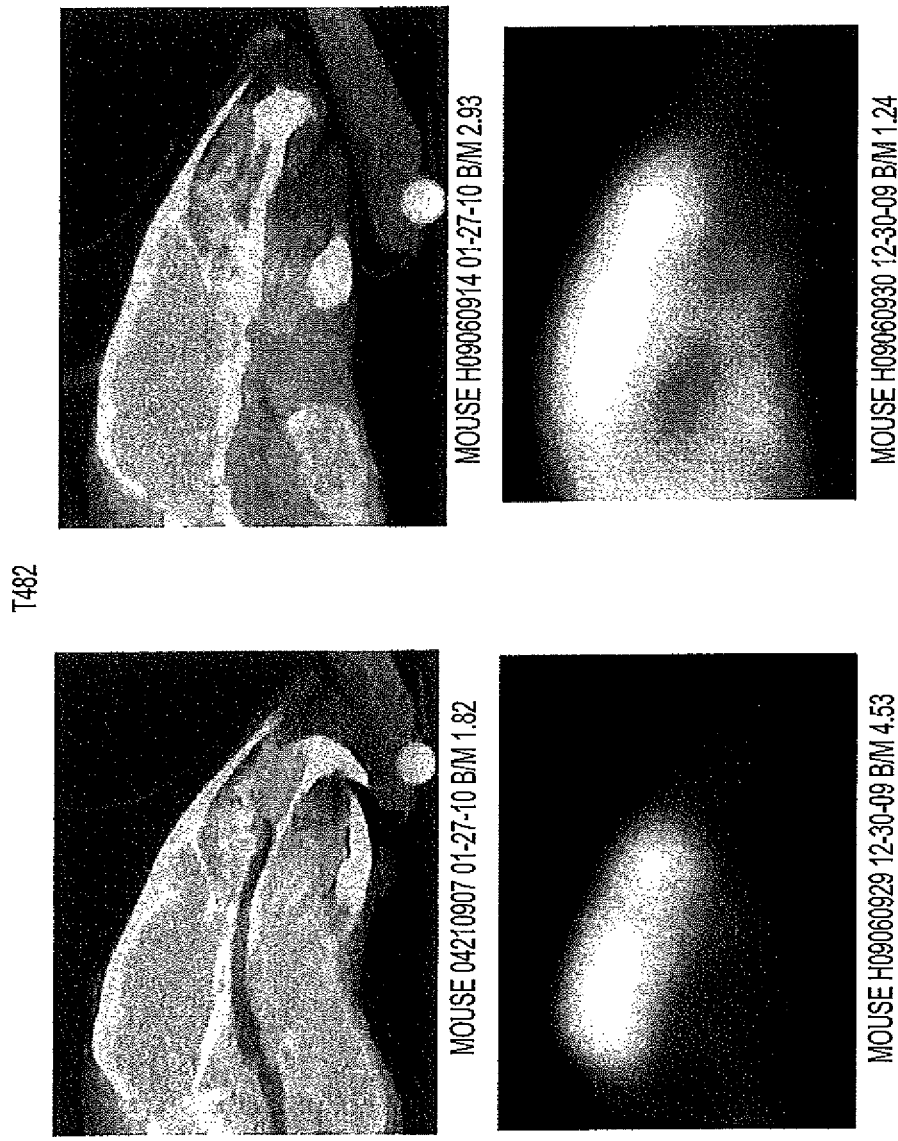
FIG. 21 shows brain images (brain uptake) for tracer T482.
Figure 22:
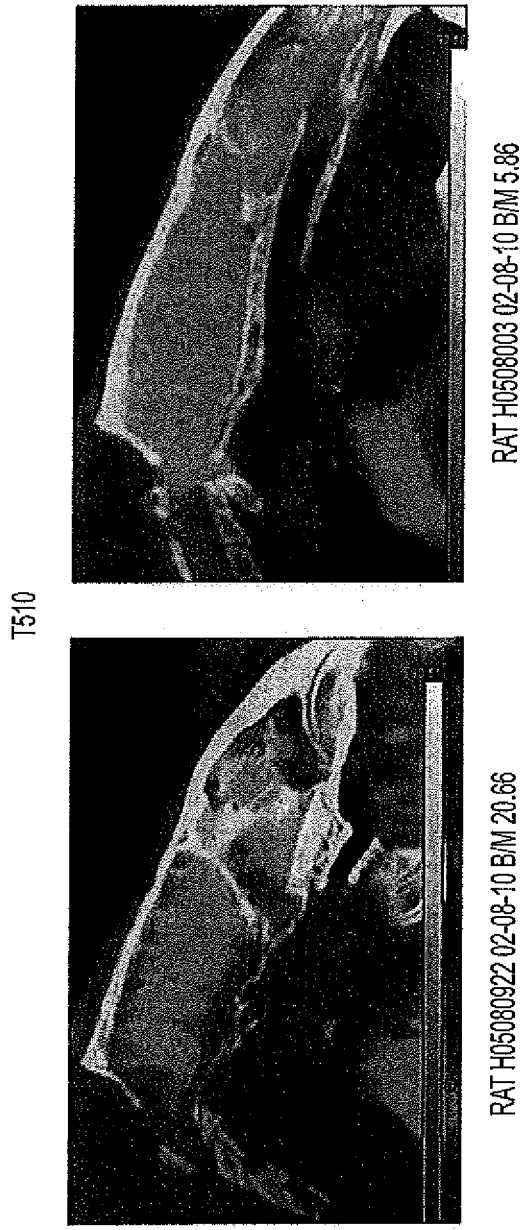
FIG. 22 shows brain images (brain uptake) for tracer T510.
Figure 23:
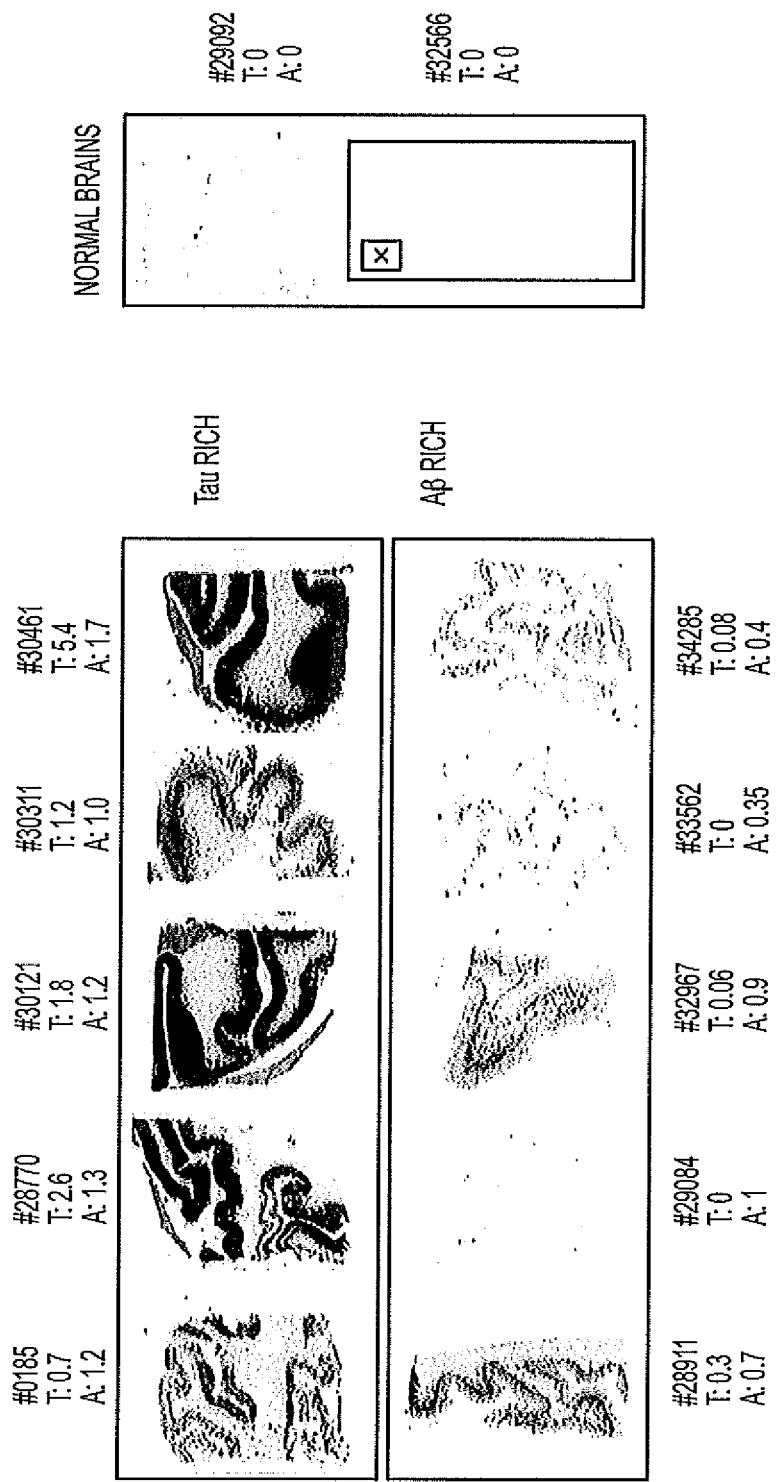
FIG. 23 shows Autoradiography of $^{18}$F-T777.
Figure 24:
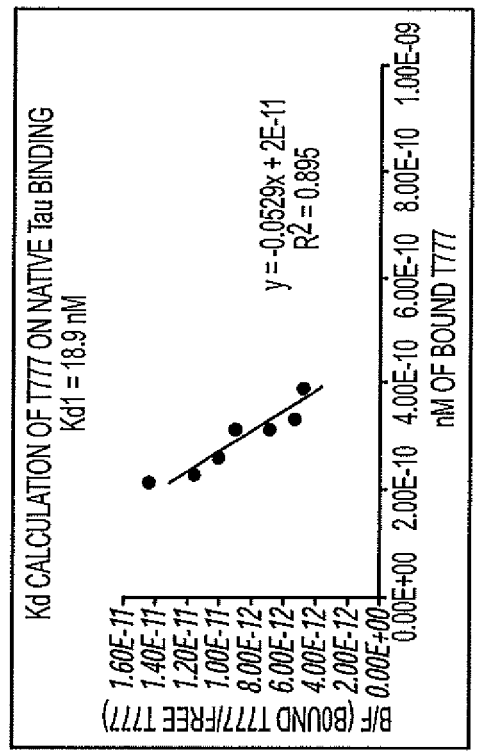
FIG. 24 shows $^{18}$F-T777 correlation with Tau and Amyloid load.
Figure 24:
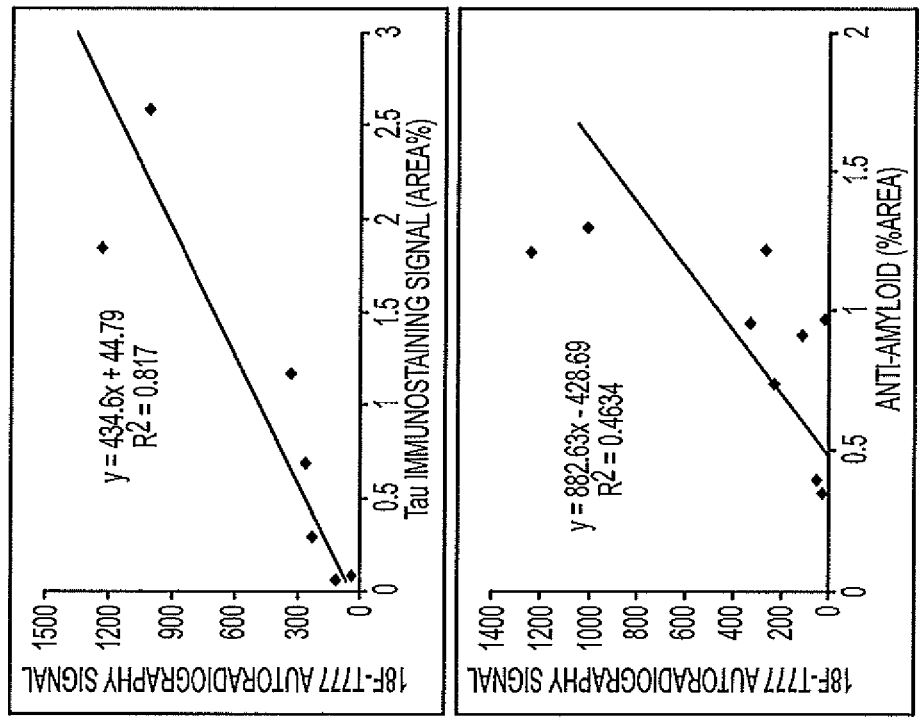
Figure 25:
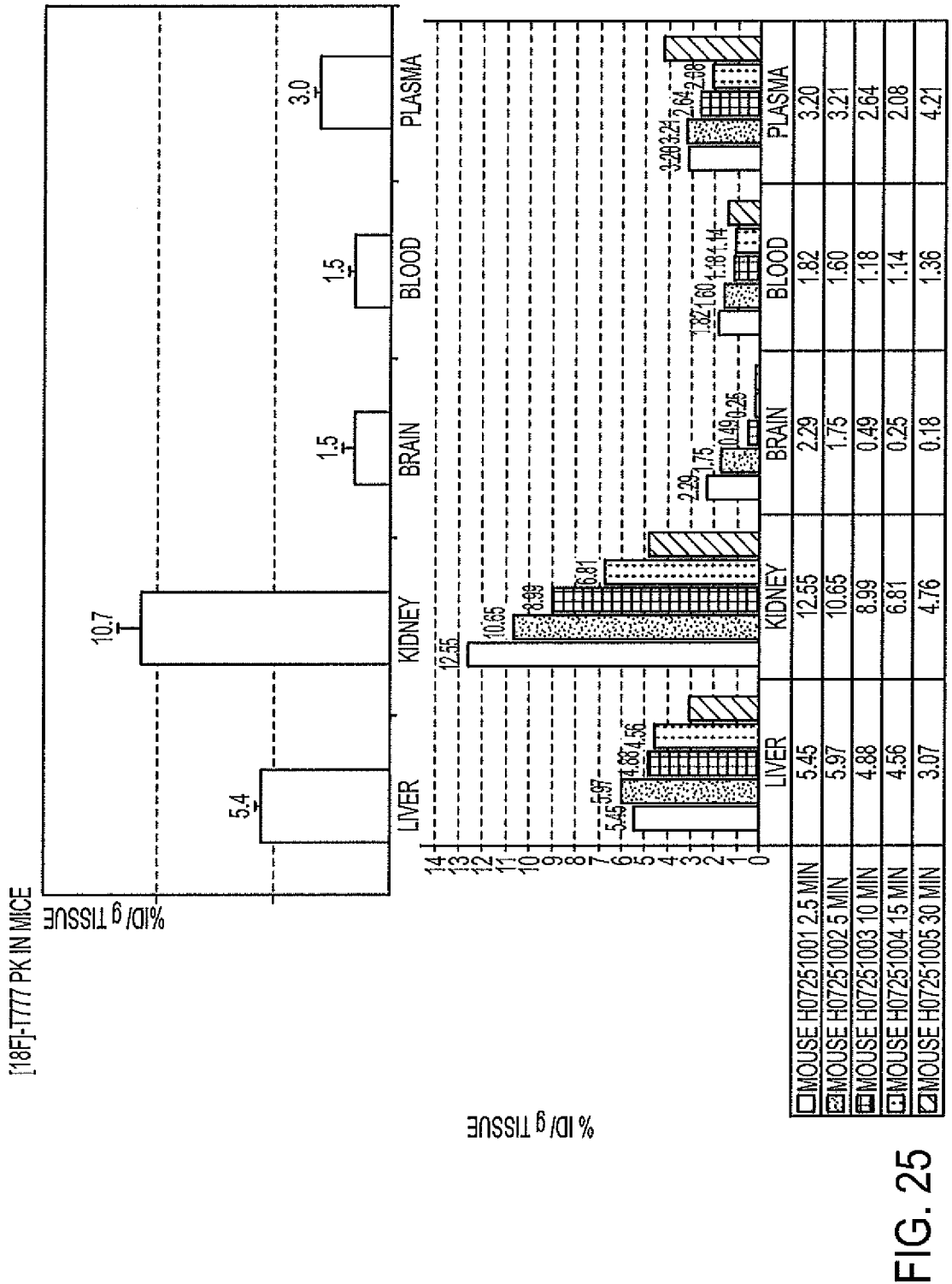
FIG. 25 shows $^{18}$F-T777 PK in mice
Figure 26:
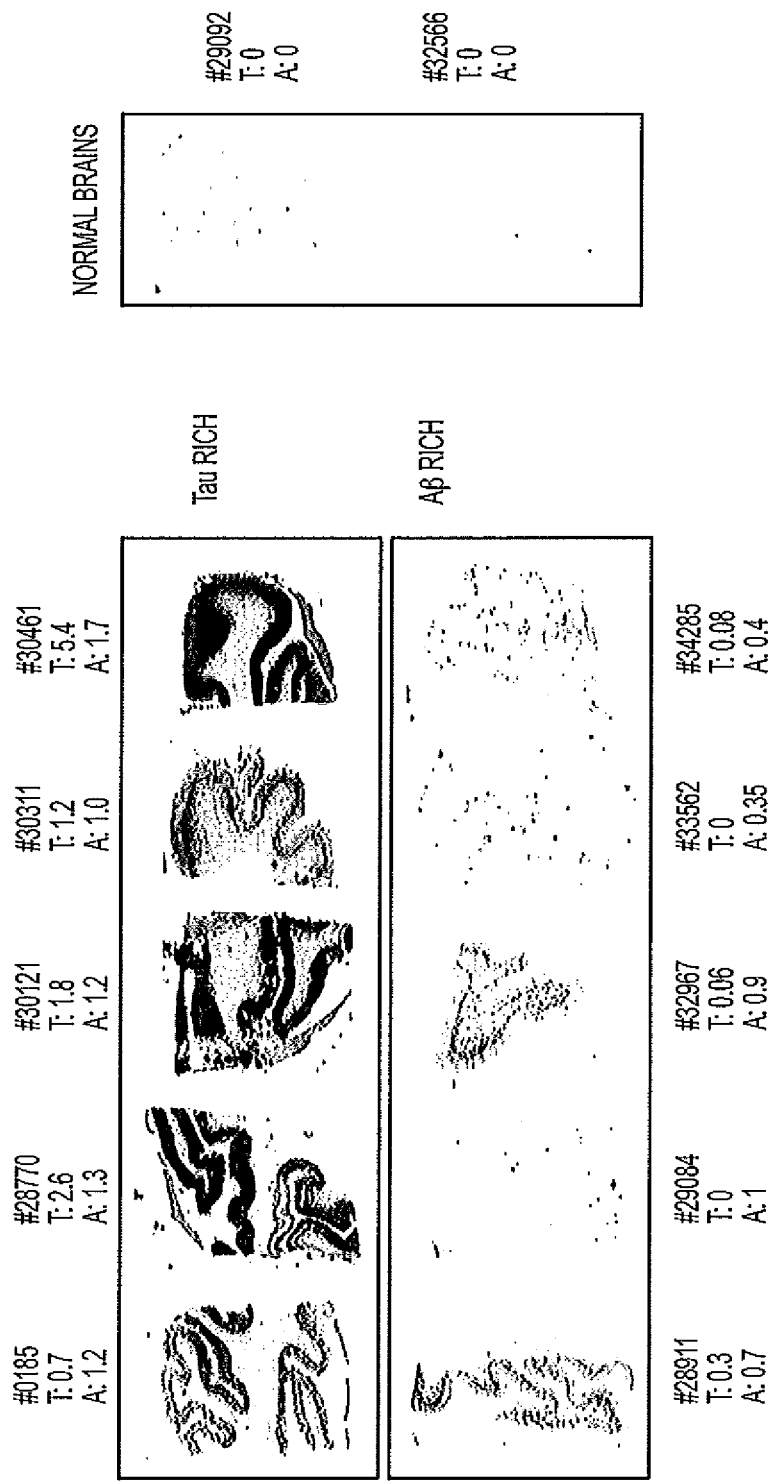
FIG. 26 shows Autoradiography of $^{18}$F-T808.
Figure 27:
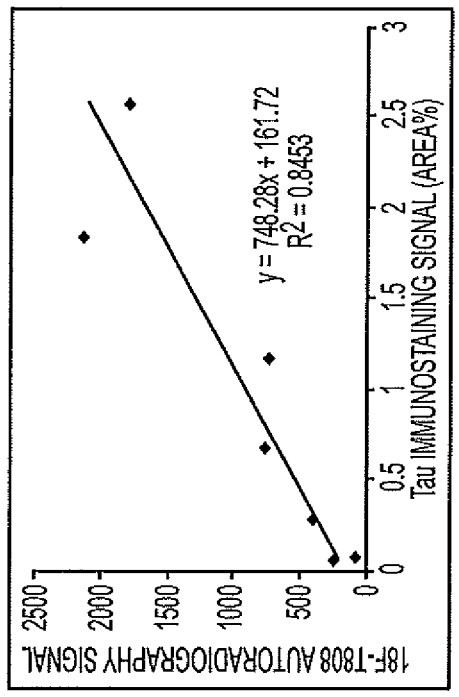
FIG. 27 shows $^{18}$F-T808 correlation with Tau and Amyloid load.
Figure 27:
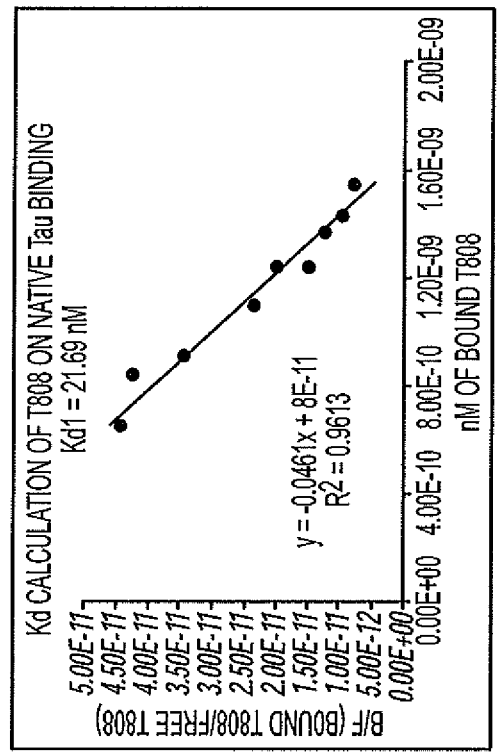
Figure 27:
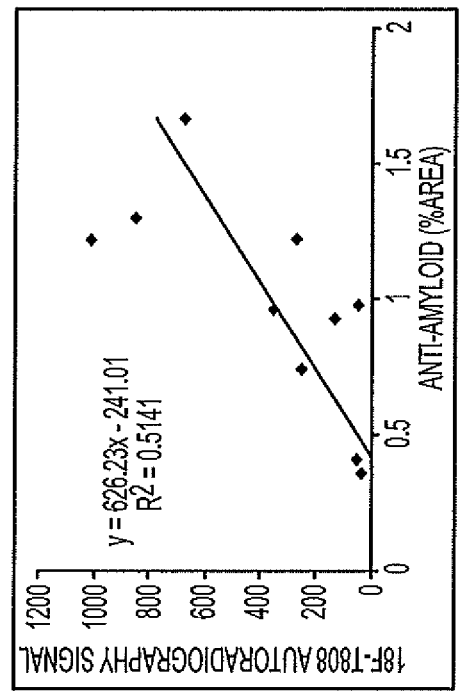
Figure 28:
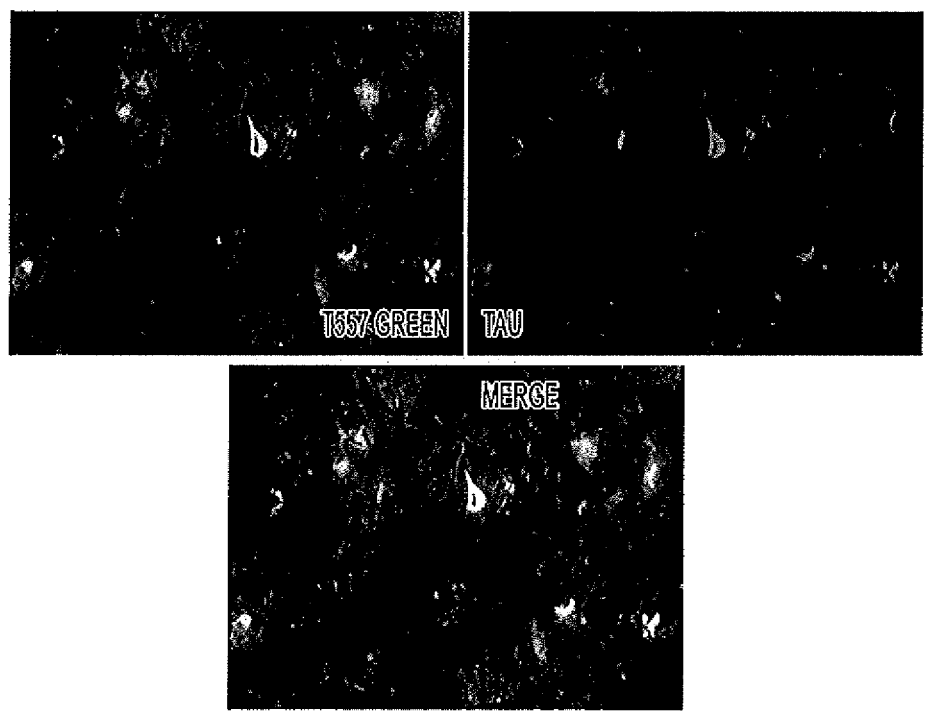
FIG. 28 shows brain images (brain uptake) for tracer T557.
Figure 29:
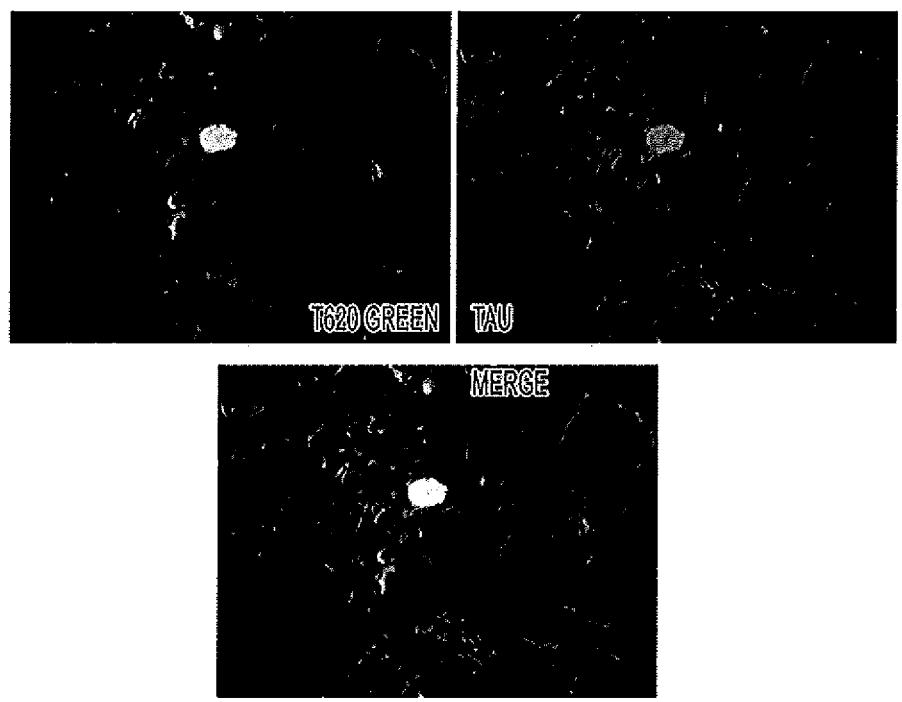
FIG. 29 shows brain images (brain uptake) for tracer T620.
Figure 30:
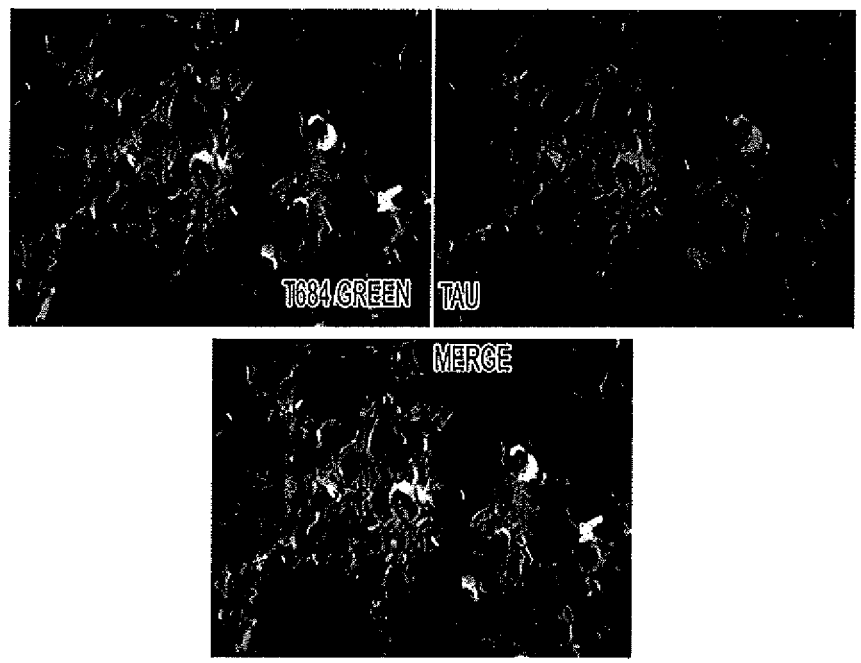
FIG. 30 shows brain images (brain uptake) for tracer T684.
Figure 31:
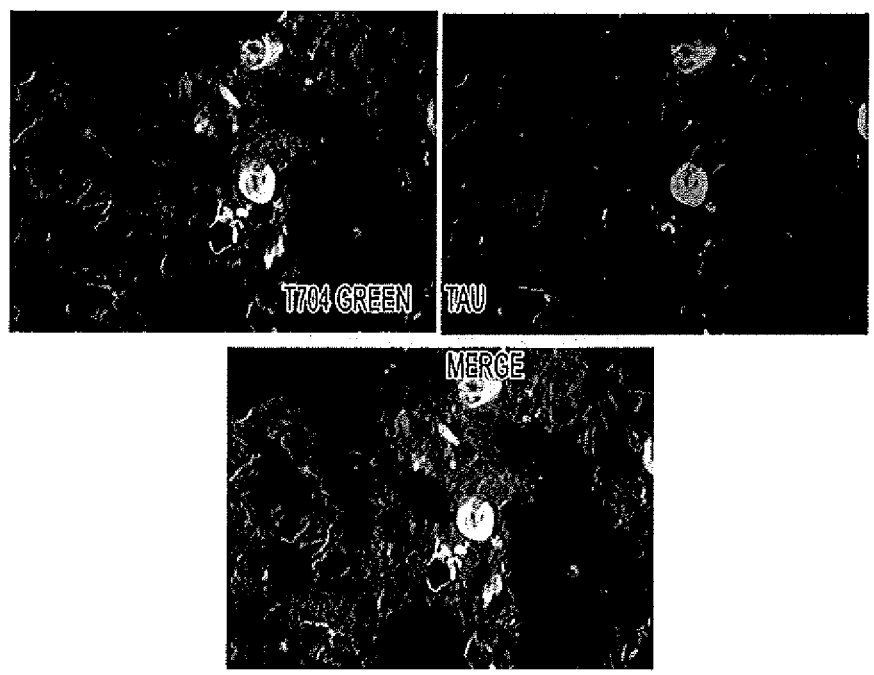
FIG. 31 shows brain images (brain uptake) for tracer T704.
Figure 32:
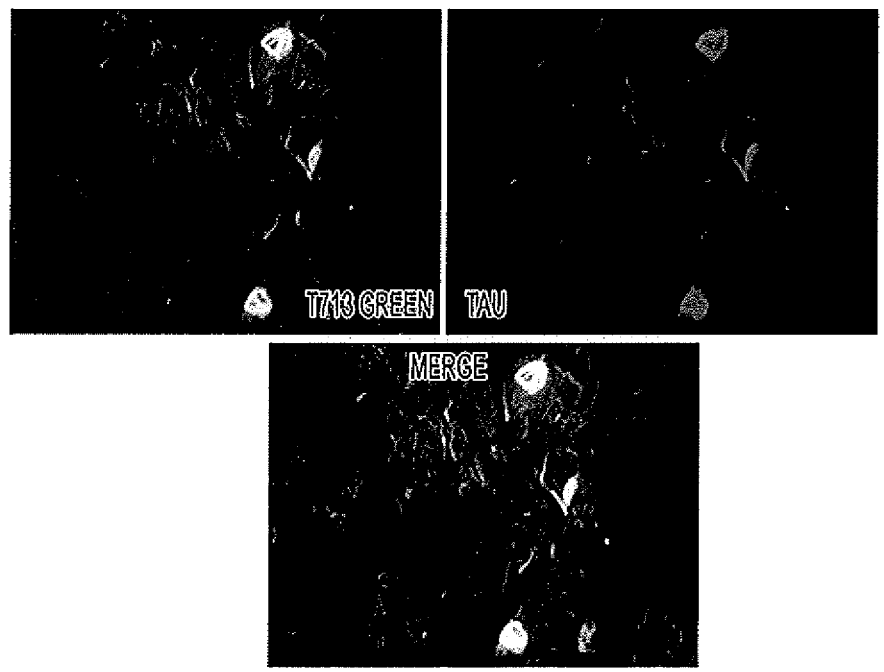
FIG. 32 shows brain images (brain uptake) for tracer T713.
Figure 33:
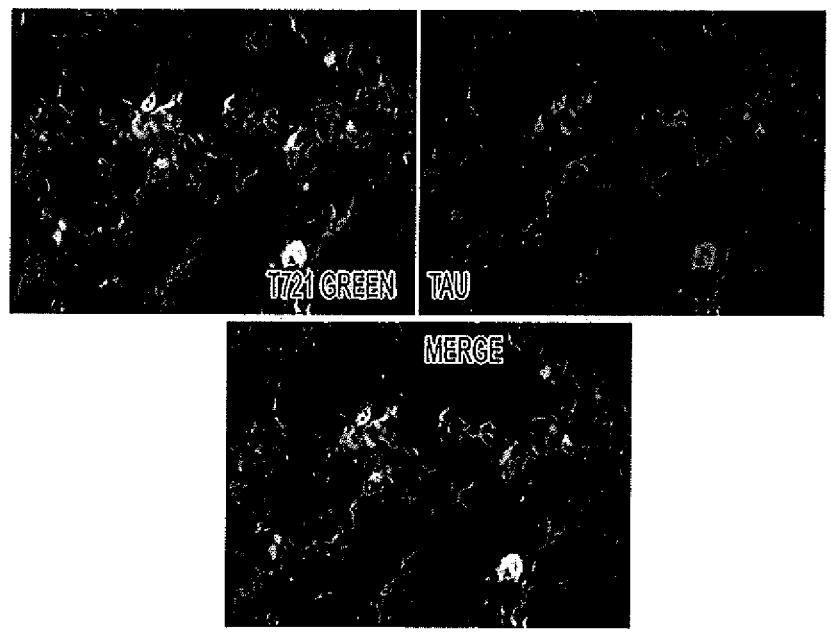
FIG. 33 shows brain images (brain uptake) for tracer T721.
Figure 34:
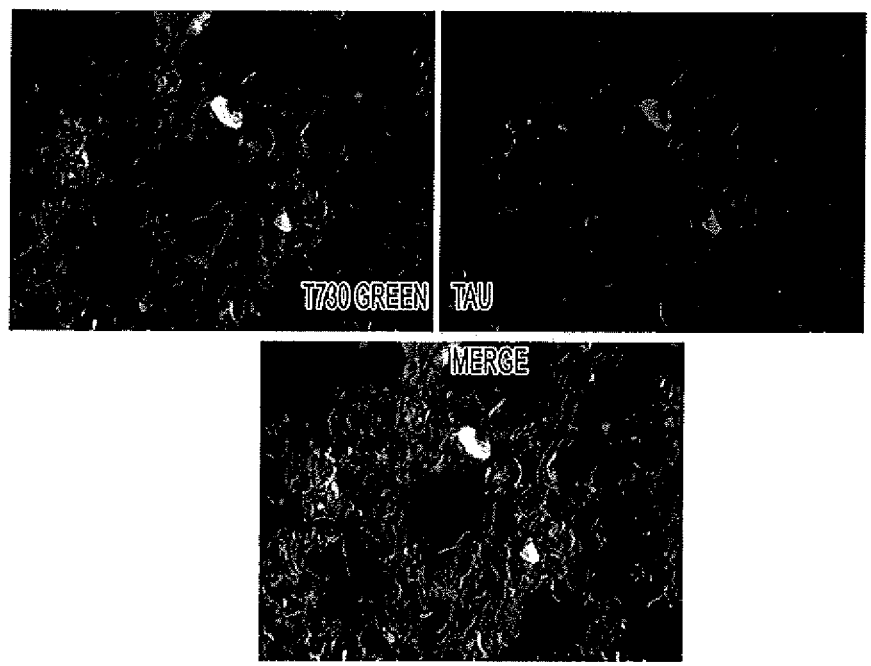
FIG. 34 shows brain images (brain uptake) for tracer T730.

FIGS. 12, 13a-13b, and 14 show binding of preferred fluorescent compounds T539, T499, and T525 to AD brain sections confirmed by immunostaining with tau or Aβ antibodies. FIG. 15 show ex vivo autoradiograph images of T525, in three different types of brain sections: Aβ+/tau− brains contain Aβ plaques, but no tau aggregates (diagnosis by brain bank as non-AD donor); Aβ+/tau+ brains contain both. Aβ plaques and tau aggregates (diagnosed by brain bank as AD patient), and normal (control) brains. The presence or absence of Aβ and/or tau is confirmed by immunostaining.

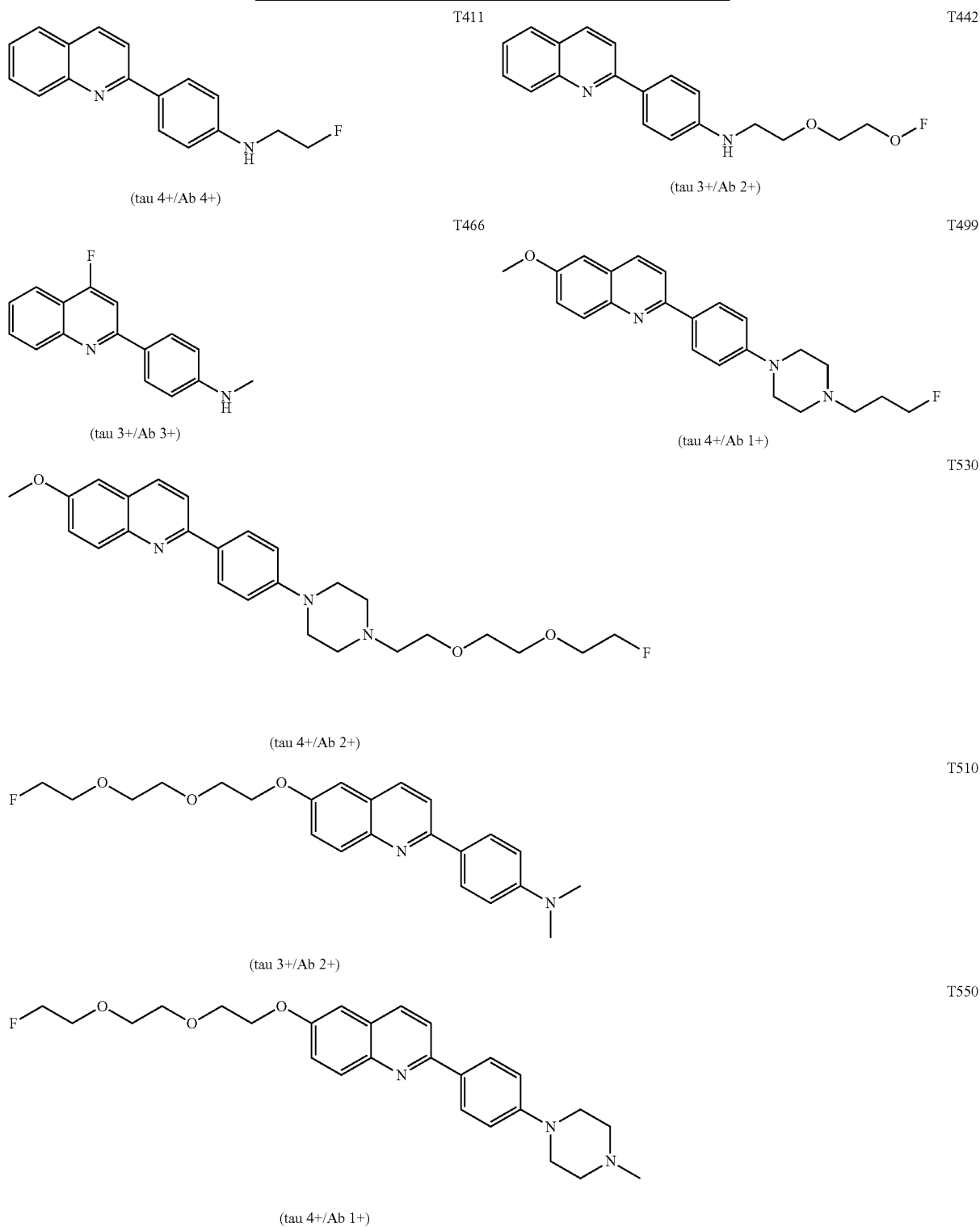

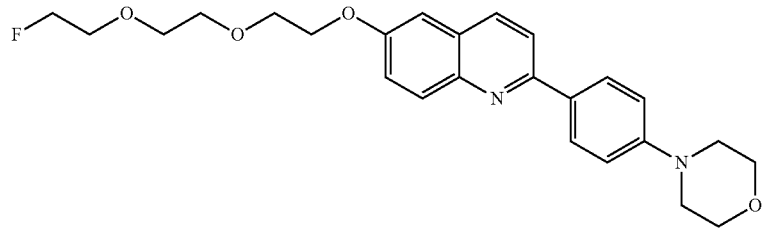
T539
(tau 3+/Ab 1+)
TABLE 1
Representative examples of quinoline compounds of the present invention.
| Comp. ID | Structure | FW | MW | Brain Section Staining | cLogP |
|---|---|---|---|---|---|
| T046 | | 270.3 | | | |
| T047 | | 220.3 | 220.1 | | |
| T048 | | 291.4 | 291.2 | binds to Ab (amyloid) (100 uM) | |
| T049 | | 256.7 | 256 | | |
| T050 | | 221.3 | 221.1 | | |

TABLE 1-continued
Representative examples of quinoline compounds of the present invention.
| Comp. ID | Structure | FW | MW | Brain Section Staining | cLogP |
|---|---|---|---|---|---|
| T051 | 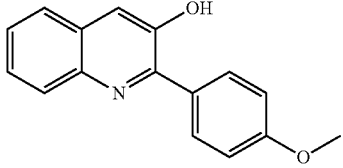 [SMILES: COc1ccc(-c2nc3ccccc3cc2O)cc1] | 251.3 | 251.1 | | |
| T123 | 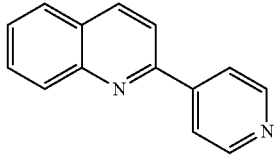 [SMILES: c1ccc2nc(-c3ccncc3)ccc2c1] | 206.2 | 206.1 | No fluorescence is detected at 100 uM | |
| T124 | 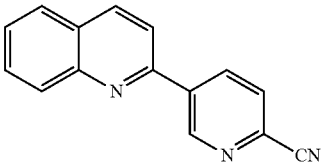 [SMILES: N#Cc1ccc(-c2ccc3ccccc3n2)cn1] | 231.3 | 231.1 | | |
| T125 | 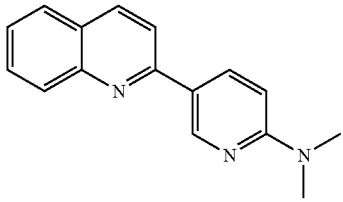 [SMILES: CN(C)c1ccc(-c2ccc3ccccc3n2)cn1] | 249.3 | 249.1 | staining shows strong binding to tau | |
| T126 | 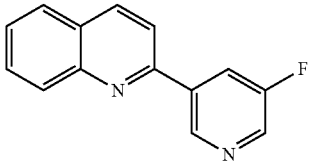 [SMILES: Fc1cncc(-c2ccc3ccccc3n2)c1] | 224.2 | 224.1 | | |
| T127 | 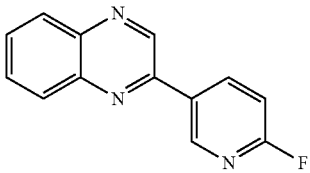 [SMILES: Fc1ccc(-c2cnc3ccccc3n2)cn1] | 225.2 | 225.1 | | |
| T128 | 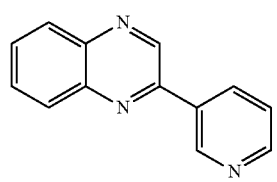 [SMILES: c1cncc(-c2cnc3ccccc3n2)c1] | 207.2 | 207.1 | | |
| T138 | 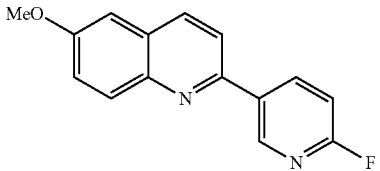 | 254.3 | 254.1 | | |

TABLE 1-continued

Representative examples of quinoline compounds of the present invention.

| Comp. ID | Stucture | FW | MW | Brain Section Staining | cLogP |
|---|---|---|---|---|---|
| T139 | (6-methoxyquinolin-2-yl)-(4-(dimethylamino)phenyl) | 278.4 | 278.1 | binds to amyloid and Tau | |
| T407 | 6-methoxyquinoline·TFA with 4-(N-methylamino)phenyl·TFA | 458.4 | | | |
| T409 | 6-(2-fluoroethoxy)quinoline·HCl with 4-(N-methylamino)phenyl·HCl | 369.3 | | binds to amyloid | |
| T411 | quinoline·HCl with 4-(N-(2-fluoroethyl)amino)phenyl·HCl | 339.2 | | binds to tau, weakly binds to Ab. (100 uM) | |
| T412 | quinoline with 4-(N-(2-(2-(2-azidoethoxy)ethoxy)ethyl)amino)phenyl | 377.4 | | binds to tau but not to amyloid | |
| T420 | 1-(4-(dimethylamino)phenyl)isoquinoline | 248.3 | | | |

TABLE 1-continued
Representative examples of quinoline compounds of the present invention.
| Comp. ID | Structure | FW | MW | Brain Section Staining | cLogP |
|---|---|---|---|---|---|
| T427 | 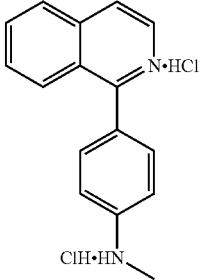 | 307.2 | | | |
| T428 | 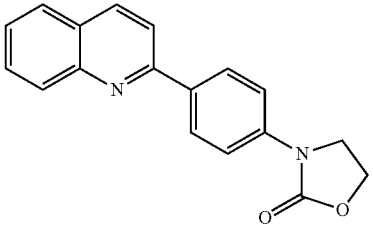 [SMILES: O=C1OCCN1c1ccc(-c2ccc3ccccc3n2)cc1] | 290.3 | | | |
| T429 | 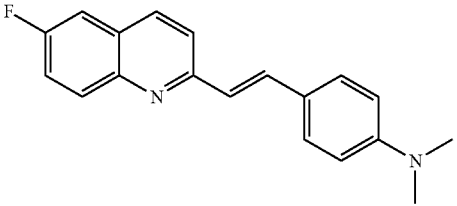 [SMILES: CN(C)c1ccc(/C=C/c2ccc3cc(F)ccc3n2)cc1] | 292.4 | | binds to Ab | |
| T433 | 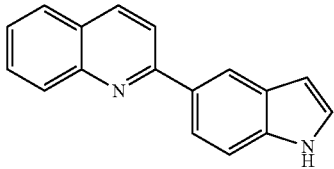 | 472.3 | | | |
| T434 | 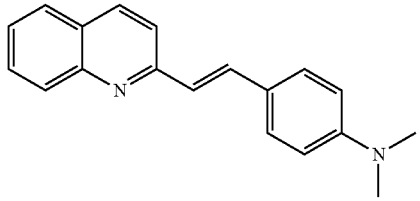 [SMILES: CN(C)c1ccc(/C=C/c2ccc3ccccc3n2)cc1] | 274.4 | | | |
| T442 | 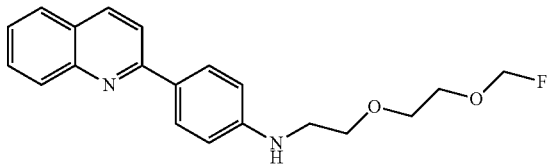 [SMILES: FCOCCOCCNc1ccc(-c2ccc3ccccc3n2)cc1] | | | binds to Tau and Ab | 3.8 |

TABLE 1-continued

Representative examples of quinoline compounds of the present invention.

| Comp. ID | Stucture | FW | MW | Brain Section Staining | cLogP |
|---|---|---|---|---|---|
| T443 | | 429.4 | | | |
| T445 | | 238.3 | | binds to Tau | |
| T446 | | 360.3 | | | |
| T447 | | 311.4 | | | |
| T453 | | 258.3 | | binds to Ab | |
| T454 | | 304.4 | | binds to Ab | |
| T455 | | 224.2 | | No fluorescence | |

TABLE 1-continued

Representative examples of quinoline compounds of the present invention.

| Comp. ID | Stucture | FW | MW | Brain Section Staining | cLogP |
|---|---|---|---|---|---|
| T458 | | 252.3 | | binds to amyloid and tau | 4.1 |
| T461 | | 304.4 | | | |
| T463 | | 279.3 | | | |
| T466 | | 366.3 | | binds to tau and amyloid | 4 |
| T467 | | 268.3 | | binds to tau and amyloid | 3.6 |
| T475 | | 275.4 | | binds to Ab mostly | |
| T476 | | 248.3 | | | |

TABLE 1-continued
Representative examples of quinoline compounds of the present invention.
| Comp. ID | Structure | FW | MW | Brain Section Staining | cLogP |
|---|---|---|---|---|---|
| T477 | 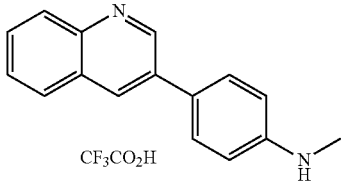 [SMILES: CNc1ccc(-c2cnc3ccccc3c2)cc1 ; "CF3CO2H"] | 348.3 | | binds to Ab mostly | 3.6 |
| T480 | 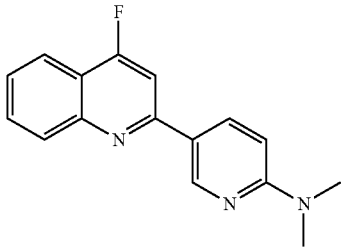 [SMILES: CN(C)c1ccc(-c2cc(F)c3ccccc3n2)cn1] | 267.3 | | | |
| T483 | 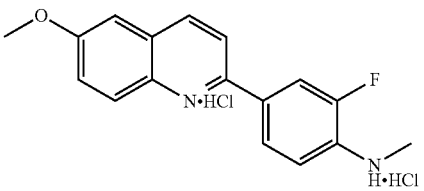 | 355.2 | | Mostly binds to Tau | |
| T484 | 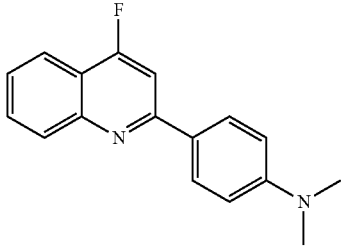 [SMILES: CN(C)c1ccc(-c2cc(F)c3ccccc3n2)cc1] | 266.3 | | binds to Tau and Ab; | 4.6 |
| T485 | 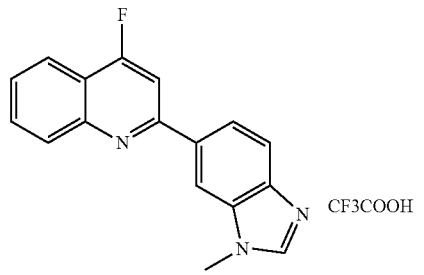 [SMILES: Cn1cnc2ccc(-c3cc(F)c4ccccc4n3)cc21 ; "CF3COOH"] | 391.3 | | weakly binds to Ab | |
| T490 | 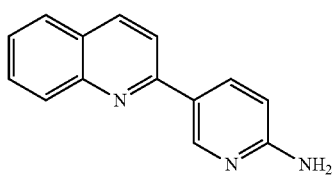 [SMILES: Nc1ccc(-c2ccc3ccccc3n2)cn1] | 221.3 | | | 2.5 |

TABLE 1-continued

Representative examples of quinoline compounds of the present invention.

| Comp. ID | Structure | FW | MW | Brain Section Staining | cLogP |
|---|---|---|---|---|---|
| T491 | | 279.3 | | | |
| T492 | | 238.3 | | | 3.3 |
| T498 | | 423.5 | | | 5.2 |
| T499 | | 379.5 | | Binds to Tau mostly (+++). Weakly binds to Ab (+) | 4.9 |
| T500 | | 248.3 | | | 4.2 |
| T501 | | 270.8 | | No fluorescence | 3.6 |
| T502 | | 369.4 | | | 3.5 |

TABLE 1-continued

Representative examples of quinoline compounds of the present invention.

| Comp. ID | Structure | FW | MW | Brain Section Staining | cLogP |
|---|---|---|---|---|---|
| T504 | | 248.3 | | binds to Ab strongly (++++) | 4.1 |
| T505 | | 248.3 | | binds to Ab weakly (+) | 4.1 |
| T507 | | 307.4 | | Binds to Ab (+++) | 4.1 |
| T510 | | 398.5 | | Binds both Tau (+++) and Ab (++) | 4.5 |
| T513 | | 267.3 | | Binds to Tau (+) and Ab (++) | 3.5 |
| T514 | | 234.3 | | | 3.4 |
| T515 | | 234.3 | | weakly to Ab (+) | 3.4 |

TABLE 1-continued

Representative examples of quinoline compounds of the present invention.

| Comp. ID | Structure | FW | MW | Brain Section Staining | cLogP |
|---|---|---|---|---|---|
| T517 | | 272.3 | 272.3 | Binds to Ab (+++) | 4.8 |
| T519 | | 365.4 | 365.4 | binds to Tau strongly (+++); weakly to Ab (+). | 4.7 |
| T523 | | 264.3 | 264.3 | Binds to Tau (++++). | 4.1 |
| T525 | | 355.4 | 355.4 | Binds to Tau (++); Binds to Ab (+) | 3.2 |
| T530 | | 453.6 | | Binds to Tau (++++); Binds to Ab (+) | 4.6 |
| T531 | | 264.4 | 264.4 | Binds to Tau. Binds to Ab (+) | 4.4 |
| T535 | | 631.4 | 289.1 | | 3.7 |

TABLE 1-continued

Representative examples of quinoline compounds of the present invention.

| Comp. ID | Structure | FW | MW | Brain Section Staining | cLogP |
|---|---|---|---|---|---|
| T536 | | 410.3 | 410.3 | | 4 |
| T537 | | 349.4 | 349.4 | | 3.4 |
| T539 | | 441.5 | 441.5 | | 2.9 |
| T545 | | 425.5 | 425.5 | Binds to Tau (+) and Ab (+) | 3.7 |
| T549 | | 440.5 | 440.5 | Binds to Tau | 3.8 |
| T550 | | 453.6 | 453.6 | Binds to Tau | 4.4 |

TABLE 1-continued

Representative examples of quinoline compounds of the present invention.

| Comp. ID | Stucture | FW | MW | Brain Section Staining | cLogP |
|---|---|---|---|---|---|
| T559 | | 321.4 | 321.4 | No fluorescence | 4.5 |
| T565 | | 440.5 | 440.5 | | 2.9 |
| T566 | | 413.4 | 413.4 | | 4.3 |
| T569 | | 310.4 | 310.4 | | 5 |

Another embodiment of the present invention is directed to acetylene compounds of formula (I) having bicyclic heteroaryl moiety and extended side chains containing radiolabel as illustrated in Scheme 3. As shown in Scheme 3 and in Table 2, compounds of this class have a high binding affinity to tau proteins. These compounds incorporate extended side chains, especially containing polyethers such as PEG in a biaryl alkyne core structure, wherein one of the aryl components is a substituted benzimidazole. Such structural modification leads to an increased selectivity of these compounds.

Scheme 3. Qualitative results of
Tau/Aβ binding of fluorescent compounds
in brain section (4+ is the strongest, 1+ is the weakest)

T540

(tau 4+/Ab 1+)

T465

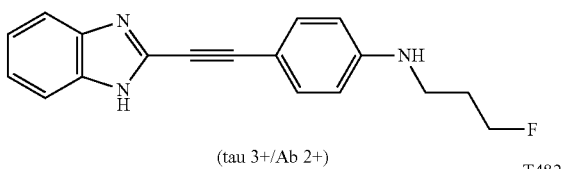

(tau 3+/Ab 2+)

T482

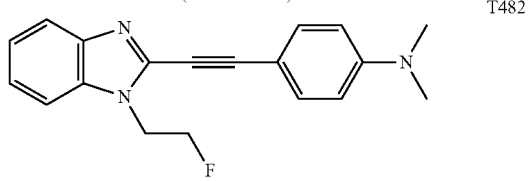

(tau 3+/Ab 1+)

T114

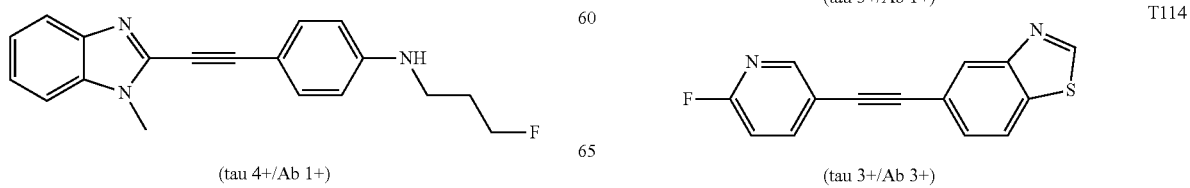

(tau 3+/Ab 3+)

-continued

T527

(tau 3+/Ab 1+)

-continued

T541

(tau 3+/Ab 1+)

TABLE 2

Representative examples of acetylene compounds of the present invention

| Comp. ID | Stucture | MW | Exact Mass | Brain Section Staining | cLogP |
|---|---|---|---|---|---|
| T110/ W294 | | 265.33 | | | |
| T114/ W313 | | 254.28 | | stains amyloid and tau | |
| T118/ W366 | | 298.33 | | binds to Ab | |
| T444 | | 244.29 | | | |
| T448 | | 312.36 | | binds to Ab | |

TABLE 2-continued

Representative examples of acetylene compounds of the present invention

| Comp. ID | Stucture | MW | Exact Mass | Brain Section Staining | cLogP |
|---|---|---|---|---|---|
| T454 | | 304.36 | | binds to Ab | |
| T464 | | 233.27 | | | |
| T465 | | 293.34 | | binds to tau and Ab | 4.2 |
| T481 | | 261.32 | | | |
| T482 | | 307.36 | | Mostly binds to Tau | 4.6 |
| T496 | | 429.37 | | Weakly binds to Ab | 4.3 |
| T508 | | 395.47 | | | 4.2 |
| T516 | | 240.28 | | Weakly binds to Tau (+) and Ab (++) | 3.6 |

TABLE 2-continued

Representative examples of acetylene compounds of the present invention

| Comp. ID | Structure | MW | Exact Mass | Brain Section Staining | cLogP |
|---|---|---|---|---|---|
| T517 | | 272.34 | 272.34 | Binds to Ab (+++) | 4.8 |
| T526 | | 295.38 | 295.38 | Binds to Tau (++); Binds to Ab (+) | 3.4 |
| T527 | | 506.45 | | Binds to Tau (+++); Binds to Ab (+) | 3.1 |
| T528 | | 375.34 | 261.32 | Binds to Tau (++++); Binds to Ab (+) | 3.9 |
| T534 | | 407.36 | 293.34 | | 4 |
| T540 | | 307.36 | 307.36 | Binds to Tau (++++). Binds to Ab (+) | 4.2 |

TABLE 2-continued

Representative examples of acetylene compounds of the present invention

| Comp. ID | Structure | MW | Exact Mass | Brain Section Staining | cLogP |
|---|---|---|---|---|---|
| T541 | | 495.47 | 381.44 | Binds to Tau (+++). Binds to Ab (+) | 3.6 |
| T546 | | 385.48 | 385.48 | | 4.1 |
| T547 | | 272.34 | 272.34 | | 4.6 |
| T551 | | 379.31 | 265.28 | | 3 |
| T552 | | 404.32 | 266.27 | | 2 |
| T553 | | 380.3 | 266.27 | | 2.8 |
| T554 | | 412.3 | 298.27 | Blue. Tau +++. Ab + | 3.2 |

TABLE 2-continued

Representative examples of acetylene compounds of the present invention

| Comp. ID | Stucture | MW | Exact Mass | Brain Section Staining | cLogP |
|---|---|---|---|---|---|
| T564 | | 506.45 | 392.43 | | 2.9 |
| T568 | | 394.32 | 280.3 | | 2.6 |

Figure 2:
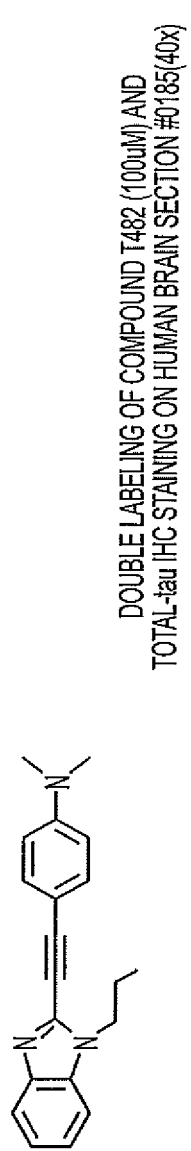
FIG. 2 shows total tau binding of fluorescent compound T482 to AD brain sections confirmed by immunostaining with tau or Aβ antibodies (double labeling of T482 at 100 uM).
Figure 2:
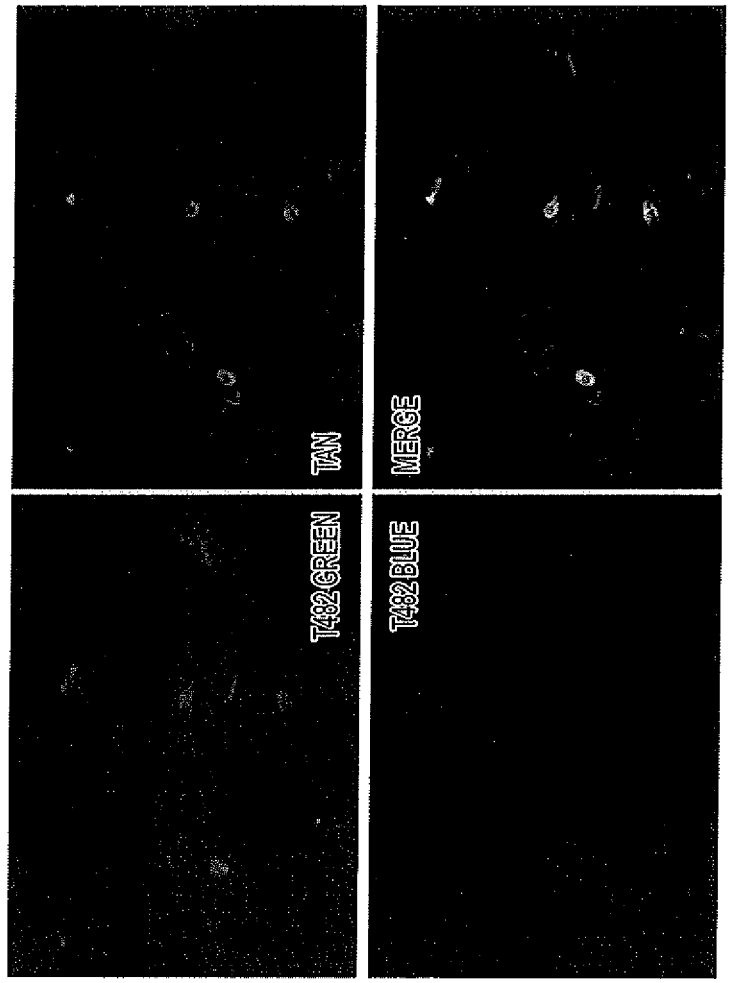
Figure 3:
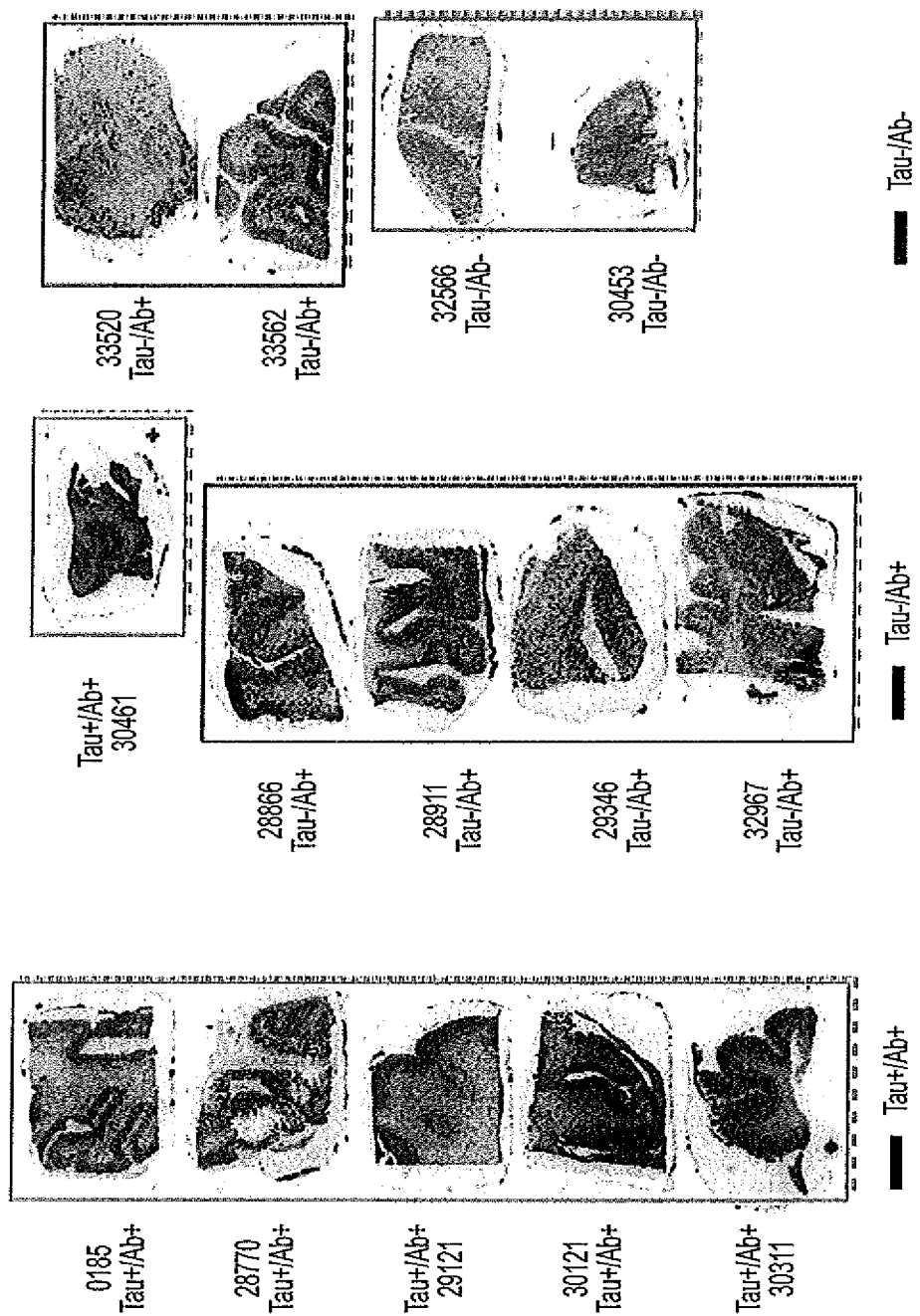
FIG. 3 shows ex vivo autoradiograph images of a preferred compound, T482.
Figure 4A:
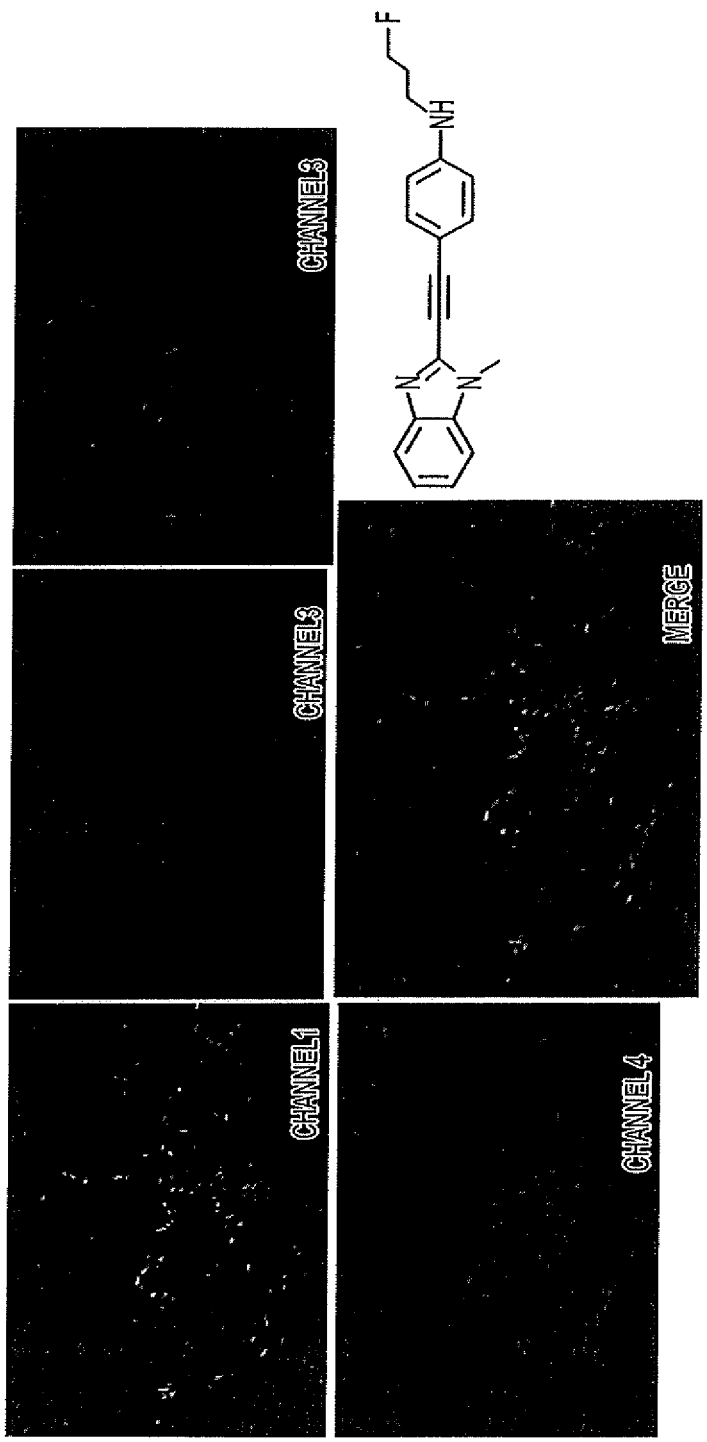
FIGS. 4a and 4b binding of fluorescent compound T540 to AD brain sections, which contain Aβ plaques and tau aggregates as confirmed by immunostaining with Aβ or tau antibodies (double labeling of T540 at 100 uM).
Figure 4B:
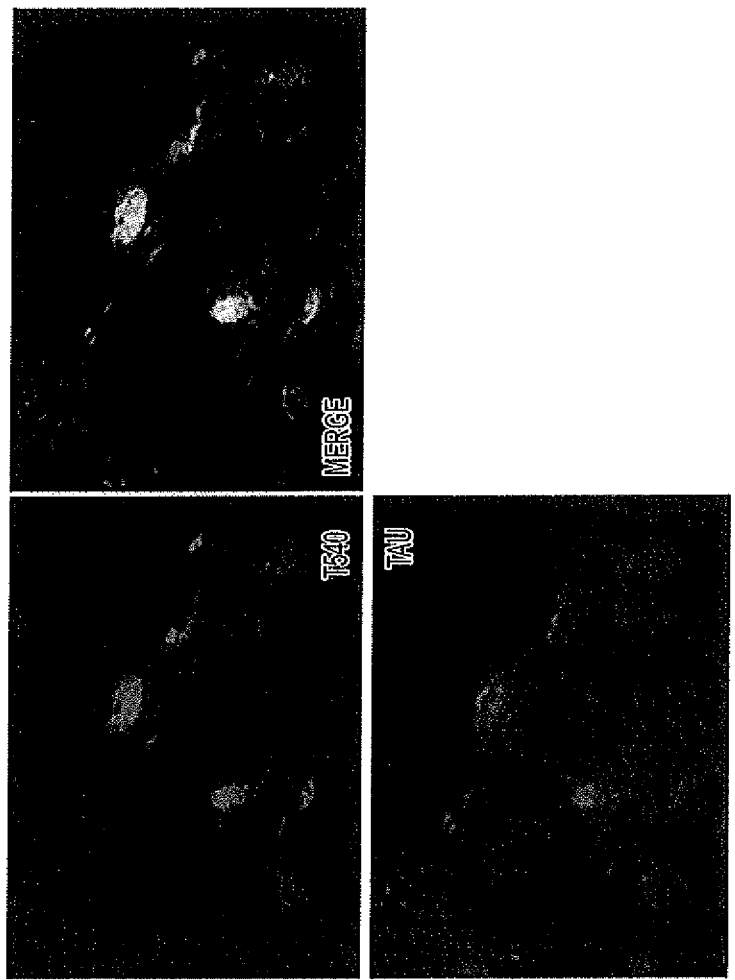
Figure 5:
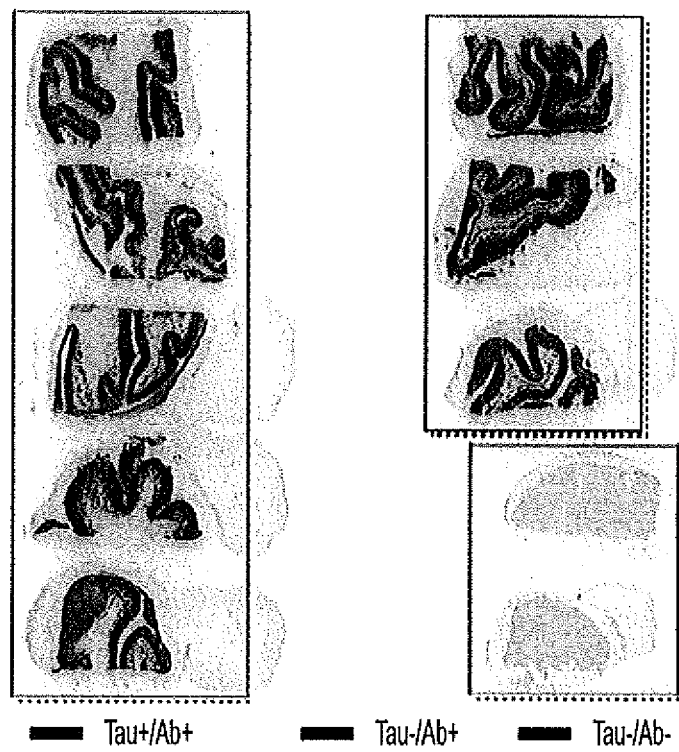
FIG. 5 shows ex vivo autoradiograph images of a preferred compound, T540, in three different types of brain sections: Aβ+/tau− brains contain Aβ plaques, but no tau aggregates (diagnosis by brain bank as non-AD donor); Aβ+/tau+ brains contain both Aβ plaques and tau aggregates (diagnosed by brain bank as AD patient), and normal (control) brains. The presence or absence of Aβ and/or tau was confirmed by immunostaining.
Figure 6A:
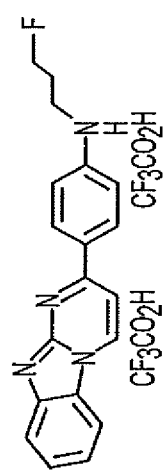
FIGS. 6a, 6b, and 6c show binding of fluorescent compound T542 to AD brain sections confirmed by immunostaining with tau or Aβ antibodies.
Figure 6A:
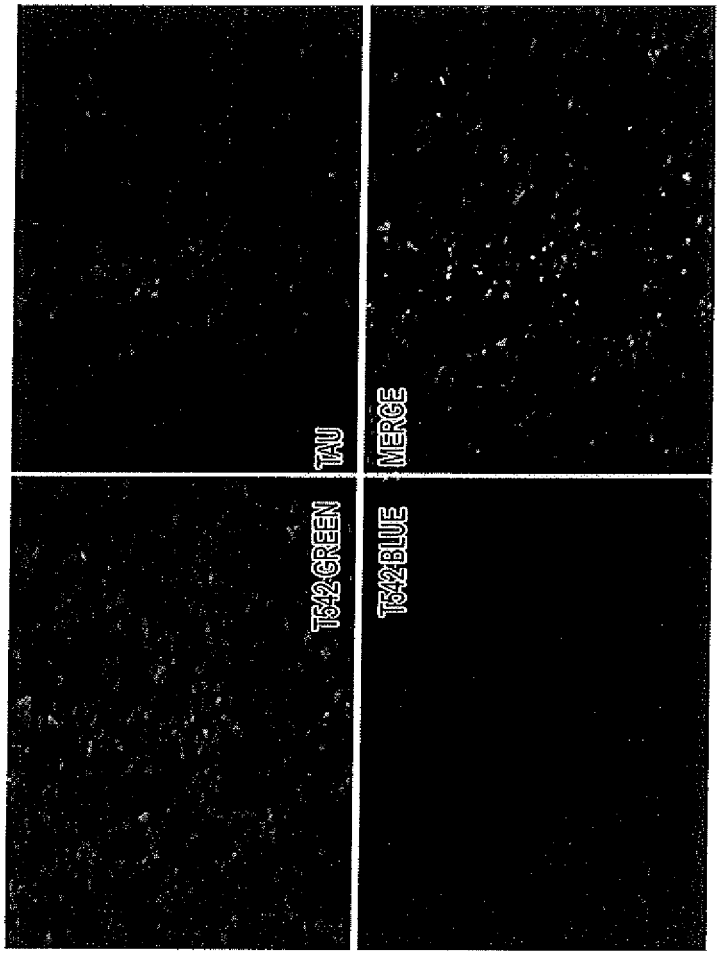
Figure 6B:
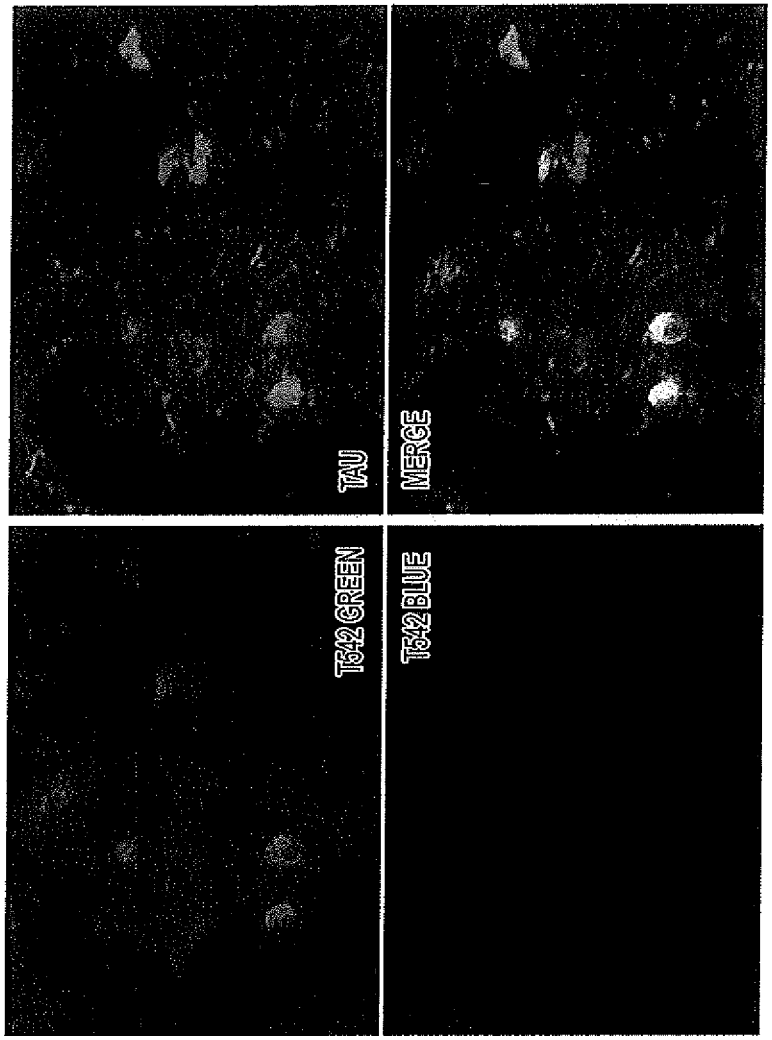
Figure 6C:
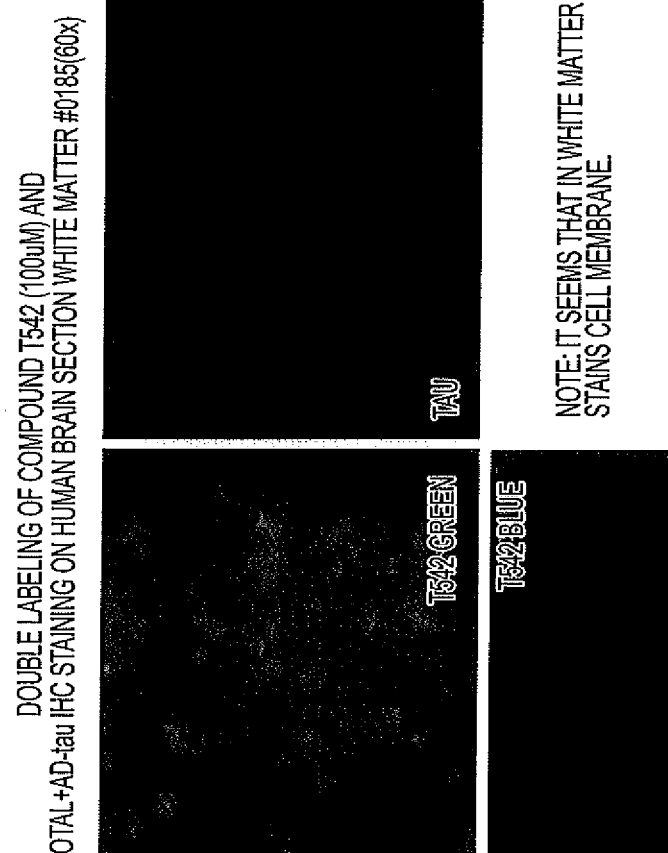
Figure 7:
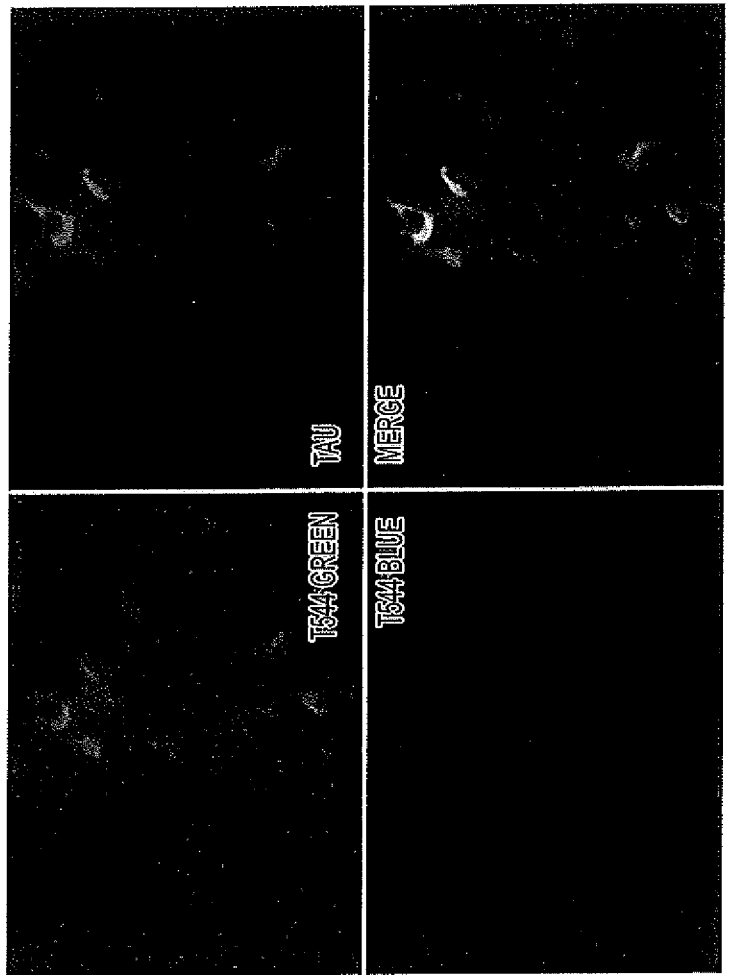
FIG. 7 binding of fluorescent compound T544 to AD brain sections confirmed by immunostaining with tau or Aβ antibodies.
Figure 7:
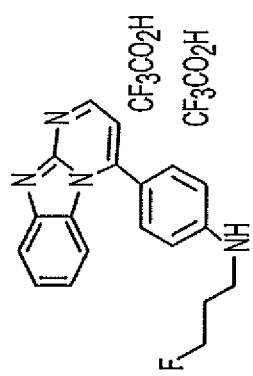
Figure 8B:
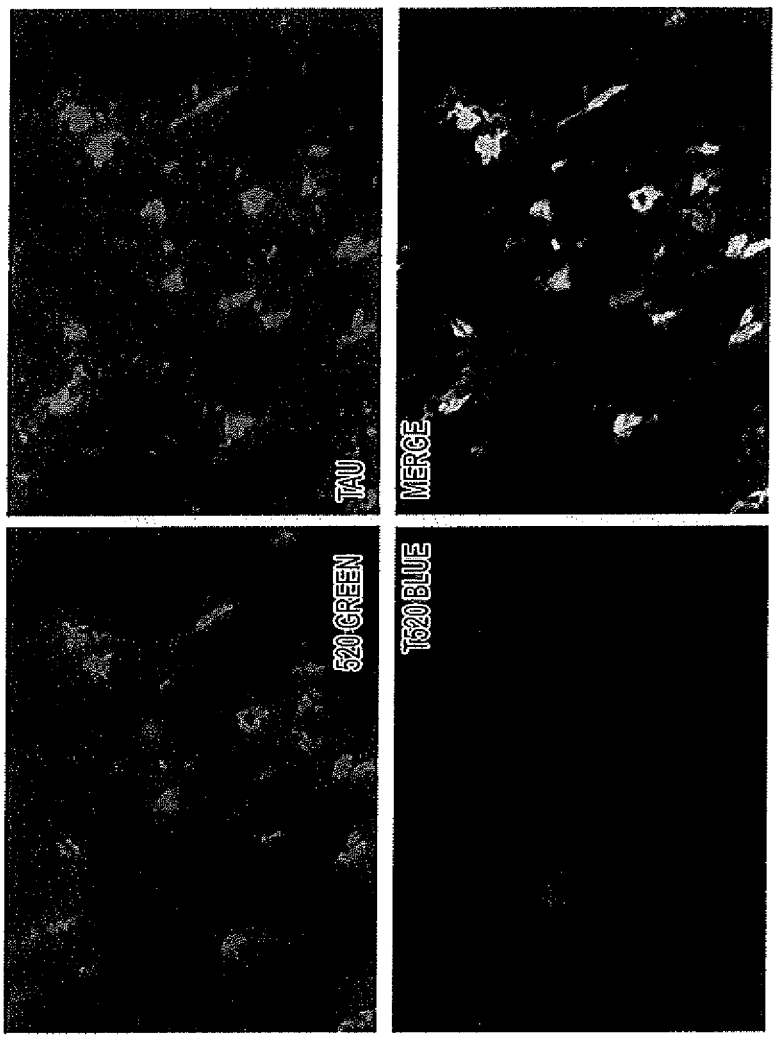
Figure 9A:
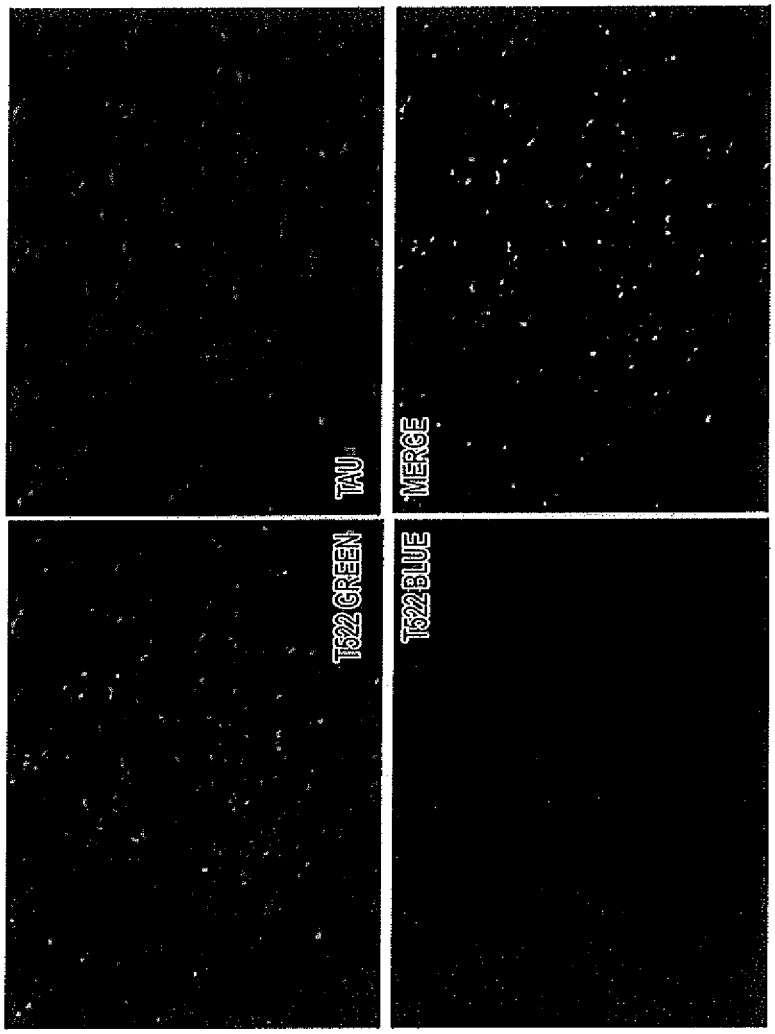
Figure 9A:
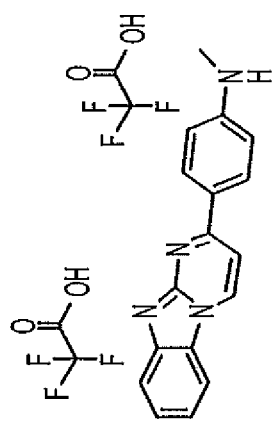
Figure 10A:
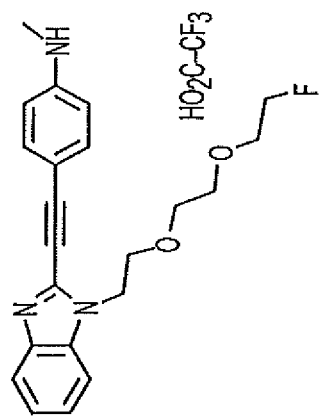
FIGS. 10a and 10b show binding of fluorescent compound T541 to AD brain sections confirmed by immunostaining with tau or Aβ antibodies.
Figure 10A:
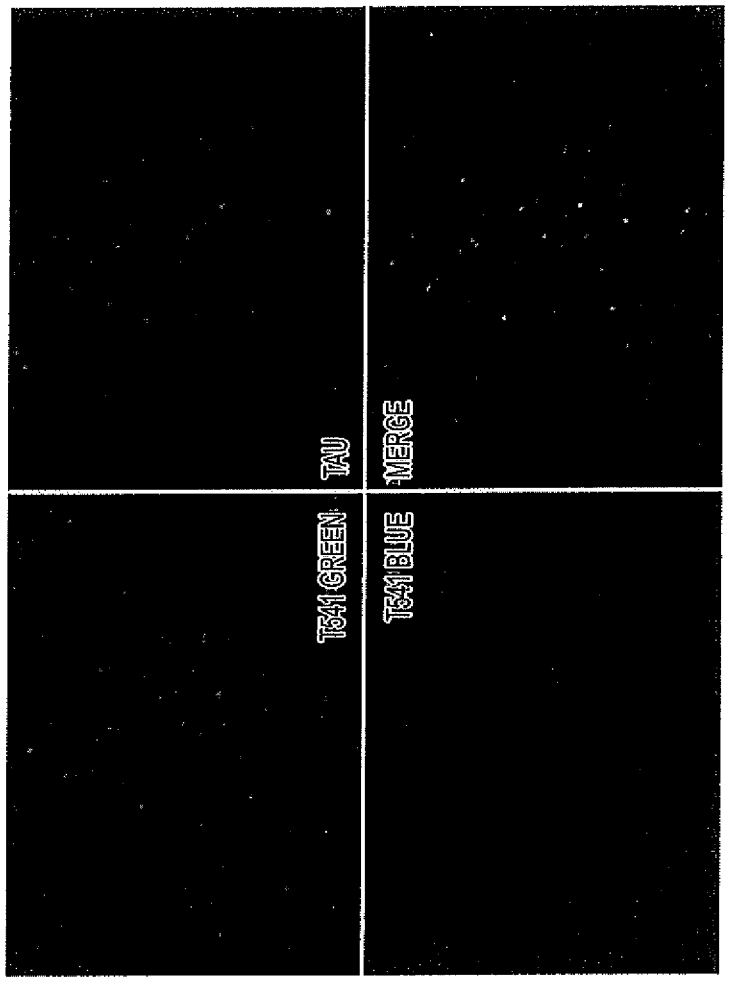
Figure 10B:
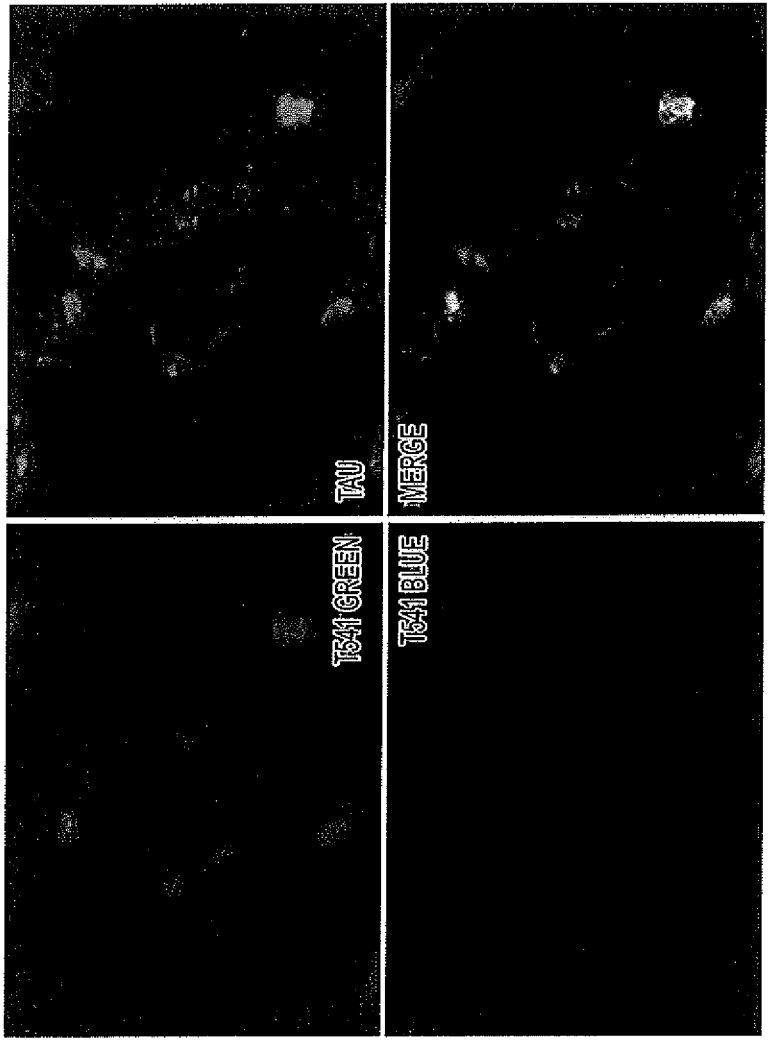
Figure 11:
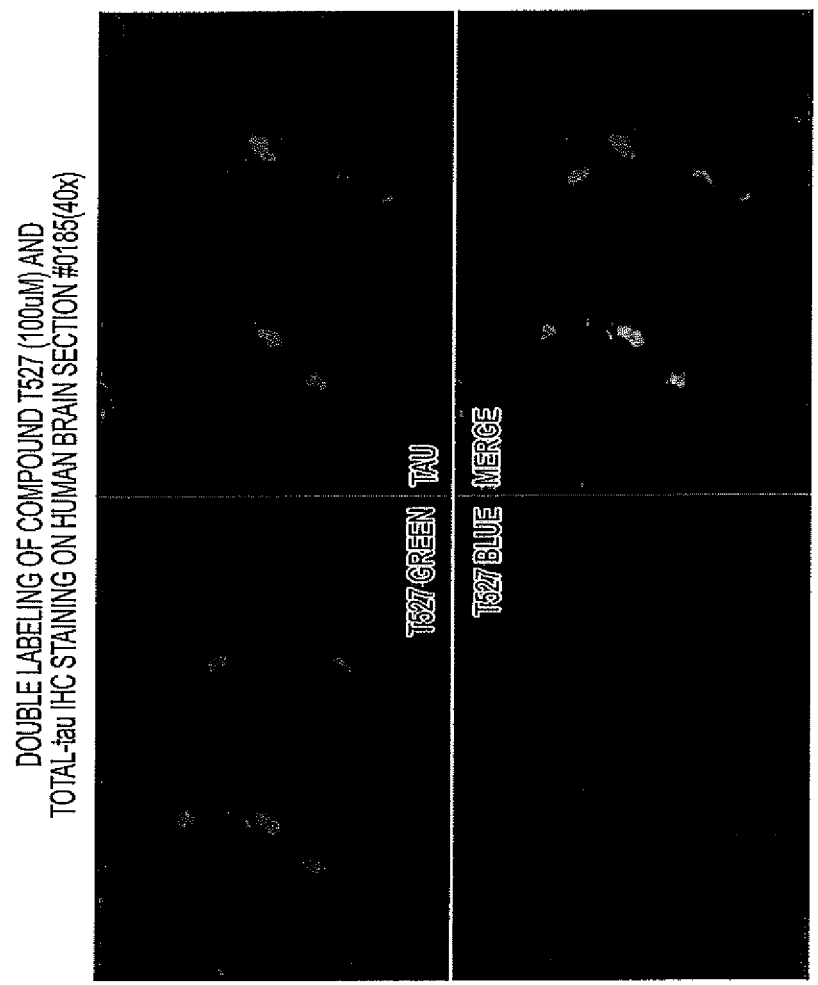
FIG. 11 shows binding of fluorescent compound T527 to AD brain sections confirmed by immunostaining with tau or Aβ antibodies.
Figure 11:
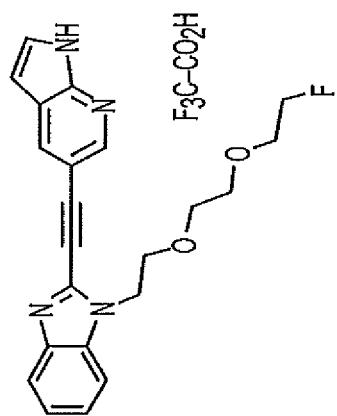
Figure 12:
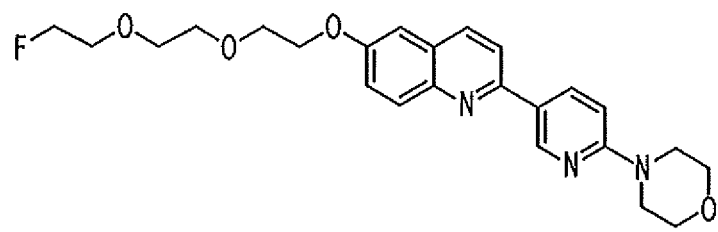
FIG. 12 shows binding of fluorescent compound T539 to AD brain sections confirmed by immunostaining with tau or Aβ antibodies.
Figure 12:
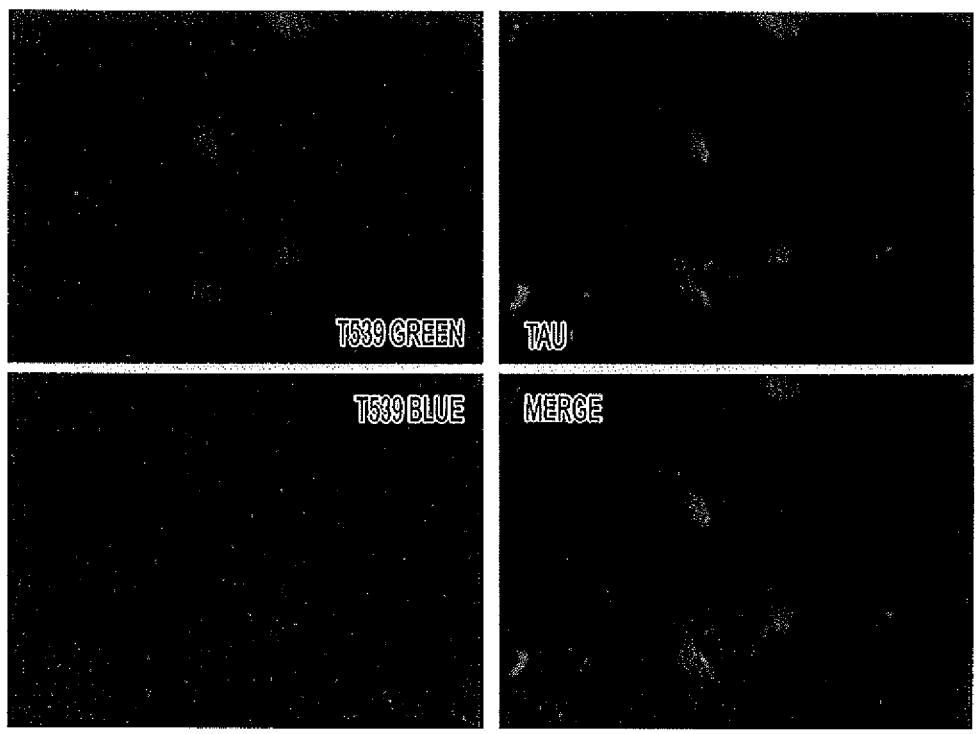
Figure 13A:
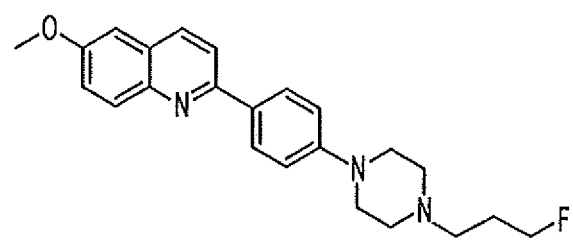
FIGS. 13a and 13b show binding of fluorescent compound T499 to AD brain sections confirmed by immunostaining with tau or Aβ antibodies.
Figure 13A:
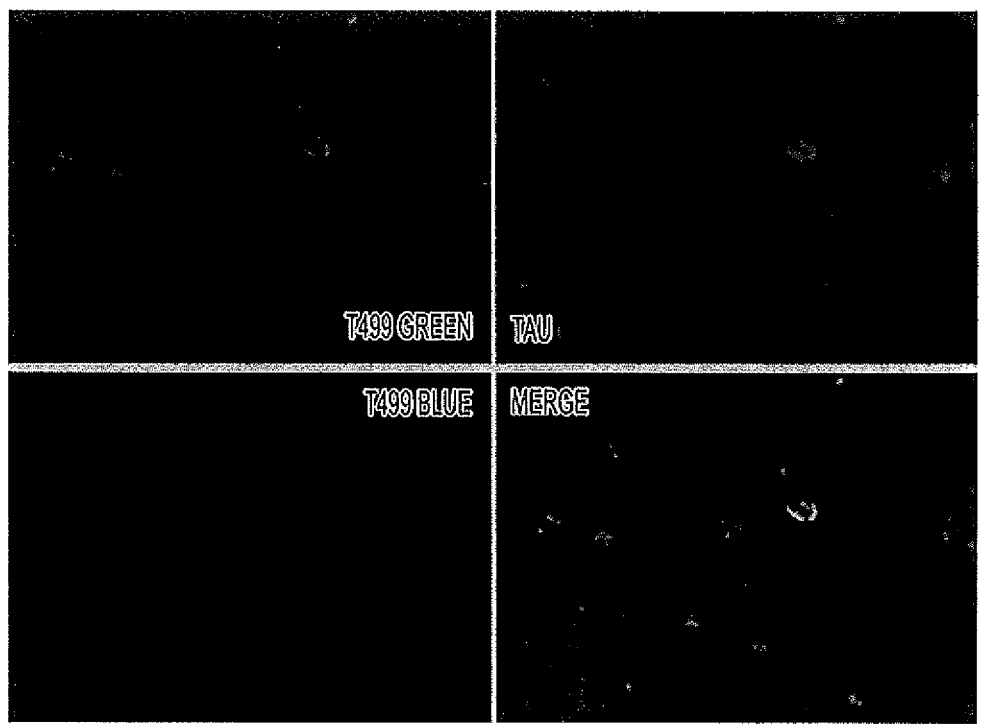
Figure 13B:
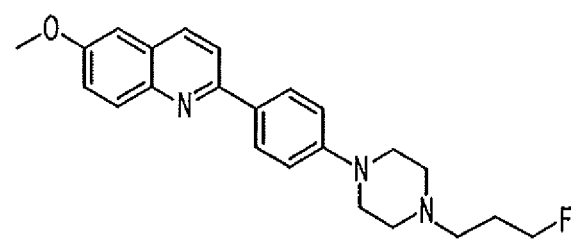
Figure 13B:
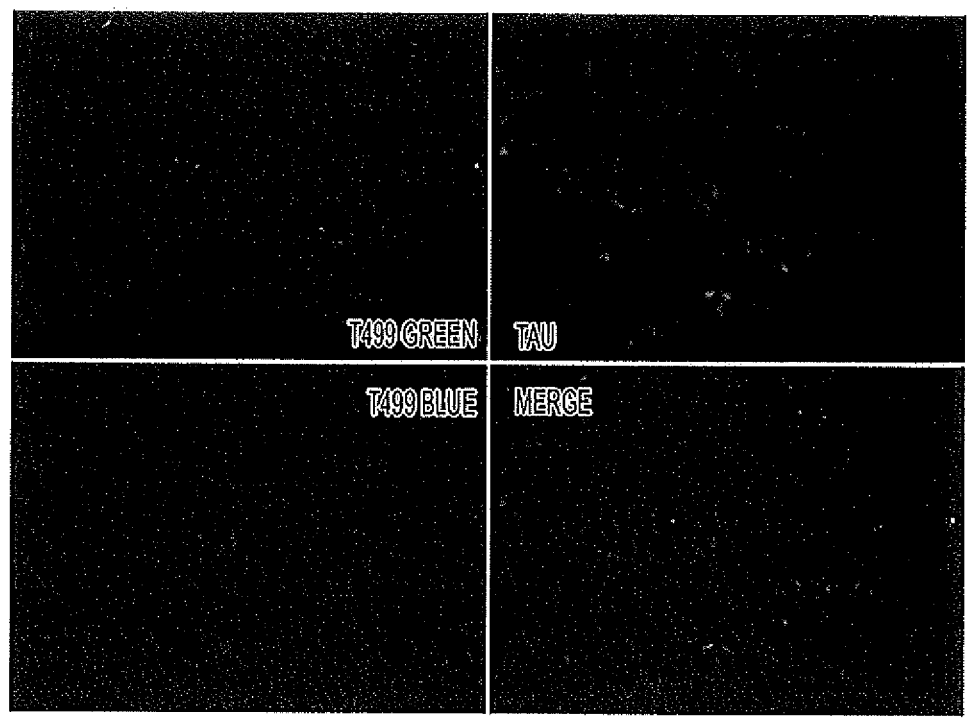
Figure 14:
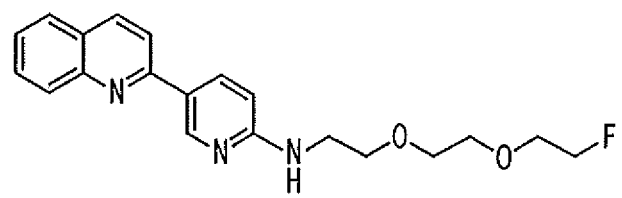
FIG. 14 shows binding of fluorescent compound T525 to AD brain sections confirmed by immunostaining with tau or Aβ antibodies.
Figure 14:

FIGS. 2 and 4a-4b show binding of fluorescent compounds T482 and T540 to AD brain sections confirmed by immunostaining with tau or Aβ antibodies. FIGS. 3 and 5 show ex vivo autoradiograph images of the preferred compounds T482 and T540, in three different types of brain sections: Aβ+/tau− brains contain Aβ plaques, but no tau aggregates (diagnosis by brain bank as non-AD donor); Aβ+/tau+ brains contain both. Aβ plaques and tau aggregates (diagnosed by brain bank as AD patient), and normal (control) brains. The presence or absence of Aβ and/or tau is confirmed by immunostaining.

Another embodiment of the present invention is directed to compounds of formula (I) comprising a tricyclic aryl moiety. For example, benzimidazole pyrimidines shown in Scheme 4, exhibit high binding affinity to tau proteins. FIGS. 6a-6c, 7, 8a-8b, 9a-9b, 10a-10b, and 11 show binding of fluorescent compounds T542, T544, T520, T522, T541, and T527 to AD brain sections confirmed by immunostaining with tau or Aβ antibodies.

Scheme 4. Qualitative results of Tau/Aβ binding of fluorescent compounds in brain section (4+ is the strongest, 1+ is the weakest)

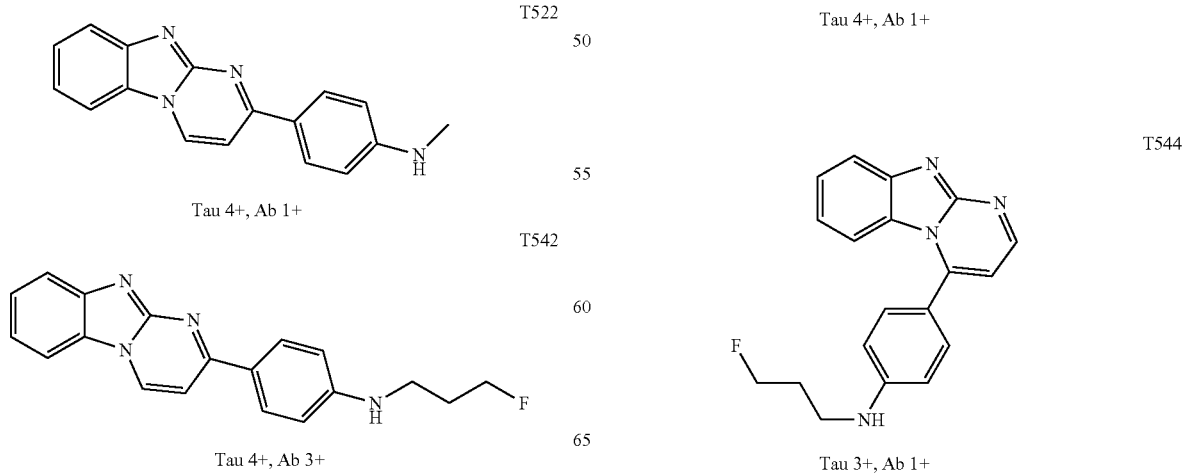

TABLE 3

Representative examples of benzimidazole and tricyclic benzimidazole compounds of the present invention.

| Compound ID | Structure | MW | Brain Section Staining |
|---|---|---|---|
| T506 | (benzimidazole fused imidazole - phenyl-NEt₂, TFA salt) | 401.4 | |
| T511 | (tricyclic benzimidazole-pyrimidine - phenyl-NO₂) | 290.28 | |
| T512 | (tricyclic benzimidazole-pyrimidine - phenyl-NO₂, isomer) | 290.28 | |
| T518 | (tricyclic benzimidazole-pyrimidine - phenyl-NH₂) | 260.29 | Aβ/1+ Tau/4+ |
| T520 | (tricyclic benzimidazole-pyrimidine - phenyl-NH₂, isomer) | 260.29 | Aβ/1+ Tau/4+ |
| T521 | (tricyclic benzimidazole-pyrimidine - phenyl-N(CH₃)₂, bis-TFA salt) | 516.39 | Aβ/1+ Tau/4+ |

TABLE 3-continued

Representative examples of benzimidazole and tricyclic benzimidazole compounds of the present invention.

| Compound ID | Structure | MW | Brain Section Staining |
|---|---|---|---|
| T522 | 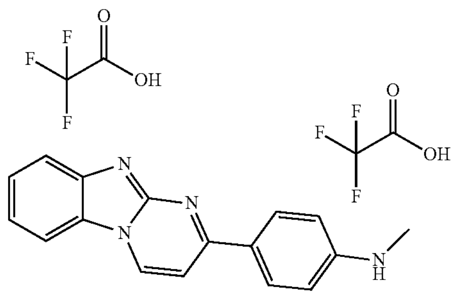 | 502.37 | Aβ/1+ Tau/4+ |
| T542 | 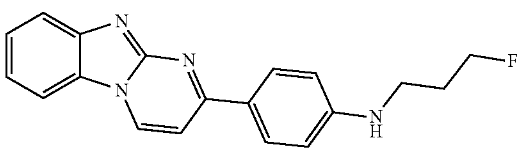 | 548.41 | Aβ/3+ Tau/4+ |
| T544 | 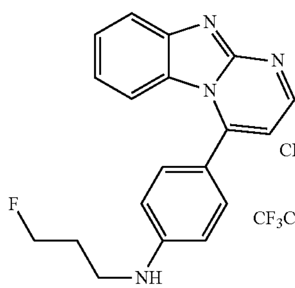 | 548.41 | Aβ/1+ Tau/3+ |
| T557 | 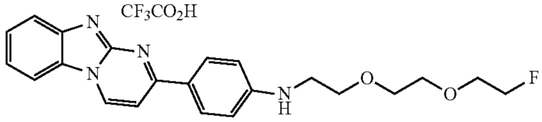 | 622.49 | Aβ/2+ Tau/4+ |
| T452 | 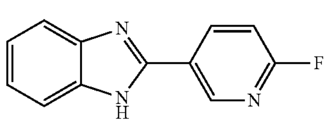 [SMILES: Fc1ccc(-c2nc3ccccc3[nH]2)cn1] | 213.21 | |
| T460 | 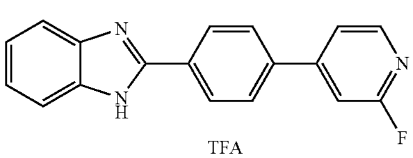 [SMILES: Fc1cc(-c2ccc(-c3nc4ccccc4[nH]3)cc2)ccn1] | 386.3 | |
| T469 | 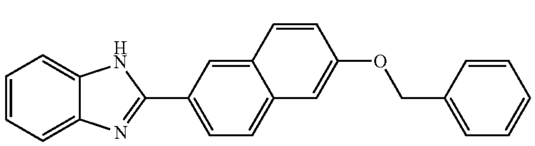 [SMILES: c1ccc(COc2ccc3cc(-c4nc5ccccc5[nH]4)ccc3c2)cc1] | 350.41 | |

TABLE 3-continued
Representative examples of benzimidazole and tricyclic benzimidazole compounds of the present invention.
| Compound ID | Structure | MW | Brain Section Staining |
|---|---|---|---|
| T470 | 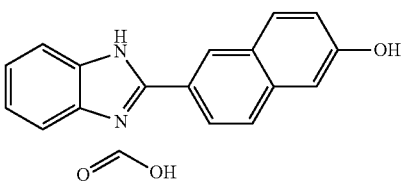 | 306.32 | |
| T473 | 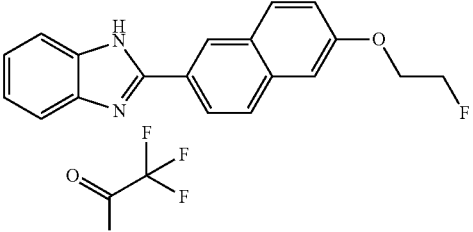 | 420.36 | |
| T474 | 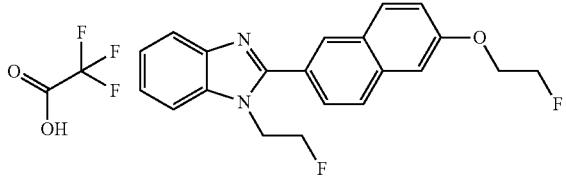 | 466.4 | |
| T487 | 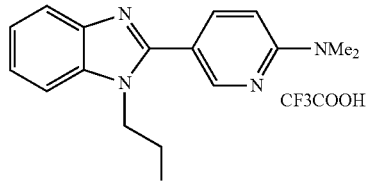 | 398.35 | |
| T488 | 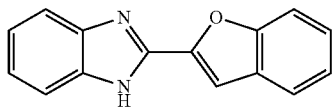 | 234.3 | |
| T489 | 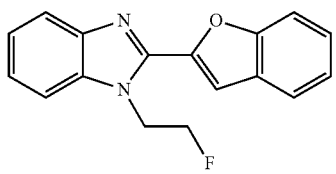 | 280.3 | |
| T493 | 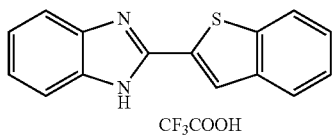 | 364.3 | |
| T494 | 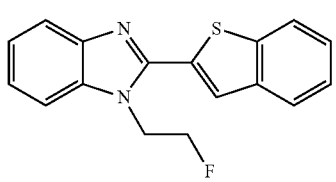 | 296.4 | |

TABLE 3-continued
Representative examples of benzimidazole and tricyclic benzimidazole compounds of the present invention.
| Compound ID | Structure | MW | Brain Section Staining |
|---|---|---|---|
| T495 | 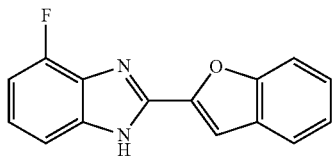 | 366.3 | |
| T497 | 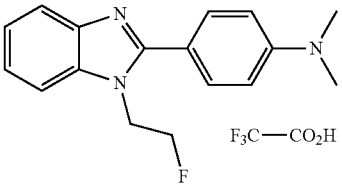 | 397.37 | |
| T524 | 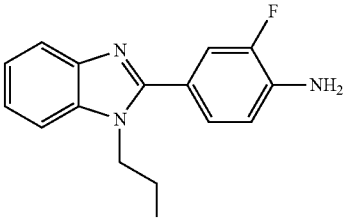 | 273.28 | Tau +++; Ab ++ |
| T538 | 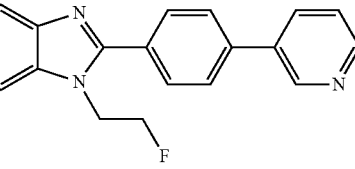 | 335.4 | |
| T543 | 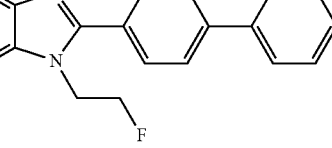 | 473.5 | Tau ++; Ab no binding |
| T548 | 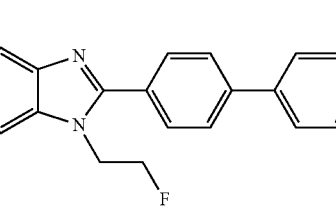 | 359.2 | |
| T556 | 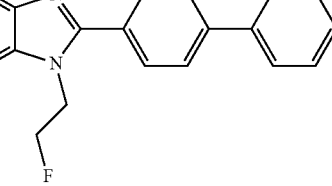 | 341.4 | |

Another embodiment of the present invention is directed to additional compounds of formula (I) comprising a tricyclic aryl moiety. For example, benzimidazole pyrimidines shown in Scheme 5, exhibit high binding affinity to tau proteins.

Scheme 5. Qualitative result of Tau/Aβ binding of fluorescent compound in brain section (4+ is the strongest, 1+ is the weakest)

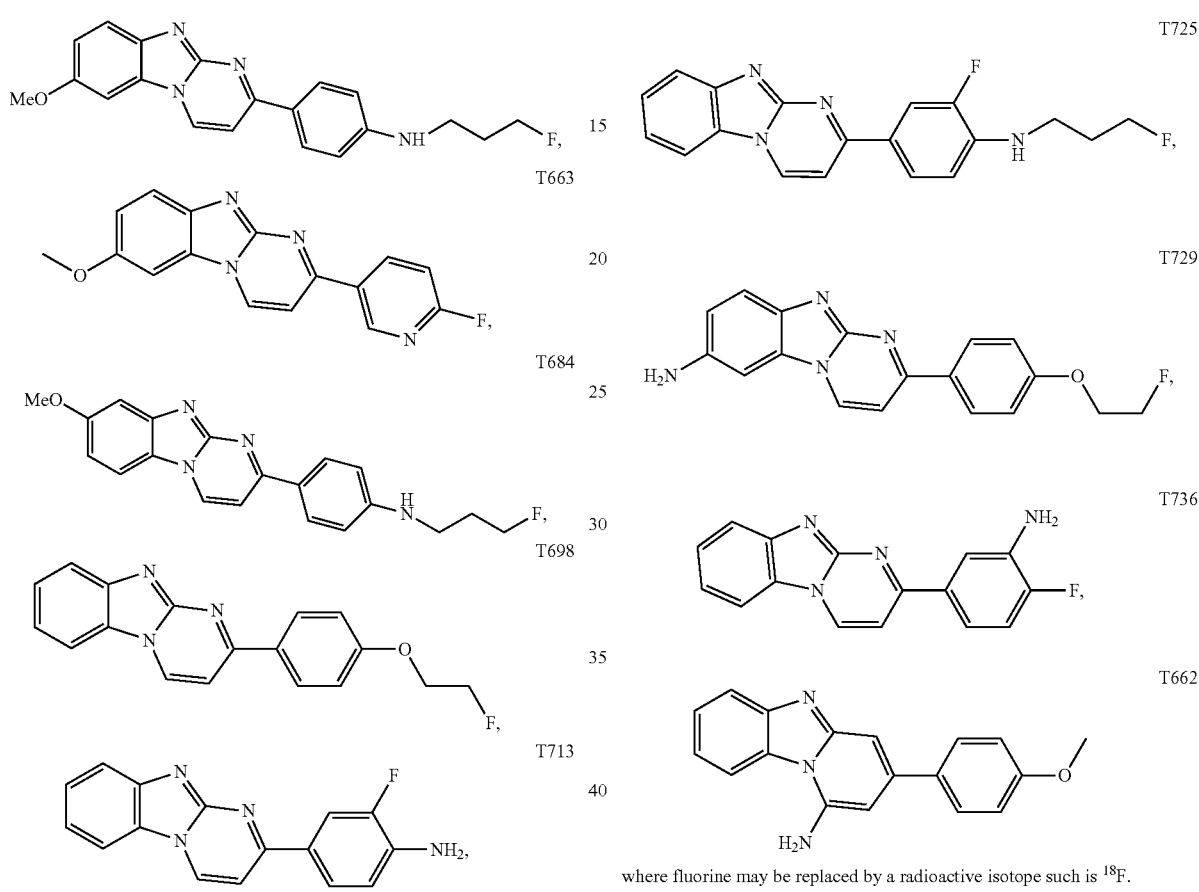

where fluorine may be replaced by a radioactive isotope such is $^{18}$F.

| Compound ID | Structure | MW | Kd (tau) | Brain Section Staining |
|---|---|---|---|---|
| T620 | T620 | 350.4 | | Tau++++ |
| T663 | T663 | 293.3 | 105 nM | |

-continued

| Compound ID | Structure | MW | Kd (tau) | Brain Section Staining |
|---|---|---|---|---|
| T684 | T684 | 350.39 | | Tau++++. Ab+ |
| T698 | T698 | 307.32 | 23 and 81 nM | Tau−. Ab+ |
| T713 | T713 | 278.28 | | Tau++++ |
| T723 | T723 | 350.39 | | Tau++++ |
| T725 | T725 | 338.35 | | Tau++++ |
| T729 | T729 | 322.34 | | Tau+. Ab++ |
| T736 | T736 | 278.28 | | Tau− |
| T662 | T662 | 289.33 | | Tau−. Ab+ |

In the above compounds, $R_1$ and/or $R_2$ may be a primary amine or a secondary amine. For example, $R_1$ and/or $R_2$ may be —NH—$(C_nH_{2n})_n$—.

It will be understood that "F" may be replaced by $^{18}$F or another radiolabel.

In another embodiment, the present invention is compounds of the general formula (IV).

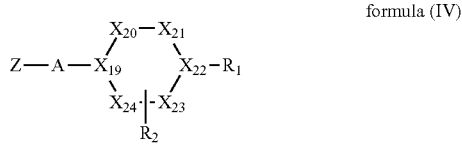
formula (IV)

wherein

A is a bond, $(C_1-C_4)$alkyl, $(C_3-C_6)$cycloalkyl, $(C_2-C_4)$alkene, or $(C_1-C_4)$alkyne;

Z is aryl selected from the group consisting of:

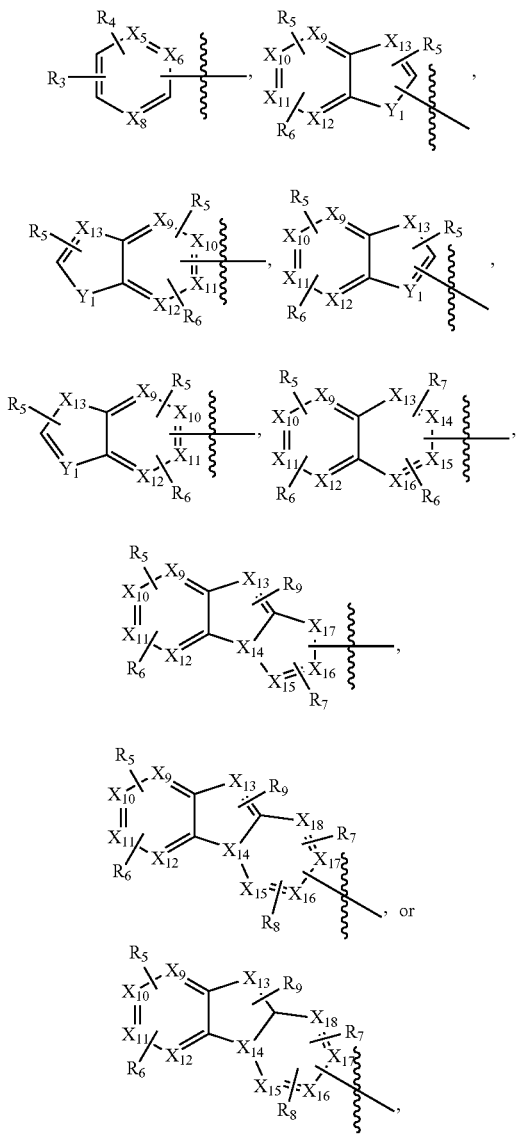

wherein $X_{19}$-$X_{24}$ are each independently $CH_2$, N, NH, O, NH, S, SH.

$X_{13}$ is each independently C, N, O, or S;

$X_5$-$X_{12}$ and $X_{14}$-$X_{18}$ are each independently C or N;

$Y_1$ is N, O, or S;

$R_1$-$R_2$ are each independently H, halogen, hydroxy, nitro, cyano, amino, alkyl, alkoxy, —(O—$CH_2$—$CH_2$)$_n$—, monoalkylamino, dialkylamino, monoarylamino, diarylamino, primary amine, secondary amine, tertiary amine, heterocycle, polycyclic heterocycle, $C_1$-$C_6$—OH, $NR_{10}$COOalkyl, $NR_{10}$ COOaryl, $NR_{10}$ COalkyl, $NR_{10}$ CO aryl, COOalkyl, COOaryl, COalkyl, COaryl, aryl, saturated heterocyclyl, wherein the last seventeen groups are unsubstituted or substituted by a halogen, leaving group or one or more radicals selected from the group consisting of halogen, alkyl, haloalkyl, cyano, hydroxyl, amino, monoalkylamino, dialkylamino, alkoxy, $R_{10}$, a radiolabel or alkyl substituted with a radiolabel; or $R_1$ and $R_2$ together form a five- or six-membered saturated or unsaturated ring which optionally contains an additional heteroatom in the ring which is selected from N, O, and S, the ring being unsubstituted or substituted by one or more halogens or radicals selected from the group consisting of halogen, alkyl, haloalkyl, cyano, hydroxyl, amino, monoalkylamino, dialkylamino, alkoxy, $R_{10}$, a radiolabel or alkyl substituted with radiolabel;

$R_3$-$R_9$ are each independently H, halogen, hydroxy, nitro, cyano, amino, alkyl, alkoxy, —(O—$CH_2$—$CH_2$)$_n$—, monoalkylamino, dialkylamino, monoarylamino, diarylamino, $NR_{10}$COOalkyl, $NR_{10}$ COOaryl, $NR_{10}$ COalkyl, $NR_{10}$ CO aryl, COOalkyl, COOaryl, COalkyl, COaryl, aryl, heterocyclyl, heterocycle, polycyclic heterocycle, wherein the last seventeen groups are unsubstituted or substituted by a halogen, leaving group or one or more radicals selected from the group consisting of halogen, alkyl, haloalkyl, cyano, hydroxyl, amino, monoalkylamino, dialkylamino, alkoxy, $R_{10}$, a radiolabel or alkyl substituted with a radiolabel;

$R_{10}$ is H, alkyl, alkene, aryl unsubstituted or substituted with halogen, hydroxyl, cyano, nitro, amino, —$OSO_2$alkyl, —$OSO_2$aryl, —OSi(alkyl)$_3$, —OTHP or a radiolabel;

n is 1, 2, or 3;

m is 0 or 1, or a pharmaceutically acceptable salt thereof.

For example, benzimidazole pyrimidines shown in Scheme 6, exhibit high binding affinity to tau proteins.

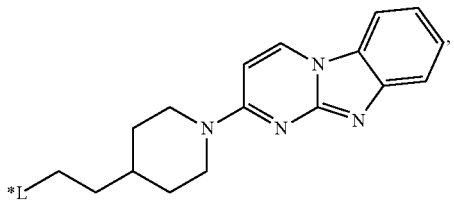

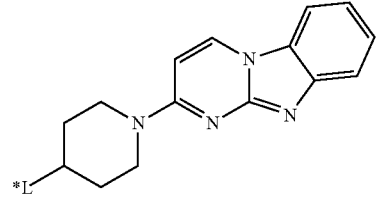

| ID | | |
|---|---|---|
| | T777 | T808 |
| | 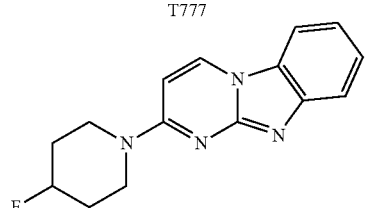 | 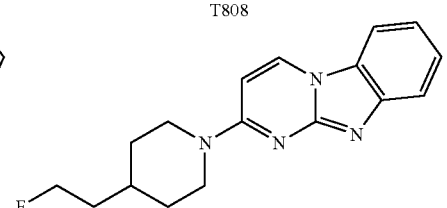 |
| MW | 270.3 | 298.4 |
| CLogP | 3.1 | 3.7 |
| KD (tau) | 19 nM | 22 nM |
| selectivity (tau/Ab) | 25× | 27× |
| GM Intensity (comp. with W372) | 9% | 18% |
| background (normal brain 32566) PSL/mm2 | 21 | 42 |
| Tx/tau/amyloid correlation | yes | yes |
| Brain uptake | yes (4 rats, 4 mice) | yes (4 rats, 5 mice) |
| in vivo metabolism | 5, 15 min | 15 min |
| in vivo metabolism: one day | | 5, 30 min |
| human hepatocytes | not stable (polar metabolites) | stable |
| PK | yes | yes |
| 45 brain panel double staining | done | done |
| AchE activity (IC50) | 3 uM | 3 uM |
| MAO inhibition | 9% (1 uM) MAO-A<br>0% (1 uM) MAO-B | 22% (1 uM) MAO-A<br>29% (1 uM) MAO-B |
| CNS selectivity panel | 10 uM<br>Bombesin BB3 (49%)<br>Monoamine transp. (49%)<br>Norepinephrine transp. (42%) | Bombesin BB3 (<20%)<br>Monoamine transp. (IC50 2.7 uM)<br>Norepinephrine transp. (IC50 0.82 uM) |
| MDS SDL/quote # | | SDL-19, #22576 |

It will be understood that "F" may be replaced by $^{18}$F or another radiolabel.

Compounds of the present invention may also have the general structure of Formula (V):

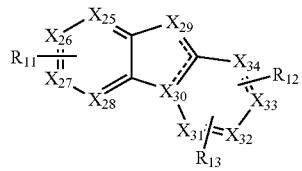

(V)

a pharmaceutically acceptable salt thereof, or stereoisomers thereof,
wherein:
$X_{25}$-$X_{28}$ are each independently CH, $CR_{11}$, or N;
$X_{29}$ is CH, N, O or S;
$X_{30}$ is CH, C, or N;
$X_{31-34}$ are each independently CH, $CR_{12}$, $CR_{13}$ or N;
$R_{11}$-$R_{13}$ are each independently H, halogen, hydroxy, nitro, cyano, amino, alkyl, alkylaryl, alkylamino, alkylamine, arylamine, arylamino, alkoxy, —(O—CH$_2$—CH$_2$)$_n$—, alkenyl, alkynyl, aryloxy, NR$_{10}$COOalkyl, NR$_{10}$ COOaryl, NR$_{10}$ COalkyl, NR$_{10}$ CO aryl, COOalkyl, COOaryl, COalkyl, COaryl, aryl, cycloalkyl, cycloalkylamino, cycloalkylamine, bicyclic, saturated heterocycle and unsaturated heterocycle, wherein at least one carbon is optionally replaced with N, O, S, triazole, or halo,
and
wherein at least one hydrogen is optionally replaced with halo, amine, amino, alkoxy, nitro, alkyl, alkenyl, alkynyl, aryloxy, alkylaryl, alkylamino, alkylamine, NR$_{10}$COOalkyl, NR$_{10}$ COOaryl, NR$_{10}$ COalkyl, NR$_{10}$ CO aryl, COOalkyl, COOaryl, COalkyl, COaryl, aryl, cycloalkyl, cycloalkylamino, cycloalkylamine, bicyclic, saturated heterocycle and unsaturated heterocycle, a leaving group, CN, OH or a radioactive isotope.

Compounds of the present invention may also have the general structure of Formula (Va):

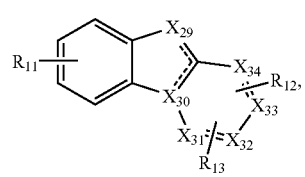

(Va)

or a pharmaceutically acceptable salt thereof, stereoisomers thereof,
wherein:
$X_{29}$ is CH, N, O or S;
$X_{30}$ is CH, C, or N;

$X_{31-34}$ are each independently CH, $CR_{12}$, $CR_{13}$ or N;

$R_{11}$-$R_{13}$ are each independently H, halogen, hydroxy, nitro, cyano, amino, alkyl, alkylaryl, alkylamino, cycloalkylamino, alkylamine, arylamine, arylamino, alkoxy, $NR_{10}$COOalkyl, $NR_{10}$ COOaryl, $NR_{10}$ COalkyl, $NR_{10}$ CO aryl, COOalkyl, COOaryl, COalkyl, COaryl, aryl, cycloalkyl, saturated heterocycle and unsaturated heterocycle, wherein at least one carbon is optionally replaced with N, O, S, or halo and wherein at least one hydrogen is optionally replaced with halo, amino, alkoxy or a radioactive isotope.

Compounds of the present invention may also have the general structure of Formula (Vb):

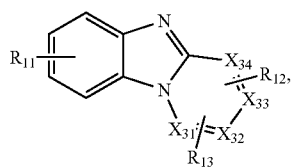

(Vb)

or a pharmaceutically acceptable salt thereof, stereoisomers thereof, wherein:

$X_{31-34}$ are each independently CH, $CR_{12}$, $CR_{13}$, N, O or S $R_{11}$-$R_{13}$ are each independently H, halogen, hydroxy, nitro, cyano, amino, alkyl, alkylaryl, alkylamino, alkylamine, arylamine, arylamino, alkoxy, $NR_{10}$COOalkyl, $NR_{10}$ COOaryl, $NR_{10}$ COalkyl, $NR_{10}$ CO aryl, COOalkyl, COOaryl, COalkyl, COaryl, aryl, cycloalkyl, saturated heterocycle and unsaturated heterocycle, wherein at least one carbon is optionally replaced with N, O, S, or halo and wherein at least one hydrogen is optionally replaced with halo, amino, alkoxy or a radioactive isotope.

Compounds of the present invention may also have the general structure of:

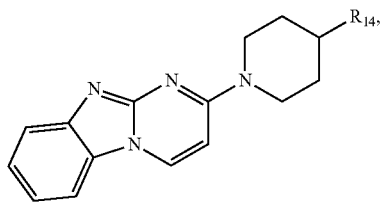

wherein $R_{14}$ is alkyl, alkylaryl, halo or a radioactive isotope.

One skilled in the art will understand that modifications to the above general structures may be made. For example, the following structures may exhibit favorable properties:

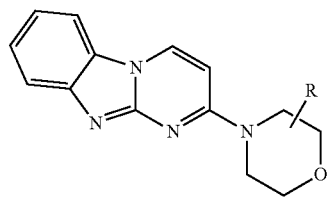

-continued

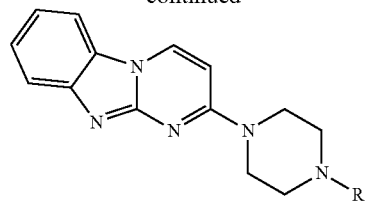

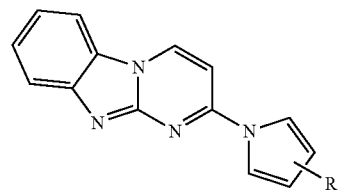

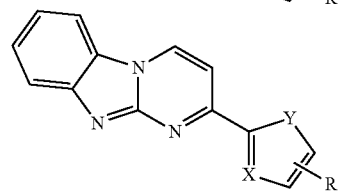

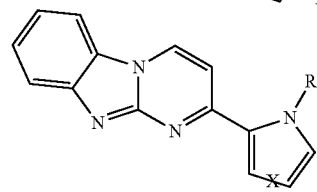

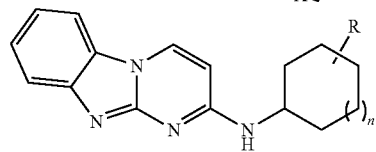

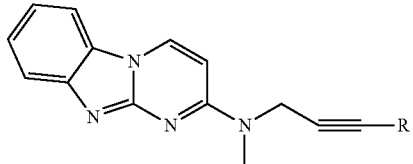

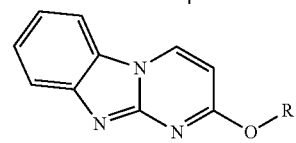

In addition, it will be understood that the radiolabel (e.g., $^{18}$F) may be replaced by a fluorescent tag. Such tags may include Ethidium bromide, Fluorescein, Green fluorescent protein, etc.

The present invention is also directed to methods of using compounds of Formulas IV and V.

In one embodiment, the invention is a method for imaging and detection of senile plaques and/or neurofibrillary tangles in a brain tissue, the method comprising treating the tissue with a compound of any of formulas (IV)-(V) for detection of neurological disorders.

In one embodiment, the invention is the method above wherein the neurological disorder is detected by measuring the affinity of compounds of any of formulas (IV)-(V) for senile plaques.

In one embodiment, the invention is a method above wherein the neurological disorder is detected by measuring the affinity of compounds of any of formulas (IV)-(V) for tau aggregates.

In one embodiment, the invention is a method for ex vivo or in vitro detection of amyloid deposit in a brain tissue, the method comprising treating the tissue with a compound of any of formulas (IV)-(V) for detection of the amyloid deposit.

In one embodiment, the invention is a method for in vivo detection of amyloid deposits in a patient, the method comprising administering an effective amount of a radiolabed compound of any of formulas (IV)-(V) to the patient, and detecting the binding level of the compound to the amyloid deposit to the patient.

In one embodiment, the invention is a method for ex vivo or in vitro detection of tau proteins in a brain tissue, the method comprising treating the tissue with a compound of any one of formulas (IV)-(V) for detectiong of the neurofibrillary tangles.

In one embodiment, the invention is a method for in vivo detection of neurofibrillary tangles in a patient, the method comprising administering an effective amount of a radiolabeled compound of any one of formulas (IV)-(V) to the patient, and detecting the binding level of the compound to tau proteins.

In one embodiment, the invention is a method above, wherein the disorder is Alzheimer's disease (AD).

In one embodiment, the invention is a method above, wherein the detection is performed using gamma imaging, magnetic resonance imaging, magnetic resonance spectroscopy or fluorescence spectroscopy.

In one embodiment, the invention is a method above, wherein the detection by gamma imaging is PET or SPECT.

In another embodiment, the present invention relates to compounds and compositions which comprise the formulae as disclosed herein, wherein the compound is an amyloid and/or tau protein binding compound. An amyloid and/or tau protein binding compound of the invention may be administered to a patient in amounts suitable for in vivo imaging of amyloid deposits and/or NTFs, and distinguish between neurological tissue with amyloid deposits and/or NTfs and normal neurological tissue.

Aβ compounds are typically evaluated in a competitive binding assay using synthetic Aβ1-42 fibrils ($IC_{50}$s). The situation is more complicated for tau, because there are 6 isoforms of tau potentially present in AD brains as products of alternate splicing of a single tau gene. Most reports in the literature rely therefore on only one recombinant isoform, Tau-441. To add more complexity, the various tau isoforms are hyperphosphorylated in vivo, something that is difficult to mimic in vitro. Furthermore, structural information on these tau fibrils is lacking, making an interpretation of binding of compounds difficult.

Native forms of tau (various isoforms, hyperphosphorylated) and amyloid aggregates are present in brain sections and therefore preferred for compound testing. Using the self-fluorescence of a test compound can give an indication of whether the compound binds to tau tangles/PHFs and/or amyloid plaques. This is further confirmed by immunostaining with Aβ and tau antibodies and overlaying the images. The drawback is that the fluorescent signals cannot be used for quantitation as some compounds might exhibit a strong fluorescent signal than others and the coexistence of Aβ plaques and tau tangles in AD brains. However, it is possible to "rate" the signal strength qualitatively and distinguish compounds that show binding to these aggregates.

Furthermore, the selectivity can be evaluated in brains containing only Aβ plaques/no tau aggregates, Aβ plaques/ and tau aggregates, and control brains. Unfortunately, there are no AD brains with only tau and no Aβ present. By testing radiolabeled tracers in these brain sections, one can more quantitative evaluate the relative binding strength (signal strength) and selectivity of various test compounds as they all contain the same radioactive tracer. For examples, if a test tracer binds only to tau, and not amyloid, it should show no signal in the Aβ plaques only brain sections. If a compound binds only to amyloid, it should show uptake in both types of brains. The difficulty of identifying and further quantifying selective compounds lies in the relative abundance of amyloid vs. tau, which is difficult to measure.

In one of the embodiments of the present invention, the self-fluorescence of the compound of formula (I) is used to determine whether the compound binds to tau/amyloid in the brain sections and to give it a qualitative rating. The next step is to proceed to the autoradiography using different brain types for further evaluation and quantitation.

Amyloid and/or tau protein probes of the invention may be used to detect and quantitate amyloid deposits and/or NTFs in diseases including, but not limited to Mediterranean fever, MuckleWells syndrome, idiopathic myeloma, amyloid polyneuropathy, amyloid cardiomyopathy, systemic senile myloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, Isolated atrial amyloid, $β_2$-microglobulin amyloid in dialysis patients, inclusion body myositis, $β_2$-amyloiddeposits in muscle wasting disease, chronic traumatic encephalopathy (CTE), and Islets of Langerhans diabetes Type II insulinoma.

The compounds and probes of the invention preferably exhibit low toxicity at dosages effective to image (including diagnostic, detection, quantification and evaluation) amyloid and/or related afflictions.

In one of the embodiment, the present invention is directed to a pharmaceutical diagnostic formulation comprising a radiolabeled compound of formula (I) or a pharmaceutically acceptable salt thereof in a suitable vehicle or diluent for imaging and detection of neurological disorders.

In another embodiment, the present invention is directed to a pharmaceutical diagnostic formulation for detection of amyloid peptides.

In another embodiment, the present invention is directed to a pharmaceutical diagnostic formulation for detection of tau proteins of neurofibrillary tangles.

In another embodiment, the present invention is directed to a pharmaceutical diagnostic formulation for detection of the neurological disorder.

In another embodiment, the present invention is directed to a pharmaceutical diagnostic formulation for detection of Alzheimer's disease.

In another embodiment of the present invention, the radioactive diagnostic agent composition may contain any additive such as pH controlling agents (e.g., acids, bases, buffers), stabilizers (e.g., ascorbic acid) or isotonizing agents (e.g., sodium chloride).

In yet another embodiment, the invention further relates to a method for imaging and detection of senile plaques and/or neurofibrillary tangles in a brain tissue, the method comprising treating the tissue with a compound of formula (V).

In yet another embodiment, the invention further relates to a method for ex vivo or in vitro detection of amyloid deposit in a brain tissue, the method comprising treating the tissue with a compound of formula (V) for detection of the amyloid deposit.

In yet another embodiment, the invention further relates to a method for in vivo detection of amyloid deposits in a patient, the method comprising administering an effective amount of the compound of formula (V) to the patient, and detecting the binding level of the compound to the amyloid deposit to the patient.

In yet another embodiment, the invention further relates to a method for ex vivo or in vitro detection of tau proteins in a brain tissue, the method comprising treating the tissue with a compound of formula (V) for detecting of the neurofibrillary tangles.

In yet another embodiment, the invention further relates to a method for in vivo detection of neurofibrillary tangles in a patient, the method comprising administering an effective amount of the compound of formula (V) to the patient, and detecting the binding level of the compound to tau proteins.

In yet another embodiment, the invention further relates to a method of detecting a SPs and NTFs characteristic for a neurological disorder.

In yet another embodiment, the invention further relates to a method of detecting Alzheimer's disease (AD).

In yet another embodiment, the invention further relates to a method of imaging and detection of neurological disorder performed by using gamma imaging, magnetic resonance imaging, magnetic resonance spectroscopy or fluorescence spectroscopy.

In yet another embodiment, the invention further relates to a method of imaging and detection of SPs and NTFs, wherein the detection is by PET or SPECT.

According to a particular embodiment of the present invention, the compounds and methods of the present invention are used for imaging, especially medical imaging.

Diagnostic techniques in nuclear medicine use radioactive tracers which emit gamma rays from within the body. These tracers are generally short-lived isotopes linked to chemical compounds which permit specific physiological processes to be scrutinized. They can be given by injection, inhalation or orally. The first type is where single photons are detected by a gamma camera which can view organs from many different angles. The camera builds up an image from the points from which radiation is emitted; this image is enhanced by a computer and viewed by a physician on a monitor for indications of abnormal conditions.

Positron Emission Tomography (PET) is a precise and sophisticated technique using isotopes produced in a cyclotron.

A positron-emitting radionuclide is introduced, usually by injection, and accumulates in the target tissue. As it decays it emits a positron, which promptly combines with a nearby electron resulting in the simultaneous emission of two identifiable gamma rays in opposite directions. These are detected by a PET camera and give very precise indication of their origin. PET's most important clinical role is in oncology, with fluorine-18 as the tracer, since it has proven to be the most accurate non-invasive method of detecting and evaluating most cancers. It is also well used in cardiac and brain imaging.

A number of medical diagnostic procedures, including PET and SPECT utilize radiolabeled compounds, are well known in the art. PET and SPECT are very sensitive techniques and require small quantities of radiolabeled compounds, called tracers. The labeled compounds are transported, accumulated and converted in vivo in exactly the same way as the corresponding non-radioactively compound. Tracers, or probes, can be radiolabeled with a radionuclide useful for PET imaging, such as $^{11}$C, $^{13}$N, $^{15}$O, $^{18}$F, $^{64}$Cu, and $^{124}$I, or with a radionuclide useful for SPECT imaging, such as $^{99}$Tc, $^{77}$Br, $^{61}$Cu, $^{153}$Gd, $^{123}$I, $^{125}$I, $^{131}$I and $^{32}$P.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

According to another embodiment, the present invention is also directed at a method of imaging amyloid deposits and NTFs. When the compounds of this invention are used as imaging agents, they are labeled with suitable radioactive isotopes or radiolabel or radioactive label, for example, radioactive halogens, such as $^{18}$F or, radioactive metals and other detectable radioactive atoms such as $^{11}$C.

Regarding radiohalogens, $^{125}$I isotopes are useful for laboratory testing but they will generally not useful for diagnostic purposes because of the relatively long half-life (60 days) and low gamma-emission (30-65 Key) of $^{125}$I. The isotope $^{123}$I has a half-life of thirteen hours and gamma energy of 159 Key, and it is therefore expected that labeling of ligands to be used for diagnostic purposes would be with this isotope or with $^{18}$F (half-life of 2 hours). Other isotopes which may be used include $^{131}$I, $^{77}$Br, and $^{76}$Br.

In another embodiment, compounds of the present invention also contain a radioactive isotope of carbon as the radiolabel. This refers to a compound that comprises one or more radioactive carbon atoms, preferably $^{11}$C, with a specific activity above that of the background level for that atom. It is well known that naturally occurring elements are present in the form of varying isotopes, some of which are radioactive. The radioactivity of the naturally occurring elements is a result of the natural distribution or abundance of these isotopes, and is commonly referred to as a background level. The carbon labeled compounds of the present invention have a specific activity that is higher than the natural abundance, and therefore above the background level. The carbon labeled compositions of the present invention can be used for tracing, imaging, radiotherapy, and the like.

Those skilled in the art are familiar with the various ways to detect labeled compounds for imaging purposes. For example, positron emission tomography (PET) or single photon emission computed tomography (SPECT) can be used to detect radiolabeled compounds. The label that is introduced into the compound can depend on the detection method desired. Those skilled in the art are familiar with PET detection of a positron-emitting atom, such as $^{18}$F. The present invention is also directed to specific compounds described herein where the $^{18}$F atom is replaced with a non-radiolabeled fluorine atom. Those skilled in the art are familiar with SPECT detection of a photon-emitting atom, such as $^{123}$I or $^{99m}$Tc.

The radioactive diagnostic agent should have sufficient radioactivity and radioactivity concentration which can assure reliable diagnosis. The desired level of radioactivity can be attained by the methods provided herein for preparing compounds of Formula I. The imaging of amyloid deposits and NTFs can also be carried out quantitatively so that the amount of amyloid deposits and NTFs can be determined.

One of the key prerequisites for an in vivo imaging agent of the brain is the ability to cross the intact blood-brain barrier after a bolus i.v. injection. In the first step of the present method of imaging, a labeled compound of Formula I is introduced into a tissue or a patient in a detectable quantity. The compound is typically part of a pharmaceutical composition and is administered to the tissue or the patient by methods well known to those skilled in the art. For example, the compound can be administered either orally, rectally, parenterally (intravenous, by intramuscularly or subcutaneously), intracisternally, intravaginally, intraperitoneally, intravesically, locally (powders, ointments or drops), or as a buccal or nasal spray.

In other embodiments of the invention, the labeled compound is introduced into a patient in a detectable quantity and after sufficient time has passed for the compound to become associated with amyloid deposits and/or tau proteins, the labeled compound is detected noninvasively. In another embodiment of the invention, a labeled compound of Formula I is introduced into a patient, sufficient time is allowed for the compound to become associated with amyloid deposits, and then a sample of tissue from the patient is removed and the labeled compound in the tissue is detected apart from the patient. In another embodiment of the invention, a tissue sample is removed from a patient and a labeled compound of Formula I is introduced into the tissue sample. After a sufficient amount of time for the compound to become bound to amyloid deposits and/or tau proteins, the compound is detected.

A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The amount of time necessary can easily be determined by introducing a detectable amount of a labeled compound of Formula I into a patient and then detecting the labeled compound at various times after administration.

The administration of the labeled compound to a patient can be by a general or local administration route. For example, the labeled compound may be administered to the patient such that it is delivered throughout the body. Alternatively, the labeled compound can be administered to a specific organ or tissue of interest. For example, it is desirable to locate and quantitate amyloid deposits in the brain in order to diagnose or track the progress of Alzheimer's disease in a patient.

The term "pharmaceutically acceptable salt" as used herein refers to those carboxylate salts or acid addition salts of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include, but are not limited to hydrobromide, hydrochloride, sulfate, bisulfate, nitrate, acetate, trifluoroacetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., *Pharmaceutical Salts, J. Pharm. Sci.* 66:1-19 (1977), which is incorporated herein by reference).

The term "alkyl" as employed herein by itself or as part of another group refers to both straight and branched chain radicals of up to 6 carbons, preferably up to 4 carbons.

The term "alkene" as employed herein by itself or as part of another group refers to both straight and branched chain radicals of up to 6 carbons, preferably up to 4 carbons, which have a double bond between any two carbon atoms.

The term "alkyne" as employed herein by itself or as part of another group refers to both straight and branched chain radicals of up to 6 carbons, preferably up to 4 carbons, which have a triple bond between any two carbon atoms. Alkynes are traditionally known as acetylenes, although the name acetylene refers specifically to $C_2H_2$.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 4 carbon atoms in length, more preferably 1 or 2 carbon atoms in length.

The term "halo" or "halogen" employed herein by itself or as part of another group refers to chlorine, bromine, fluorine or iodine, unless defined otherwise in specific uses in the text and/or claims.

The term "radiohalogen" employed herein by itself or as part of another group refers to $^{18}F$, $^{123}I$, $^{125}I$, $^{131}I$ $^{76}Br$ and $^{77}Br$.

The term "haloalkyl" as employed herein refers to any of the above alkyl groups substituted by one or more chlorine, bromine, fluorine or iodine with fluorine being preferred. Most preferably, the alkyl is substituted with a single halo, such as fluorine, at the distal end of the alkyl.

The term "radiohaloalkyl" refers to a haloalkyl group as defined above that contains a halogen radioisotope. One example of this type of group is $^{18}F$—$(C_{1-4})$alkyl-.

The term "hydroxyalkyl" as employed herein by itself or as part of another group refers to linear or branched alkyl groups containing an —OH substituent.

The term "aryl" as employed herein by itself or as part of another group refers to monocyclic, bicyclic, tricyclic or polycyclic aromatic groups containing from 5 to 14 atoms in the ring portion. Aryl compounds of the present invention include, but are not limited to non-substituted or further substituted phenyl, naphthyl, tetrahydronaphthyl and the like. The aryl group can also contain at least one heteroatom, such as N, S or O, to form a "heteroaryl." Examples of heteroaryls include, but are not limited to non-substituted or further substituted thienyl, benzo[b]thienyl, benzothiazolyl, furyl, pyranyl, isobenzofuranyl, benzofuranyl, benzoxazolyl, 2H-pyrrolyl, pyrrolyl, imidazolyl, benzopyrazolyl, benzoimidazolyl, benzoimidazole pyrimidines, imidazoimidazole pyridine, benzofuropyridine, benzofuropyrimidine, pyrazolyl, pyridyl, pyrazinyl, pyrimidinyl, pyridazinyl, indolizinyl, isoindolyl, 3H-indolyl, indolyl, indazolyl, 4H-quinolizinyl, isoquinolyl, quinolyl, quinazolinyl, isothiazolyl, phenothiazinyl, isoxazolyl, furazanyl, phenoxazinyl groups and the like.

The term "aryloxy" as employed herein refers to an "aryl" group bonded to an oxygen atom, and include benzyloxy and phenoxy, which can be further substituted and the like.

The term "tissue" means a part of a patient's body. It is an ensemble of cells, not necessarily identical, but from the same origin, that together carry out a specific function. Examples of tissues include, but are not limited to the brain, heart, liver, blood vessels, and arteries.

The term "patient" or "subject" means humans and other animals.

Those skilled in the art are also familiar with determining the amount of time sufficient for a compound to become associated with amyloid deposits for imaging purposes.

The term "associated" means a chemical interaction between the labeled compound and the amyloid deposit. Examples of associations include covalent bonds, ionic bonds, hydrophilic-hydrophilic interactions, hydrophobichydrophobic interactions, and complexes.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXPERIMENTAL EXAMPLES

Note: equivalents refer to molar equivalents. Actual volumes are calculated by multiplying the molar equivalents by liters. Thus, 1 mmol times 5 vol equals 5 mmol.

1. General Experimental Procedures for the Preparation of Disclosed compounds:

Method A: General Procedure for Suzuki Coupling Reactions:

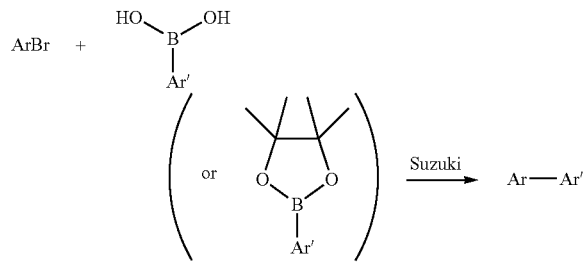

A mixture of aryl/heterocyclic halide (1.0 equiv.), boronic acid or boronate ester (1.1-1.5 equiv.), $K_2CO_3$ (3.0 equiv.) and Pd[PPh$_3$]$_4$ (0.01-0.05 equiv) in DMF (30 mL) was irradiated in a Biotage Emrys Initiator microwave reactor (250 W) at 100° C. for 30 min. After cooling to room temperature, the solvent was removed in vacuo. The residue was purified on flash column chromatography over silica gel using EtOAc:Hexanes or EtOAc:DCM or MeOH:DCM as the eluent to afford the desired biaryl products.

Method B: General Procedure for Sonogashira Coupling Reaction:

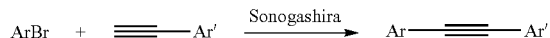

A mixture of halide (1.0 equiv.), acetylene (1.1-1.5 equiv.), CuI (0.05 equiv.), Pd[PPh$_3$]$_4$ or PdCl$_2$(PPh$_3$)$_2$ (0.01-0.05 equiv.) and DIPEA (3.0 equiv.) in ACN (30 mL) was irradiated in a Biotage Emrys Initiator microwave reactor (250 W) at 100° C. for 30 min. After cooling to room temperature, the solvent was removed in vacuo. The residue was purified on flash column chromatography over silica gel using EtOAc:Hexanes or EtOAc:DCM or MeOH:DCM as the eluent to afford the disubstituted acetylene derivatives.

Method C: General Procedure for Phenolic Alkylation:

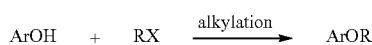

A mixture of phenol derivatives (1.0 equiv.), alkylating agent (1.1 equiv.), and $Cs_2CO_3$ (3.0 equiv.) in DMF (10 mL) was heated at 60° C. under Ar for 1-3 hrs. After the reaction was completed, the solvents were removed in vacuo. The residue was purified on flash column chromatography over silica gel using EtOAc:Hexanes or EtOAc:DCM or MeOH:DCM as the eluent to afford the alkylated products.

Method D: General Procedure for N-Alkylation Using NaH as the Base:

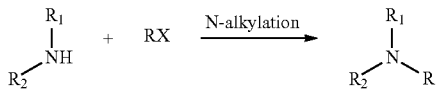

To a solution of amine (1.0 equiv.) in DMF (10 mL) was added NaH (1.5-6 equiv.), followed by alkylating agent (1.1-2 equiv.). The reaction mixture was allowed to stir at room temperature for 1-15 hrs and monitored by LCMS. The reaction mixture was then poured into water (50 mL) and extracted with EtOAc (4×20 mL). The combined organic layers were washed with $H_2O$ (3×20 mL), brine (50 mL), dried (Na$_2$SO$_4$) and concentrated in vacuo. The residue was purified on a flash column chromatography over silica gel using EtOAc:Hexanes or EtOAc:DCM or MeOH:DCM as the eluent to afford the N-alkylated products.

Method E: General Procedure for N-Alkylation Using $Cs_2CO_3$ as the Base:

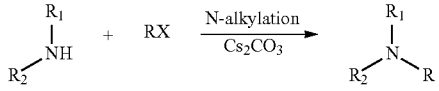

To a solution of amine (1.0 equiv.) in DMF (10 mL) was added alkylating agent (1.1-2 equiv.) and $Cs_2CO_3$ (2-3 equiv.). The reaction mixture was allowed to stir at 60° C. for 1-15 hrs. After the reaction was completed, the solvents were removed in vacuo. Water (30 mL) was added was added to the residue. If the desired products are precipitated as a solid, they are filtered, washed with water and dried to give the pure products. If the desired products are not precipitated out, the mixtures are extracted with EtOAc (4×40 mL). The combined organic layers were washed with $H_2O$ (3×40 mL), brine (50 mL), dried (Na$_2$SO$_4$) and concentrated in vacuo. The residue was purified on a flash column chromatography over silica gel using EtOAc:Hexanes or EtOAc:DCM or MeOH:DCM as the eluent to afford the N-alkylated products.

Method F: General Procedure of Tosylation of Alcohol:

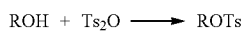

To a cooled solution of alcohol (1.0 equiv.) in DCM (20 mL) was added Ts$_2$O (1.5 equiv.) and Et$_3$N (3.0 equiv.). The reaction mixture was stirred at 0° C. and then gradually warmed to room temperature, and stirred at room temperature for 1-5 hrs. After the reaction was completed, DCM was removed in vacuo. The residue was purified on flash column chromatography over silica gel using EtOAc:Hexanes as the eluent to afford the final tosylates.

Method G: General Procedure for Demethylation of Aryl Methyl Ether:

To a cooled solution of aryl methyl ether (1.0 equiv.) in DCM (10 mL) was added BBr$_3$ (5.0 equiv.) slowly. The resulting mixture was stirred at 0° C. and then warmed gradually to room temperature, and stirred at room temperature for 15 hrs. After the reaction was completed, the reaction was quenched with NaHCO$_3$ solution (50 mL) and extracted with DCM (4×10 mL). The combined organic layers were washed with H$_2$O (3×10 mL), dried (Na$_2$SO$_4$) and concentrated in vacuo to afford the expected phenols.

Method H: General Procedure for Click Reaction Between Azides and Acetylenes Using CuI and DIPEA:

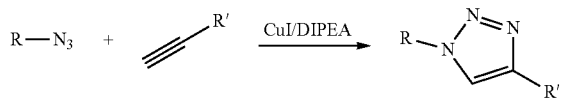

To a solution of azide derivatives (1.0 equiv.) in THF (29 mL) was added acetylene derivatives (1.0 equiv.), CuI (0.2 equiv.), DIPEA (0.4 equiv.). The reaction mixture was allowed to stir at room temperature under Ar until deemed completion of reaction by LCMS. The reaction mixture was then concentrated in vacuo. The residue was purified on a flash column chromatography over silica gel using EtOAc:Hexanes as the eluent to afford the final triazoles.

Method I: General Procedure for Silyl Deprotection Using K$_2$CO$_3$:

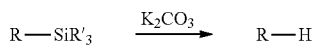

To a solution of silyl protected compounds (1.0 equiv.) in MeOH (20 mL) was added K$_2$CO$_3$ (1.2 equiv.). The reaction mixture was allowed to stir at room temperature for 1 h. After the reaction was completed, the solvent was removed in vacuo. The residue was purified on a flash column chromatography over silica gel using EtOAc:Hexanes as the eluent to give the deprotected products.

Method J: General Procedure for Silyl Deprotection with TBAF:

To a solution of silyl protected compound (1.0 equiv.) in THF (20 mL) was added a solution of TBAF in THF (1.0M, 1.0 equiv.). The reaction mixture was allowed to stir at room temperature for 10 min. After the reaction was completed, the solvents were removed in vacuo. The residue was purified on a flash column chromatography over silica gel using EtOAc:Hexanes as the eluent to afford the deprotected products.

Method K: General Procedure for the Deprotection of Boc, THP and Ketal Derivatives:

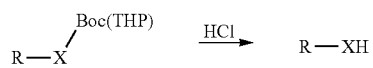

To a solution of protected derivatives (1.0 equiv.) in 1,4-dioxane (20 mL) was added a solution of HCl in 1,4-dioxane (4.0M, 3.8 mL). The reaction mixture was allowed to stir at room temperature and monitored by LCMS. After the reaction was completed, the solvents were removed in vacuo to afford the desired deprotected products.

Method L: General Procedure for the Conversion of Nitropyridyl to Fluoropyridyl compounds:

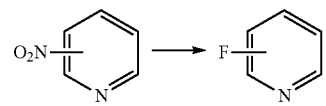

To a solution of nitropyridyl derivatives (1.0 equiv.) in DMSO (10 mL) was added KF (5 equiv.). The reaction mixture was allowed to stir at 140° C. for 1.5 hrs. After the reaction was completed, the reaction was quenched with water (10 mL) and extracted with DCM (4×10 mL). The combined organic layers were washed with H$_2$O (3×10 mL), dried (Na$_2$SO$_4$) and concentrated in vacuo. The residue was purified on a flash column chromatography over silica gel using EtOAc:Hexanes or EtOAc:DCM or MeOH:DCM as the eluent to afford the F-pyridyl compounds.

Method M: General Procedure for the Conversion of Fluoropyridyl to Aminopyridyl Compounds:

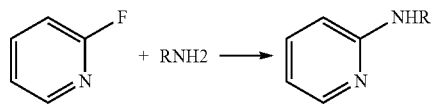

A suspension of fluoropyridyl derivatives (1.0 equiv.) and amine derivatives (excess) was irradiated in a Biotage Emrys Initiator microwave reactor (250 W) at 120° C. for 10 min. After the reaction was completed, the reaction was quenched with water (10 mL) and extracted with DCM (4×10 mL). The combined organic layers were washed with H$_2$O (3× to mL), dried (Na$_2$SO$_4$) and concentrated in vacuo. The residue was purified on a flash column chromatography over silica gel using EtOAC:DCM as the eluent to afford the aminopyridyl compounds.

Method N: General Procedure for Click Reaction Between Azides and Acetylenes Using CuSO$_4$.H$_2$O and Sodium Ascorbate:

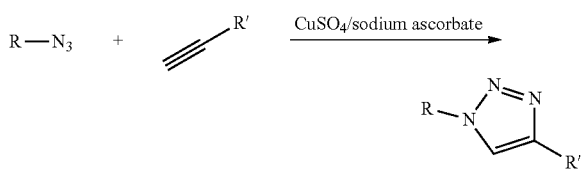

To a solution of azide derivatives (1.0 equiv.) in a mixture of tert-BuOH:H$_2$O (1:1, 100 mL) was added acetylene (0.9-1.2 equiv.), CuSO$_4$.5H$_2$O (0.2 equiv.), and sodium L-ascorbate (0.4 equiv.). The resulting reaction mixture was allowed to stir at room temperature under Ar until deemed complete by LCMS. After the reaction was completed, the solvents were removed in vacuo. The residue was mixed with water (100 mL), cooled to 0° C., and filtered. The solid collected was washed with ether (5×10 mL) and dried in vacuo to afford the final triazoles.
Method O: General Procedure for Fluorination:

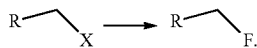

X = OTs or Br

To a solution of precursor (alkyl tosylates/bromides, 1.0 equiv.) in acetonitrile (1.0 mL) was added a solution Bu$_4$NF in THF (4M, 1.0 equiv.). The reaction mixture was allowed to stir at 90° C. for 30 min and cooled. The reaction mixture was diluted with water/acetonitrile (1 mL), filtered through 0.45 µm filter prior to purification by HPLC using ACN:Water both containing 0.05% TFA to afford the fluorinated product.
Method P: General Procedure for Boc and Ketal Deprotections Using TFA:

To a solution of protected compound (1.0 equiv.) in DCM (100 mL) was added TFA (10 mL). The resulting reaction mixture was stirred at room temperature for 15 hrs, and then poured into water (200 mL). The mixture was extracted with DCM (2×100 mL). The combined organic layers were washed with sat. NaHCO$_3$ solution (50 mL), brine (50 mL), dried (Na$_2$SO$_4$) and concentrated in vacuo. The residue was purified on a flash column chromatography over silica gel using EtOAc:Hexanes as the eluent to afford the deprotected products.
Method Q: General Procedure for One-Pot Reductive Amination of Anilines from Alcohols.

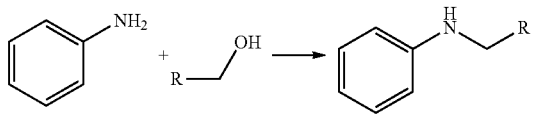

To a solution of alcohols (0.2 mmol) in DCE (1 mL) was added Dess-martin reagent (0.2 mmol). The mixture was stirred at room temperature for 15 minutes and filtered off solid with syringe filter. The filtrate was added to a solution of substituted anilines (0.1 mmol) and NaBH(OAc)$_3$ (0.3 mmol) in DCE (1 mL). The mixture was stirred 5 to 10 min at room temperature and quickly quenched with 1 N NaOH solution (1 mL). The DCE layer was separated and concentrated in vacuo. The residue was purified by flash chromatography (silica gel, 0-20% EtOAc/DCM) to give the desired mono alkylated anilines.
Method R: General Procedure for Reductive Dimethylation of Anilines with Paraformaldehyde.

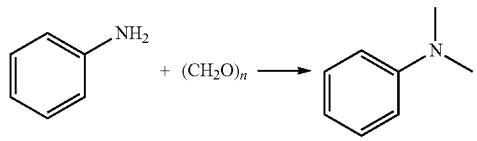

To a suspension of paraformaldehyde (1.0 mmol) in THF (5 mL) was added concentrated sulfuric acid (98%, 0.1 mL, 1.9 mmol). The mixture was stirred at room temperature while a suspension of anilines (0.1 mmol) and NaBH$_4$ (1.0 mmol) in THF (5 mL) was added to above paraformaldehyde suspension. The mixture was stirred at room temperature for 30 minutes and quenched by adding 1 N NaOH solution (1 mL). The mixture was concentrated and the residue was partitioned between DCM and water. The DCM layer was separated and concentrated in vacuo. The residue was purified by flash chromatography (silica gel, 0-10% EtOAc/DCM) to give the desired N,N-dimethyl anilines.
Method S: General Procedure for the Preparation of Benzimidazole Derivatives:

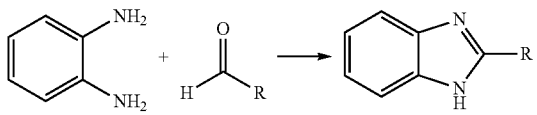

A solution of 2-aminoaniline (1.0 equiv.), benzoaldehyde/aldehyde derivatives (1.0 equiv.) and 1,4-benzoquinone (1.0 equiv.) in EtOH (10 mL) was heated at 95° C. for 4-6 hrs, and then cooled and concentrated in vacuo. The residue was purified on flash column chromatography (silica gel, 0-5% EtOAc/DCM) to give the desired products.
2. The Preparation of Claimed Compounds According to the General Procedures Described Above:
Preparation of W366

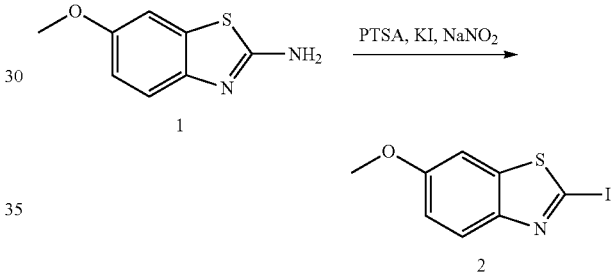

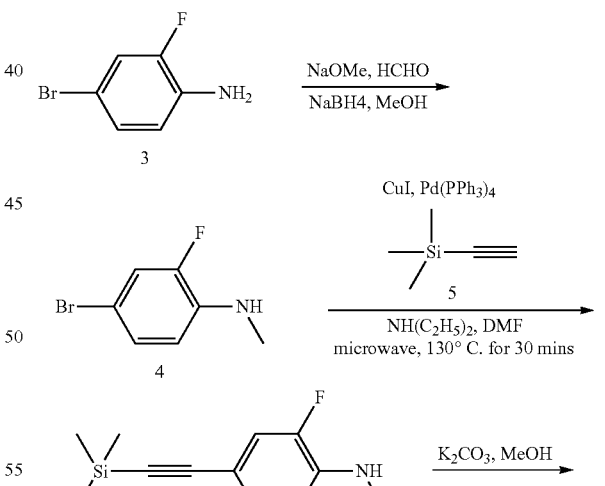

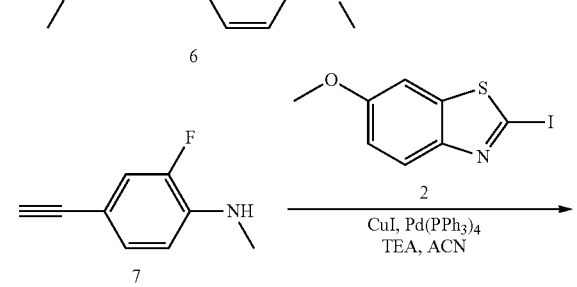

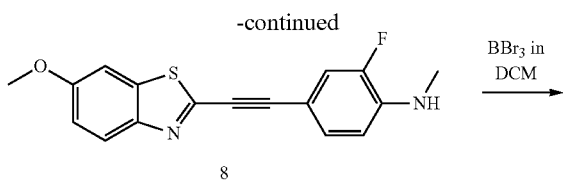

8

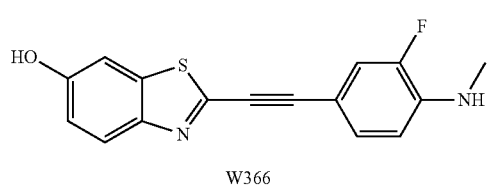

W366

Preparation of 2-iodo-6-methoxybenzo[d]thiazole (2).

To a 100 mL round bottomed flask equipped with a magnetic stir bar, ACN (33.0 mL) and PTSA (6.3 g, 33.33 mmol), 1 (2.0 g, 11.11 mmol) was added at 0° C. and stirred for 15 min. To this, a solution of NaNO$_2$ (1.5 g, 22.22 mmol) and KI (4.6 g, 27.78 mmol) in H20 (7 mL) was added and stirred for 4 hr at RT. To the reaction mixture was added H$_2$0 (175 mL) and was then made basic with sat. NaHCO$_3$ (pH=9) and Na$_2$S$_2$O$_3$ (2M, 23 mL). The resulting reaction mixture was extracted with EtOAc (3×50 mL). The combined organic extracts were washed with water (50 mL), brine (50 mL), dried over MgSO$_4$ and concentrated in vacuo. The residue was purified over silica gel using EtOAc:Hexanes (0.5:9.5) as the eluent to afford 2 (1.62 g, 50%) as a white crystalline solid. $^1$H NMR (400 MHz, CDCl$_3$), δ: 3.85 (s, 3H), 7.00 7.04 (m, 1H), 7.24-7.27 (m, 1H), 7.89 (d, J=9.19 Hz, 1H); MS (ESI) 291.9 (M+H$^+$).

Preparation of 4-bromo-2-fluoro-N-methylaniline (4).

To a 100 mL round bottomed flask equipped with a magnetic stir bar was added at RT MeOH (26.0 mL), 3 (0.5 g, 2.63 mmol), NaOMe (0.71 g, 13.16 mmol) and paraformaldehyde (0.394 g, 13.16 mmol). The reaction was refluxed for 2 hr. The reaction mixture was then cooled to 0° C. and NaHB$_4$ (0.5 g, 13.16 mmol) was added in portions. After the addition, the reaction mixture was again refluxed for 1 hr. After the reaction is complete, MeOH was removed, water (50 mL) added and extracted with EtOAc (3×30 mL). The combined organic extracts were washed with water (30 mL), brine (30 mL), dried over MgSO$_4$ and concentrated in vacuo. The residue was purified over silica gel using EtOAc:Hexanes (0.5:9.5) as the eluent to afford 4 (0.5 g, 93%) as a brown oil. $^1$H NMR (400 MHz, CDCl$_3$), δ: 2.86 (s, 3H), 6.64 6.68 (m, 1H), 7.11-7.15 (m, 2H); MS (ESI): 203.9 (M+H$^+$).

Preparation of 2-fluoro-N-methyl-4-((trimethylsilyl)ethynyl)aniline (6).

A 5 mL microwave tube was charged with 4 (0.5 g, 2.45 mmol), 5 (0.7 mL, 4.9 mmol), [Pd(PPh$_3$)$_4$] (0.3 g, 0.245 mmol), CuI (0.07 g, 0.37 mmol) and NH(C$_2$H$_5$)$_2$ (0.8 mL, 7.35 mmol) in DMF (2.5 mL). The suspension was irradiated in a Biotage Emrys Optimizer microwave reactor (250 W) at 100° C. for 15 min. After cooling to room temperature water (50 mL) was added and then extracted with EtOAc (3×30 mL). The combined organic extracts were washed with water (30 mL), brine (30 mL), dried over MgSO$_4$ and the crude mixture was used for the next step. MS (ESI): 222.1 (M+H$^+$).

Preparation of 4-ethynyl-2-fluoro-N-methylaniline (7).

To a 25 mL round bottom flask equipped with a magnetic stir bar, 6 (crude 0.4 g), MeOH (9 mL) and K$_2$CO$_3$ (0.5 g, 3.62 mmol) were added. The reaction was stirred at RT for 30 min. To the reaction mixture, silica gel added (approximately 10 g) and concentrated in vacuo. The residue was purified over silica gel using EtOAc:Hexanes (1:3) as the eluent to afford 7 (0.26 g, 96%) as brown oil. MS (ESI): 150.1 (M+H$^+$).

Preparation of 2-fluoro-4-{(6-methoxybenzo[d]thiazol-2-yl)ethynyl)-N-methylaniline (8).

A 5 mL microwave tube was charged with 2 (0.2 g, 0.68 mmol), 7 (0.1 g, 0.68 mmol) [Pd(PPh$_3$)$_4$] (0.08 g, 0.034 mmol), CuI (0.02 g, 0.05 mmol) and TEA (0.28 mL, 2.04 mmol) in ACN (2.0 mL). The suspension was irradiated in a Biotage Emrys Optimizer microwave reactor (250 W) at 100° C. for 5 min. After cooling to room temperature the solvent was evaporated in vacuo. The residue was purified over silica gel using Hexanes:Dichloromethane (DCM) (0-100%) as the eluent to afford the coupling product 8 (0.084 g, 39%) as yellow solid. $^1$H NMR (400 MHz, CDCl$_3$), δ: 2.92 (s, 3H), 3.87 (s, 3H), 6.64 (t, J=8.4 Hz, 1H), 7.11 (dd, J=12.0, 4.0 Hz, 1H), 7.22 (dd, J=10.4, 2 Hz, 1H), 7.27 (d, J=2.4, 1H), 7.33-7.35 (m, 1H), 7.96 (d, J=12 Hz, 1H); MS (ESI): 313.0 (M+H$^+$).

Preparation of 2-((3-fluoro-4-(methylamino)phenyl)ethynyl)benzo[d]thiazol-6-ol (W366).

To a 25 mL round bottomed flask equipped with a magnetic stir bar containing DCM (5.2 mL) was placed 8 (0.08 g, 0.26 mmol). The reaction mixture was cooled to 0° C. and BBr$_3$ (0.75 mL of 1M in DCM) was added drop wise. The reaction was stirred at RT for 8 hr. The reaction was then neutralized with sat. NaHCO$_3$ and extracted into DCM (2×10 mL). The combined organic extracts were washed with water (10 mL), brine (10 mL), dried over MgSO$_4$ and concentrated in vacuo. The residue was purified over silica gel using EtOAc:Hexanes (1:3) as the eluent to afford W366 (0.02 g, 26%) as a brown solid. $^1$H NMR (400 MHz, DMSO-d$_6$), δ: 2.5 (d, J=10.4 Hz, 3H), 6.06-6.08 (m, 1H), 6.42 (t, J=8.8 Hz, 1H), 6.74 (dd, J=8.8, 2.4 Hz, 1H), 7.05-7.14 (m, 2H), 7.54 (d, J=8.8, 1H), 9.76 (br s, 1H); MS (ESI): 299.0 (M+H$^+$).

Preparation of W378 standard:

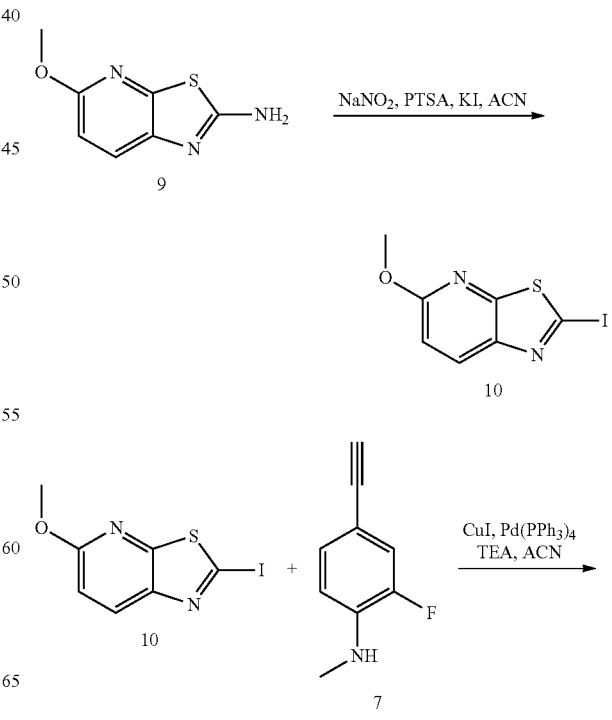

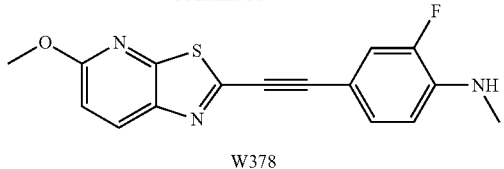
W378

Preparation of 2-iodo-5-methoxythiazolo[5,4-b]pyridine (10).

To a 25 mL round bottomed flask equipped with a magnetic stir bar, ACN (4.0 mL), PTSA (0.79 g, 4.14 mmol) and 9 (0.25 g, 1.38 mmol) were added at 0° C. and stirred for 15 min. To this, a solution of $NaNO_2$ (0.19 g, 2.76 mmol) and KI (0.57 g, 3.45 mmol) in $H_2O$ (0.9 mL) was added and stirred for 4 hr at RT. The reaction mixture was then added to $H_2O$ (15 mL), made basic with sat. $NaHCO_3$ (pH=9) and $Na_2S_2O_3$ (2M, 3 mL) was added. The resulting reaction mixture was extracted with EtOAc (3×20 mL). The combined organic extracts were washed with water (20 mL), brine (20 mL), dried over $MgSO_4$ and concentrated in vacuo. The residue was purified over silica gel using EtOAc:Hexanes (1:4) as the eluent to afford 10 (0.12 g, 30%) as a white crystalline solid. $^1$H NMR (400 MHz, $CDCl_3$), δ: 3.97 (s, 3H), 6.77 (d, J=8.8 Hz, 1H), 8.08 (d, J=8.8 Hz, 1H); MS (ESI): 292.9 (M+H$^+$).

Preparation of 2-fluoro-4-((5-methoxythiazolo[5,4-b]pyridin-2-yl)ethynyl)-N-methylaniline (W378).

A 5 mL microwave tube was charged with 10 (0.12 g, 0041 mmol), 7 (0.06 g, 0041 mmol) [Pd(PPh$_3$)$_4$] (0.05 g, 0.004 mmol), CuI (0.012 g, 0.06 mmol) and TEA (0.2 mL, 1.23 mmol) in ACN (2.0 mL). The suspension was irradiated in a Biotage Emrys Optimizer microwave reactor (250 W) at 100° C. for 5 min. After cooling to room temperature the solvent was evaporated in vacuo. The residue was purified over silica gel using Hexanes:DCM (O-100%) as the eluent to afford the coupling product W378 (0.04 g, 31%) as yellow solid. MS (ESD: 314.0 (M+H$^+$).

Preparation of W366 labeling precursor:

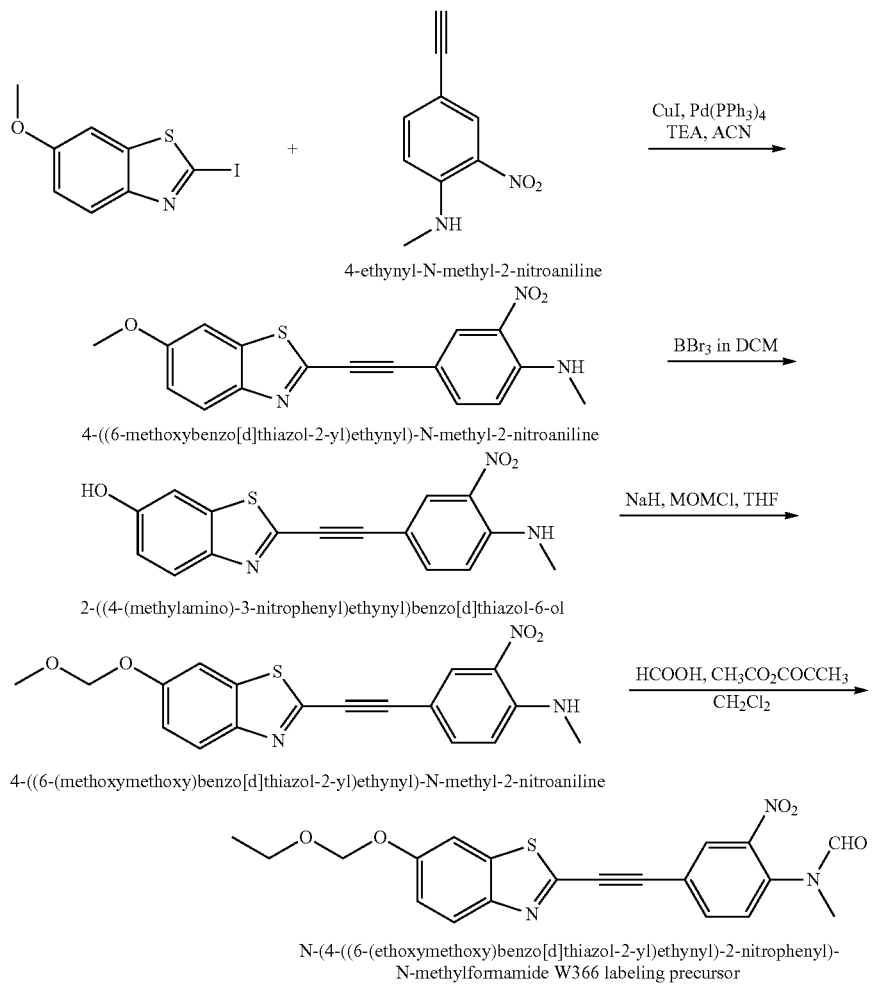

Preparation of 4-((6-methoxybenzo[d]thiazol-2-yl)ethynyl)-N-methyl-2-nitroaniline.

A 5 mL microwave tube is charged with 2 (1 equiv), 4-ethynyl-N-methyl-2-nitroaniline (1 equiv) [Pd(PPh$_3$)$_4$] (0.05 equiv), CuI (0.05 equiv) and TEA (5 equiv) in ACN (5 vol). The suspension is irradiated in a Biotage Emrys Optimizer microwave reactor (250 W) at 100° C. for 5 min. After cooling to room temperature, the solvent is evaporated in vacuo. The residue is purified over silica gel using Hexanes:DCM (0-100%) as the eluent to afford the coupling product.

Preparation of 2-((4-(methylamino)-3-nitrophenyl)ethynyl)benzo[d]thiazol-6-ol.

To a round bottomed flask equipped with a magnetic stir bar containing DCM (5 vol) is placed 4-((6-methoxybenzo[d]thiazol-2-yl)ethynyl)-N-methyl-2-nitroaniline (1 equiv). The reaction mixture is cooled to 0° C., BBr$_3$ (5 equiv of 1M in DCM) is added dropwise and the reaction is stirred at RT for 8 hours. The reaction is neutralized with sat. NaHCO$_3$, extracted into DCM (2×5 vol). The combined organic extracts are washed with water (5 vol), brine (5 vol), dried over MgSO$_4$ and concentrated in vacuo. The residue is purified over silica gel using EtOAc:Hexanes (1:3) as an eluent to afford the desired product.

Preparation of 4-((6-(ethoxymethoxy)benzo[d]thiazol-2-yl)ethynyl)-N-methyl-2-nitroaniline.

To a round bottom flask under Ar containing 2-((4-(methylamino)-3-nitrophenyl)ethynyl)benzo[d]thiazol-6-ol (1 equiv) is added THF (5 vol). To this solution is added NaH (1.3 equiv). The solution is stirred at RT for 30 min. To this solution is added MOM-Cl (1.5 equiv). The reaction is stirred overnight at RT. The reaction is poured onto water (10 vol) and extracted into DCM (10 vol). The organic layer is washed with water (10 vol), dried (MgSO$_4$), filtered and concentrated to dryness. The material is purified using EtOAc:Hexanes as the eluent over silica gel to afford the final product.

Preparation of N-(4-((6-(ethoxymethoxy)benzo[d]thiazol-2-yl)ethynyl)-2-nitrophenyl)-N-methylformamide (W366 labeling precursor).

To a round bottom flask containing 4-((6-(ethoxymethoxy)benzo[d]thiazol-2-yl)ethynyl)N-methyl-2-nitroaniline (1 equiv) is added formic acid (5 equiv), acetic anhydride (5 equiv) and DCM (5 vol). The reaction is warmed to 60° C. for 7 days. The rxn is then concentrated in vacuo and the material is purified using EtOAc:Hexanes as the eluent over silica gel to afford the final product.

Preparation of 2-(Pyridin-4-yl)quinoline (T123)

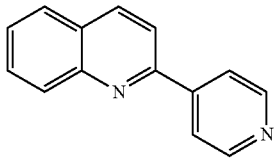 [SMILES: c1ccc2nc(-c3ccncc3)ccc2c1]

2-(Pyridin-4-yl)quinoline T123 was prepared using general procedure A from 2-chloroquinoline (82 mg, 0.5 mmol) and pyridin-4-ylboronic acid (61.5 mg, 0.5 mmol). The product was obtained as an off white solid (100 mg, 97%). NMR (400 MHz, CDCl$_3$): δ 8.75 (dd, J=5.0, 1.6 Hz, 2H), 8.26 (d, J=8.8 Hz, 1H), 8.16 (d. J=8.4 Hz, 1H), 8.04 (m, 2H), 7.87 (d, J=8.4 Hz, 1H), 7.83 (d, J=8.0 Hz, 1H), 7.74 (m, 1H), 7.55 (m, J=1H); MS (ESI): 207 (M+H$^+$).

Preparation of 5-(Quinolin-2-yl)picolinonitrile (T124)

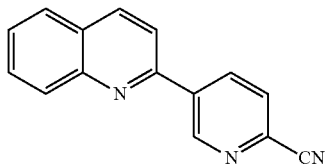 [SMILES: N#Cc1ccc(-c2ccc3ccccc3n2)cn1]

5-(Quinolin-2-yl)picolinonitrile T124 was prepared using general procedure

A from 2-chloroquinoline (82 mg, 0.5 mmol) and 5-(4,4,5,5-tetramethyl-1,3,2-dioxaborolan-2-yl)picolinonitrile (115 mg, 0.5 mmol). The product was obtained as yellow solid (3 mg, 3%). $^1$H NMR (400 MHz, CDCl$_3$): δ 9.48 (dd, J=2.4, 0.8 Hz, 1H), 8.69 (dd, J=8.0, 2.0 Hz, 1H), 8.33 (d, J=8.8 Hz, 1H), 8.19 (d, J=8.4 Hz, 1H), 7.93 (d, J=8.4 Hz, 1H), 7.90 (dd, J=8.4, 1.2 Hz, 1H), 7.87 (dd, J=8.4, 0.8 Hz, 1H), 7.81 (m, 1H), 7.63 (m, 1H); MS (ESI):232 (M+H$^+$).

Preparation of N,N-Dimethyl-5-(quinolin-2-yl)pyridin-2-amine (T125)

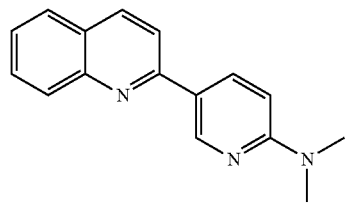 [SMILES: CN(C)c1ccc(-c2ccc3ccccc3n2)cn1]

N,N-Dimethyl-5-(quinolin-2-yl)pyridin-2-amine T125 was prepared using general procedure A from 2-chloroquinoline (82 mg, 0.5 mmol) and (6-(dimethylamino)-pyridin-3-yl)boronic acid (83 mg, 0.5 mmol). The product was obtained as yellow solid (90 mg, 72%). $^1$H NMR (400 MHz, CDCl$_3$): δ 8.93 (dd, J=2.4, 1H), 8.40 (dd, J=8.8, 2.4 Hz, 1H), 8.15 (d, J=8.4 Hz, 1H), 8.09 (d, J=8.6 Hz, 1H), 7.78 (d, J=7.2 Hz, 1H), 7.70 (m, 1H), 7.47 (m, 1H), 6.65 (dd, J=8.8, 0.8 Hz, 1H), 3.18 (s, 6H); MS (ESI): 250 (M+H$^+$).

Preparation of 2-(4-Fluoropyridin-3-yl)quinoline (T126)

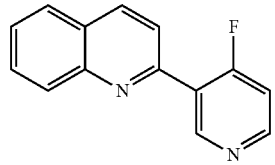 [SMILES: Fc1ccncc1-c1ccc2ccccc2n1]

2-(4-Fluoropyridin-3-yl)quinoline T126 was prepared using general procedure A from 2-chloroquinoline (82 mg, 0.5 mmol) and (5-fluoropyridin-3-yl)boronic acid (70 mg, 0.5 mmol). The product was obtained as white solid (80 mg, 71%). $^1$H NMR (400 MHz, CDCl$_3$): δ 8.93 (m, 1H), 8.63 (m, 1H), 8.24 (d, J=8.8 Hz, 1H), 8.13 (dd, J=8.8, 0.8 Hz, 1H), 7.82 (m, 2H), 7.74 (m, 1H), 7.06 (m, 1H); MS (ESI): 225 (M+H$^+$).

Preparation of 2-(6-Fluoropyridin-3-yl)quinoxaline (T127)

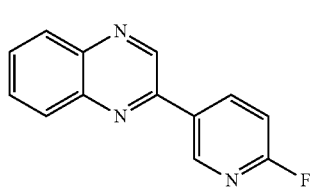 [SMILES: Fc1ccc(-c2cnc3ccccc3n2)cn1]

2-(6-Fluoropyridin-3-yl)quinoxaline T127 was prepared using general procedure A from 2-(6-fluoropyridin-3-yl)quinoxaline (82 mg, 0.5 mmol) and 2-fluoro-5-(4,4,5,5-tetramethyl-1,3,2-dioxaborolan-2-yl)pyridine (111 mg, 0.5 mmol). The product was obtained as white solid (93 mg, 82%). $^1$H NMR (400 MHz, CDCl$_3$): δ 9.32 (s, 1H), 9.00 (m, 1H), 8.66 (m, 1H), 8.15 (m, 2H), 7.82 (m, 2H), 7.15 (m, 1H); MS (ESI): 226 (M+H$^+$)—

Preparation of 2-(Pyridin-3-yl)quinoxaline (T128)

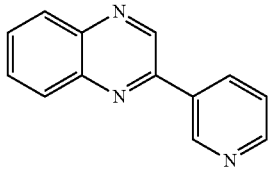 [SMILES: c1cncc(-c2cnc3ccccc3n2)c1]

2-(Pyridin-3-yl)quinoxaline T128 was prepared using general procedure A from 2-chloroquinoline (82 mg, 0.5 mmol) and (5-fluoropyridin-3-yl)boronic acid (70 mg, 0.5 mmol). The product was obtained as white solid (80 mg, 71%). $^1$H NMR (400 MHz, CDCl$_3$): δ 9.40 (d, J=2.0 Hz, 1H), 9.33 (s, 1H), 8.75 (dd, J=4.8 Hz, 1 Hz, 8.51 (m, 1H), 8.15 (m, 2H), 7.79 (m, 2H), 7.49 (m, 1H); MS (ESI): 208 (M+H$^+$).

Preparation of

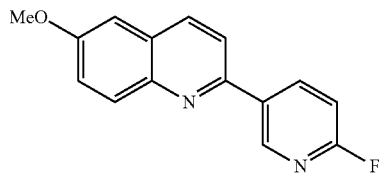 [SMILES: COc1ccc2nc(-c3ccc(F)nc3)ccc2c1]

2-(6-Fluoropyridin-3-yl)-6-methoxyquinoline T138 was prepared using general procedure A from 2-chloro-6-methoxyquinoline (65 mg, 0.33 mmol) and 2-fluoro-5-(4,4,5,5-tetramethyl-1,3,2-dioxaborolan-2-yl)pyridine (75 mg, 0.33 mmol). The product was obtained as yellow solid (30 mg, 35%). $^1$H NMR (400 MHz, CDCl$_3$): δ 8.91 (m, 1H), 8.63 (m, 1H), 8.16 (d, J=8.4 Hz, 1H), 8.05 (d, J=9.2 Hz, 1H), 7.80 (d, J=8.8 Hz, 1H), 7.41 (dd, J=9.2, 2.8 Hz, 1H), 7.11 (d, J=2.8 Hz, 1H), 7.08 (m, 1H); 3.96 (s, 3H); MS (ESI): 255 (M+H$^+$).

Preparation of

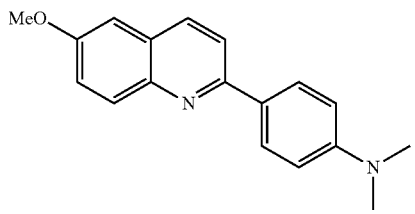 [SMILES: COc1ccc2nc(-c3ccc(N(C)C)cc3)ccc2c1]

4-(6-Methoxyquinolin-2-yl)-N,N-dimethylaniline T139 was prepared using general procedure A from 2-chloro-6-methoxyquinoline (65 mg, 0.33 mmol) and (4-(dimethylamino)phenyl)boronic acid (55 mg, 0.33 mmol). The product was obtained as yellow solid (30 mg, 33%). $^1$H NMR (400 MHz, CDCl$_3$): δ 8.06 (d, J=8.8 Hz, 2H), 8.02 (dd, J=8.4, 6.4 Hz, 2H), 7.78 (d, J=8.8 Hz, 1H), 7.33 (dd, J=9.2, 2.8 Hz, 1H), 7.06 (d, J=2.8 Hz, 1H), 6.83 (m, 2H), 3.93 (s, 3H), 3.03 (s, 6H); MS (ESI): 279 (M+H$^+$).

Preparation of

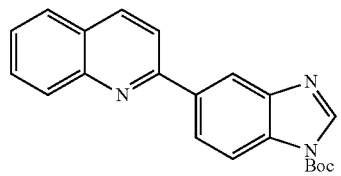 [SMILES: CC(C)(C)OC(=O)n1cnc2cc(-c3ccc4ccccc4n3)ccc21]

tert-Butyl 5-(quinolin-2-yl)-1H-benzo[d]imidazole-1-carboxylate T432 was prepared using general procedure A from 2-chloroquinoxaline (24 mg, 0.145 mmol) and tert-butyl 5-(4,4,5,5-tetramethyl-1,3,2-dioxaborolan-2-yl)-1H-indole-1-carboxylate (50 mg, 0.145 mmol). The product was obtained as white wax (30 mg, 60%). $^1$H NMR (400 MHz, CDCl$_3$): δ 8.55 (dd, J=1.6, 0.8 Hz, 1H), 8.41 (dd, J=8.8, 2.0 Hz, 1H), 8.32 (d, J=8.8 Hz, 1H), 8.29 (s, 1H), 8.26 (d, J=8.4 Hz, 1H), 8.18 (d, J=8.4 Hz, 1H), 7.95 (d, J=8.8 Hz, 1H), 7.75 (m, 1H), 7.55 (m, 1H), 1.76 (s, 9H); MS (ESI): 346 (M+H$^+$).

Preparation of

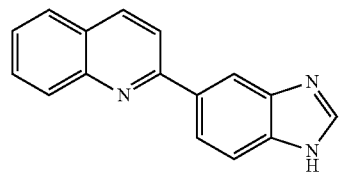 [SMILES: c1ccc2nc(-c3ccc4[nH]cnc4c3)ccc2c1]

2-(1H-Indol-5-yl)quinoline T433 was prepared using general procedure P. The reaction was performed on a 10 mg scale of T432. T433 was isolated as a yellow solid (5 mg, 35%). $^1$H NMR (400 MHz, CDCl$_3$): δ 8.83 (t, 1H), 8.70-8.51 (m, 4H), 8.24-8.22 (m, 1H), 8.14-8.08 (m, 3H), 8.00 (d, J=8.8 Hz, 0.5H), 7.88 (m, 1H), 7.68 (d, J=8.4 Hz, 0.5H); MS (ESI): 246 (M+H$^+$).

Preparation of

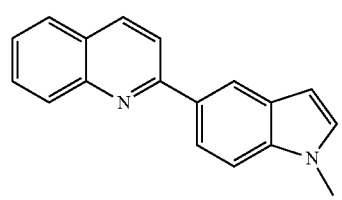 [SMILES: Cn1ccc2cc(-c3ccc4ccccc4n3)ccc21]

2-(1-Methyl-1H-indol-5-yl)quinoline T453 was prepared using general procedure A from 2-chloroquinoline (32 mg, 0.2 mmol) and 1-methyl-5-(4,4,5,5-tetramethyl-1,3,2-dioxaborolan-2-yl)-1H-indole (51 mg, 0.2 mmol). The product was obtained as off-white solid (22 mg, 42%). $^1$H NMR (400 MHz, CDCl$_3$): δ 8.43 (dd, J=2.0, 0.8 Hz, 1H), 8.17 (d, J=8.8 Hz, 2H), 8.12 (dd, J=8.8, 2.0 Hz, 1H), 7.95 (d, J=8.8 Hz, 1H), 7.80 (dd, J=8.4, 1.6 Hz, 1H), 7.70 (m, 1H), 7.48 (m, 1H), 7.44 (d, J=8.8 Hz, 1H), 7.09 (d, J=3.2 Hz, 1H), 6.60 (dd, J=3.2, 0.8 Hz, 1H), 3.82 (s, 3H); MS (ESI): 259 (M+H$^+$).

Preparation of 2-(1-(3-fluoropropyl)-1H-indol-5-yl)quinoline (T461)

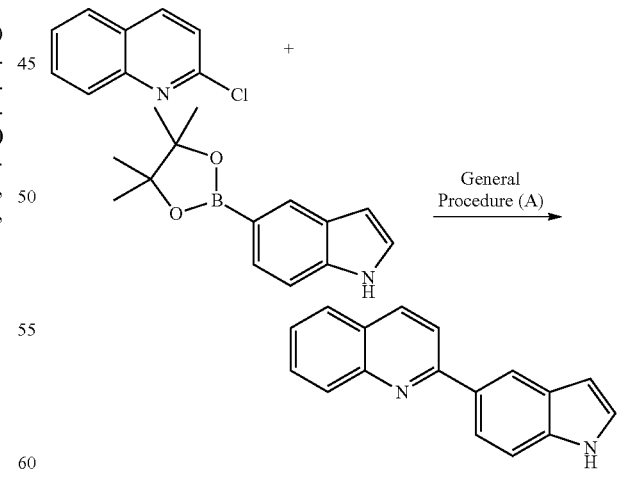

2-(1H-indol-5-yl)quinoline

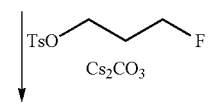

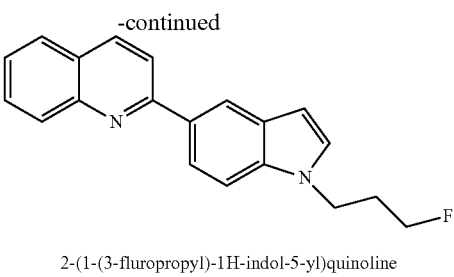

2-(1-(3-fluropropyl)-1H-indol-5-yl)quinoline

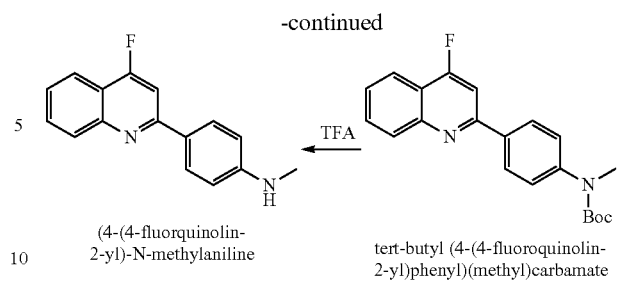

(4-(4-fluorquinolin-2-yl)-N-methylaniline tert-butyl (4-(4-fluoroquinolin-2-yl)phenyl)(methyl)carbamate 2-(1H-indol-5-yl)quinoline was prepared using general procedure A from 2-chloroquinoline (32 mg, 0.2 mmol) and 1-methyl-5-(4,4,5,5-tetramethyl-1,3,2-dioxaborolan-2-yl)-1H-indole (51 mg, 0.2 mmol). The product was obtained as off-white solid (22 mg, 42%). MS (ESI): 245 (M+H$^+$).

2-(1-(3-fluoropropyl)-1H-indol-5-yl)quinoline T461 was prepared using general procedure E. The reaction was performed on a 24 mg scale of 2-(1H-indol-5-yl)quinoline. T461 was isolated as a yellow wax (0.8 mg, 2.6%). $^1$H NMR (400 MHz, CDCl$_3$): δ 8.70 (d, J=8.4 Hz, 1H), 8.67 (d, J=8.8 Hz, 1H), 8.44 (d, J=1.2 Hz, 1H), 8.10 (d, J=9.2 Hz, 1H), 8.03-7.98 (m, 3H), 7.78 (t, J=7.2 Hz, 1H), 7.56 (d, J=8.8 Hz, 1H), 7.24 (d, J=3.2 Hz, 1H), 6.71 (d, J=3.2 Hz, 1H), 4.47 (t, J=5.2 Hz, 1H), 4.36 (m, 3H), 2.29-2.16 (m, 2H); MS (ESI): 305 (M+H$^+$).

Preparation of 4-(4-fluoroquinolin-2-yl)-N-methylaniline (T466)

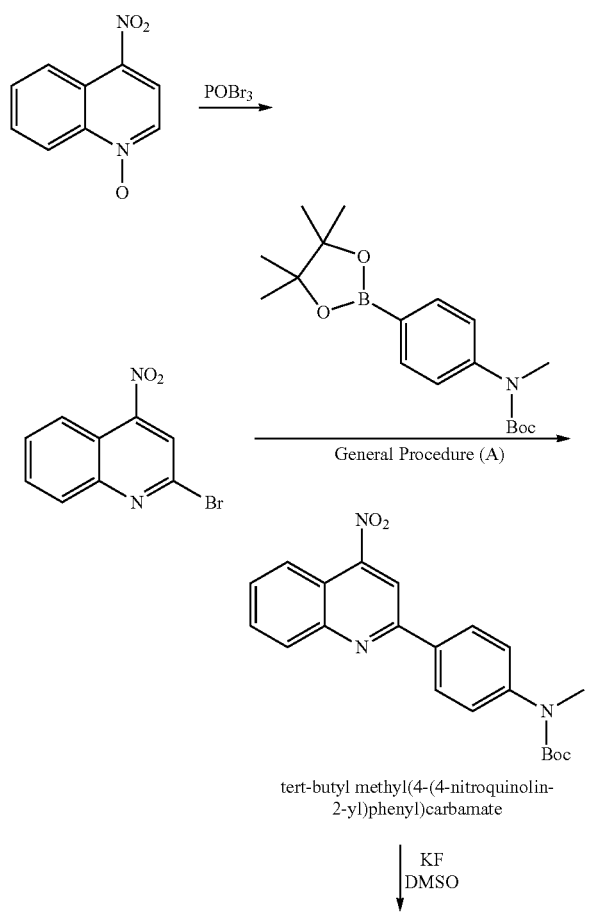

tert-butyl methyl(4-(4-nitroquinolin-2-yl)phenyl)carbamate

↓ KF
DMSO tert-Butyl methyl(4-(4-nitroquinolin-2-yl)phenyl)carbamate
4-Nitroquinoline 1-oxide (940 mg, 4.9 mmol) in chloroform (12 mL) was cooled to 0° C. To this solution, POBr$_3$ (1.77 g, 6.2 mmol) was added in small portions. The mixture was stirred at 0° C. for 2 h and diluted with DCM (50 mL), and poured on ice (50 g). To this suspension, 1 M NaOH was added to adjust pH to about 9. Layers were separated and the organic layer was washed with water (2×50 mL) and dried over MgSO4 and concentrated. The crude product was purified by silica chromatography to afford 2-bromo-4-nitroquinoline as a yellow solid (620 mg, 50%). $^1$H NMR (400 MHz, CDCl$_3$): δ 7.63-7.94 (m, 2H), 8.06 (s, 1H), 8.17 (t, J=7.16, 6.84 Hz, 1H), 8.38 (d, J=8.76 Hz, 1H).

2-Bromo-4-nitroquinoline (50 mg, 0.2 mmol) and tert-butyl methyl(4-(4,4,5,5-tetramethyl-1,3,2-dioxaborolan-2-yl)phenyl)carbamate (66 mg, 0.2 mmol) were reacted using General Procedure (A) to afford tert-butyl methyl(4-(4-nitroquinolin-2-yl)phenyl)carbamate as a yellow oil (52 mg, 68%). $^1$H NMR (400 MHz, CDCl$_3$): δ 8.43-8.40 (m, 2H), 8.28 (m, 1H), 8.19 (m, 2H), 7.87 (m, 1H), 7.73 (m, 1H), 7.46 (m, 2H), 3.35 (s, 3H), 1.59 (s, 3H), 1.50 (s, 9H); MS (ESI): 380 (M+H$^+$).

4-(4-fluoroquinolin-2-yl)-N-methylaniline T466
tert-Butyl methyl(4-(4-fluoroquinolin-2-yl)phenyl)carbamate was prepared using general procedure M from tert-butyl methyl(4-(4-nitroquinolin-2-yl)phenyl)carbamate (10 mg, 0.026 mmol) and KF (60 mg, 1 mmol). tert-butyl (4-(4-fluoroquinolin-2-yl)phenyl)(methyl)carbamate was isolated as a clear oil (4.5 mg, 49%). $^1$H NMR (400 MHz, CDCl$_3$): δ 8.16 (m, 1H), 8.12-8.07 (m, 3H), 7.78 (m, 1H), 7.59-7.54 (m, 2H), 7.41 (m, 1H), 3.32 (s, 3H), 1.48 (s, 9H); MS (ESI): 353 (M+H$^+$).

tert-Butyl (4-(4-fluoroquinolin-2-yl)phenyl)(methyl)carbamate (4.5 mg, 0.013 mmol) was treated with TFA by using general procedure P. The crude product was purified by HPLC to afford T466 as an orange-colored solid (1.8 mg, 55%). $^1$H NMR (400 MHz, CDCl$_3$): δ 8.57 (d, J=8.4 Hz, 1H), 8.02-7.97 (m, 3H), 7.75 (t, J=7.6 Hz, 1H), 7.56 (d, J=10.0 Hz, 1H), 6.72 (d, J=8.4 Hz, 2H), 2.95 (s, 3H); MS (ESI): 253 (M+H$^+$).

Preparation of N-Methyl-4-(quinolin-3-yl)aniline (T477)

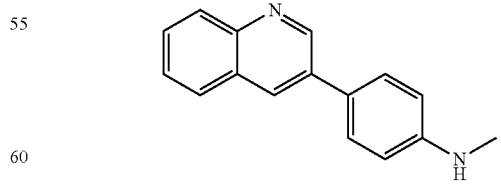

3-Bromoquinoline (42 mg, 0.2 mmol) and tert-butyl methyl(4-(4,4,5,5-tetramethyl-1,3,2-dioxaborolan-2-yl)phenyl)carbamate (66 mg, 0.2 mmol) were reacted using General Procedure (A) to afford tert-butyl methyl(4-(quinolin-3-yl)phenyl)carbamate a clear wax (44 mg, 66%). $^1$H NMR (400 MHz, CDCl$_3$): δ 9.18 (d, J=2.4 Hz, 1H), 8.31 (d, J=2.0 Hz, 1H), 8.15 (m, 1H), 7.89 (m, 1H), 7.73 (m, 1H), 7.68 (m, 2H), 7.59 (m, 1H), 7.42 (m, 2H), 3.3 (s, 3H), 1.50 (s, 9H); MS (ESI): 335 (M+H⁺). tert-Butyl methyl(4-(quinolin-3-yl)phenyl)carbamate (44 mg, 0.13 mmol) was then treated with TFA by using the general procedure P. The crude product was purified by HPLC to afford T477 as an orange-colored wax (13 mg, 29%). ¹H NMR (400 MHz, CDCl₃): δ 9.46 (d, J=2.0 Hz, 1H), 8.79 (d, J=1.6 Hz, 1H), 8.47 (d, J=8.4 Hz, 1H), 8.08 (d, J=8.4 Hz, 1H), 7.95 (m, 1H), 7.83 (m, 1H), 7.62 (m, 2H), 6.82 (m, 2H), 2.94 (s, 3H); MS (ESI): 235 (M+H⁺).
Preparation of

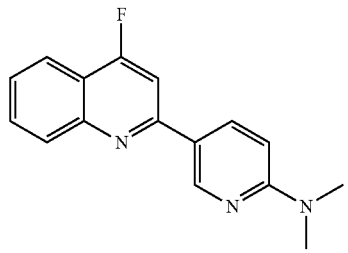 [SMILES: CN(C)c1ccc(-c2cc(F)c3ccccc3n2)cn1]

5-(4-Fluoroquinolin-2-yl)-N,N-dimethylpyridin-2-amine T480 was prepared using general procedure M from N,N-dimethyl-5-(4-nitroquinolin-2-yl)pyridin-2-amine (4 mg, 0.014 mmol) and KF (16 mg, 0.28 mmol). The crude product was purified by silica chromatography to afford 5-(4-fluoroquinolin-2-yl)-N,N-dimethylpyridin-2-amine as a light-brown solid (1.4 mg, 37%). ¹H NMR (400 MHz, CDCl₃): δ 8.89 (d, J=2.8 Hz, 1H), 8.36 (dd, J=11.6 Hz, 1H), 8.09 (m, 1H), 8.04 (m, 1H), 7.73 (m, 1H), 7.51 (m, 1H), 7.47 (d, J=11.6 Hz, 1H), 6.64 (d, J=9.2 Hz, 1H), 3.19 (s, 6H); MS (ESI): 268 (M+H⁺).
Preparation of

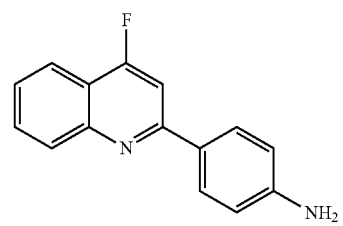

4-(4-Fluoroquinolin-2-yl)aniline T492 was prepared by using general procedure M from 4-(4-Nitroquinolin-2-yl)aniline (6 mg, 0.02 mmol) and KF (26 mg, 0.45 mmol), The crude product was purified by silica chromatography to afford 4-(4-fluoroquinolin-2-yl)aniline as a yellow solid (2 mg, 42%). ¹H NMR (400 MHz, CDCl₃): δ 8.11 (m, 1H), 8.03 (m, 1H), 8.00 (m, 2H), 7.72 (m, 1H), 7.51 (m, 1H), 7.48 (d, J=11.6 Hz, 1H), 6.80 (m, 2H), 3.93 (br s, 2H); MS (ESI): 239 (M+H⁺).
Preparation of

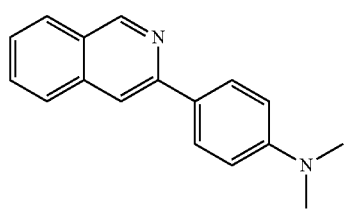 [SMILES: CN(C)c1ccc(-c2cc3ccccc3cn2)cc1]

4-(Isoquinolin-3-yl)-N,N-dimethylaniline T500 was by prepared using general procedure A from 3-chloroisoquinoline (41 mg, 0.25 mmol) and (4-(dimethylamino)phenyl)boronic acid (41 mg, 0.25 mmol). The product T500 was obtained as a white solid (11 mg, 17%). ¹H NMR (400 MHz, CDCl₃): δ 9.27 (s, 1H), 8.05 (m, 2H), 7.94 (s, 1H), 7.93 (d, J=6.8 Hz, 1H), 7.81 (d, J=8.4 Hz, 1H), 7.63 (m, 1H), 7.49 (m, 1H), 6.84 (m, 2H), 3.03 (s, 6H); MS (ESI): 249 (M+H⁺).
Preparation of

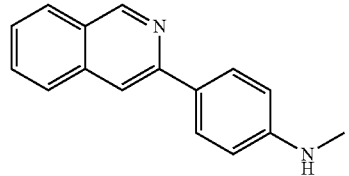 [SMILES: CNc1ccc(-c2cc3ccccc3cn2)cc1]

3-Chloroisoquinoline (33 mg, 0.2 mmol) and tert-butyl methyl(4-(4,4,5,5-tetramethyl-1,3,2-dioxaborolan-2-yl)phenyl)carbamate (66 mg, 0.2 mmol) were reacted using general procedure A to afford tert-butyl (4-(isoquinolin-3-yl)phenyl)(methyl)carbamate as a clear oil (12 mg, 18%). ¹H NMR (400 MHz, CDCl₃): δ 9.33 (s, 1H), 8.09 (m, 2H), 8.05 (s, 1H), 7.99 (m, 1H), 7.87 (m, 1H), 7.69 (m, 1H), 7.58 (m, 1H), 7.38 (m, 2H), 3.32 (s, 3H), 1.48 (s, 9H); MS (ESI): 335 (M+H⁺).
4-(Isoquinolin-3-yl)-N-methylaniline T501 was prepared using general procedure K. The reaction was performed on a 12 mg scale of tert-Butyl (4-(isoquinolin-3-yl)phenyl)(methyl). T501 was isolated as a off-white solid (7 mg, 72%). ¹H NMR (400 MHz, CDCl₃): δ 9.71 (s, 1H), 8.68 (s, 1H), 8.47 (d, J=8.4 Hz, 1H), 8.29 9d, J=8.0 Hz, 1H), 8.19 (m, 1H), 8.01-7.95 (m, 3H), 7.34 9d, J=8.8 Hz, 2H), 3.02 (s, 3H); MS (ESI): 235 (M+H⁺).
Preparation of

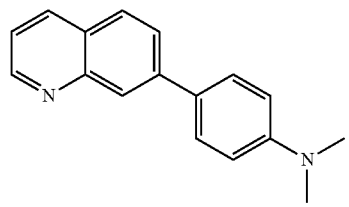 [SMILES: CN(C)c1ccc(-c2ccc3cccnc3c2)cc1]

N,N-Dimethyl-4-(quinolin-7-yl)aniline T504 was prepared using general procedure A from 7-bromoquinoline (52 mg, 0.25 mmol) and (4-(dimethylamino)phenyl)boronic acid (41 mg, 0.25 mmol). The product T504 was obtained as a yellow solid (52 mg, 83%). ¹H NMR (400 MHz, CDCl₃): δ 8.89 (dd, J=4.4, 1.6 Hz, 1H), 8.28 (m, 1H), 8.12 (dq, J=8.4, 0.8 Hz, 1H), 7.81 (d, J=1.2 Hz, 2H), 7.68 (m, 2H), 7.33 (dd, J=8.4, 4.4 Hz, 1H), 6.84 (m, 2H), 3.00 (s, 3H); MS (ESI): 249 (M+H⁺).
Preparation of

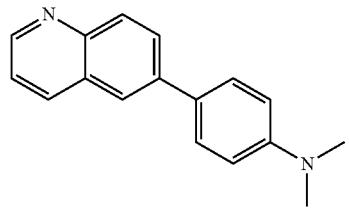 [SMILES: CN(C)c1ccc(-c2ccc3ncccc3c2)cc1]

N,N-Dimethyl-4-(quinolin-6-yl)aniline T505 was prepared using general procedure A from 6-bromoquinoline (52 mg, 0.25 mmol) and (4-(dimethylamino)phenyl)boronic acid (41 mg, 0.25 mmol). The product T505 was obtained as a yellow solid (42 mg, 67%). $^1$H NMR (400 MHz, CDCl$_3$): δ 8.85 (dd, J=4.4, 1.6 Hz, 1H), 8.15 (m. 2H), 7.97 (dd, J=8.4, 1.6 Hz, 1H), 7.92 (d, J=2.0 Hz, 1H), 7.63 (m, 2H), 7.38 (dd, J=8.4, 4.4 Hz, 1H), 6.84 (m, 2H), 3.01 (s, 6H); MS (ESI): 249 (M+H$^+$).

Preparation of

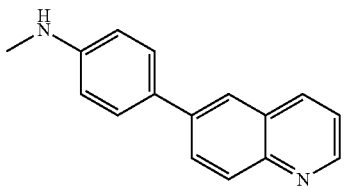 [SMILES: CNc1ccc(-c2ccc3ncccc3c2)cc1]

N-Methyl-4-(quinolin-6-yl)aniline T514 was prepared using general procedure A from 6-bromoquinoline (41 mg, 0.2 mmol) and N-methyl-4-(4,4,5,5-tetramethyl-1,3,2-dioxaborolan-2-yl)aniline (46 mg, 0.2 mmol). The product T514 was obtained as a black solid (20 mg, 43%). $^1$H NMR (400 MHz, CDCl$_3$): δ 8.86 (dd, J=4.4, 1.6 Hz, 1H), 8.18 9m, 1H), 8.13 (d, J=9.2 Hz, 1H), 7.96 (dd, J=8.8, 2.4 Hz, 1H), 7.92 (d, J=2.0 Hz, 1H), 7.59 (m, 2H), 7.40 (dd, J=8.4, 4.4 Hz, 1H), 6.74 (m, 2H), 2.91 (s, 3H); MS (ESI): 235 (M+H$^+$).

Preparation of

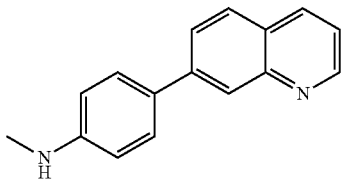 [SMILES: CNc1ccc(-c2ccc3cccnc3c2)cc1]

N-Methyl-4-(quinolin-7-yl)aniline T515 was prepared using general procedure A from 7-bromoquinoline (41 mg, 0.2 mmol) and N-methyl-4-(4,4,5,5-tetramethyl-1,3,2-dioxaborolan-2-yl)aniline (46 mg, 0.2 mmol). T515 was obtained as a yellow wax (18 mg, 38%). $^1$H NMR (400 MHz, CDCl$_3$): δ 8.90 (dd, J=4.0, 1.2 Hz, 1H), 8.26 (m, 1H), 8.13 (m, 1H), 7.82-7.81 (m, 2H), 7.64 (m, 2H), 7.34 (dd, J=8.4, 4.4 Hz, 1H), 6.73 (m, 2H), 2.90 (s, 3H); MS (ESI): 235 (M+H$^+$).

Preparation of

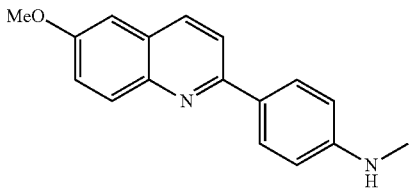 [SMILES: CNc1ccc(-c2ccc3cc(OC)ccc3n2)cc1]

4-(6-Methoxyquinolin-2-yl)-N-methylaniline T523 was prepared using general procedure A from 2-chloro-6-methoxyquinoline (39 mg, 0.2 mmol) and N-methyl-4-(4,4,5,5-tetramethyl-1,3,2-dioxaborolan-2-yl)aniline (46 mg, 0.2 mmol). T523 was obtained as a brown solid (27 mg, 51%). NMR (400 MHz, CDCl$_3$): δ 8.03-7.99 (m, 4H), 7.75 (d, J=8.4 Hz, 1H), 7.33 (dd, J=9.2, 2.8 Hz, 1H), 7.04 (d, J=2.8 Hz, 1H), 6.71 (m, 2H), 3.92 (s, 3H), 2.89 (s, 3H); MS (ESI): 235 (M+H$^+$).

Preparation of

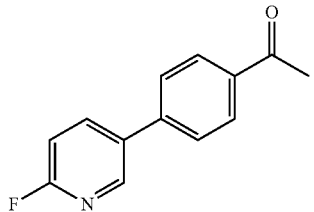 [SMILES: CC(=O)c1ccc(-c2ccc(F)nc2)cc1]

1-(4-(6-Fluoropyridin-3-yl)phenyl)ethanone T405 was prepared using general procedure A from 1-(4-bromophenyl)ethanone (117 mg, 0.5 mmol) and 2-fluoro-5-(4,4,5,5-tetramethyl-1,3,2-dioxaborolan-2-yl)pyridine (100 mg, 0.5 mmol). T405 was obtained as a yellow solid (64 mg, 59%). $^1$H NMR (400 MHz, CDCl$_3$): δ 8.47 (m, 1H), 8.06 9m, 2H), 8.04-7.99 (m, 1H), 7.65 (m, 2H), 7.05 (ddd, J=8.4, 3.2, 0.8 Hz, 1H), 2.65 (s, 3H); MS (ESI): 216 (M+H$^+$).

Preparation of 5-((1-(2-Fluoroethyl)-1H-benzo[d]imidazol-2-yl)ethynyl)pyridin-2-amine (T568)

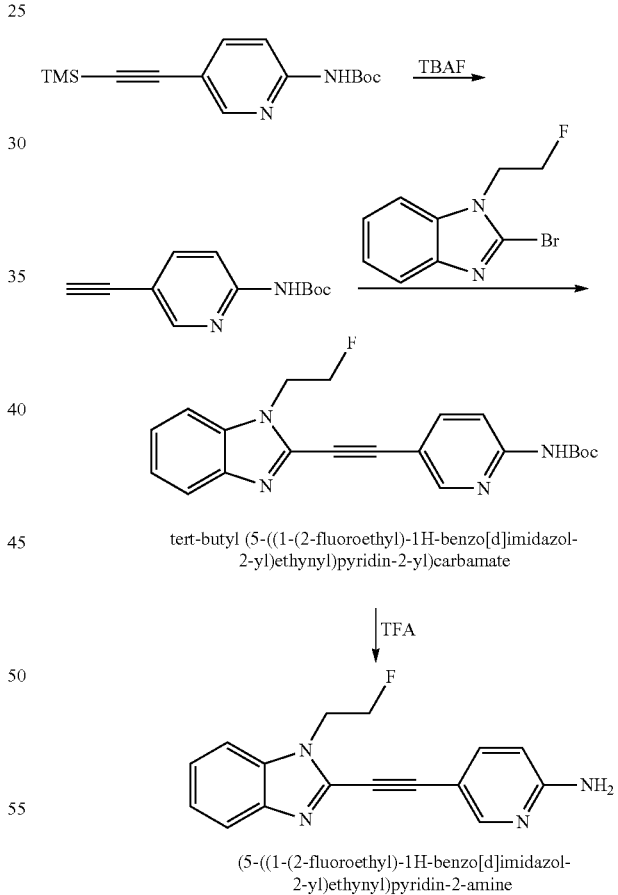

tert-Butyl (5-ethynylpyridine-2-yl)carbamate was prepared from tert-butyl (5-((trimethylsilyl)ethynyl)pyridin-2-yl)carbamate (200 mg, 0.69 mmol) using general procedure J. The product was obtained as a white solid (98 mg, 65%). $^1$H NMR (300 MHz, CDCl$_3$): δ 8.44 (dd, J=2.0, 0.8 Hz, 1H), 7.69 (dd, J=8.4, 2.4 Hz, 1H), 7.33 (dd, J=8.4, 0.8 Hz, 1H), 6.09 (s, 1H), 3.17 (s, 1H), 1.26 (s, 9H).

tert-Butyl (5-ethynylpyridin-2-yl)carbamate (22 mg, 0.1 mmol) and 2-bromo-1-(2-fluoroethyl)-1H-benzo[d]imidazole (24.3 mg, 0.1 mmol) was reacted using general procedure B to afford tert-butyl (5-((1-(2-fluoroethyl)-1H-benzo[d]imidazol-2-yl)ethynyl)pyridin-2-yl)carbamate (12 mg, 31%). $^1$H NMR (300 MHz, CDCl$_3$): 8.51 (d, J=1.6 Hz, 1H), 8.47 (m, 1H), 7.88 (dd, J=8.8, 2.4 Hz, 7.40-7.34 (m, 3H), 7.31 (d, J=12.8 Hz, 6.22 (s, 1H), 4.80 (t, J=4.8 Hz, 1H), 4.68 (t, J=4.8 Hz, 1H), 4.53 (m, 1H), 4.47 (m, 1H), 1.55 (s, 9H).

5-((1-(2-Fluoroethyl)-1H-benzo[d]imidazol-2-yl)ethynyl)pyridin-2-amine was prepared using general procedure P from tert-butyl (5-((1-(2-fluoroethyl)-1H-benzo[d]imidazol-2-yl)ethynyl)pyridin-2-yl)carbamate (10 mg, 0.026 mmol). The product T568 was obtained as a yellow solid (0.5 mg, 5%). $^1$H NMR (300 MHz, MeOH-d4): δ 8.32 (br s, 1H), 8.01 (dd, J=9.2, 1.6 Hz, 1H), 7.71-7.66 (m, 2H), 7.45 (t, J=7.2 Hz, 1H), 7.412 (m, 1H), 6.98 (d, J=9.2 Hz, 1H), 4.89-4.76 (m, 4H); MS (ESI): 281 (M+H$^+$).

Preparation of

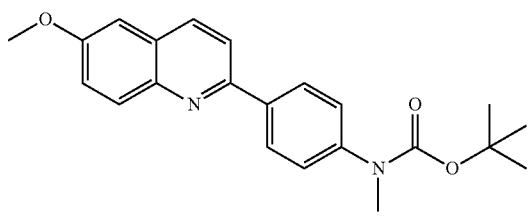 [SMILES: COc1ccc2nc(-c3ccc(N(C)C(=O)OC(C)(C)C)cc3)ccc2c1]

tert-Butyl-4-(6-methoxyquinolin-2-yl)phenyl)(N-methyl) carbamate T406 was prepared using general procedure A. Reaction was performed on a 0.1 g scale. T406 was isolated as off white solid (0.118 g, 62%). $^1$H NMR (400 MHz, CDCl$_3$): δ 8.10-8.07 (m, 4H), 7.80 (d, J=8.4 Hz, 1H), 7.36 (dt, J=8.4, 2.0 Hz, 3H), 7.07 (d, J=2.8 Hz, 1H), 3.93 (s, 3H), 3.30 (s, 3H), 1.46 (s, 9H), 2.56 (br s, 2H); MS (ESI): 365.2 (M+H$^+$):

Preparation of

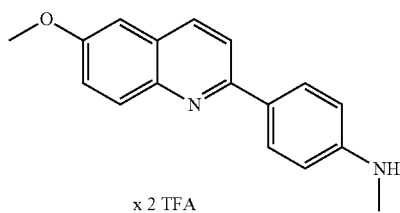

4-(6-Methoxyquinolin-2-yl)-N-methylaniline bis TFA salt T407 was prepared using general procedure P. Reaction was performed on a 0.045 g scale. The crude mixture was purified by HPLC (Acetnitrile: H$_2$O: 0.05% TFA) system. T407 was isolated as an orange solid (0.018 g, 33%). $^1$H NMR (400 MHz, CD$_3$OD): δ 8.72 (d, J=9.2 Hz, 1H), 8.17 (d, J=9.2 Hz, 1H), 8.10 (d, J=9.2 Hz, 1H), 7.95 (dt, J=9.2, 2.8 Hz, 2H), 7.64 (dd, J=9.2, 2.8 Hz, 1H), 7.56 (d, J=2.8 Hz, 1H), 6.81 (dt, J=9.2, 2.8 Hz, 2H), 3.98 (s, 3H), 2.89 (s, 3H); MS (ESI): 265.1 (M+H$^+$).

Preparation of

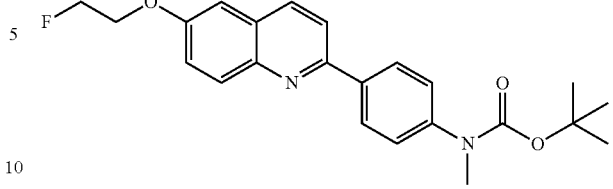

tert-Butyl 4-(6-fluoroethoxy)quinolin-2-yl)-N-methylaniline carbamate T408 was prepared using general procedure A and general procedure C sequentially. Reaction was performed on a 0.042 g scale. T408 was isolated as an off white solid (0.070 g, 76%, in two steps). $^1$H NMR (400 MHz, CDCl$_3$): δ 8.10-8.08 (m, 4H), 7.80 (d, J=8.8 Hz, 1H), 7.40 (dd, J=9.2, 2.8 Hz, 1H), 7.37 (br d, J=8.8 Hz, 2H), 7.08 (d, J=2.4 Hz, 1H), 4.88 (t, J=4.0 Hz, 1H), 4.76 (t, J=4.0 Hz, 1H), 4.37 (t, J=4.4 Hz, 1H), 4.30 (t, J=4.4 Hz, 1H), 3.30 (s, 3H), 1.46 (s, 9H); MS (ESI): 397.2 (M+H$^+$).

Preparation of

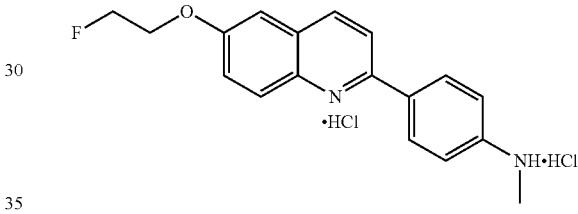

4-(6-Fluoroethoxy)quinolin-2-yl)-N-methylaniline dihydrochloride T409 was prepared using general procedure K. Reaction was performed on a 0.045 g scale. T409 was isolated as an orange solid (0.035 g, 83%). $^1$H NMR (400 MHz, CD$_3$OD): δ 8.74 (d, J=8.4 Hz, 1H), 8.18 (dd, J=15.2, 9.2 Hz, 2H), 7.98 (d, J=7.2 Hz, 2H), 7.71 (br d, J=9.2 Hz, 1H), 7.61 (br s, 1H), 6.88 (dt, J=9.2, 2.8 Hz, 2H), 4.84 (t, J=4.0 Hz, 1H), 4.74 (t, J=4.0 Hz, 1H), 4.46 and 4.39 (t, J=4.0 Hz, 1H), 2.91 (s, 3H); MS (ESI): 297.1 (M+H$^+$).

Preparation of

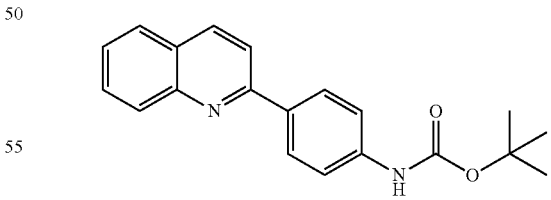

tert-Butyl (4-(quinolin-2-yl)phenyl)carbamate T410 was prepared using general procedure A. Reaction was performed on a 0.164 g scale. T410 was isolated as an off white solid (0.203 g, 64%). $^1$H NMR (400 MHz, CDCl$_3$): δ 8.16 (t, J=8.0 Hz, 2H), 8.12 (dt, J=8.8, 2.4 Hz, 2H), 7.83 (d, J=8.4 Hz, 1H), 7.79 (dd, J=8.0, 1.2 Hz, 1H), 7.69 (ddd, J=8.4, 7.2, 1.6 Hz, 1H), 7.55-7.47 (m, 3H), 6.63 (br s, 1H), 1.53 (s, 9H); MS (ESI): 321.1 (M+H$^+$).

Preparation of

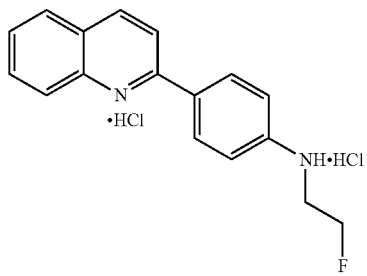

N-(2-Fluoroethyl)-4-(quinolin-2-yl)aniline dihydrochloride T411 was prepared using general procedure A and general procedure D sequentially. Reaction was performed on a 0.036 g scale. T411 was isolated as an orange solid (0.018 g, 48%, in two steps). $^1$H NMR (400 MHz, CD$_3$OD): δ 9.11 (br s, 1H), 8.72 (d, J=8.8 Hz, 1H), 8.38 (dt, J=9.2, 2.8 Hz, 1H), 8.10 (d, J=8.8 Hz, 2H), 8.007 (td, J=8.8, 1.6 Hz, 1H), 7.78 (td, J=8.8, 1.6 Hz, 1H), 6.83 (dt, J=9.2, 2.8 Hz, 2H), 4.68 (t, J=4.8 Hz, 1H), 4.56 (t, J=4.8 Hz, 1H), 3.57 (q, J=4.8 Hz, 1H), 3.51 (q, J=4.8 Hz, 1H); MS (ESI): 267.1 (M+H$^+$).

Preparation of

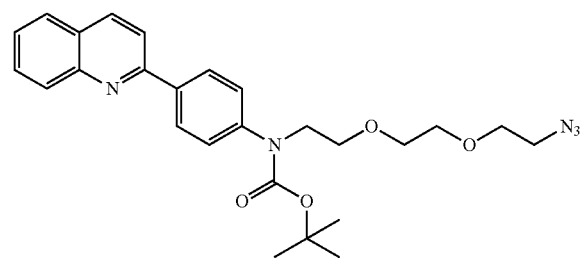 [SMILES: CC(C)(C)OC(=O)N(CCOCCOCCN=[N+]=[N-])c1ccc(-c2ccc3ccccc3n2)cc1]

tert-butyl-(2-(2-(2-azidoethoxy)ethoxy)ethyl)(4-(quinolin-2-yl)phenyl-carbamate (AS-5306-190 Boc) was prepared using general procedure D. Reaction was performed on 0.020 g scale. AS-5332-190 Boc was isolated as an off semi solid (0.020, 70%). $^1$H NMR (400 MHz, CDCl$_3$): δ 8.21 (br d, J=8.8 Hz, 2H), 8.11 (dt, J=8.8, 2.0 Hz, 2H), 7.85 (d, J=8.4 Hz, 1H), 7.81 (dd, J=9.2, 1.6 Hz, 1H), 7.71 (ddd, J=8.4, 7.2, 1.2 Hz, 1H), 7.51 (ddd, J=8.4, 7.2, 1.2 Hz, 1H), 7.40 (br d, J=8.4 Hz, 2H), 3.86 (t, J=6.0 Hz, 2H), 165 (t, J=6.0 Hz, 2H), 3.62-3.59 (m, 6H), 3.34 (t, J=5.2 Hz, 2H), 1.44 (s, 9H); MS (ESI): 478.1 (M+H$^+$).

Preparation of

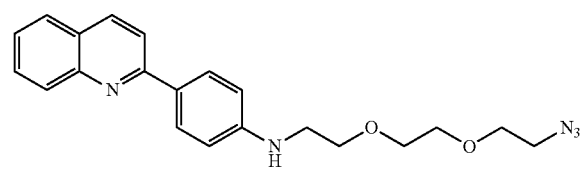 [SMILES: [N-]=[N+]=NCCOCCOCCNc1ccc(-c2ccc3ccccc3n2)cc1]

N-(2-(2-(2-azidoethoxy)ethoxy)ethyl)(4-(quinolin-2-yl)aniline T412 was prepared using general procedure K. Reaction was performed on a 0.020 g scale. The crude product was neutralized with NaHCO$_3$ and purified. T412 was isolated as yellow oil (0.010 g, 63%). $^1$H NMR (400 MHz, CDCl$_3$): δ 8.26-8.14 (m, 4H), 7.88-7.72 (m, 3H), 7.57-7.48 (m, 1H), 7.45 (d, J=8.0 Hz, 1H), 6.75 (d, J=8.8 Hz, 2H), 3.74 (t, J=4.8 Hz, 2H), 3.70-3.60 (m, 6H), 3.39 (t, J=5.2 Hz, 4H); MS (ESI): 378.1 (M+H$^+$).

Preparation of

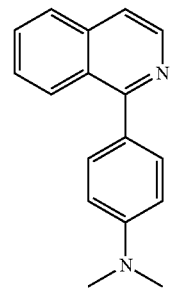

4-(Isoquinolin-1-yl)-N,N-dimethylaniline T420 was prepared using general procedure A. Reaction was performed on a 0.105 g scale. T420 was isolated as off white solid (0.115 g, 72%). $^1$H NMR (400 MHz, CDCl$_3$): δ 8.55 (d, J=5.6 Hz, 1H), 8.25 (d, J=8.8 Hz, 1H), 7.85 (d, J=7.6 Hz, 1H), 7.69 (t, J=7.6 Hz, 1H), 7.66 (dt, J=8.8, 2.0 Hz, 2H), 7.53 (d, J=6.0 Hz, 1H), 7.54 (t, J=7.6 Hz, 1H), 6.86 (dt, J=8.8, 2.0 Hz, 2H), 3.05 (s, 6H); MS (ESI): 249.1 (M+H$^+$).

Preparation of

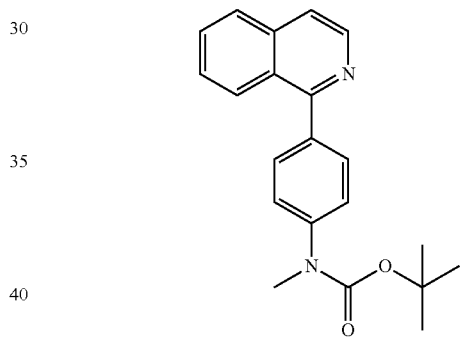

tert-Butyl (4-(isoquinolin-1-yl)phenyl)-N-methyl)carbamate T426 was prepared using general procedure A. Reaction was performed on a 0.082 g scale. T426 was isolated as a colorless oil (0.0.78 g, 46%). $^1$H NMR (400 MHz, CDCl$_3$): δ 8.56 (dd, J=6.8, 0.8 Hz, 1H), 8.10 (d, J=8.4 Hz, 1H), 7.84 (d, J=8.4 Hz, 1H), 7.67-7.64 (m, 3H), 7.60 (d, J=5.6 Hz, 1H), 7.50 (td, J=8.4, 1.6 Hz, 1H), 7.39 (br d, J=8.8 Hz, 2H), 3.31 (s, 3H), 1.47 (s, 9H); MS (ESI): 335.1 (M+H$^+$).

Preparation of

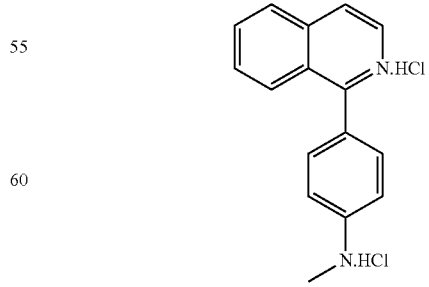

4-(Isoquinolin-1-yl)phenyl)-N-methylaniline dihydrochloride T427 was prepared using general procedure K.

Reaction was performed on a 0.048 g scale. T427 was isolated as yellow solid (0.038 g, 72%). $^1$H NMR (400 MHz, CD$_3$CN): δ 8.42 (d, J=7.6 Hz, 1H), 8.35 (d, J=6.4 Hz, 1H), 8.24 (d, J=8.0 Hz, 1H), 8.18 (d, J=7.2 Hz, 1H), 8.14 (ddd, J=8.4, 7.2, 1.2 Hz, 1H), 7.94 (ddd, J=8.4, 7.2, 1.2 Hz, 1H), 7.72 (dt, J=8.8, 2.0 Hz, 2H), 7.08 (d, J=8.8 Hz, 2H), 2.93 (s, 3H); MS (ESI): 235.1 (M+H$^+$).

Preparation of

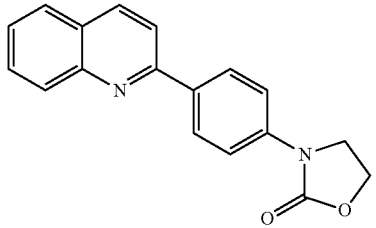 [SMILES: O=C1OCCN1c1ccc(-c2ccc3ccccc3n2)cc1]

3(4-(Quinolin-2-yl)phenyl)oxazolidin-2-one T428 was isolated as a by-product during N-alkylation of T-410 using NaH as the base (0.010 g, 33%); $^1$H NMR (400 MHz, CDCl$_3$): δ 8.20 (dt, J=9.2, 2.4 Hz, 2H), 8.15 (d, J=8.4 Hz, 2H), 7.86 (d, J=8.4 Hz, 1H), 7.81 (dd, J=9.2, 1.2 Hz, 1H), 7.71 (ddd, J=8.4, 7.2, 1.2 Hz, 1H), 7.70 (dt, J=9.2, 2.4 Hz, 2H), 7.51 (ddd, J=8.4, 7.2, 1.2 Hz, 1H), 4.52 (t, J=8.0 Hz, 2H), 4.14 (t, J=8.0 Hz, 2H); MS (ESI): 291.1 (M+H$^+$).

Preparation of

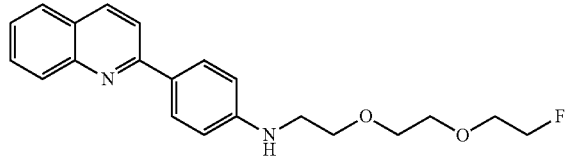 [SMILES: FCCOCCOCCNc1ccc(-c2ccc3ccccc3n2)cc1]

N-(2-(2-(2-Fluoroethoxy)ethoxy)ethyl-4-(quinolin-2-yl) aniline T442 was prepared using general procedure D. Reaction performed on a 0.031 g scale. T442 was isolated as a yellow oil (0.015 g, 42%). $^1$H NMR (400 MHz, CDCl$_3$): δ 8.12 (d, J=8.0 Hz, 2H), 8.05 (dd, J=8.0 Hz, 2H), 7.79 (d, J=8.0 Hz, 1H), 7.76 (d, J=8.0 Hz, 1H), 7.66 (dt, J=8.4, 1.6 Hz, 1H), 7.45 (dt, J=8.4, 1.6 Hz, 1H), 6.75-6.72 (m, 3H), 4.64 (m, 1H), 4.52 (m, 1H), 4.38 (br s, 1H), 3.80-3.67 (m, 8H), 3.38 (m, 2H), MS (ESI): 355.2 (M+H$^+$).

Preparation of

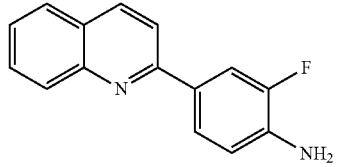 [SMILES: Nc1ccc(-c2ccc3ccccc3n2)cc1F]

2-Fluoro-4-(quinolin-2-yl) aniline T445 was prepared using general procedure A. Reaction was performed on a 0.090 g scale. T445 was isolated as white solid (0.120 g, 91%). $^1$H NMR (400 MHz, CDCl$_3$): δ 8.17 (d, J=8.8 Hz, 2H), 7.92 (dd, J=12.8, 2.0 Hz, 1H), 7.82-7.62 (m, 3H), 7.70 (t, J=8.0 Hz, 1H), 7.49 (t, J=8.0 Hz, 1H), 6.88 (t. J=8.0 Hz, 1H), 3.95 (br s, 2H); MS (ESI): 239.1 (M+H$^+$).

Preparation of

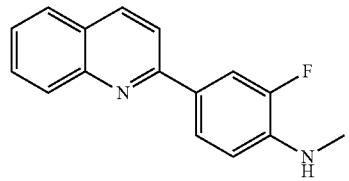 [SMILES: CNc1ccc(-c2ccc3ccccc3n2)cc1F]

A mixture of T445 (0.024 g, 0.95 mmol) and paraformaldehyde (0.06 g, 2.0 eq) in DCE-AcOH (10:1, 5 ml) was stirred at room temperature for 2 hrs, and then Sodium triacetoxyborohydride (0.061 g, 3.0 eq) was added. The resulting mixture was stirred overnight. After the reaction was complete, the solvents were removed in vacuo and product was purified on a Combiflash purification system (silica gel, 0-10% EtOAc:DCM). T458 was isolated as off white semi solid (0.005 g, 20%). $^1$H NMR (400 MHz, CDCl$_3$): δ 8.14 (dt, J=8.4, 5.6 Hz, 2H), 7.93 (dd, J=13.6, 2.0 Hz, 1H), 7.87 (d, J=8.0 Hz, 1H), 7.78 (d, J=8.4 Hz, 1H), 7.77 (ddd, J=8.4, 6.8, 1.2 Hz, 1H), 7.68 (ddd, J=8.4, 6.8, 1.2 Hz, 1H), 6.77 (t, J=8.8 Hz, 1H), 2.95 (s, 3H); MS (ESI): 253.1 [M+H$^+$].

Preparation of

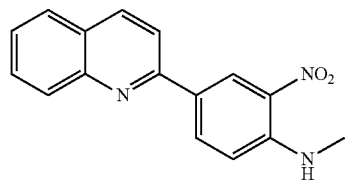 [SMILES: CNc1ccc(-c2ccc3ccccc3n2)cc1[N+](=O)[O-]]

N-Methyl-2-nitro-4-(quinolin-2-yl)aniline T463 was prepared using general procedure A. Reaction was performed on a 0.045 g scale. T463 was isolated as yellow solid (0.068 g, 88%). $^1$H NMR (400 MHz, CDCl$_3$): δ 8.97 (d, J=2.4 Hz, 1H), 8.49 (dd, J=9.2, 2.0 Hz, 1H), 8.25 (br s, 1H), 8.19 (d, J=8.4 Hz, 1H), 8.12 (d, J=8.0 Hz, 1H), 7.86 (d, J=8.8 Hz, 2H), 7.80 (dd, J=9.6, 1.2 Hz, 1H), 7.71 (ddd, J=8.8, 6.8, 1.6 Hz, 1H), 7.50 (ddd, J=8.8, 6.8, 1.6 Hz, 1H), 7.00 (d, J=9.2 Hz, 1H), 3.10 (d, J=5.2 Hz, 3H); MS (ESI): 280.1 (M+H$^+$).

Preparation of

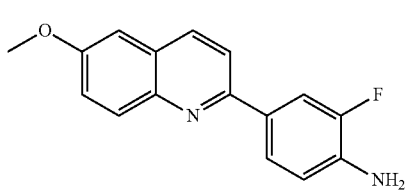 [SMILES: COc1ccc2nc(-c3ccc(N)c(F)c3)ccc2c1]

2-Fluoro-4-(6-methoxyquinolin-2-yl)aniline T467 was prepared using general procedure A. Reaction was performed on a 0.1 g scale. T467 was isolated as off white solid (0.112 g, 81%). $^1$H NMR (400 MHz, CDCl$_3$): δ 8.08 (br d, J=8.8 Hz, 2H), 7.87 (dd, J=12.4, 2.0 Hz, 1H), 7.77 (br d, J=7.6 Hz, 1H), 7.73 (d, J=8.8 Hz, 1H), 7.36 (dd, J=9.2, 2.8 Hz, 1H), 7.06 (d, J=2.4 Hz, 1H), 6.87 (t, J=8.4 Hz, 1H), 3.32 (s, 3H); MS (ESI): 269.0 (M+H$^+$).

Preparation of

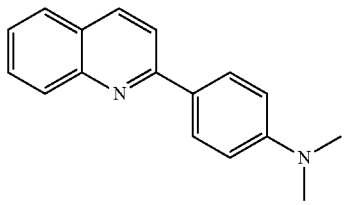

N—N-Dimethyl-4-(quinolin-2-yl)aniline T476 was prepared using general procedure A. Reaction was performed on a 0.092 g scale. T-467 was isolated as yellow solid (0.120 g, 86%). ¹H NMR (400 MHz, CDCl₃): δ 8.11 (br t, J=7.6 Hz, 4H), 7.81 (d, J=8.8 Hz, 1H), 7.75 (dd, J=9.6, 1.6 Hz, 1H), 7.66 (ddd, J=9.2, 6.8, 1.6 Hz, 1H), 7.44 (ddd, J=9.2, 6.8, 1.6 Hz, 1H), 6.82 (dt, J=9.2, 2.8 Hz, 1H), 3.94 (s, 6H); MS (ESI): 249.1 (M+H⁺).

Preparation of

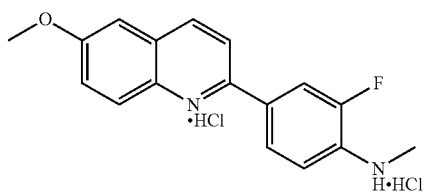

2-Fluoro-4-(6-methoxyquinolin-2-yl)-N-methylaniline dihydrochloride T483 was prepared using general procedure D and general procedure K sequentially. Reaction was performed on a 0.030 g scale. T483 was isolated as an orange color solid (0.025 g, 86% in two steps). ¹H NMR (400 MHz, CDCl₃): δ 9.07 (d, J=9.2 Hz, 1H), 8.65 (d, J=8.8 Hz, 1H), 8.21 (dd, J=13.6, 2.4 Hz, 1H), 8.09 (dd, J=8.4, 2.4 Hz, 1H), 8.05 (d, J=9.2 Hz, 1H), 7.64 (dd, J=9.6, 2.8 Hz, 1H), 7.49 (d, J=2.8 Hz, 1H), 6.85 (t, J=8.8 Hz, 1H), 3.98 (s, 3H), 2.91 (s, 3H); MS (ESI): 283.1 (M+H⁺).

Preparation of

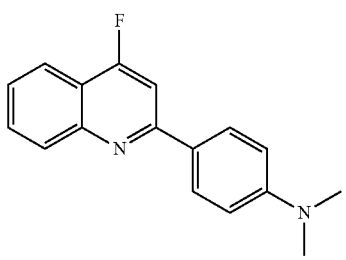 [SMILES: CN(C)c1ccc(-c2cc(F)c3ccccc3n2)cc1]

4-(4-Fluoroquinolin-2-yl)-N—N-dimethylaniline T484 was prepared using general procedure L. Reaction was performed on a 0.030 g scale. T484 was isolated as a light yellow color solid (0.012 g, 44%), ¹H NMR (400 MHz, CDCl₃): δ 8.11 (d, J=8.4 Hz, 1H), 8.04 (dt, J=9.2, 2.8 Hz, 2H), 8.01 (dd, J=8.8, 0.8 Hz, 1H), 7.70 (td, J=8.4, 1.2 Hz, 1H), 7.50-7.46 (m, 2H), 6.80 (dt, J=9.2, 2.8 Hz, 2H), 3.04 (s, 6H); MS (ESI): 267.1 (M+H⁺).

Preparation of

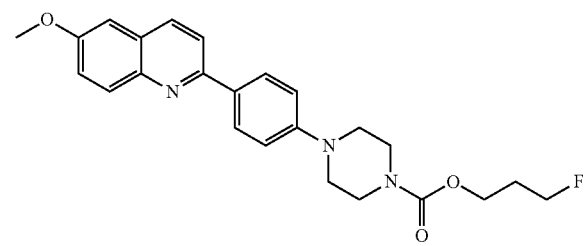 [SMILES: COc1ccc2nc(-c3ccc(N4CCN(C(=O)OCCCF)CC4)cc3)ccc2c1]

3-Fluoroprpyl 4-(4-(6-methoxyquinolin-2-yl)phenyl)piperazine-1-carboxylate T498 was prepared using general procedure E. Reaction performed on a 0.032 g scale. T498 was isolated as off white solid (0.030 g, 70%). ¹H NMR (400 MHz, CDCl₃): δ 8.07 (br t, J=8.0 Hz, 4H), 7.78 (d, J=8.8 Hz, 1H), 7.35 (dd, J=9.2, 2.8 Hz, 1H), 7.06 (d, J=2.8 Hz, 1H), 7.02 (dt, J=9.2, 2.8 Hz, 2H), 4.61 (t, J=6.0 Hz, 1H), 4.49 (t, J=6.0 Hz, 1H), 4.26 (t, J=6.0 Hz, 2H), 3.93 (s, 3H), 3.65 (t, J=4.8 Hz, 4H), 2.57 (t, J=4.8 Hz, 4H), 2.09 (quintet, J=6.0 Hz, 1H), 2.02 (quintet, J=6.0 Hz, 1H); MS (ESI): 224.1 (M+H⁺).

Preparation of

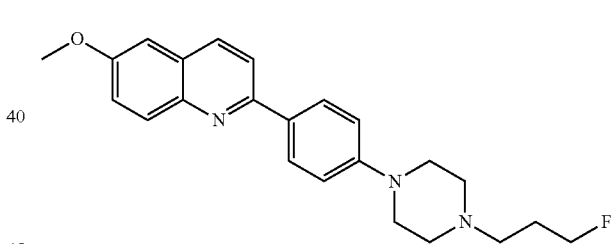

2-(4-(4-(3-Fluoropropyl)piperazin-1-yl)phenyl)-6-methoxyquinoline T499 was prepared using general procedure E. Reaction performed on a 0.032 g scale. T499 was isolated as off white solid (0.005 g, 13%). ¹H NMR (400 MHz, CDCl₃): δ 8.05 (dt, J=9.2, 2.8 Hz, 2H), 8.03 and 8.00 (d, J=7.6 and 9.2 Hz, 2H), 7.77 (d, J=8.8 Hz, 1H), 7.54 (dd, J=9.2, 3.2 Hz, 1H), 7.05 (d, J=2.8 Hz, 1H), 7.02 (dt, J=9.2, 2.8 Hz, 2H), 4.60 (t, J=6.0 Hz, 1H), 4.48 (t, J=6.0 Hz, 1H), 3.92 (s, 3H), 3.34 (br s, 4H), 2.68 (br s, 4H), 2.56 (br s, 2H), 1.97 (br d, J=24.8 Hz, 2H); MS (ESI): 380.2 (M+H⁺).

Preparation of

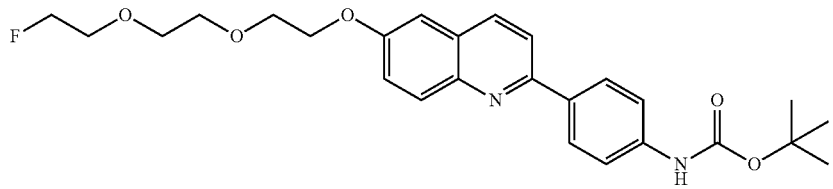 [SMILES: CC(C)(C)OC(=O)Nc1ccc(-c2ccc3cc(OCCOCCOCCF)ccc3n2)cc1]

tert-Butyl-(4-(6-(2-(2-(2-fluoroethoxy)ethoxy)ethoxy)quinoline-2-yl)-phenyl)-carbamate T509 was prepared using general procedure C and general procedure A sequentially. Reaction was performed on a 0.045 g scale T509 was isolated as off white solid (0.010 g, 8.4% in two steps). $^1$H NMR (400 MHz, CDCl$_3$): δ 8.05 (dt, J=8.0, 2.0 Hz, 2H), 8.04 (t, J=10.4 Hz, 2H), 7.78 (d, J=8.8 Hz, 1H), 7.49 (d, J=8.4 Hz, 1H), 7.38 (dd, J=9.2, 2.8 Hz, 1H), 7.07 (d, J=2.8 Hz, 1H), 6.59 (s, 1H), 4.61 (td, J=4.4, 0.4 Hz, 1H), 4.49 (td, J=4.4, 0.4 Hz, 1H), 4.26 (t, J=4.8 Hz, 2H), 3.93 (t, J=4.8 Hz, 2H), 3.80-3.76 (m, 3H), 3.74-3.70 (m, 3H), 1.53 (s, 9H); MS (ESI): 471.2 (M+H$^+$).

Preparation of

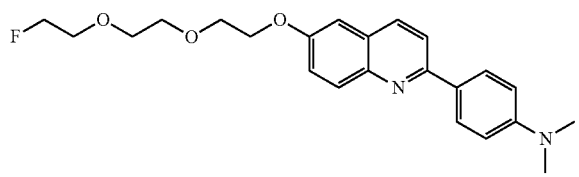 [SMILES: CN(C)c1ccc(-c2ccc3cc(OCCOCCOCCF)ccc3n2)cc1]

4-(6-(2-(2-(Fluoroethoxy)ethoxy)ethoxy)quinoline-2-yl)-N—N-dimethylaniline T510 was prepared using general procedure C and general procedure A sequentially. Reaction was performed on a 0.037 g scale. T510 was isolated as a light yellow color solid (0.006 g, 7.2% in two steps). $^1$H NMR (400 MHz, CDCl$_3$): δ 8.05 (d, J=8.0 Hz, 2H), 8.0 (d, J=8.0 Hz, 2H), 7.76 (d, J=8.8 Hz, 1H), 7.34 (dd, J=9.2, 2.8 Hz, 1H), 7.05 (d, J=2.4 Hz, 1H), 6.81 (m, 1H), 4.61 (m, 1H), 4.49 (m, 1H), 4.25 (t, J=4.4 Hz, 2H), 3.93 (t, J=4.4 Hz, 2H), 3.80-3.70 (m, 5H), 3.02 (s, 6H); MS (ESI): 399.2 (M+H$^+$).

Preparation of

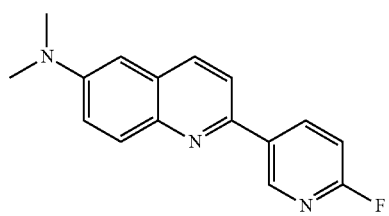 [SMILES: CN(C)c1ccc2nc(-c3ccc(F)nc3)ccc2c1]

2-(6-Fluoropyridin-3-yl)-N—N-dimethylquinolin-6-amine T513 was prepared using general procedure A. Reaction was performed on a 0.0.036 g scale. T513 was isolated as a yellow color solid (0.015 g, 54%). $^1$H NMR (400 MHz, CDCl$_3$): δ 8.86 (m, 1H), 8.57 (td, J=10.0, 2.4 Hz, 1H), 8.02 (d, J=8.8 Hz, 1H), 7.97 (d, J=9.6 Hz, 1H), 7.69 (d, J=8.8 Hz, 1H), 7.38 (dd, J=9.2, 2.8 Hz, 1H), 7.02 (dd, J=8.4, 0.8 Hz, 1H), 6.80 (d, J=2.8 Hz, 1H), 3.09 (s, 6H); MS (ESI): 268.1 [M+H$^+$].

Preparation of

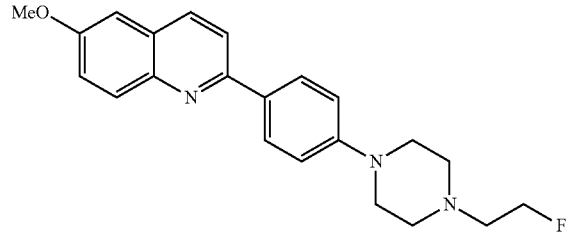 [SMILES: COc1ccc2nc(-c3ccc(N4CCN(CCF)CC4)cc3)ccc2c1]

2-(4-(4-(2-Fluoroethyl)piperazin-1-yl)-6-methoxyquinoline T519 was prepared using general procedure E. Reaction performed on a 0.050 g scale. T519 was isolated as a off white solid (0.010 g, 17.5%). $^1$H NMR (400 MHz, CDCl$_3$): δ 8.01 (dt, J=6.8, 2.0 Hz, 2H), 7.95 (d, J=10.4 Hz, 2H), 7.71 (d, J=8.4 Hz, 1H), 7.27 (dd, J=9.2, 2.4 Hz, 1H), 6.99 (d, J=2.4 Hz, 1H), 6.96 (dt, J=6.8, 2.0 Hz, 2H), 4.62 (t, J=4.0 Hz, 1H), 4.50 (t, J=4.0 Hz, 1H), 3.86 (s, 3H), 3.27 (t, J=5.2 Hz, 4H), 2.75 (t, J=5.2 Hz, 1H), 2.69-2.66 (m, 5H); MS (ESI): 366.1 (M+H$^+$).

Preparation of

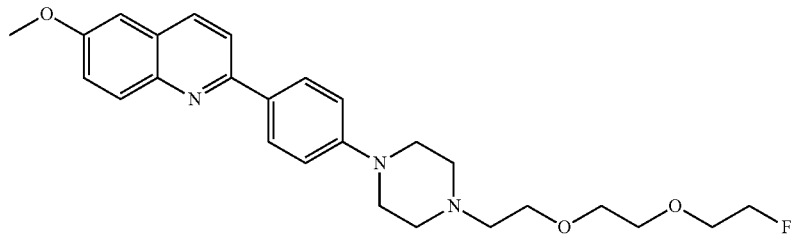 [SMILES: COc1ccc2nc(-c3ccc(N4CCN(CCOCCOCCF)CC4)cc3)ccc2c1]

2-(4-(4-(2-(2-Fluoroethoxy)ethyl)piperazin-1-yl)phenyl)-6-methoxyquinoline T530 was prepared using general procedure D. Reaction performed on a 0.032 g scale. T530 was isolated as off white semi solid (0.004 g, 9%). $^1$H NMR (400 MHz, CDCl$_3$): δ 8.04 (dt, J=8.0, 1.2 Hz, 2H), 8.01 (dd, J=10.4, 7.6 Hz, 2H), 7.77 (d, J=8.0 Hz, 1H), 7.32 (dd, J=9.2, 2.8 Hz, 1H), 7.05 (d, J=2.8 Hz, 1H), 7.01 (dt, J=8.0, 1.2 Hz, 2H), 4.62 (t, J=4.4 Hz, 1H), 4.50 (t, J=4.4 Hz, 1H), 3.92 (s, 3H), 3.78 (t, J=4.4 Hz, 1H), 3.72-3.64 (m, 4H), 3.19 (t, J=4.8 Hz, 2H), 2.70 (m, 3H); MS (ESI): 454.1 (M+H$^+$).

Preparation of

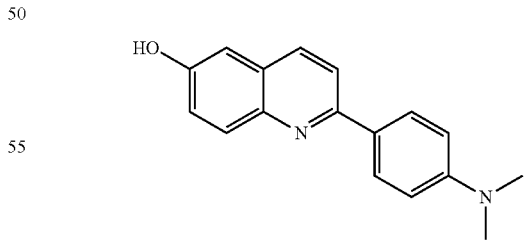

2-(4-Dimethylamino)phenyl)quinoline-6-ol T531 was prepared using general procedure A. Reaction was performed on a 0.0.236 g scale. T531 was isolated as a yellow solid (0.218 g, 53%). $^1$H NMR (400 MHz, CD$_3$CN): δ 8.08 (td, J=8.4, 2.0 Hz, 3H), 7.86 (dd, J=8.8, 5.2 Hz, 1H), 7.28 (ddd, J=8.8, 5.6, 2.8 Hz, 1H), 7.14 (d, J=2.8 Hz, 1H), 6.86 (dt, J=8.8, 2.0 Hz, 2H), 3.03 (s, 6H); MS (ESI): 365.1 (M+H$^+$).

Preparation of

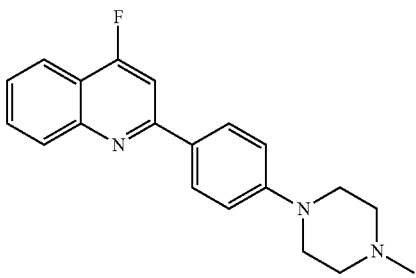 [SMILES: CN1CCN(c2ccc(-c3cc(F)c4ccccc4n3)cc2)CC1]

4-Fluoro-2-(4-(4-methylpiperazin-1-yl)phenylquinoline T559 was prepared using general procedure L. Reaction was performed on a 0.005 g scale. T559 was isolated as light yellow solid (0.004 g, 89%). $^1$H NMR (400 MHz, CDCl$_3$): δ 8.06-7.96 (m, 4H), 7.66 (td, J=8.4, 1.6 Hz, 1H), 7.44 (td, J=8.4, 1.6 Hz, 1H), 7.43 (d, J=11.2 Hz, 1H), 6.96 (dt, J=9.2, 2.4 Hz, 2H), 3.28 (t, J=4.8 Hz, 4H), 2.54 (t, J=4.8 Hz, 4H), 2.31 (s, 3H); MS (ESI): 322.1 (M+H$^+$).

Preparation of

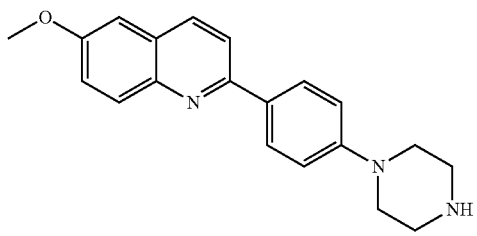 [SMILES: COc1ccc2nc(-c3ccc(N4CCNCC4)cc3)ccc2c1]

6-Methoxy-2-(4-(piperazine-1-yl)phenyl) quinoline AS-5332-52 was prepared using general procedure A. Reaction was performed on a 0.194 g scale. AS-5332-52 was isolated as a off white solid (0.269 g, 84%). $^1$H NMR (400 MHz, CDCl$_3$): δ 8.01 (dt, J=8.0, 4.0 Hz, 2H), 7.98 (d, J=9.2 Hz, 1H), 7.95 (d, J=9.2 Hz, 1H), 7.72 (d, J=8.8 Hz, 1H), 7.27 (dd, J=8.0, 4.0 Hz, 1H), 7.01-6.96 (m, 3H), 3.87 (s, 2H), 3.24 (td, J=5.2, 2.8 Hz, 4H), 3.06 (td, J=5.2, 2.8 Hz, 4H); MS (ESI): 320.1 (M+H$^+$).

Preparation of

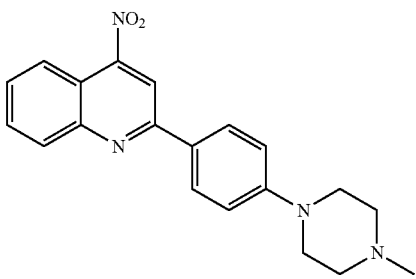 [SMILES: CN1CCN(c2ccc(-c3cc([N+](=O)[O-])c4ccccc4n3)cc2)CC1]

2-(4-(4-Methylpiperazin-1-yl)phenyl)-4-nitroquinoline AS-5332-80 was prepared using general procedure A. Reaction was performed on a 0.06 g scale. AS-5332-80 was isolated as red color solid (0.062 g, 75%). NMR (400 MHz, CDCl$_3$): δ 8.35 (dd, J=9.2, 0.4 Hz, 2H), 8.25 (dd, J=9.2, 0.4 Hz, 1H), 8.13 (dt, J=9.2, 2.0 Hz, 2H), 7.80 (td, J=8.0, 1.2 Hz, 1H), 7.64 (td, J=8.0, 1.2 Hz, 1H), 7.03 (dt, J=8.8, 2.0 Hz, 2H), 3.36 (t, J=6.4 Hz, 4H), 2.59 (t, J=6.4 Hz, 4H), 2.36 (s, 3H); MS (ESI): 349 (M+H$^+$).

Preparation of

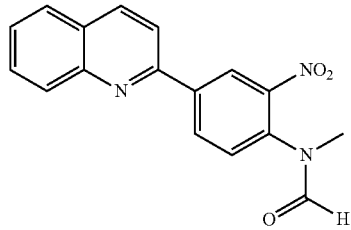 [SMILES: CN(C=O)c1ccc(-c2ccc3ccccc3n2)cc1[N+](=O)[O-]]

N-methyl-N-(2-nitro-4-(quinolin-2-yl)phenyl)formamide AS-5332-30. A mixture of acetic anhydride (0.600 g, 22 equiv.) and HCO$_2$H (0.252 g, 22 equiv.) was heated at 60° C. for 15 min. To this mixture was added a solution of T463 (0.078 g) in DCM (5 mL). The resulting mixture was heated at 80° C. for 2 days. The volatiles were removed in vacuo. The crude product was purified on a Combiflash purification system (silica gel, 0-20% EtOAc:DCM). AS-5332-30 was isolated as yellow solid (0.054 g, 70%). $^1$H-NMR (400 MHz, CDCl$_3$) δ: 8.84 and 8.82 (d, J=2.0 Hz, 1H each), 8.52-8.49 (m, 1H), 8.29 and 8.27 (d, J=8.8 Hz, 1H each), 8.26 (s, 1H), 8.18 and 8.15 (d, J=8.8 Hz, 1H each), 7.89 (d, J=8.4 Hz, 1H), 7.88-7.84 (m, 2H), 7.79-7.75 (m, 1H), 7.61-7.57 (m, 1H), 7.47 (d, J=8.4 Hz, 1H), 3.7 and 3.28 (s, 3H each); MS (ESI): 308.1 (M+H$^+$).

Preparation of

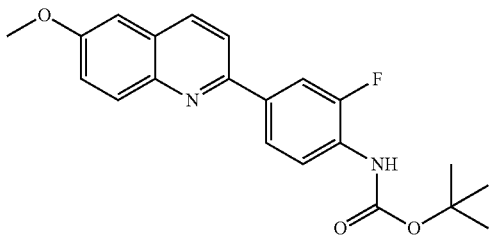 [SMILES: COc1ccc2nc(-c3ccc(NC(=O)OC(C)(C)C)c(F)c3)ccc2c1]

tert-Butyl 2-fluoro-4-(6-methoxyquinolin-2-yl)phenyl) carbamate AS-5332-32): To a solution of T467 (0.050 g, 0.186 mmol) in THF (3.0 mL) was added Boc anhydride (0.82 g, 0.373 mmol). The resulting reaction mixture was heated at 100° C. overnight. The volatiles were removed in vacuo and residue was purified on a Combiflash purification system silica gel, 0-20% EtOAc:DCM). AS-5332-32 was isolated as off white solid (0.040 g, 58%). $^1$H-NMR (400 MHz, CDCl$_3$): δ 8.22 (br, 1H), 8.09 (d, J=8.4 Hz, 1H), 8.12 (d, J=9.2 Hz, 1H), 7.98 (dd, J=8.8, 2.0 Hz, 1H), 7.83 (d, J=8.8 Hz, 1H), 7.77 (d, J=8.8 Hz, 1H), 7.35 (dd, J=9.2 Hz, 2.8 Hz, 1H), 7.06 (d, J=2.8 Hz 1H), 6.83 (br, 1H), 3.93 (s, 3H), 1.54 (s, 9H); MS (ESI): 369.2 (M+H$^+$).

Preparation of

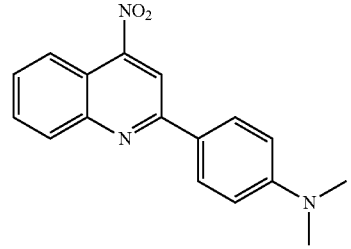 [SMILES: CN(C)c1ccc(-c2cc([N+](=O)[O-])c3ccccc3n2)cc1]

N—N-Dimethyl-4-(4-nitroquinolin-2-yl)aniline AS-5332-36 was prepared using general procedure A. Reaction was performed on a 0.126 g scale. AS-5332-36 was isolated as yellow solid (0.103 g, 70%). NMR (400 MHz, CDCl$_3$): δ 8.34-8.32 (m, 2H), 8.20 (d, J=8.8 Hz, 1H), 8.13 (dt, J=9.2, 2.8 Hz, 2H), 7.78 (ddd, J=8.4, 7.2, 1.2 Hz, 1H), 7.62 (ddd, J=8.4, 7.6, 1.2 Hz, 1H), 6.82 (br d, J=9.2 Hz, 2H), 3.07 (s, 6H); MS (ESI): 294.1 (M+H$^+$).

Preparation of

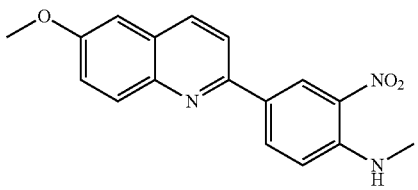

4-(6-Methoxyquinolin-2-yl)-N-methyl-2-nitroaniline AS-5332-42 was prepared using general procedure A. Reaction was performed on a 0.050 g scale. AS-5332-42 was isolated as yellow solid (0.080 g, 100%). $^1$H NMR (400 MHz, CDCl$_3$): δ 8.92 (d, J=2.0 Hz 1H), 8.50 (br, 1H), 8.23 (br, 1H), 8.12 (d, J=8.4 Hz, 1H), 7.83 (d, J=8.8 Hz, 1H), 7.37 (dd, J=9.2 Hz, 2.8 Hz, 1H), 7.08 (d, J=2.8 Hz, 1H), 7.00 (d, J=8.8 Hz 1H), 3.94 (s, 3H), 3.11 (d, J=4.8 Hz, 3H); MS (ESI): 310.1 (M+H$^+$).

Preparation of

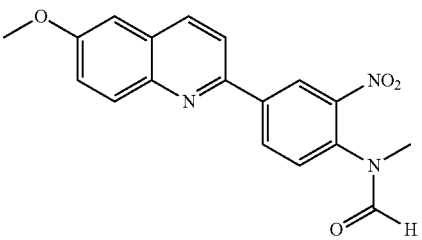

N-(4-(6-Methoxyquinolin-2-yl)-2-nitrophenyl)-N-methylformamide AS-5332-43: A mixture of acetic anhydride (0.305 g, 22 eq) and HCO$_2$H (0.137 g, 22 eq) was heated at 60° C. for 15 min. To this mixture was added a solution of AS-5332-42 (0.042 g) in DCM (5 mL). The resulting mixture was heated at 80° C. for 3 days. The volatiles were removed in vacuo. The residue was purified on a Combiflash purification system (silica gel, 0-20% EtOAc:DCM) to give AS-5332-43 as a yellow solid (0.034 g, 74%). $^1$H-NMR (400 MHz, CDCl$_3$) δ: 8.80 and 8.76 (d, J=2.0 Hz, 1H), 8.47-8.46 (m, 1H), 8.25 and 8.24 (s, 1H each), 8.17 (t, J=8.4 Hz, 1H), 8.05 (d, J=9.2 Hz, 1H), 7.85 and 7.83 (d, J=5.2 Hz, 1H each), 7.45 (d, J=8.4 Hz, 1H), 7.44-7.40 (m, 1H), 7.11 and 7.10 (d, J=0.8 Hz, 1H each), 3.96 and 3.95 (s, 3H each), 3.46 and 3.27 (s, 3H each); MS (ESI): 338.1 (M+H$^+$).

Preparation of

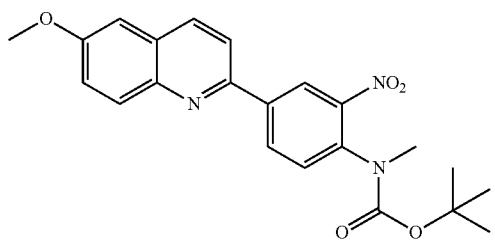 [SMILES: COc1ccc2nc(-c3ccc(N(C)C(=O)OC(C)(C)C)c([N+](=O)[O-])c3)ccc2c1]

tert-Butyl 4-(6-methoxyquinolin-2-yl)-2-nitrophenyl(methyl)carbamate AS-5332-46: To a solution AS-5332-42 (0.030 g, 0.186 mmol) in THF (3.0 mL) was added Boc anhydride (0.063 g, 0.0291 mmol) and DMAP (0.012 g, 0.097 mmol). The resulting reaction mixture was heated at 100° C. for 30 min. The volatiles were removed in vacuo and residue was purified on a Combiflash purification system (silica gel, 0-7% EtOAc:DCM) to afford AS-5332-43 as a off white solid (0.040 g, 100%). $^1$H-NMR (400 MHz, CDCl$_3$) δ: 8.69 (d, J=2.0 Hz, 1H), 8.40 (d, J=8.0 Hz, 1H), 8.16 (d, J=8.8 Hz, 1H), 8.07 (d, J=9.2 Hz, 1H), 7.85 (d, J=8.8 Hz, 1H), 7.44 (d, J=8.0 Hz, 1H), 7.41 (dd, J=9.2, 2.8 1H), 7.10 (d, J=2.8 Hz, 1H), 3.95 (s, 3H), 3.34 (s, 3H), 1.32 (s, 9H); MS (ESI): 410.1 (M+H$^+$).

Preparation of

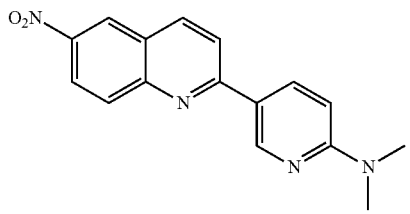 [SMILES: CN(C)c1ccc(-c2ccc3cc([N+](=O)[O-])ccc3n2)cn1]

N,N-dimethyl-5-(6-nitroquinolin-2-yl)pyridin-2-amine AS-5332-49 was prepared using general procedure A. for Suzuki coupling (method A) was followed. Reaction was performed on a 0.104 g scale. AS-5332-49 was isolated as a orange red color solid (0.1 g, 68%). $^1$H-NMR (400 MHz, CDCl$_3$) δ: 8.99 (d, J=2.4 Hz, 1H), 8.72 (d, J=2.4 Hz, 1H), 8.44-8.41 (m, 2H), 8.27 (d, J=8.8 Hz, 1H), 8.14 (d, J=8.8 Hz, 1H), 7.93 (d, J=8.8 Hz, 1H), 6.66 (d, J=8.8 Hz, 1H), 3.21 (s, 6H); MS (ESI): 295.1 (M+H$^+$).

Preparation of

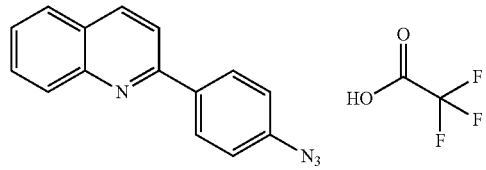 [SMILES: [N-]=[N+]=Nc1ccc(-c2ccc3ccccc3n2)cc1 ; O=C(O)C(F)(F)F]

2-(4-Azidophenyl)quinoline *TFA: T446 To a solution of 4-(quinolin-2-yl)aniline dihydrochloride (29.0 mg, 0.1 mmol) in 1 N HCl (1 mL) was added NaNO$_2$ solution (7.0 mg in 0.3 mL water, 0.1 mmol) at 0° C. The mixture was stirred at 0° C. for 2 hrs before NaN$_3$ (7.8 mg in 1.0 mL water, 0.12 mmol) was added at 0° C. The mixture was stirred at 0° C. for 1 hour and concentrated. The residue was purified by HPLC (acetonitrile/water) to give T446 as a light yellow solid (23.0 mg, 64%). $^1$H NMR (400 MHz, CD$_3$OD): δ 8.31 (d, J=8.8 Hz, 1H), 8.10 (m, 2H), 8.00 (m, 1H), 7.90 (d, J=8.8 Hz, 1H), 7.85 (dd, J=8.2, 1.4 Hz, 1H), 7.69 (m, 1H), 7.50 (m, 1H), 7.16 (m, 2H); MS (ESI): 247 (M+H$^+$).

Preparation of

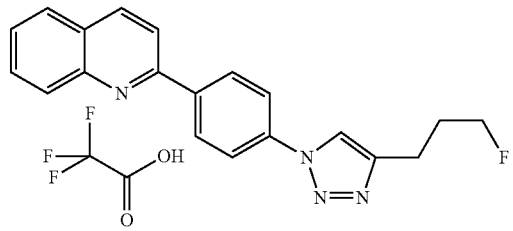

2-(4-(4-(3-Fluoropropyl)-1H-1,2,3-triazol-1-yl)phenyl)quinoline*TFA: T443 was prepared using general procedure N. Reaction was performed on a 4.0 mg scale of T446. T443 was isolated as a brown solid (2.7 mg, 39%). ¹H NMR (400 MHz, CD₃OD): δ 8.72 (d, J=8.8 Hz, 1H), 8.50 (s, 1H), 8.34-8.38 (m, 2H), 8.19-8.24 (m, 2H), 8.09-8.14 (m, 3H), 7.94 (m, 1H), 7.74 (m, 1H), 4.59 (t, J=6.0 Hz, 1H), 4.47 (t, J=6.0 Hz, 1H), 2.94 (t, J=7.6 Hz, 1H), 2.14 (m, 2H); MS (ESI): 333 (M+H⁺).

Preparation of

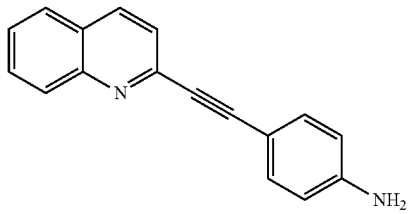 [SMILES: Nc1ccc(C#Cc2ccc3ccccc3n2)cc1]

4-(Quinolin-2-ylethynyl)aniline: T444 was prepared using general procedure B. Reaction was performed on a 16.0 mg scale of 2-chloroquinoline. T444 was isolated as a light yellow solid (6.0 mg, 25%). ¹H NMR (400 HMz, CDCl₃): δ 8.11 (d, J=8.4 Hz, 2H), 7.79 (dd, J=8.0, 1.4 Hz, 1H), 7.72 (m, 1H), 7.57 (d, J=8.4 Hz, 1H), 7.53 (m, 1H), 7.48 (m, 2H), 6.66 (m, 2H), 3.91 (br s, 2H); MS (ESI): 245 (M+H⁺).

Preparation of

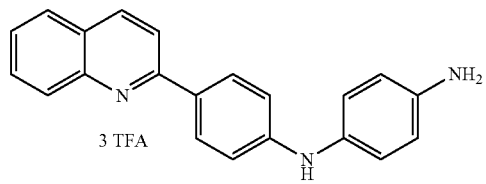 [SMILES: Nc1ccc(Nc2ccc(-c3ccc4ccccc4n3)cc2)cc1]

N-(4-(Quinolin-2-yl)phenyl)benzene-1,4-diamine *3TFA: T447 To a solution of 4-(quinolin-2-yl)aniline dihydrochloride (7.6 mg, 0.026 mmol) in DCM (1.0 mL) was added 4-(tert-butoxycarbonylamino)phenylboronic acid (12.4 mg, 0.052 mmol), Cu(OAc)₂ (4.8 mg, 0.026 mmol) and triethylamine (0.036 mL, 0.26 mmol). The mixture was stirred at room temperature for 3 hrs. LCMS showed that the desired product was formed. To the mixture was added 4 N HCl in dioxane (1.0 mL) and stirred for another hour. The mixture was concentrated in vacuo and purified by HPLC (acetonitrile/water) to give T447 as a brown solid (4.3 mg, 25%). ¹H NMR (400 MHz, CD₃OD): δ 8.77 (d, J=8.8 Hz, 1H), 8.16 (m, 2H), 8.10 (d, J=8.4 Hz, 1H), 8.01 (m, 2H), 7.96 (m, 1H), 7.73 (m, 1H), 7.21-729 (m, 6H); MS (ESI): 312 (M+H⁺).

Preparation of

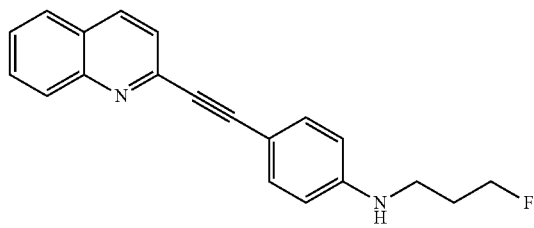 [SMILES: FCCCNc1ccc(C#Cc2ccc3ccccc3n2)cc1]

N-(3-Fluoropropyl)-4-(quinolin-2-ylethynyl)aniline: T454 was prepared using general procedure Q. Reaction was performed on a 4.0 mg scale of T444. T454 was isolated as a light yellow solid (2.3 mg, 46%). ¹H NMR (400 MHz, CDCl₃): δ 8.11 (d, J=8.4 Hz, 2H), 7.79 (dd, J=8.0, 1.4 Hz, 1H), 7.26-7.58 (m, 4H), 6.59 (m, 2H), 4.66 (t, J=5.6 Hz, 1), 4.54 (t, J=5.6 Hz, 1H), 4.05 (m, 1H), 3.36 (m, 2H), 2.05 (m, 2H); MS (ESI): 305 (M+H⁺).

Preparation of

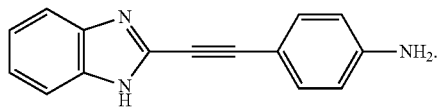 [SMILES: Nc1ccc(C#Cc2nc3ccccc3[nH]2)cc1]

4-((1H-Benzo[d]imidazol-2-yl)ethynyl)aniline: T464 was prepared using general procedure B. Reaction was performed on a 60.0 mg scale of 2-bromo-1H-benzo[d]imidazole. T464 was isolated as a light yellow solid (35.9 mg, 51%). ¹H NMR (400 MHz, CD₃OD): δ 7.50 (br s, 2H), 7.31 (m, 2H), 7.24 (m, 2H), 6.64 (m, 2H); MS (ESI): 234 (M+H⁺).

Preparation of

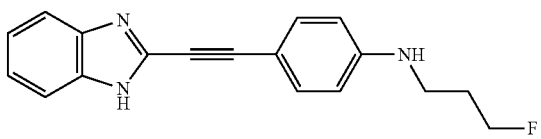

4-((1H-Benzo[d]imidazol-2-yl)ethynyl)-N-(3-fluoropropyl)aniline: T465 was prepared using general procedure Q. Reaction was performed on a 33.3 mg scale of T464. T465 w isolated as a white solid (8.9 mg, 21%). ¹H NMR (400 MHz, CD₃OD): 7.50 (m, 2H), 7.35 (m, 2H), 7.26 (m, 2H), 6.61 (m, 2H), 4.58 (t, J=5.6 Hz, 1H), 4.46 (t, J=5.6 Hz, 1H), 3.27 (m, 2H), 1.95 (m, 2H); MS (ESI): 294 (M+H⁺).

Preparation of

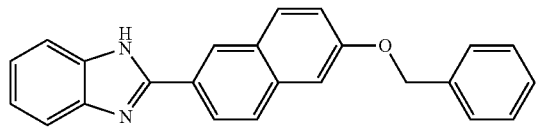

2-(6-(Benzyloxy)naphthalen-2-yl)-1H-benzo[d]imidazole: T469 was prepared using general procedure A. Reaction was performed on a 100 mg scale of 2-bromo-1H-benzo[d]imidazole. T469 was isolated as a white solid (75.0 mg, 42%). NMR (400 MHz, DMSO-d₆): δ 12.95 (s, 1H), 8.63 (d, J=1.2 Hz, 1H), 8.22 (dd, J=8.4, 2.0 Hz, 1H), 7.93 (t, J=9.2 Hz, 2H), 7.64 (m, 1H), 7.50 (m, 4H), 7.40 (m, 2H), 7.34 (m, 1H), 7.29 (m, 1H), 7.17 (m, 2H), 5.24 (s, 2H); MS (ESI): 351 (M+H⁺).

Preparation of

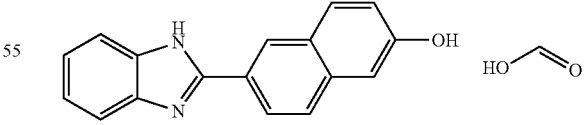

6-(1H-Benzo[d]imidazol-2-yl)naphthalen-2-ol*formate: T470 To a solution of 2-(6-(benzyloxy)naphthalen-2-yl)-1H-benzo[d]imidazole (73 mg, 0.21 mmol) in THF (2 mL) was added MeOH (2 mL), Pd—C (10%, 30 mg), and formic acid (0.30 mL). The mixture was flushed with argon and sealed in a microwave vial. The mixture was heated at 100° C. for 5 minutes in a microwave synthesizer. The mixture was filtered off Pd—C and the filtrate was concentrated to give T470 as a white solid (60 mg, 94%). ¹H NMR (400 MHz, CD₃OD): δ

8.46 (t, J=1.0 Hz, 1H), 8.12 (s, 1H), 8.05 (dd, J=8.8, 2.0 Hz, 1H), 7.85 (d, J=9.6 Hz, 1H), 7.79 (d, J=8.8 Hz, 1H), 7.62 (m, 2H), 7.29 (m, 2H), 7.16 (m, 2H); MS (ESI): 261 (M+H⁺).
Preparation of

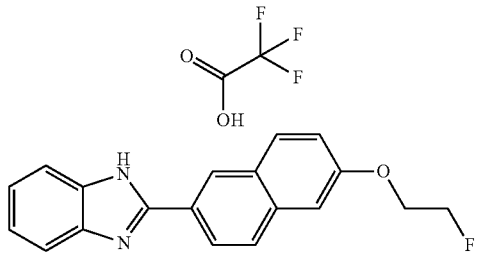

2-(6-(2-Fluoroethoxy)naphthalen-2-yl)-1H-benzo[d]imidazole*TFA: T473 was prepared using general procedure. Reaction was performed on a 16 mg scale of T470. T473 was isolated as a light yellow solid (1.9 mg, 8.6%). NMR (400 MHz, CD₃OD): δ 8.63 (d, J=1.6 Hz, 1H), 8.01-8.11 (m, 3H), 7.82 (m, 2H), 7.62 (m, 2H), 7.45 (m, 1H), 7.38 (dd, J=9.0, 2.6 Hz, 1H), 4.87 (t, J=4.0 Hz, 1H), 4.75 (t, J=4.0 Hz, 1H), 4.44 (t, J=4.0 Hz, 1H), 4.37 (t, J=4.0 Hz, 1H); MS (ESI): 307 (M+H⁺).
Preparation of

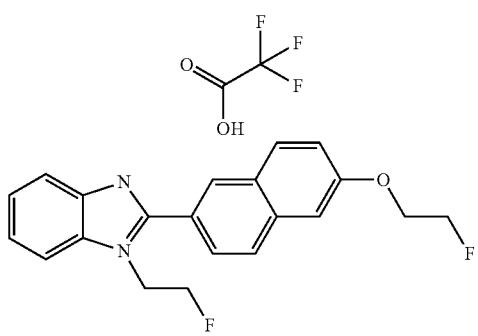

2-(6-(2-Fluoroethoxy)naphthalen-2-yl)-1-(2-fluoroethyl)-1H-benzo[d]imidazole*TFA: T474 was prepared using general procedure C. Reaction was performed on a 16 mg scale T470. T474 was isolated as a light yellow solid (9.4 mg, 39%). ¹H NMR (400 MHz, CD₃OD): δ 8.41 (d, J=1.6 Hz, 1H), 8.12 (d, J=8.4 Hz, 1H), 8.02 (m, 2H), 7.82-7.89 (m, 2H), 7.71 (m, 2H), 7.47 (d, J=2.4 Hz, 1H), 7.38 (dd, J=9.0, 2.6 Hz, 1H), 4.95-5.00 (m, 2H), 4.86-4.92 (m, 3H), 4.75 (m, 1H), 4.44 (m, 1H), 4.37 (m, 1H); MS (ESI): 353 (M+H⁺).
Preparation of

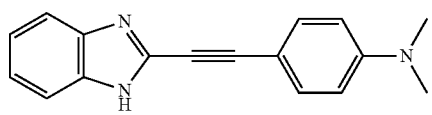 [SMILES: CN(C)c1ccc(C#Cc2nc3ccccc3[nH]2)cc1]

4-((1H-Benzo[d]imidazol-2-yl)ethynyl)-N,N-dimethylaniline: T481 was prepared using general procedure R. Reaction was performed on a 26.0 mg scale of T464. T481 was isolated as a light yellow solid (11.2 mg, 39%). ¹H NMR (400 MHz, CD₃OD): δ 7.51 (m, 2H), 7.44 (m, 2H), 7.25 (m, 2H), 6.73 (m, 2H), 3.00 (s, 6H); MS (ESI): 262 (M+H⁺).

Preparation of

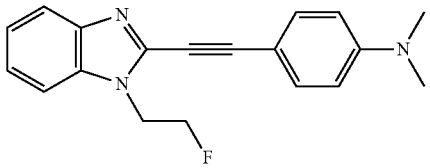 [SMILES: CN(C)c1ccc(C#Cc2nc3ccccc3n2CCF)cc1]

4-((1-(2-Fluoroethyl)-1H-benzo[d]imidazol-2-yl)ethynyl)-N,N-dimethylaniline: T482 was prepared using general procedure E. Reaction was performed on a 10.1 mg scale of T481. T482 was isolated as a light yellow solid (9.6 mg, 81%). ¹H NMR (400 MHz, CDCl₃): δ 7.76 (m, 1H), 7.48 (m, 2H), 7.37 (m, 1H), 7.28 (m, 2H), 4.87 (t, J=5.2 Hz, 1H), 4.76 (t, J=5.2 Hz, 1H), 4.66 (t, J=5.2 Hz, 1H), 4.60 (t, J=5.2 Hz, 1H), 3.02 (s, 6H); MS (ESI): 308 (M+H⁺).
Preparation of

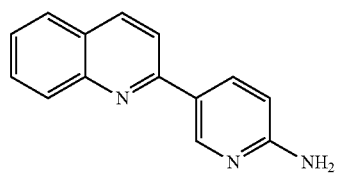 [SMILES: Nc1ccc(-c2ccc3ccccc3n2)cn1]

5-(Quinolin-2-yl)pyridin-2-amine: T490 was prepared using general procedure A. Reaction was performed on a 106 mg scale of 2-chloroquinoline. T490 was isolated as a white solid (135 mg, 94%). ¹H NMR (400 MHz, CDCl₃): δ 8.85 (d, J=2.4 Hz, 1H), 8.37 (dd, J=8.4, 2.4 Hz, 1H), 8.18 (d, J=8.8 Hz, 1H), 8.11 (d, J=8.8 Hz, 1H), 7.79 (m, 2H), 7.71 (m, 1H), 7.50 (m, 1H), 6.65 (dd, J=8.4, 0.8 Hz, 1H), 4.66 (br s, 2H); MS (ESI): 222 (M+H⁺).
Preparation of

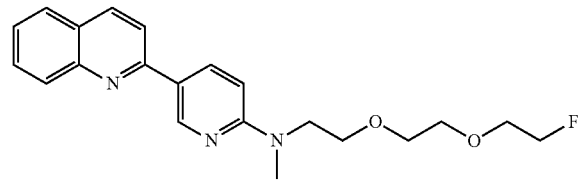 [SMILES: CN(CCOCCOCCF)c1ccc(-c2ccc3ccccc3n2)cn1]

N-(2-(2-(2-Fluoroethoxy)ethoxy)ethyl)-N-methyl-5-(quinolin-2-yl)pyridin-2-amine: T502 was prepared using general procedure S. Reaction was performed on a 7.4 mg scale of T502-precursor. T502 as light yellow oil (3.8 mg, 73%). ¹H NMR (400 MHz, CDCl₃): δ 8.92 (dd, J=2.4, 0.8 Hz, 1H), 8.38 (dd, J=8.8, 2.4 Hz, 1H), 8.15 (d, J=8.4 Hz, 1H), 8.09 (dd, J=8.4, 1.2 Hz, 1H), 7.79 (m, 2H), 7.69 (m, 1H), 7.47 (m, 1H), 6.67 (dd, J=8.8, 0.8 Hz, 1H), 4.61 (t, J=4.2 Hz, 1H), 4.49 (t, J=4.2 Hz, 1H), 3.86 (t, J=5.8 Hz, 2H), 3.65-3.78 (m, 8H), 3.19 (s, 3H); MS (ESI): 370 (M+H⁺).
Preparation of

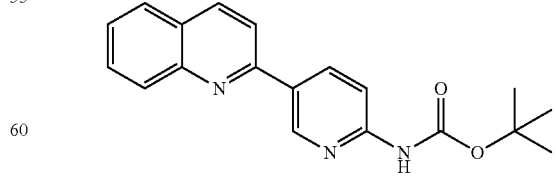

tert-Butyl 5-(quinolin-2-yl)pyridin-2-yl-carbamate T503: To a solution of 5-(quinolin-2-yl)pyridin-2-amine (130 mg, 0.59 mmol) in DCM (5 mL) was added Boc₂O (154 mg, 0.71 mmol), DIEA (76 mg, 0.59 mmol) an DMAP (14 mg, 0.11 mmol). The mixture was stirred at room temperature for 24 hrs. LCMS showed that mono-Boc, di-Boc product, and starting material were present. The solvent was removed and the residue was dissolved in a mixture of ethyl acetate and DCM. As DCM evaporated, and needle crystals were formed. The crystals were collected by filtration, washed with ethyl acetate, and dried to give T503 white needles (67 mg, 35%). NMR (400 MHz, DMSO-d$_6$): δ 10.03 (s, 1H), 9.11 (dd, J=2.4, 0.8 Hz, 1H), 8.60 (dd, J=8.8, 2.4 Hz, 1H), 8.43 (d, J=8.8 Hz, 1H), 8.15 (d, J=8.8 Hz, 1H), 8.04 (dd, J=8.2, 1.0 Hz, 1H), 7.96 (m, 2H), 7.76 (m, 1H), 7.57 (m, 1H), 1.47 (s, 9H); MS (ESI): 322 (M+H$^+$).

Preparation of

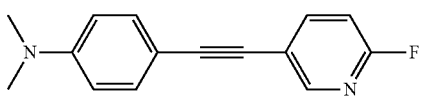 [SMILES: CN(C)c1ccc(C#Cc2ccc(F)nc2)cc1]

4-((6-Fluoropyridin-3-yl)ethynyl)-N,N-dimethylaniline: T516 was prepared using general procedure B. Reaction was performed on a 90 mg scale of 5-bromo-2-fluoropyridine. T516 was isolated as a light yellow solid (50 mg, 41%). NMR (400 MHz, CDCl$_3$): δ 8.34 (m, 1H), 7.85 (m, 1H), 7.39 (m, 2H), 6.90 (m, 1H), 6.66 (m, 2H), 3.00 (s, 6H); MS (ESI): 241 (M+H$^+$).

Preparation of

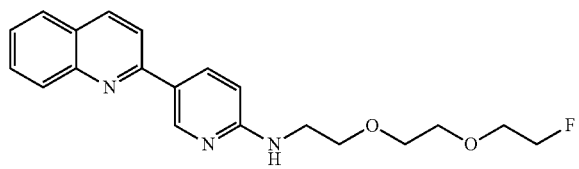 [SMILES: FCCOCCOCCNc1ccc(-c2ccc3ccccc3n2)cn1]

N-(2-(2-(2-Fluoroethoxy)ethoxy)ethyl)-5-(quinolin-2-yl)pyridin-2-amine: T525 was prepared using general procedure D. Reaction was performed on a 22.0 mg scale of T490. T525 was isolated as light yellow oil (3.3 mg, 9.3%). $^1$H NMR (400 MHz, CDCl$_3$): δ 8.86 (d, J=2.4 Hz, 1H), 8.35 (dd, J=8.8, 2.4 Hz, 1H), 8.15 (d, J=8.8 Hz, 1H), 8.09 (d, J=8.4 Hz, 1H), 7.79 (d, J=8.4 Hz, 2H), 7.69 (m, 1H), 7.48 (m, 1H), 6.57 (dd, J=8.8, 0.8 Hz, 1H), 5.15 (m, 1H), 4.65 (t, J=4.0 Hz, 1H), 4.53 (t, J=4.0 Hz, 1H), 3.81 (t, J=4.0 Hz, 1H), 3.68-3.77 (m, 7H), 6.63 (dd, J=10.6, 5.0 Hz, 2H); MS (ESI): 356 (M+H$^+$).

Preparation of

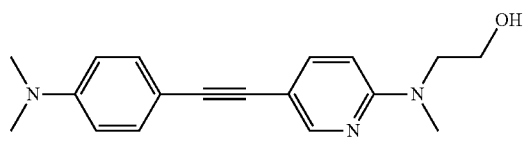 [SMILES: CN(C)c1ccc(C#Cc2ccc(N(C)CCO)nc2)cc1]

2-((5-((4-(Dimethylamino)phenyl)ethynyl)pyridin-2-yl)(methyl)amino)ethanol: T526 was prepared using general procedure M from 2-fluoropyridine derivatives and 2-(methylamino)ethanol. Reaction was performed on a 45 mg scale of T516. T526 was isolated as a light yellow solid (40 mg, 72%). $^1$H NMR (400 MHz, CDCl$_3$): δ 8.22 (dd, J=2.4, 0.8 Hz, 1H), 7.57 (dd, J=8.8, 2.4 Hz, 1H), 7.37 (m, 2H), 6.65 (m, 2H), 6.90 (d, J=8.8, 0.8 Hz, 1H), 4.58 (br s, 1H), 3.85 (t, J=4.8 Hz, 2H), 3.74 (t, J=4.8 Hz, 2H), 3.09 (s, 3H), 2.98 (s, 6H); MS (ESI): 296 (M+H$^+$).

Preparation of

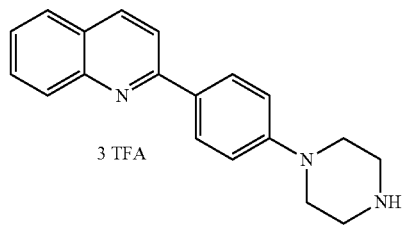 [SMILES: c1ccc2nc(-c3ccc(N4CCNCC4)cc3)ccc2c1]

2-(4-(piperazin-1-yl)phenyl)quinoline*3TFA: T535 was prepared using general procedure A. Reaction was performed on a 17.0 mg scale of 2-chloroquinoline. T535 was isolated as a light yellow solid (10.0 mg, 42%). $^1$H NMR (400 MHz, CD$_3$OD): δ 8.74 (d, J=8.8 Hz, 1H), 8.11-8.21 (m, 5H), 7.96 (t, J=7.2 Hz, 1H), 7.75 (t, J=7.2 Hz, 1H), 7.26 (m, 2H), 3.66 (br t, J=5.4 Hz, 4H), 3.40 (br t, J=5.4 Hz, 4H); MS (ESI): 290 (M+H$^+$).

Preparation of

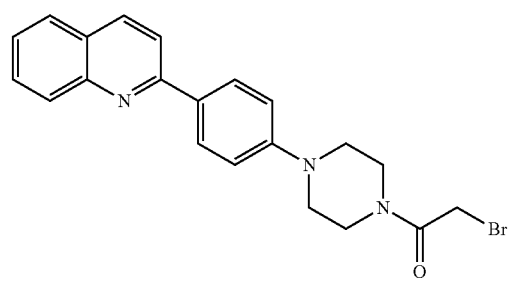 [SMILES: O=C(CBr)N1CCN(c2ccc(-c3ccc4ccccc4n3)cc2)CC1]

2-Bromo-1-(4-(4-(quinolin-2-yl)phenyl)piperazin-1-yl)ethanone T536: To a solution of 2-(4-(piperazin-1-yl)phenyl)quinoline*3TFA (8.6 mg, 0.014 mmol) in DCM (2 mL) was added TEA (9.0 mg, 0.089 mmol), followed by 2-bromoacetyl bromide (12.0 mg, 0.059 mmol). The mixture was stirred at room temperature for 1 hour and quenched by adding NaHCO$_3$ solution. The DCM layer was separated and concentrated. The residue was purified by flash chromatography (silica gel, 0-30% ethyl acetate/DCM) to give T536 as a white solid (3.7 mg, 66%). $^1$H NMR (400 MHz, CDCl$_3$): δ 8.11-8.18 (m, 4H), 7.84 (d, J=8.8 Hz, 1H), 7.80 (dd, J=8.0, 1.6 Hz, 1H), 7.72 (m, 1H), 7.49 (m, 1H), 7.05 (m, 2H), 3.91 (s, 2H), 3.83 (br t, J=5.2 Hz, 2H), 3.72 (br t, J=5.2 Hz, 2H), 3.39 (br t, J=5.2 Hz, 2H), 3.32 (br t, J=5.2 Hz, 2H); MS (ESI): 410 (M+H$^+$).

Preparation of

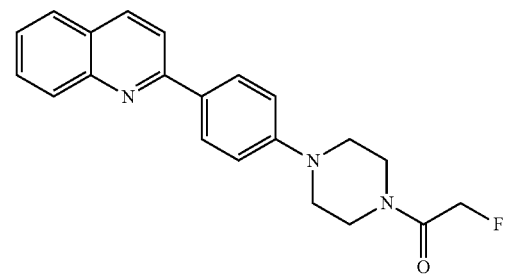 [SMILES: O=C(CF)N1CCN(c2ccc(-c3ccc4ccccc4n3)cc2)CC1]

2-Fluoro-1-(4-(4-(quinolin-2-yl)phenyl)piperazin-1-yl)ethanone: T537 was prepared using general procedure O.

Reaction was performed on a 2.8 mg scale of T536. T537 was isolated as a white solid (1.9 mg, 80%). ¹H NMR (400 MHz, CDCl₃): δ 8.11-8.18 (m, 4H), 7.84 (d, J=8.8 Hz, 1H), 7.80 (d, J=8.4 Hz, 1H), 7.70 (m, 1H), 7.49 (m, 1H), 7.05 (m, 2H), 5.11 (s, 1H), 4.99 (s, 1H), 3.84 (br s, 2H), 3.67 (br s, 2H), 3.33 (br t, J=5.0 Hz, 2H); MS (ESI): 350 (M+H⁺).
Preparation of

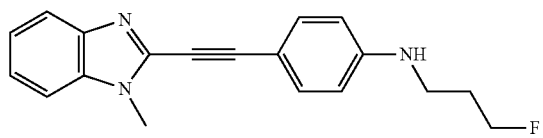 [SMILES: Cn1c(C#Cc2ccc(NCCCF)cc2)nc2ccccc21]

N-(3-Fluoropropyl)-4-((1-methyl-1H-benzo[d]imidazol-2-yl)ethynyl)aniline: T540 was prepared using general procedure E. Reaction was performed on a 6.7 mg scale of T465. T540 was isolated as a white solid (5.9 mg, 84%). ¹H NMR (400 MHz, CDCl₃): δ 7.74 (m, 1H), 7.46 (m, 2H), 7.27-7.32 (m, 3H), 6.59 (m, 2H), 4.66 (t, J=5.6 Hz, 1H), 4.54 (t, J=5.6 Hz, 1H), 4.15 (br s, 1H), 191 (s, 3H), 3.36 (m, 2H), 2.02 (m, 2H); MS (ESI): 308 (M+H⁺).
Preparation of

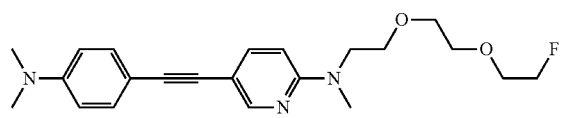 [SMILES: CN(C)c1ccc(C#Cc2ccc(N(C)CCOCCOCCF)nc2)cc1]

5-((4-(Dimethylamino)phenyl)ethynyl)-N-(2-(2-(2-fluoroethoxy)ethoxy)ethyl)-N-methylpyridin-2-amine: T546 was prepared using general procedure O. Reaction was performed on a 30.2 mg scale of T546-precursor. T546 was isolated as a light yellow gum (11.6 mg, 53%). ¹H NMR (400 Hz, CDCl₃): δ 8.27 (d, J=2.4 Hz, 1H), 7.52 (dd, J=8.8, 2.4 Hz, 1H), 7.36 (m, 2H), 6.64 (br d, J=8.8 Hz, 2H), 6.47 (d, J=8.8 Hz, 1H), 4.59 (t, J=4.2 Hz, 1H), 4.47 (t, J=4.2 Hz, 1H), 3.60-3.79 (m, 10H), 3.11 (s, 3H), 2.97 (br s, 6H); MS (ESI): 386 (M+H⁺).
Preparation of

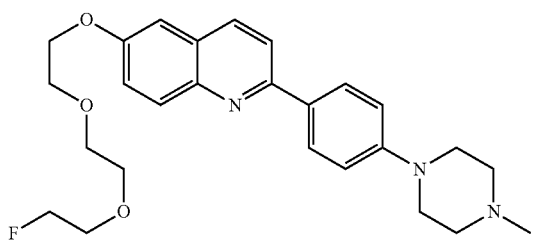 [SMILES: CN1CCN(c2ccc(-c3ccc4cc(OCCOCCOCCF)ccc4n3)cc2)CC1]

6-(2-(2-(2-Fluoroethoxy)ethoxy)ethoxy)-2-(4-(4-methylpiperazin-1-yl)phenyl)quinoline: T550 was prepared using general procedure A. Reaction was performed on a 38.6 mg scale of 2-chloro-6-(2-(2-(2-fluoroethoxy)ethoxy)ethoxy)quinoline. T550 was isolated as a white crystal (7.2 mg, 13%). ¹H NMR (400 MHz, CDCl₃): δ 7.99-8.08 (m, 4H), 7.77 (d, J=9.2 Hz, 1H), 7.37 (dd, J=9.2, 2.8 Hz, 1H), 7.07 (d, J=2.8 Hz, 1H), 7.02 (m, 2H), 4.62 (t, J=4.4 Hz, 1H), 4.50 (t, J=4.4 Hz, 1H), 4.26 (t, J=5.0 Hz, 2H), 3.94 (t, J=5.0 Hz, 2H), 3.70-3.81 (m, 6H), 3.43 (br s, 4H), 2.78 (br s, 4H), 2.50 (br s, 3H); MS (ESI): 454 (M+H⁺).
Preparation of

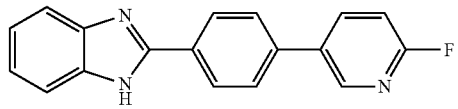 [SMILES: Fc1ccc(-c2ccc(-c3nc4ccccc4[nH]3)cc2)cn1]

2-(4-(6-Fluoropyridin-3-yl)phenyl)-1H-benzo[d]imidazole: T468 was prepared using general procedure S. Reaction was performed on a 0.029 g scale of 2-aminoaniline. The desired product T468 was isolated as a yellow solid (0.043 g, 55%). ¹H NMR (400 MHz, MeOH-d₄): δ 8.61 (d, J=2.8 Hz, 1H), 8.33 (dd, J=8.4, 2.8 Hz, 1H), 8.24 (d, J=8.8 Hz, 2H), 8.03 (d J=8.8 Hz, 2H), 7.82 (dd, J=8.8, 2.4 Hz, 2H), 7.61 (dd, J=8.8, 2.4 Hz, 2H), 7.22 (dd, J=8.8, 2.8 Hz, 1H); MS (ESI): 290 (M+H⁺).
Preparation of

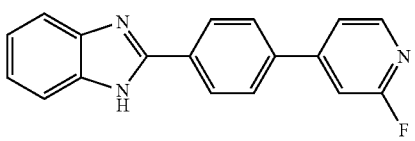 [SMILES: Fc1cc(-c2ccc(-c3nc4ccccc4[nH]3)cc2)ccn1]

2-(4-(2-Fluoropyridin-4-yl)phenyl)-1H-benzo[d]imidazole: T460 was prepared using general procedure S. Reaction was performed on a 0.027 g scale of 2-aminoaniline. The desired product T460 as a yellow solid (0.010 g, 14%). ¹H NMR (400 MHz, MeOH-d₄): δ 8.25 (d, J=5.2 Hz, 1H), 8.19 (d, J=8.8 Hz, 2H), 8.04 (d, J=8.8 Hz, 2H), 8.03 (d, J=8.8 Hz, 2H), 7.72 (q, J=3.2 Hz, 2H), 7.64 (dt, J=5.2, 1.6 Hz, 1H), 7.49 (q, J=3.2 Hz, 2H), 7.42 (s, 1H); MS (ESI): 290 (M+H⁺).
Preparation of

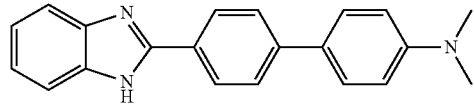 [SMILES: CN(C)c1ccc(-c2ccc(-c3nc4ccccc4[nH]3)cc2)cc1]

4'-(1H-Benzo[d]imidazol-2-yl)-N,N-dimethyl-[1,1'-biphenyl]-4-amine: EW5338-028 was prepared using general procedure S. Reaction was performed on a 0.052 g scale of 2-aminoaniline. EW5338-028 was isolated as a yellow solid (0.076 g, 50%). ¹H NMR (400 MHz, MeOH-d₄): δ 8.08 (d, J=8.8 Hz, 2H), 7.72 (d, J=8.8 Hz, 2H), 7.51-7.62 (m, 4H), 7.23 (dd, J=8.8, 2.8 Hz, 2H), 6.84 (d, J=8.8 Hz, 2H), 2.97 (s, 6H); MS (ESI): 314 (M+H⁺).
Preparation of

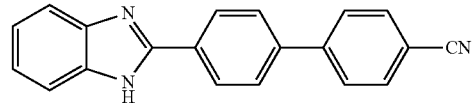 [SMILES: N#Cc1ccc(-c2ccc(-c3nc4ccccc4[nH]3)cc2)cc1]

4'-(1H-Benzo[d]imidazol-2-yl)-[1,1'-biphenyl]-4-carbonitrile: EW5338-043 was prepared using general procedure S. Reaction was performed on a 0.052 g scale of 2-aminoaniline. EW5338-043 was isolated as a yellow solid (0.076 g, 50%). ¹H NMR (DMSO-d₆): δ8.66 (s, 2H), 8.28 (d, J=8.4 Hz, 2H), 7.92-8.02 (m, 6H), 7.16-7.22 (m, 2H); MS (ESI): 296 (M+H⁺).

Preparation of

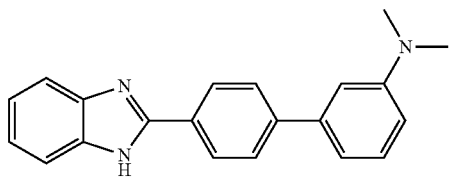 [SMILES: CN(C)c1cccc(-c2ccc(-c3nc4ccccc4[nH]3)cc2)c1]

4'-(1H-Benzo[d]imidazol-2-yl)-N,N-dimethyl-[1,1'-biphenyl]-3-amine: EW5338-036 was prepared using general procedure S. Reaction was performed on a 0.052 g scale of 2-aminoaniline. EW5338-036 was isolated as a yellow solid (0.076 g, 50%). $^1$H NMR (400 MHz, MeOH-d$_4$): δ 8.08 (d, J=8.8 Hz, 2H), 7.56-7.62 (m, 3H), 7.20-7.51 (m, 4H), 6.99 (s, 1H), 6.84-6.91 (m, 2H), 3.02 (s, 6H); MS (ESI): 314 (M+H$^+$).

Preparation of

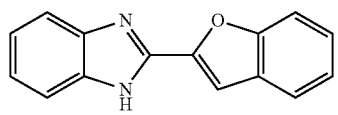 [SMILES: c1ccc2oc(-c3nc4ccccc4[nH]3)cc2c1]

2-(Benzofuran-2-yl)-1H-benzo[d]imidazole: T488 was prepared using general procedure S. Reaction was performed on a 0.34 g scale of 2-aminoaniline. T488 was isolated as a yellow solid (0.1 g, 14%). $^1$H NMR (400 MHz, MeOH-d$_4$): δ 7.54-7.74 (m, 5H), 7.36-7.44 (m, 1H), 7.26-7.34 (m, 3H); MS (ESI): 235 (M+H$^+$).

Preparation of

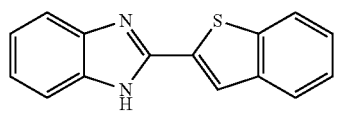 [SMILES: c1ccc2sc(-c3nc4ccccc4[nH]3)cc2c1]

2-(Benzo[b]thiophen-2-yl)-1H-benzo[d]imidazole: T493 was prepared using general procedure S. Reaction was performed on a 0.4 g scale of 2-aminoaniline. T493 was isolated as a yellow solid (0.7 g, 76%). $^1$H NMR (400 MHz, MeOH-d$_4$): δ 8.25 (d, J=0.8 Hz, 1H), 7.98-8.06 (m, 2H), 7.73 (dd, J=8.8, 2.4 Hz, 2H), 7.48-7.56 (m, 4H); MS (ESI): 251 (M+H$^+$).

Preparation of

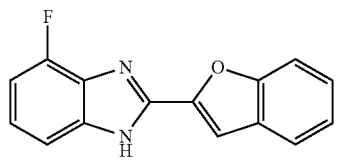 [SMILES: Fc1cccc2[nH]c(-c3cc4ccccc4o3)nc12]

2-(Benzofuran-2-yl)-4-fluoro-1H-benzo[d]imidazole: T495 was prepared using general procedure S. Reaction was performed on a 0.34 g scale of 2-aminoaniline. T495 was isolated 0 as a solid (0.3 g, 50%). NMR (400 MHz, MeOH-d$_4$): δ 7.72-7.78 (m, 1H), 7.71 (d, J=1.2 Hz, 1H), 7.62-7.68 (m, 1H), 7.43-7.49 (m, 2H), 7.30-7.38 (m, 2H), 7.09 (dd, J=8.0, 0.8 Hz, 1H); MS (ESI): 253 (M+H$^+$).

Preparation of

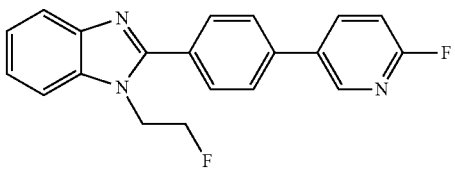 [SMILES: FCCn1c(-c2ccc(-c3ccc(F)nc3)cc2)nc2ccccc21]

1-(2-Fluoroethyl)-2-(4-(6-fluoropyridin-3-yl)phenyl)-1H-benzo[d]imidazole: T538 was prepared using general procedure E. Reaction was performed on a 0.01 g scale of T468. T538 was isolated as a white solid (0.012 g, 100%). $^1$H NMR (400 MHz, CDCl$_3$): δ 8.49 (dt, J=2.4, 0.8 Hz, 1H), 8.30 (dd, J=8.4, 2.4 Hz, 1H), 7.93-7.97 (m, 1H), 7.90 (d, J=8.8 Hz, 2H), 7.72 (d, J=8.8 Hz, 2H), 7.38-7.51 (m, 3H), 7.05 (dd, J=8.8, 0.4 Hz, 1H), 4.84 (dt, J=46.4, 5.2 Hz, 2H), 4.61 (dt, J=24, 4.8 Hz, 2H); MS (ESI): 336 (M+H$^+$).

Preparation of

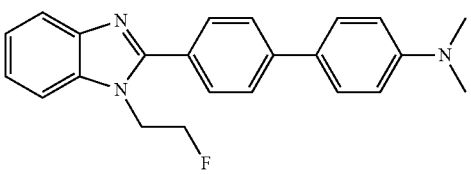

4'-(1-(2-Fluoroethyl)-1H-benzo[d]imidazol-2-yl)-N,N-dimethyl-[1,1'-biphenyl]-4-amine: T543 was prepared using general procedure E. Reaction was performed on a 0.030 g scale of EW5338-028. T543 was isolated as a yellow solid (0.007 g, 20%). $^1$H NMR (400 MHz, MeOH-d$_4$): δ 7.83-8.20 (m, 6H), 7.67-7.73 (m, 4H), 6.97 (d, J=8.8 Hz, 2H), 4.96 (dt, J=46.4, 5.2 Hz, 2H), 4.61 (dt, J=24, 4.8 Hz, 2H), 3.05 (s, 6H); MS (ESI): 360 (M+H$^+$).

Preparation of

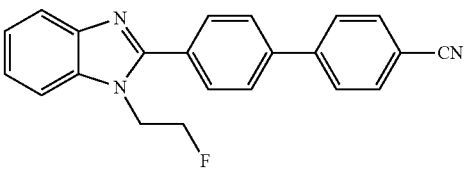 [SMILES: N#Cc1ccc(-c2ccc(-c3nc4ccccc4n3CCF)cc2)cc1]

4'-(1-(2-Fluoroethyl)-1H-benzo[d]imidazol-2-yl)-[1,1'-biphenyl]-4-carbonitrile: T556 was prepared using general procedure E. Reaction was performed on a 0.036 g scale of EW5338-043. T556 was isolated as a yellow solid (0.009 g, 22%). $^1$H NMR (400 MHz, CDCl$_3$): δ 7.89 (d, J=8.0 Hz, 3H), 7.72-7.79 (m, 6H), 7.42-7.48 (m, 1H), 7.34-7.41 (m, 2H), 4.83 (dt, J=46, 4.8 Hz, 2H), 4.59 (dt, J=24, 5.2 Hz, 2H); MS (ESI): 342 (M+H$^+$).

Preparation of

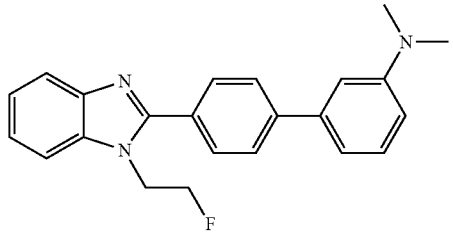 [SMILES: CN(C)c1cccc(-c2ccc(-c3nc4ccccc4n3CCF)cc2)c1]

4'-(1-(2-Fluoroethyl)-1H-benzo[d]imidazol-2-yl)-N,N-dimethyl-[1,1'-biphenyl]-3-amine: T548 was prepared using general procedure E. Reaction was performed on a 0.036 g scale of EW5338-036. T548 was isolated as a yellow solid (0.014 g, 33%). $^1$H NMR (400 MHz, CDCl$_3$): δ 7.85-7.89 (m, 1H), 7.79 (d, J=8.4 Hz, 2H), 7.75 (d, J=8.4 Hz, 2H), 7.42-7.47 (m, 1H), 7.31-7.37 (m, 3H), 6.95-7.02 (m, 2H), 6.78 (dd, J=8.4, 0.8 Hz, 1H), 3.02 (s, 6H); MS (ESI): 360 (M+H$^+$).

Preparation of

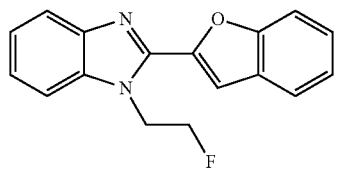 [SMILES: FCCn1c(-c2cc3ccccc3o2)nc2ccccc21]

2-(Benzofuran-2-yl)-1-(2-fluoroethyl)-1H-benzo[d]imidazole: T489 was prepared using general procedure E. Reaction was performed on a 0.052 g scale of T488. T489 was isolated as a yellow solid (0.076 g, 50%). $^1$H NMR (400 MHz, CDCl$_3$): δ 7.81-7.88 (m, 1H), 7.69-7.74 (m, 1H), 7.55-7.63 (m, 2H), 7.45-7.51 (m, 1H), 7.30-7.44 (m, 4H), 4.92-5.03 (m, 2H), 4.85-4.95 (m, 2H); MS (ESI): 281 (M+H$^+$).

Preparation of

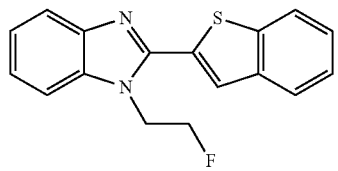 [SMILES: FCCn1c(-c2cc3ccccc3s2)nc2ccccc21]

2-(Benzo[b]thiophen-2-yl)-1-(2-fluoroethyl)-1H-benzo[d]imidazole: T494 was prepared using general procedure E. Reaction was performed on a 0.052 g scale of T493. T494 was isolated as a yellow solid (0.076 g, 50%). $^1$H NMR (400 MHz, CDCl$_3$): δ 7.85-7.92 (m, 3H), 7.77 (s, 1H), 7.81-7.95 (m, 3H), 7.60-7.75 (m, 2H), 4.91 (dt, J=46.4, 4.8 Hz, 2H), 4.75 (dt, J=24, 4.8 Hz, 2H); MS (ESI): 297 (M+H$^+$).

Preparation of

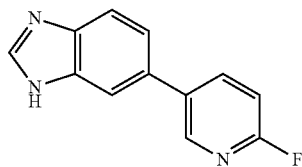 [SMILES: Fc1ccc(-c2ccc3nc[nH]c3c2)cn1]

6-(6-Fluoropyridin-3-yl)-1H-benzo[d]imidazole: T532 was prepared using general procedure A. Reaction was performed on a 0.08 g scale of 6-bromobenzimidazole. T532 was isolated as a yellow solid (0.025 g, 29%). $^1$H NMR (400 MHz, MeOH-d$_4$): δ 9.16 (s, 1H), 8.15 (d, J=2.8 Hz, 1H), 8.26 (dd, J=10, 2.4 Hz, 1H), 8.0-8.04 (m, 1H), 7.90 (d, J=8.8 Hz, 1H), 7.83 (dd, J=8.4, 1.6 Hz, 1H), 7.19 (dd, J=8.4, 1.6 Hz, 1H); MS (ESI): 214 (M+H$^+$).

Preparation of

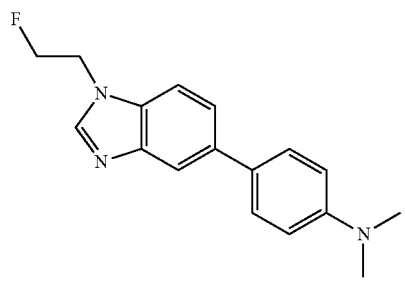 [SMILES: CN(C)c1ccc(-c2ccc3c(c2)ncn3CCF)cc1]

4-(1-(2-Fluoroethyl)-1H-benzo[d]imidazol-5-yl)-N,N-dimethylaniline: T533 was prepared using general procedure A. Reaction was performed on a 0.08 g scale of 6-bromo-N-2-fluoroethylbenzoimidazole. T533 was isolated as a yellow solid (0.025 g, 29%). $^1$H NMR (400 MHz, D$_2$O): δ 9.23 (s, 1H), 8.05 (d, J=1.2 Hz, 1H), 7.81-7.89 (m, 4H), 7.64 (d, J=8.8 Hz, 2H), 4.90 (dt, J=27.2, 5.2 Hz, 2H), 4.78-4.83 (m, 2H), 3.25 (s, 6H); MS (ESI): 284 (M+H$^+$).

Preparation of

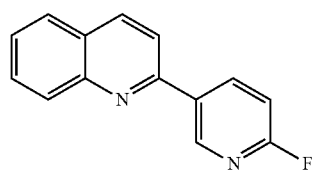 [SMILES: Fc1ccc(-c2ccc3ccccc3n2)cn1]

2-(6-Fluoropyridin-3-yl)quinoline: T455 was prepared using general procedure A. Reaction was performed on a 0.1 g scale. T455 was isolated as a white solid (0.14 g, 100%). $^1$H NMR (400 MHz, CDCl$_3$): δ 8.94 (d, J=2.4 Hz, 1H), 8.66 (ddd, J=10.4, 7.6, 2.4 Hz, 1H), 8.27 (d, J=8.0 Hz, 1H), 8.14 (dd, J=8.4, 1.2 Hz, 1H), 7.75 (ddd, J=8.4, 6.8, 1.6 Hz, 1H), 7.85 (d, J=8.8 Hz, 2H), 7.56 (ddd, J=8.0, 6.3, 1.2 Hz, 1H), 7.09 (ddd, J=8.8, 3.2, 0.2 Hz, 1H); MS (ESI): 225.0 (M+H$^+$).

Preparation of

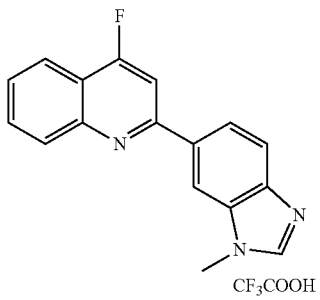 [SMILES: Cn1cnc2ccc(-c3cc(F)c4ccccc4n3)cc21 ; "CF3COOH"]

4-Fluoro-2-(1-methyl-1H-benzo[d]imidazol-6-yl)quinoline 2,2,2-trifluoroacetate: T485 was prepared using general procedure L. Reaction was performed on a 0.017 g scale. Product was purified by HPLC using ACN(0.05% TFA)/H2O (0.05% TFA). T485 was isolated as a white solid (0.09 g, 58%). $^1$H NMR (400 MHz, CD$_3$OD): δ 9.24 (s, 1H), 8.65-8.64 (m, 1H), 8.44 (dd, J=8.8, 2.4 Hz, 1H), 8.13-8.07 (m, 2H), 7.95 (d, J=11.6 Hz, 1H), 7.90-7.88 (m, 1H), 7.81 (ddd, J=8.4, 6.8, 1.6 Hz, 1H), 7.62 (ddd, J=8.0, 6.8, 0.8 Hz, 1H), 4.14 (s, 3H); MS (ESI): 278.1 (M+H$^+$).

Preparation of

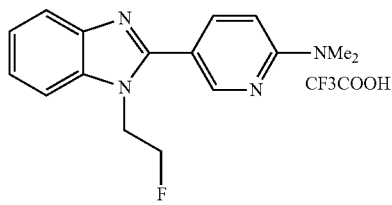

5-(1-(2-Fluoroethyl)-1H-benzo[d]imidazol-2-yl)-N,N-dimethylpyridin-2-amine 2,2,2-trifluoroacetate: T487 was prepared using general procedure A. Reaction was performed on a 0.02 g scale. Product was purified by HPLC using ACN (0.05% TFA)/$H_2O$ (0.05% TFA). T487 was isolated as a white solid (0.018 g, 77%). $^1$H NMR (400 MHz, $CD_3OD$): δ 8.55 (d, J=2.4 Hz, 1H), 7.98 (ddd, J=9.2, 2.4, 0.4 Hz, 1H), 7.93-7.91 (m, 1H), 7.81-7.78 (m, 1H), 7.63 (ddd, J=5.6, 2.4, 1.2 Hz, 1H), 6.93 (dd, J=9.2, 0.8 Hz, 1H), 5.00 (t, J=4.4 Hz, 1H), 4.89 (m, 1H), 4.83 (s, 6H), 4.84 (m, 1H), 4.79 (t, J=4.4 Hz, 1H); MS (ESI): 285.1 (M+H$^+$).

Preparation of

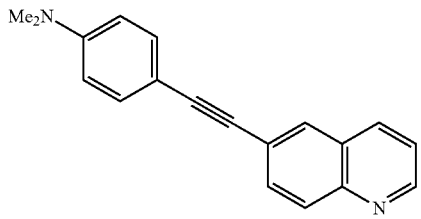 [SMILES: CN(C)c1ccc(C#Cc2ccc3ncccc3c2)cc1]

N,N-Dimethyl-4-(quinolin-6-ylethynyl)aniline: T517 was prepared using general procedure B. Reaction was performed on a 0.1 g scale. T517 was isolated as a yellow solid (0.1 g, 76%). NMR (400 MHz, $CDCl_3$): δ 8.87 (dd, J=4.4, 2.0 Hz, 1H), 8.09 (d, J=8.0 Hz, 1H), 8.03 (d, J=8.8 Hz, 1H), 7.95 (d, J=1.6 Hz, 1H), 7.78 (dd, J=8.8, 2.0 Hz, 1H), 7.44 (d, J=8.8 Hz, 2H), 7.39 (dd, J=8.4, 4.4 Hz, 1H), 6.67 (d, J=9.2 Hz, 2H), 3.00 (s, 6H); MS (ESI): 273.1 (M+H$^+$).

Preparation of

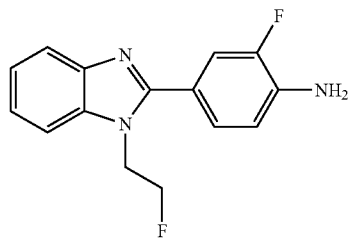 [SMILES: Nc1ccc(-c2nc3ccccc3n2CCF)cc1F]

2-Fluoro-4-O-(2-fluoroethyl)-1H-benzo[d]imidazol-2-yl) aniline: T524 was prepared using general procedure A. Reaction was performed on a 0.1 g scale. T524 was isolated as a white solid (0.09 g, 76%). $^1$H NMR (400 MHz, $CDCl_3$): δ 7.81-7.78 (m, 1H), 7.43-7.37 (m, 2H), 7.33-7.29 (m, 3H), 6.87 (dd, J=8.8, 8.4 Hz, 1H), 4.84 (t, J=4.8 Hz, 1H), 4.72 (t, J=5.2 Hz, 1H), 4.54 (t, J=4.8 Hz, 1H), 4.48 (t, J=5.2 Hz, 1H); MS (ESI): 274.1 (M+H$^+$).

Preparation of

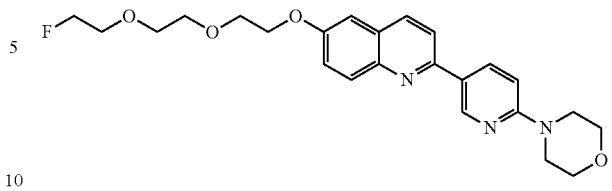

4-(5-(6-(2-(2-(2-Fluoroethoxy)ethoxy)ethoxy)quinolin-2-yl)pyridin-2-yl)morpholine: T539 was prepared using general procedure A. Reaction was performed on a 0.037 g scale. T539 was isolated as white solid (0.04 g, 77%). $^1$H NMR (400 MHz, DMSO-$d_6$): δ 8.99 (d, J=2.0 Hz, 1H), 8.41 (dd, J=8.8, 2.8 Hz, 1H), 8.25 (d, J=8.8 Hz, 1H), 8.03 (d, J=8.8 Hz, 1H), 7.91 (d, J=8.8 Hz, 1H), 7.41-7.37 (m, 2H), 6.98 (d, J=9.6 Hz, 1H), 4.58 (t, J=4.0 Hz, 1H), 4.46 (t, J=4.0 Hz, 1H), 4.25 (t, J=4.4 Hz, 2H), 3.84 (t, J=4.8 Hz, 2H), 3.74-3.69 (m, 6H), 3.66-3.56 (m, 4H), 3.58-3.56 (m, 4H); MS (ESI): 442.1 (M+H$^+$).

Preparation of

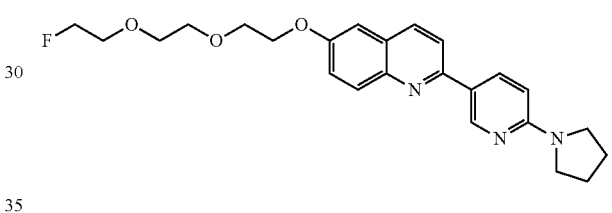

6-(2-(2-(2-Fluoroethoxy)ethoxy)ethoxy)-2-(6-(pyrrolidin-1-yl)pyridin-3-yl)quinoline: T545 was prepared using general procedure A. Reaction was performed on a 0.039 g scale. T545 was isolated as white solid (0.035 g, 66%). $^1$H NMR (400 MHz, $CDCl_3$): δ 8.86 (d, J=2.4 Hz, 1H), 8.34 (dd, J=8.8, 2.4 Hz, 1H), 8.01 (d, J=8.4 Hz, 1H), 7.97 (d, J=9.2 Hz, 1H), 7.73 (d, J=8.8 Hz, 1H), 7.36 (dd, J=9.2, 2.8 Hz, 1H), 7.06 (d, J=2.04 Hz, 1H), 6.49 (d, J=8.8 Hz, 1H), 4.62 (t, J=4.0 Hz, 1H), 4.50 (t, J=4.0 Hz, 1H), 4.26 (t, J=4.8 Hz, 2H), 3.94 (t, J=4.0 Hz, 2H), 3.80-3.71 (m, 6H), 3.55-3.52 (m, 4H), 2.05-2.02 (m, 4H); MS (ESI): 426.1 (M+H$^+$).

Preparation of

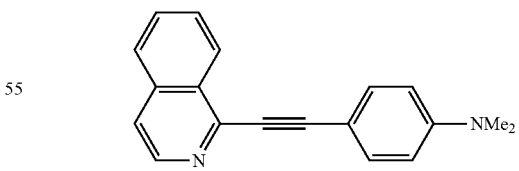

4-(Isoquinolin-1-ylethynyl)-N,N-dimethylaniline: T547 was prepared using general procedure B. Reaction was performed on a 0.064 g scale. T547 was isolated as yellow solid (0.1 g, 76%). $^1$H NMR (400 MHz, $CDCl_3$): δ 8.52 (d, J=7.2 Hz, 1H), 8.49 (d, J=6.0 Hz, 1H), 7.82 (d, J=8.0 Hz, 1H), 7.73-7.65 (m, 2H), 7.622-7.56 (m, 3H), 6.70 (d, J=9.2 Hz, 2H), 3.03 (s, 6H); MS (ESI): 273.1 (M+H$^+$).

Preparation of

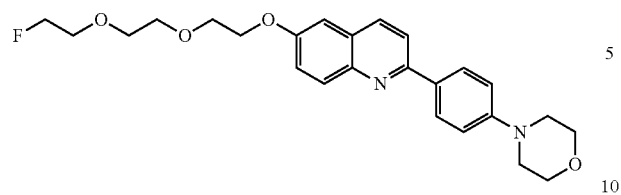

4-(4-(6-(2-(2-(2-Fluoroethoxy)ethoxy)ethoxy)quinolin-2-yl)phenyl)morpholine: T549 was prepared using general procedure A. Reaction was performed on a 0.033 g scale. T549 was isolated as white solid (0.035 g, 76%). $^1$H NMR (400 MHz, CDCl$_3$): δ 8.02 (d, J=8.8 Hz, 2H), 7.96 (dd, J=9.6, 8.8 Hz, 2H), 7.72 (d, J=8.4 Hz, 1H), 7.31 (dd, J=9.2, 3.2 Hz, 1H), 7.01 (d, J=2.4 Hz, 1H), 6.96 (d, J=9.2 Hz, 2H), 4.56 (t, J=4.0 Hz, 1H), 4.44 (t, J=4.4 Hz, 1H), 4.20 (t, J=4.8 Hz, 2H), 3.88 (t, J=4.8 Hz, 2H), 3.83 (t, J=4.8 Hz, 4H), 3.75-3.65 (m, 6H), 3.19 (t, J=4.8 Hz, 4H); MS (ESI): 441.1 (M+H$^+$).

Preparation of

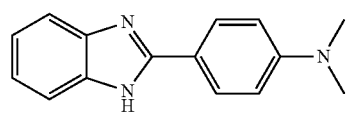 [SMILES: CN(C)c1ccc(-c2nc3ccccc3[nH]2)cc1]

T450: A mixture of 1,2-phenylenediamine (80 mg, 0.740 mmol) and 4-dimethylamino-benzyl chloride (80 mg, 0.436 mmol) in DMF (1.0 mL) was heated at 200° C. for 15 mins in a microwave. The crude product was purified by prepHPLC and neutralized with NaHCO3 to afford T450 (20 mg, 19.35%). $^1$H NMR (400 MHz, DMSO-d$_6$) δ 8.03-8.01 (d, 2H), 7.72-7.69 (m, 2H), 7.47-7.45 (m, 2H), 6.95-6.93 (m, 2H), 3.06 (s, 6H); MS (ESI): 238.1 (M+H$^+$).

Preparation of

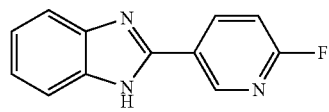

T452 A mixture of 2-bromobenzimidazole (0.05 g, 0.254 mmol), 2-fluoropyridine-5-boronic acid (0.036 g, 0.254 mmol), Potassium carbonate (0.190 ml, 0.381 mmol), and PdCl$_2$(dppf)$_2$DCM (10.36 mg, 0.013 mmol) in DMF (1.0 mL) was heated at 150° C. for 15 min. The crude product was purified by prepHPLC to afford T452 (6 mg, 11.09%). $^1$H NMR (400 MHz, CD$_3$CN) □ 9.01 (s, 1H), 8.70-8.65 (m, 1H), 7.81-7.79 (m, 2H), 7.45-7.43 (m, 2H), 7.29-7.26 (m, 1H); MS (ESI): 214.0 (M+H$^+$).

Preparation of

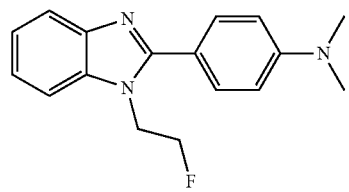 [SMILES: CN(C)c1ccc(-c2nc3ccccc3n2CCF)cc1]

T497 was prepared using general procedure D. The reaction was performed on a 20 mg scale of T450. T497 TFA salt was isolated (6 mg, 25.1%). $^1$H NMR (400 MHz, CD$_3$CN) δ 7.96-7.93 (m, 1H), 7.77-7.75 (m, 1H), 7.70-7.67 (m, 2H), 7.56-7.53 (m, 2H), 6.94-6.90 (m, 2H), 4.94-4.92 (m, 1H), 4.83-4.80 (m, 2H), 4.76-4.74 (m, 1H), 3.04 (s, 6H); MS (ESI): 284.10 (M+H$^+$).

Preparation of

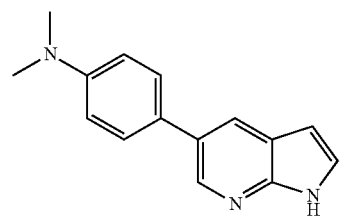 [SMILES: CN(C)c1ccc(-c2cnc3[nH]ccc3c2)cc1]

T555: To a solution of 5-bromo-7-azaindole (0.1 g, 0.508 mmol), 4-Dimethylaminophenyl boronic acid (0.084 g, 0.508 mmol), Copper(I) iodide (9.67 mg, 0.051 mmol), and Potassium carbonate (0.508 ml, 1.015 mmol) in DMF (2.0 mL) was added a solution of [1,1′-bis(diphenylphosphino)ferrocnee] dichloropalladium(II) (0.021 g, 0.025 mmol) in DCM (2.0 mL). The resulting mixture was heated at 120° C. in a microwave for 30 min. and then cooled to room temperature. The crude product was purified by prep HPLC to afford T555 TFA salt (0.010 g, 5.61%). $^1$H NMR (400 MHz, DMSO-d$_6$) δ 11.80 (s, 1H), 8.48-8.47 (m, 1H), 8.22-8.21 (m, 1H), 7.61-7.58 (m, 2H), 7.51-7.50 (m, 1H), 6.98-6.96 (m, 2H), 6.51-6.50 (m, 1H), 2.97 (s, 6H); MS (ESI): 238.7 (M+H$^+$).

Preparation of

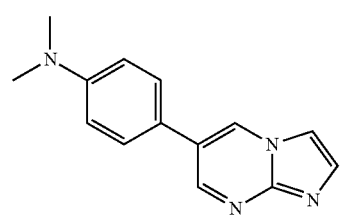 [SMILES: CN(C)c1ccc(-c2cnc3nccn3c2)cc1]

T558: To a solution of 6-bromoimidazo[1,2-a]pyrimidine (0.08 g, 0.404 mmol), 4-dimethylaminophenylboronic acid (0.087 g, 0.525 mmol), Copper(I) iodide (7.69 mg, 0.040 mmol) and Potassium carbonate (0.404 ml, 0.808 mmol) in DMF (2.0 mL) was added a solution of [1,1′-bis(diphenylphosphino)ferrocnee]dichloropalladium(11) (0.016 g, 0.020 mmol) in DCM (2.0 mL). The resulting mixture was microwaved at 120° C. for 30 min., cooled and filtered. The filtrate was concentrated in vacuo. The residue was purified on prep HPLC to afford T558 TFA salt (0.008 g, 0.023 mmol, 5.62% yield). $^1$H NMR (400 MHz, DMSO-d$_6$) δ 9.44 (m, 1H), 9.26 (m, 1H), (m, 2H), 7.69-7.66 (m, 2H), 6.90-6.88 (m, 2H), 2.99 (s, 3H); MS (ESI): 239.1 (M+H$^+$).

Preparation of

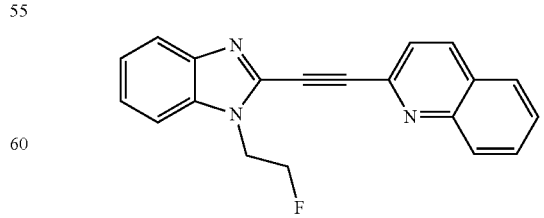

T496 was prepared using general procedure B. Reaction was performed on a 50 mg scale. Filtered and purified on prep HPLC to afford T496 TFA salt (0.02 g, 30.8%). $^1$H NMR (400 MHz, DMSO-d$_6$) δ 8.52-8.50 (m, 1H), 8.07-8.04 (m, 2H), 7.90-7.82 (m, 2H), 7.74-7.69 (m, 3H), 7.40-7.37 (m, 1H), 7.34-7.32 (m, 1H), 4.92-4.90 (m, 1H), 4.87-4.86 (m, 1H), 4.80 (m, 2H); MS (ESI): 316.1 (M+H⁺).

Preparation of

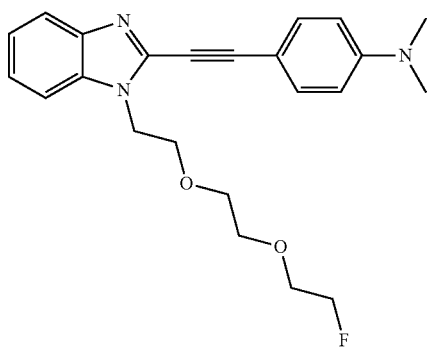 [SMILES: CN(C)c1ccc(C#Cc2nc3ccccc3n2CCOCCOCCF)cc1]

T508 was prepared using general procedure D from T481 and 2-(2-(2-fluoroethoxy)-ethoxy)ethyl 4-methylbenzenesulfonate. The reaction was performed on a 60 mg scale of T481. The crude product was purified by prep HPLC to afford T508 (5 mg, 5.51%). ¹H NMR (400 MHz, CD₃CN) δ 7.83-7.77 (m, 2H), 7.59-7.52 (m, 4H), 6.79-6.77 (m, 2H), 4.66-4.63 (m, 2H), 4.43-4.41 (m, 1H), 4.31-4.29 (m, 1H), 3.96-3.94 (m, 2H), 3.57-3.52 (m, 3H), 3.48-3.44 (m, 3H), 3.05 (s, 6H); MS (ESI): 396.20 (M+H⁺).

Preparation of

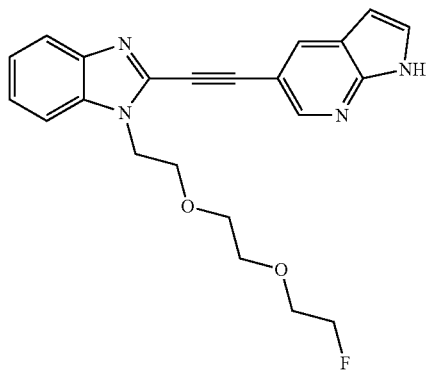 [SMILES: FCCOCCOCCn1c(C#Cc2cnc3[nH]ccc3c2)nc2ccccc21]

T527 was prepared using general procedure B from 2-bromo-1-(2-(2-(2-fluoroethoxy)ethoxy)ethyl)-1H-benzo[d]imidazole and 5-ethynyl-7-azaindole. The reaction was performed on a 105 mgs scale of 2-bromo-1-(2-(2-(2-fluoroethoxy)ethoxy)ethyl)-1H-benzo[d]imidazole. The crude product was purified by Prep HPLC to afford T527 TFA salt (0.01 g, 6.24%). ¹H NMR (400 MHz, CD₃CN) δ 10.14 (s, 1H), 8.59-8.58 (m, 1H), 8.32 (m, 1H), 7.82-7.80 (m, 1H), 7.73-7.71 (m, 1H), 7.52-7.45 (m, 3H), 6.61-6.59 (m, 1H), 4.69-4.67 (m, 2H), 4.42-4.40 (m, 1H), 4.30-4.28 (m, 1H), 3.98-3.95 (m, 2H), 3.58-3.52 (m, 3H), 3.49-3.44 (m, 3H); MS (ESI): 393.10 (M+H⁺).

Preparation of

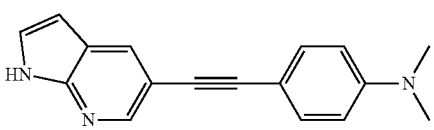

T528 was prepared using general procedure B. Reaction was performed on a 63 mgs scale. The crude product was purified by prep HPLC to afford T528 TFA salt (0.005 g, 4.21%). ¹H NMR (400 MHz, CD₃CN) δ 8.28 (m, 1H), 7.98 (m, 1H), 7.33-7.28 (m, 3H), 6.66-6.64 (m, 2H), 6.42-6.41 (m, 1H), 2.88 (s, 6H); MS (ESI): 261.1 (M+H⁺).

Preparation of

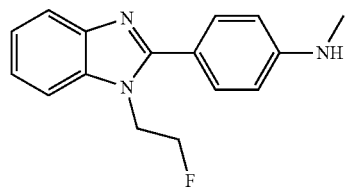 [SMILES: CNc1ccc(-c2nc3ccccc3n2CCF)cc1]

T534 was prepared using general procedure B from 2-bromo-1-(2-fluoroethyl)-1H-benzo[d]imidazole and tert-butyl methyl-4-(ethynyl)phenylcarbamate. Reaction was performed on a 53 mgs scale of 2-bromo-1-(2-fluoroethyl)-1H-benzo[d]imidazole. The crude product was purified by ISCO column to afford tert-butyl 4-((1-(2-fluoroethyl)-1H-benzo[d]imidazol-2-yl)ethynyl)phenyl(methyl)carbamate (0.03 g, 35.3%). It was dissolved in acetonitrile (0.5 mL). To this solution was added a solution of 20% sulfuric acid (1.5 mL, 5.63 mmol). The resulting mixture was stirred at room temperature for 20 minutes, diluted with water (2.0 mL) and purified by preparative HPLC to afford T534 as TFA salt (0.004 g, 12.88%). ¹H NMR (400 MHz, CD₃CN) δ 7.81-7.79 (m, 1H), 7.67-7.65 (m, 1H), 7.52-7.48 (m, 4H), 6.66-6.64 (m, 2H), 4.95-4.93 (m, 1H), 4.83-4.478 (m, 2H), 4.74-4.73 (m, 1H), 2.82 (s, 3H); MS (ESI): 294.1 (M+H⁺).

Preparation of

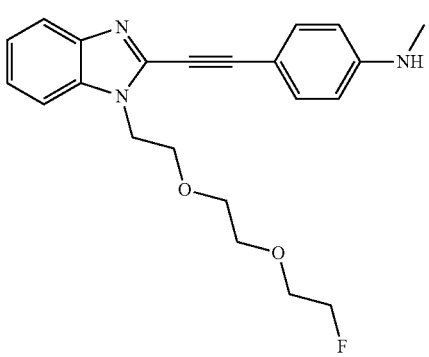 [SMILES: CNc1ccc(C#Cc2nc3ccccc3n2CCOCCOCCF)cc1]

T541 was prepared using general procedure B from 2-bromo-1-(2-(2-(2-fluoroethoxy)ethoxy)ethyl)-1H-benzo[d]imidazole and tert-butyl methyl-4-(ethynyl)phenylcarbamate. Reaction was performed on a 72 mgs scale of 2-bromo-1-(2-(2-(2-fluoroethoxy)ethoxy)ethyl)-1H-benzo[d]imidazole. The crude product was purified by ISCO column to afford tert-butyl 4-((1-(2-(2-(2-fluoroethoxy)ethoxy)ethyl)-1H-benzo[d]imidazol-2-yl)ethynyl)phenyl(methyl)carbamate (0.02 g, 19.21%). It was then dissolved in acetonitrile (1.0 mL). To this solution was added 20% Sulfuric acid (1.0 mL, 3.75 mmol). The reaction mixture was stirred at room temperature for 30 mins. The crude product was purified by prep HPLC to afford T541 TFA salt (0.004 g, 19.44%). ¹H NMR (400 MHz, CD₃CN) δ 7.78-7.76 (m, 1H), 7.70-7.68 (m, 1H), 7.51-7.45 (m, 4H), 6.66-6.64 (m, 2H), 4.63-4.60 (m, 2H), 4.44-4.42 (m, 1H), 4.32-4.30 (m, 1H), 3.95-3.92 (m, 2H), 3.57-3.53 (m, 3H), 3.48-3.45 (m, 3H), 2.82 (m, 3H). MS (ESI): 382.1 (M+H⁺).

Preparation of

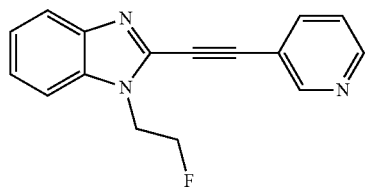

T551 was prepared using general procedure B from 2-ethynyl-1-(2-fluoroethyl)-1H-benzo[d]imidazole and 3-bromopyridine. Reaction was performed on a 40 mgs scale of 2-ethynyl-1-(2-fluoroethyl)-1H-benzo[d]imidazole. The crude product was purified by prep HPLC to afford T551 TFA salt (0.006 g, 7.44%). $^1$H NMR (400 MHz, CD$_3$CN): δ 8.92-8.91 (m, 1H), 8.70-8.69 (m, 1H), 8.14-8.11 (m, 1H), 7.79-7.77 (m, 1H), 7.64-7.62 (m, 1H), 7.55-7.40 (m, 3H), 4.94-4.92 (m, 1H), 4.82-4.80 (m, 2H), 4.76-4.73 (m, 1H); MS (ESI): 266.1 (M+H$^+$).

Preparation of

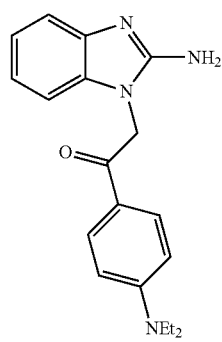

2-(2-amino-1H-benzo[d]imidazol-1-yl)-1-(4-(diethylamino)phenyl)ethanone: A solution of 2-aminobenzimidazole (197 mg, 1.5 mmol) and 2-Bromo-4'-(diethylamino)acetophenone (402 mg, 1.5 mmol) in MeOH (7 mL) was stirred at r.t. for 18 hours. The volatiles were removed in vacuo and NaHCO$_3$ (sat. aq., 30 mL) was added. The aqueous mixture was extracted with EtOAc (3×30 mL). The combined EtOAc extracts were dried with MgSO$_4$ and concentrated in vacuo. The residue was purified on silica gel eluting with a gradient up to 5:95 (MeOH:DCM) to isolate 2-(2-amino-1H-benzo[d]imidazol-1-yl)-1-(4-(diethylamino)phenyl)ethanone (176 mg, 36%) as a beige solid.

Preparation of

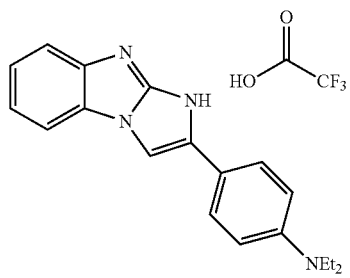

4-(1H-benzo[d]imidazo[1,2-a]imidazol-2-yl)-N,N-diethylaniline trifluoroacetate T506: A solution of 2-(2-amino-1H-benzo[d]imidazol-1-yl)-1-(4-(diethylamino)phenyl)ethanone (50 mg, 0.155 mmol) was heated to reflux in AcOH (2 mL) for several hours. The volatiles were removed in vacuo. The residue was dissolved in ACN and purified by semi-prep HPLC to isolate T506 (15 mg, 24%) as a beige solid. $^1$H NMR (400 MHz, CD$_3$OD): δ 1.19 (t, 6H), 3.48 (q, 4H), 6.92 (m, 2H), 7.42-7.51 (m, 2H), 7.62 (m, 3H), 7.91 (m, 1H), 8.06 (s, 1H); MS (ESI): 305.1 (M+H$^+$).

Preparation of

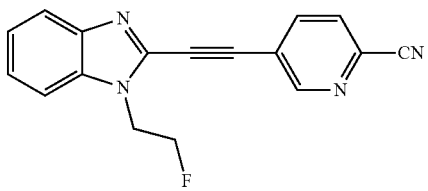 [SMILES: N#Cc1ccc(C#Cc2nc3ccccc3n2CCF)cn1]

T552 was prepared using general procedure B. Reaction was performed on a 40 mgs scale. The crude product was purified by prep HPLC to afford T552 TFA salt (0.006 g, 6.98%). $^1$H NMR (400 MHz, CD$_3$CN) δ 9.08-9.07 (m, 1H), 8.42-8.40 (m, 1H), 8.19-8.16 (m, 1H), 7.71-7.67 (m, 2H), 7.40-7.29 (m, 2H), 4.86 (m, 2H), 4.79-4.74 (m, 2H); MS (ESI): 291.0 (M+H$^+$).

Preparation of

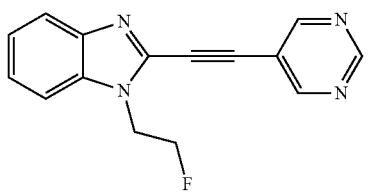 [SMILES: FCCn1c(C#Cc2cncnc2)nc2ccccc21]

T553 was prepared using general procedure B. Reaction was performed on a 40 mgs scale. The crude product was purified by prep HPLC to afford T553 TFA salt (0.006 g, 7.42%). NMR (400 MHz, CD$_3$CN) δ 9.23 (s, 1H), 9.05 (s, 2H), 7.82-7.79 (m, 1H), 7.67-7.65 (m, 1H), 7.52-7.43 (m, 2H), 4.94-4.92 (m, 1H), 4.84-4.80 (m, 2H), 4.78-4.75 (m, 1H); MS (ESI): 267.1 (M+H$^+$).

Preparation of

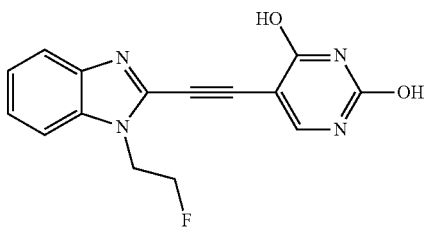 [SMILES: Oc1ncc(C#Cc2nc3ccccc3n2CCF)c(O)n1]

T554 was prepared using general procedure B. Reaction was performed on a 40 mgs scale. The crude product was purified by prep HPLC to afford T554 TFA salt (0.006 g, 6.85%). $^1$H NMR (400 MHz, DMSO-d$_6$) δ 11.63-11.61 (m, 1H), 11.56 (s, 1H), 8.17-8.16 (m, 1H), 7.64-7.59 (m, 2H), 7.33-7.23 (m, 2H), 4.84-4.83 (m, 1H), 4.76-4.68 (m, 3H); MS (ESI): 299.6 (M+H$^+$).

Preparation of

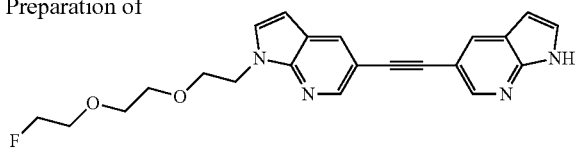

T564 was prepared using general procedure B from 5-bromo-1-(2-(2-(2-fluoroethoxy)ethoxy)ethyl)-1H-pyrrolo[2,3-b]pyridine and tert-butyl 5-ethynyl-1H-pyrrolo[2,3-b]pyridine-1-carboxylate, followed by a hydrolysis with NaOH. The reaction was performed on a 85 mg scale of 5-bromo-1-(2-(2-(2-fluoroethoxy)ethoxy)ethyl)-1H-pyrrolo[2,3-b]pyridine. T564 TFA salt was isolated (0.007 g, 5.40%). NMR (400 MHz, CD$_3$CN) δ 11.53 (s, 1H), 8.50-8.49 (m, 2H), 8.41-8.4 (m, 2H), 8.17 (m, 2H), 7.59-7.58 (m, 1H), 7.53-7.52 (m, 1H), 6.69-6.68 (m, 1H), 6.54-6.53 (m, 1H), 4.53-4.51 (m, 1H), 4.48-4.46 (m, 2H), 4.41-4.39 (m, 1H), 3.86-3.84 (m, 2H), 3.64-3.62 (m, 1H), 3.59-3.53 (m, 5H); MS (ESI): 393.5 (M+H$^+$).

Preparation of

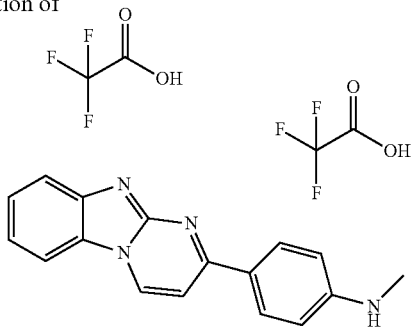

4-(Benzo[4,5]imidazo[1,2-a]pyrimidin-2-yl)-N-methylaniline bistrifluoracetate T522: To a suspension of 4-(benzo[4,5]imidazo[1,2-a]pyridin-2-yl)-aniline (25 mg, 0.10 mmol) in MeOH (3 mL) at r.t. was added paraformaldehyde (110 mg, 3.7 mmol) followed by NaCNBH$_3$ (40 mg, 0.63 mmol). The mixture was heated in a microwave reactor at 100° C. for 20 minutes. The volatiles were removed in vacuo. The residue was dissolved in EtOAc (15 mL), washed with NaHCO$_3$ (2×15 mL), and brine (15 mL). The EtOAc layer was dried with MgSO$_4$, filtered and evaporated to obtain an oil that was purified by semi-prep HPLC. 4-(benzo[4,5]imidazo[1,2-a]pyrimidin-2-yl)-N,N-dimethylaniline bistrifluoracetate (2.0 mg, 4%) was obtained as an orange solid. $^1$H NMR (400 MHz, CD$_3$OD) δ 3.17 (s, 6H), 6.91 (m, 2H), 7.64 (m, 1H), 7.73-7.80 (m, 2H), 8.07 (d, J=7.6 Hz, 1H), 8.26 (m, 1H), 8.34 (m, 2H), 9.33 (d, J=7.6 Hz, 1H). MS (ESI): 275.1 (M+H$^+$).

Preparation of

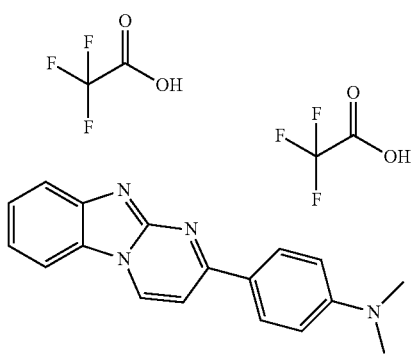 [SMILES: CN(C)c1ccc(-c2ccn3c(n2)nc2ccccc23)cc1 ; O=C(O)C(F)(F)F ; O=C(O)C(F)(F)F]

4-(Benzo[4,5]imidazo[1,2-a]pyrimidin-2-yl)-N,N-dimethylaniline bistrifluoracetate T521 was also obtained from the preceding reaction (1 mg, 2%). $^1$H NMR (400 MHz, CD$_3$OD) δ 2.92 (s, 3H), 6.75 (m, 2H), 7.63 (m, 1H), 7.71-7.79 (m, 2H), 8.02 (d, J=7.6 Hz, 1H), 8.24-8.30 (m, 3H), 9.30 (d, J=7.6 Hz, 1H). MS (ESI): 289.1 (M+H$^+$)

Preparation of

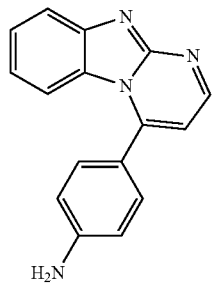 [SMILES: Nc1ccc(-c2ccnc3nc4ccccc4n23)cc1]

4-(Benzo[4,5]imidazo[1,2-a]pyrimidin-4-yl)aniline T520: To a solution of 4-(4-nitrophenyl)benzo[4,5]imidazo[1,2-a]pyrimidine (35 mg, 0.12 mmol) in MeOH:THF:H2O (1:1:3, 2 mL) was added a large excess of Na$_2$S$_2$O$_4$. The reaction was quenched with NaHCO$_3$ (sat. aq.) and extracted with EtOAc. The EtOAc layer was washed with H$_2$O and then brine. The EtOAc layer was dried with MgSO4. The residue was purified by semi-prep HPLC to give T520 as TFA salt (3 mg, 7%). $^1$H NMR (400 MHz, DMSO-d$_6$) δ 6.81 (m, 2H), 7.27 (m, 1H), 7.36 (m, 2H), 7.45 (m, 2H), 7.67 (m, 1H), 7.88 (m, 1H), 9.01 (d, J=4.8 Hz, 1H). MS (ESI): 261.1 (M+H$^+$).

Preparation of

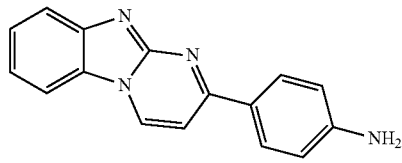 [SMILES: Nc1ccc(-c2ccn3c(n2)nc2ccccc23)cc1]

4-(Benzo[4,5]imidazo[1,2-a]pyrimidin-2-yl)aniline T518: To a suspension of 2-(4-nitrophenyl)benzo[4,5]imidazo[1,2-a]pyrimidine (58 mg, 0.20 mmol) in ethanol (3 mL) was added SnCl$_2$.2H$_2$O (361 mg, 1.6 mmol). The solution was refluxed for 1.5 hours and then the volatiles were removed under vacuum. The residue was dissolved in DCM, washed with 1 N NaOH, and then H$_2$O. The DCM layer was dried with MgSO$_4$. The crude product was purified on flash chromatography (silica gel, 5% MeOH/DCM) to provide T518 as a yellow solid (35 mg, 67%). $^1$H NMR (400 MHz, DMSO-d$_6$) δ 5.94 (s, 2H), 6.70 (m, 2H), 7.34 (m, 1H), 7.47 (m, 1H), 7.61 (d, J=7.6 Hz, 1H), 7.75 (m, 1H), 8.08 (m, 2H), 8.21 (m, 1H), 9.34 (d, J=7.6 Hz, 1H). MS (ESI): 261.1 (M+H$^+$).

Preparation of

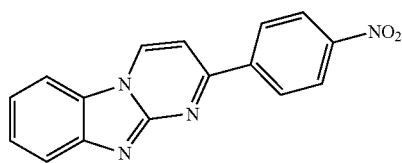 [SMILES: O=[N+]([O-])c1ccc(-c2ccn3c(n2)nc2ccccc23)cc1]

2-(4-Nitrophenyl)benzo[4,5]imidazo[1,2-a]pyrimidine T511: A solution of (E)-3-(dimethylamino)-1-(4-nitrophenyl)prop-2-en-1-one (410 mg, 1.9 mmol) and 1H-benzo[d]imidazol-2-amine (248 mg, 1.9 mmol) in AcOH (10 ml) was heated to reflux overnight. The volatiles were removed by rotary evaporation and the residue was partitioned between DCM and aqueous NaHCO$_3$. The mixture was filtered to obtain pure 2-(4-nitrophenyl)benzo[4,5]imidazo[1,2-a]pyrimidine (85 mg, 15%) as a yellow solid. $^1$H NMR (400 MHz, DMSO-d$_6$) δ 7.47 (m 1H), 7.59 (m, 1H), 7.90 (d, J=7.2 Hz, 1H), 7.96 (m, 1H), 8.38 (m, 1H), 8.44 (m, 2H), 8.61 (m, 2H), 9.72 (d, J=7.2 Hz, 1H). MS (ESI): 291.0 (M+H$^+$)

Preparation of

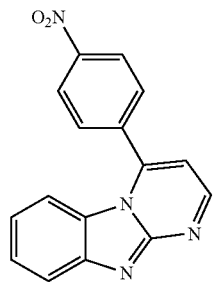 [SMILES: O=[N+]([O-])c1ccc(-c2ccnc3nc4ccccc4n23)cc1]

4-(4-Nitrophenyl)benzo[4,5]imidazo[1,2-a]pyrimidine T512: The DCM layer from the preceding reaction was washed with H$_2$O and dried (MgSO$_4$). The residue was purified by flash chromatography (silica gel, 100% EtOAc) to give 4-(4-nitrophenyl)benzo[4,5]imidazo[1,2-a]pyrimidine (120 mg, 22%) as a yellow solid. $^1$H NMR (400 MHz, DMSO-d$_6$) δ 6.65 (m 1H), 7.09-7.14 (m, 2H), 7.47-7.52 (m, 1H), 7.90 (m, 1H), 8.08 (m, 2H), 8.54 (m, 2H), 8.91 (d, J=4.0 Hz, 1H). MS (ESI): 291.1 (M+H$^+$)

Preparation of

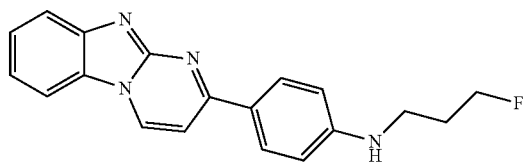 [SMILES: FCCCNc1ccc(-c2ccn3c(n2)nc2ccccc23)cc1]

4-(Benzo[4,5]imidazo[1,2-a]pyrimidin-2-yl)-N-(3-fluoropropyl)aniline T542: To 3-fluoropropan-1-ol (4 mg, 0.05 mmol) in 0.5 mL DCM was added Dess-Martin reagent (42 mg, 0.1 mmol). The mixture was stirred at rt for 1 h and filtered directly into a mixture of 4-(benzo[4,5]imidazo[1,2-a]pyrimidin-2-yl)aniline (4 mg, 0.015 mmol) and NaBH(OAc)$_3$ (43 mg, 0.2 mmol) with stirring. After vigorously stirred for 5 min, reaction was quenched by adding 0.5 M NaOH (2 mL). The mixture was extracted with EtOAc (3×10 mL) and the organic phase was dried over MgSO4 and concentrated. The crude product was purified by HPLC to afford 4-(Benzo[4,5]imidazo[1,2-a]pyrimidin-2-yl)-N-(3-fluoropropyl)aniline as a yellow solid (2.7 mg, 33%). $^1$H NMR (400 MHz, CDCl$_3$): δ 8.76 (d, J=7.2 Hz, 1H), 7.88 (m, 4H), 7.55 (d, J=7.2 Hz, 1H), 7.53 (m, 1H), 7.40 (m, 1H), 6.47 (d, J=9.2 Hz, 1H), 4.68 (t, J=5.2 Hz, 1H), 4.56 (t, J=5.2 Hz, 1H), 3.34 (t, J=6.8 Hz, 2H), 2.09 (m, 1H), 2.02 (m, 1H); MS (ESI): 321 (M+H$^+$).

Preparation of

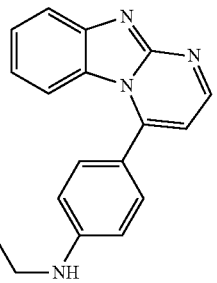

4-(Benzo[4,5]imidazo[1,2-a]pyrimidin-4-yl)-N-(3-fluoropropyl)aniline T544 was prepared using the procedure for 4-(Benzo[4,5]imidazo[1,2-a]pyrimidin-2-yl)-N-(3-fluoropropyl)aniline from 4-(benzo[4,5]imidazo[1,2-a]pyrimidin-2-yl)aniline (10 mg, 0.038 mmol) and 3-fluoropropan-1-ol (8 mg, 0.1 mmol). The product T544 was obtained as a yellow solid (7 mg, 33%). $^1$H NMR (400 MHz, CDCl$_3$): δ 8.93 (d, J=4.4 Hz, 1H), 8.19 (d, J=8.4 Hz, 1H), 7.65 (m, 1H), 7.45 (m, 2H), 7.35 (d, J=8.0 Hz, 1H), 7.29 (m, 1H), 7.17 (d, J=4.4 Hz, 1H), 6.83 (m, 2H), 4.73 (t, J=5.2 Hz, 1H), 4.61 (t, J=5.2 Hz, 1H), 3.47 (t, J=6.8 Hz, 2H), 2.16 (m, 1H), 2.08 (m, 1H); MS (ESI): 321 (M+H$^+$).

Preparation of

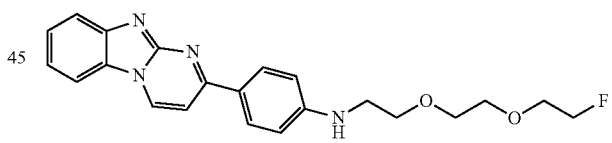

4-(Benzo[4,5]imidazo[1,2-a]pyrimidin-2-yl)-N-(2-(2-(2-fluoroethoxy)ethoxy)ethyl)-aniline T557: 4-(benzo[4,5]imidazo[1,2-a]pyrimidin-2-yl)-N-(2-(2-(2-fluoroethoxy)ethoxy)ethyl)aniline was prepared using the procedure for 4-(Benzo[4,5]imidazo[1,2-a]pyrimidin-2-yl)-N-(3-fluoropropyl)aniline from 4-(benzo[4,5]imidazo[1,2-a]pyrimidin-2-yl)aniline (10 mg, 0.038 mmol) and 2-(2-(2-hydroxyethoxy)ethoxy)ethyl 4-methylbenzenesulfonate (23 mg, 0.075 mmol). The product T557 was obtained as a yellow solid (1.2 mg, 5.1%). NMR (400 MHz, CDCl$_3$): δ 9.31 (d, J=7.6 Hz, 1H), 8.25 (m, 2H), 8.02 (d, J=7.2 Hz, 1H), 7.78-7.75 (m, 1H), 7.72 (m, 1H), 7.61 (m, 1H), 6.80 (d, J=9.2 Hz, 2H), 4.56 (m, 1H), 4.45 (m, 1H), 3.75 (m, 1H), 3.71 (t, J=5.2 Hz, 2H), 3.69-3.65 (m, H), 3.47-3.43 (m, H); MS (ESI): 395 (M+H$^+$).

Preparation of

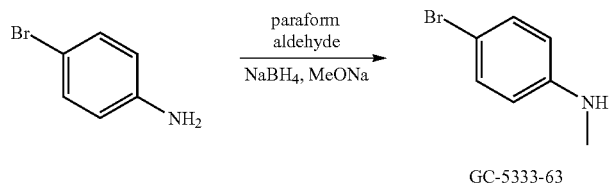

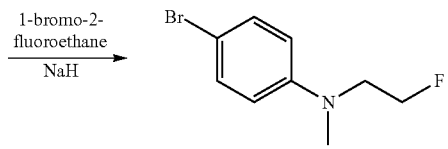

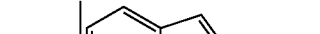

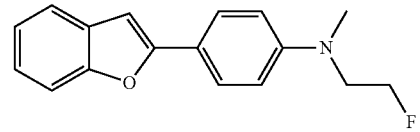

T478

Synthesis of GC-5333-63: 4-Bromoaniline (10 g, 58 mmol) was dissolved in MeOH (20 ml). To the reaction mixture was added paraformaldehyde (5.18 ml, 174 mmol) and 25% sodium methoxide solution (48.3 ml, 291 mmol). The mixture was heated at 65° C. for 1 h and allowed to cool to room temperature. Sodium borohydride (6.17 ml, 174 mmol) was added into the reaction mixture portionwise. The reaction mixture was heated for another 2 h. The mixture was concentrated, diluted with water (50 mL), extracted with EtOAc (3×50 mL). The organic layers were combined, dried and concentrated in vacuo. The residue was purified on flash column chromatography (silca gel, 10% EtOAc/DCM) to afford GC-5333-63 (7.5 g, 69%). $^1$H-NMR (400 MHz, CDCl$_3$): δ 7.27-7.25 (m, 2H), 6.50-6.48 (m, 2H), 3.80. (br, 1H), 2.81 (s, 3H); MS (ESI): 186.1 (M+H$^+$).

GC-5333-65 was prepared using general procedure D. Reaction was performed on a 4 g scale. GC-5333-65 was eluted out in 20% EtOAc: Hexanes mixture in a gradient elution on a Biotage purification system (500 mg, 10%) as a colorless oil. $^1$H-NMR (400 MHz, CDCl$_3$): δ 7.31-7.29 (m, 2H), 6.59-5.58 (m, 2H), 4.59 (dt, J=47.2, 5.2 Hz, 2H), 3.62 (dt, J=24.8, 5.2 Hz, 2H), 2.99 (s, 3H); MS (ESI): 232.1 (M+H$^+$).

T478 was prepared using general procedure A. Reaction was performed on a 30 mg scale. T78 was isolated as a solid (8 mg, 23%). $^1$H-NMR (400 MHz, CDCl$_3$): δ 7.75-7.72 (m, 2H), 7.57-7.52 (m, 2H), 7.24-7.19 (m, 2H), 6.81-6.76 (m, 3H), 4.63 (dt, J=47.2, 5.2 Hz, 2H), 3.70 (dt, J=24.8, 5.2 Hz, 2H), 3.01 (s, 3H); MS (ESI): 270.1 (M+H$^+$).

3. Preparation of Radiolabeling Precursors:
Preparation of

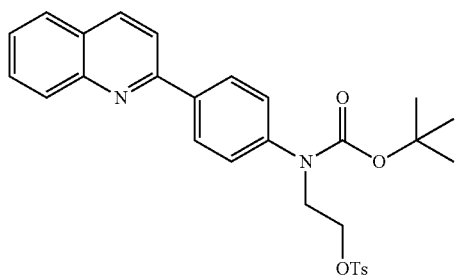 [SMILES: Cc1ccc(S(=O)(=O)OCCN(C(=O)OC(C)(C)C)c2ccc(-c3ccc4ccccc4n3)cc2)cc1]

2-((tert-Butoxycarbonyl)(4-(quinolin-2-yl)phenyl)amino) ethyl-4-methyl-benzene-sulfonate T411P was prepared using general procedure D. Reaction was performed on 0.187 g scale. T411P was isolated as an oil (0.014 g, 6%); $^1$H NMR (400 MHz, CDCl$_3$): δ 8.28-8.19 (m, 2H), 8.09 (dt, J=8.8, 2.4 Hz, 1H), 7.88-7.82 (m, 2H), 7.76-7.70 (m, 3H), 7.54 (ddd, J=8.0, 6.8, 0.8 Hz, 1H), 7.30-7.24 (m, 4H), 4.21 (t, J=5.6 Hz, 2H), 3.90 (t, J=5.6 Hz, 2H), 2.34 (s, 3H), 1.40 (s, 9H); MS (ESI): 519.1 [M+H$^+$], 541.1 (M+Na$^+$).

Preparation of

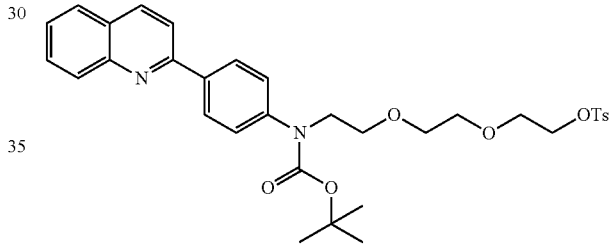

2,2-Dimethyl-4-oxo-5-(4-(quinolin-2-yl)phenyl)3,8,11-trioxa-azamidecan-13-yl-4-methylbenzenesulfonate T442P was prepared using general procedure D.

Reaction performed on a 0.032 g scale. T442P was isolated as a light yellow oil (0.028 g, 46%); $^1$H NMR (400 MHz, CDCl$_3$): δ 8.21 (d, J=8.4 Hz, 2H), 8.11 (d, J=8.8 Hz, 2H), 7.86 (d, J=8.8 Hz, 1H), 7.82 (d, J=8.0 Hz, 1H), 7.75 (dt, J=8.0, 2.0 Hz, 2H), 7.70 (d, J=6.8 Hz, 1H), 7.52 (t, J=8.0 Hz, 1H), 7.38 (d, J=8.4 Hz, 1H), 7.27 (d, J=8.0 Hz, 1H), 4.12 (t, J=4.8 Hz, 2H), 3.83 (t, J=4.8 Hz, 2H), 3.64-3.59 (m, 4H), 3.52 (s, 4H), 2.38 (s, 3H), 1.43 (s, 9H); MS (ESI): 607.2 M+H$^+$).

Preparation of

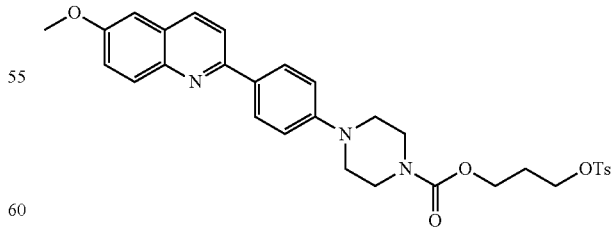

3-(Tosyloxy)propyl-4-(4-(6-methoxyquinolin-2-yl)phenyl)piperazine-1-carboxylate T498P was prepared using General experimental procedure E for N-alkylation using Cs$_2$CO$_3$ as the base (method E) was used. Reaction performed on a 0.032 g scale. Product eluted out in 20% EtOAc:DCM mixture in a gradient elution on a Combiflash purification system. T498P was isolated as a light yellow color solid (0.010 g, 18%). $^1$H NMR (400 MHz, CDCl$_3$): δ 8.06 (br t, J=8.8 Hz, 4H), 7.79 (dt, J=8.4 and 1.6 Hz, 2H), 7.77 (d, J=8.4 Hz, 1H), 7.36-7.32 (m, 3H), 7.06 (d, J=2.4 Hz, 1H), 7.00 (dt, J=8.8 and 1.6 Hz, 2H), 4.14 (q, J=7.2 Hz, 4H), 3.93 (s, 3H), 3.60 (br s, 4H), 3.22 (br s, 4H), 2.43 (s, 3H), 2.01 (q, J=8.0 Hz, 2H); LC-MS (ESI): (M+H$^+$).

Preparation of

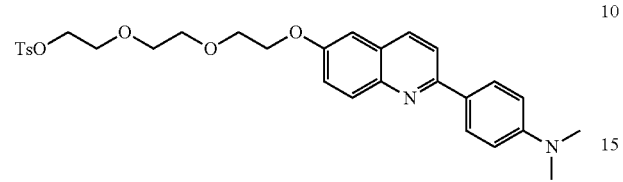

2-(2-(2-((2-(4-(Dimethylamino)phenyl)quinolin-6-yl)oxy)ethoxy)ethoxy)ethyl-4-methylbenzenesulfonate T510P was prepared using general procedure E. Reaction performed on a 0.050 g scale. T510P was isolated as yellow solid (0.030 g, 29%). $^1$H NMR (400 MHz, CDCl$_3$): δ 8.05 (dt, J=8.0, 2.0 Hz, 2H), 7.98 (d, J=8.8 Hz, 2H), 7.77 (dt, J=8.8, 2.0 Hz, 2H), 7.76 (d, J=8.8 Hz, 1H), 7.33 (dd, J=9.2, 2.8 Hz, 1H), 7.28 (dd, J=8.4, 0.4 Hz, 2H), 7.04 (d, J=2.8 Hz, 1H), 6.81 (dt, J=8.8, 2.0 Hz), 4.21 (t, J=4.8 Hz, 2H), 4.15 (t, J=4.8 Hz, 2H), 3.88 (t, J=4.8 Hz, 2H), 3.70-3.66 (m, 3H), 3.63-3.60 (m, 3H), 3.01 (s, 3H), 3.39 (s, 6H); MS (ESI): 551.2 (M+H$^+$), 324 (M+Na$^+$).

Preparation of

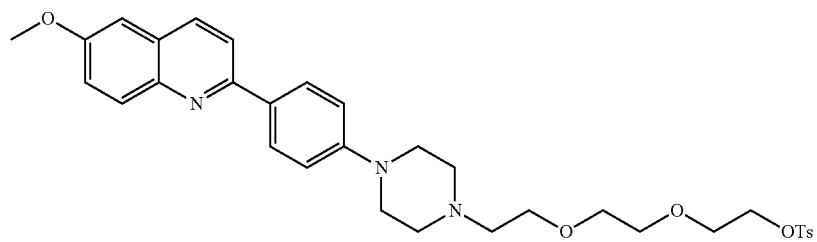 [SMILES: COc1ccc2nc(-c3ccc(N4CCN(CCOCCOCCOS(=O)(=O)c5ccc(C)cc5)CC4)cc3)ccc2c1]

2-(4-(4-(2-(6-Methoxyquinolin-2-yl)phenyl)piperazin-1-yl)ethoxy)ethoxy)ethyl-4-methylbenzenesulfonate T530P was prepared using general procedure E. Reaction was performed on a 0.1 g scale. T530P was isolated as off white oil (0.046 g, 24%). $^1$H NMR (400 MHz, CDCl$_3$): δ 7.99 (dt, J=8.8, 2.0 Hz, 2H), 8.01 (d, J=8.4 Hz, 1H), 7.97 (d, J=9.2 Hz, 1H), 7.73 (dt, J=8.4, 2.0 Hz, 1H), 7.71 (d, J=9.2 Hz, 1H), 7.29-7.25 (m, 2H), 6.99 (d, J=2.8 Hz, 1H), 6.95 (dt, J=8.8, 2.0 Hz, 2H), 4.09 (t, J=4.8 Hz, 2H), 3.86 (s, 3H), 3.64 (t, J=4.8 Hz, 2H), 3.61-3.52 (m, 6H), 3.25 (t, J=4.8 Hz, 4H), 2.64-2.60 (m, 6H); MS (ESI): 606.1 (M+H$^+$).

Preparation of

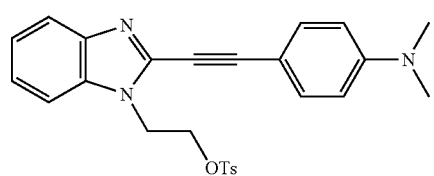 [SMILES: Cc1ccc(S(=O)(=O)OCCn2c(C#Cc3ccc(N(C)C)cc3)nc3ccccc32)cc1]

2-(2-((4-(Mimethylamino)phenyl)ethynyl)-1H-benzo[d]imidazol-1-yl)ethyl-4-methylbenzenesulfonate: T482P was prepared using general procedure E. Reaction was performed on a 140 mg scale of T481. T482P was isolated as a white solid (135 mg, 55%). $^1$H NMR (400 MHz, CDCl$_3$): δ 7.67 (m, 1H), 7.44-7.48 (m, 4H), 7.25-7.27 (m, 3H), 7.05 (d, J=8.4 Hz, 2H), 6.68 (m, 2H), 4.57 (t, J=5.6 Hz, 2H), 4.43 (t, J=5.6 Hz, 2H), 3.04 (s, 6H), 2.33 (s, 3H); MS (ESI): 460 (M+H$^+$).

Preparation of

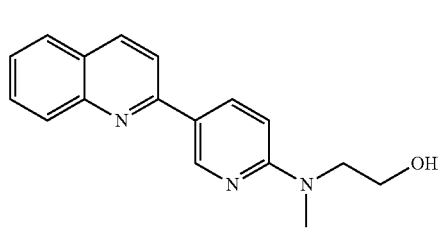 [SMILES: CN(CCO)c1ccc(-c2ccc3ccccc3n2)cn1]

2-(Methyl(5-(quinolin-2-yl)pyridin-2-yl)amino)ethanol: T491 was prepared using general procedure M. Reaction was performed on a 110 mg scale of T455. T491 was isolated as a light yellow solid (120 mg, 88%). NMR (400 MHz, CDCl$_3$): δ 8.86 (dd, J=2.4, 0.8 Hz, 1H), 8.41 (dd, J=8.8, 2.4 Hz, 1H), 8.15 (d, J=8.4 Hz, 1H), 8.09 (dd, J=8.4, 0.8 Hz, 1H), 7.78 (m, 2H), 7.69 (m, 1H), 7.48 (m, 1H), 6.69 (dd, J=8.8, 0.8 Hz, 1H), 4.92 (br s, 1H), 3.90 (t, J=4.6 Hz, 2H), 3.81 (t, J=4.6 Hz, 2H), 3.15 (s, 3H); MS (ESI): 280 (M+H$^+$).

Preparation of

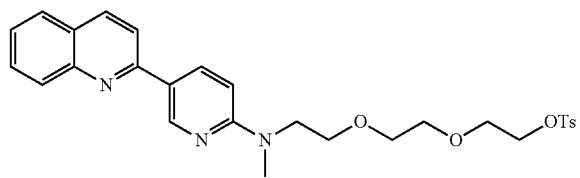 [SMILES: Cc1ccc(S(=O)(=O)OCCOCCOCCN(C)c2ccc(-c3ccc4ccccc4n3)cn2)cc1]

2-(2-(2-(Methyl(5-(quinolin-2-yl)pyridin-2-yl)amino)ethoxy)ethoxy)ethyl 4-methylbenzenesulfonate: T502P was prepared using general procedure D. Reaction was performed on a 94 mg scale of T491. T502P was isolated as light yellow oil (86 mg, 49%). $^1$H NMR (400 MHz, CDCl$_3$): δ 8.92 (dd, J=2.4, 0.8 Hz, 1H), 8.37 (dd, J=8.8, 2.4 Hz, 1H), 8.15 (d, J=8.8 Hz, 1H), 8.09 (dd, J=8.4, 1.0 Hz, 1H), 7.80 (m, 2H), 7.69 (m, 1H), 7.48 (m, 1H), 6.65 (dd, J=8.4, 0.8 Hz, 1H), 4.15 (m, 2H), 3.84 (t, J=6.2 Hz, 2H), 3.66-3.72 (m, 4H), 3.57 (t, J=1.4 Hz, 2H), 3.17 (s, 3H), 2.42 (s, 3H); MS (ESI): 522 (M+H$^+$).

Preparation of

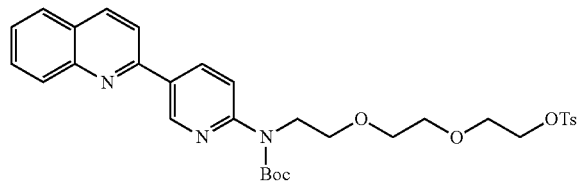 [SMILES: Cc1ccc(S(=O)(=O)OCCOCCOCCN(C(=O)OC(C)(C)C)c2ccc(-c3ccc4ccccc4n3)cn2)cc1]

2,2-Dimethyl-4-oxo-5-(5-(quinolin-2-yl)pyridin-2-yl)-3,8,11-trioxa-5-azamidecan-13-yl 4-methylbenzenesulfonate: T525P was prepared using general procedure D. Reaction was performed on a 67.0 mg scale of T503. T525P was isolated as colorless oil (80.5 mg, 65%). $^1$H NMR (400 MHz, CDCl$_3$): δ 9.10 (dd, J=2.8, 0.8 Hz, 1H), 8.44 (dd, J=4.6, 2.6 Hz, 1H), 8.22 (d, J=8.4 Hz, 1H), 8.14 (d, J=8.4 Hz, 1H), 7.71-7.86 (m, 6H), 7.54 (m, 1H), 7.29 (m, 2H), 4.22 (t, J=6.4 Hz, 2H), 4.10 (m, 2H), 3.70 (t, J=6.4 Hz, 2H), 3.61 (m, 2H), 3.53 (m, 2H), 3.49 (m, 2H), 2.40 (s, 3H); MS (ESI): 608 (M+H$^+$).

Preparation of

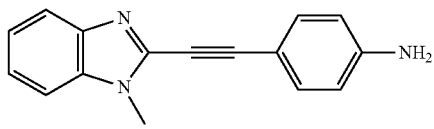 [SMILES: Cn1c(C#Cc2ccc(N)cc2)nc2ccccc21]

4-((1-Methyl-1H-benzo[d]imidazol-2-yl)ethynyl)aniline: CL-5311-144 Intermediate for T540P was prepared using general procedure E. Reaction was performed on a 277 mg scale of T464. CL-5311-144 was isolated as a light yellow solid (140 mg, 48%). $^1$H NMR (400 MHz, CD$_3$OD): δ 7.58 (m, 1H), 7.47 (m, 1H), 7.09-7.38 (m, 4H), 6.66 (m, 2H), 3.91 (s, 3H); MS (ESI): 248 (M+H$^+$).

Preparation of

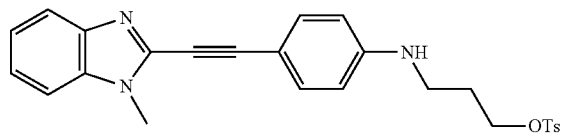 [SMILES: Cc1ccc(S(=O)(=O)OCCCNc2ccc(C#Cc3nc4ccccc4n3C)cc2)cc1]

3-(4-((1-Methyl-1H-benzo[d]imidazol-2-yl)ethynyl)phenylamino)propyl 4-methylbenzenesulfonate: T540P was prepared using general procedure Q. Reaction was performed on an 80.0 mg scale of CL-5311-144. T540P was isolated as a light yellow solid (83.0 mg, 56%). $^1$H NMR (400 MHz, CD$_2$Cl$_2$): δ 7.77 (m, 2H), 7.68 (m, 1H), 7.44 (m, 2H), 7.24-7.38 (m, 5H), 6.53 (m, 2H), 4.14 (t, J=6.0 Hz, 2H), 4.09 (br t, J=6.0 Hz, 2H), 3.89 (s, 3H), 3.24 (m, 2H), 2.44 (s, 3H), 1.95 (m, 2H); MS (ESI): 460 (M+H$^+$).

Preparation of

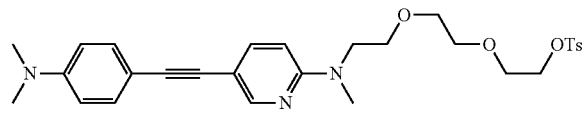

2-(2-(2-((5-((4-(Dimethylamino)phenyl)ethynyl)pyridin-2-yl)(methyl)amino)ethoxy)ethoxy)ethyl 4-methylbenzenesulfonate: T546P was prepared using general procedure D. Reaction was performed on a 35 mg scale of T526. T546P was isolated as a colorless gum (30.2 mg, 47%). $^1$H NMR (400 MHz, CDCl$_3$): δ 8.26 (dd, J=2.4, 0.8 Hz, 1H), 7.78 (m, 2H), 7.50 (dd, J=8.8, 2.4 Hz, 1H), 7.35 (m, 2H), 7.31 (m, 2H), 6.64 (m, 2H), 6.44 (d, J=8.8 Hz, 1H), 4.12 (t, J=4.8 Hz, 2H), 3.74 (t, J=5.6 Hz, 2H), 3.61-3.64 (m, 4H), 3.52-3.53 (m, 4H), 3.07 (s, 3H), 2.96 (s, 6H), 2.42 (s, 3H); MS (ESI): 538 (M+H$^+$).

Preparation of

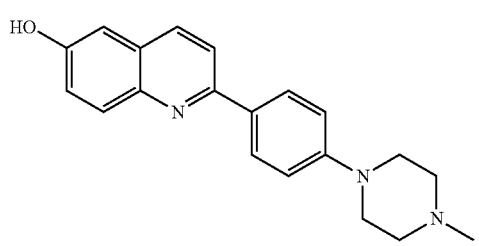 [SMILES: CN1CCN(c2ccc(-c3ccc4cc(O)ccc4n3)cc2)CC1]

2-(4-(4-Methylpiperazin-1-yl)phenyl)quinolin-6-ol: CL-5311-146 Intermediate for T550P was prepared using general procedure A. Reaction was performed on a 208 mg scale of 2-chloroquinolin-6-ol. CL-5311-146 was isolated as a grey solid (214 mg, 58%). $^1$H NMR (400 Hz, DMSO-d$_6$): δ 9.88 (s, 1H), 8.10 (d, J=8.8 Hz, 1H), 8.06 (m, 2H), 7.89 (d, J=8.8 Hz, 1H), 7.81 (d, J=9.2 Hz, 1H), 7.25 (dd, J=9.2, 2.8 Hz, 1H), 7.09 (d, J=2.8 Hz, 1H), 7.02 (m, 2H), 3.22 (br, 4H), 2.45 (br s, 4H), 2.22 (s, 3H); MS (ESI): 320 (M+H$^+$).

Preparation of

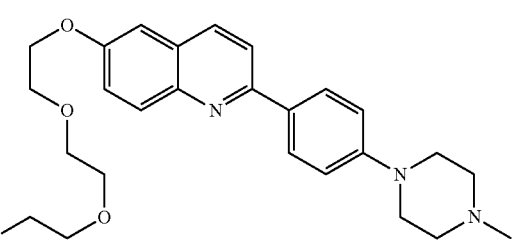

2-(2-(2-(2-(4-(4-Methylpiperazin-1-yl)phenyl)quinolin-6-yloxy)ethoxy)-ethoxy)ethyl 4-methylbenzenesulfonate: T550P was prepared using general procedure C. Reaction was performed on a 101 mg scale of CL-5311-146. T550P was isolated as a white solid (90.0 mg, 47%). $^1$H NMR (400 MHz, CDCl$_3$): δ 7.97-8.08 (m, 4H), 7.75-7.79 (m, 3H), 7.35 (dd, J=9.2, 2.8 Hz, 1H), 7.29 (m, 2H), 7.06 (d, J=2.8 Hz, 1H), 7.02 (m, 2H), 4.24 (t, J=4.6 Hz, 2H), 4.15 (t, J=4.8 Hz, 2H), 3.89 (t, J=4.8 Hz, 2H), 3.67-3.70 (m, 4H), 3.61-3.64 (m, 2H), 3.35 (br s, 4H), 2.66 (br s, 4H), 2.40 (s, 3H), 2.39 (s, 3H); MS (ESI): 606 (M+H$^+$).

Preparation of

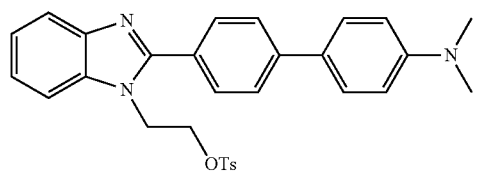 [SMILES: Cc1ccc(S(=O)(=O)OCCn2c(-c3ccc(-c4ccc(N(C)C)cc4)cc3)nc3ccccc32)cc1]

2-(2-(4'-(Dimethylamino)-[1,1'-biphenyl]-4-yl)-1H-benzo[d]imidazol-1-yl)ethyl-4-methylbenzenesulfonate T543P was prepared using general procedure E. Reaction was performed on a 0.082 g scale. T543P was isolated s a yellow solid (0.050 g, 38%). $^1$H NMR (400 MHz, CDCl$_3$): δ 7.78 (d, J=7.6 Hz, 1H), 7.62-7.71 (m, 4H), 7.56 (d, J=8.4 Hz, 2H), 7.39 (d J=8.4 Hz, 2H), 7.22-7.34 (m, 3H), 7.05 (d, J=8.8, Hz, 2H), 6.83 (d, J=8.8 Hz, 2H), 3.02 (s, 6H), 2.32 (s, 3H); MS (ESI): 512 (M+H$^+$).

Preparation of

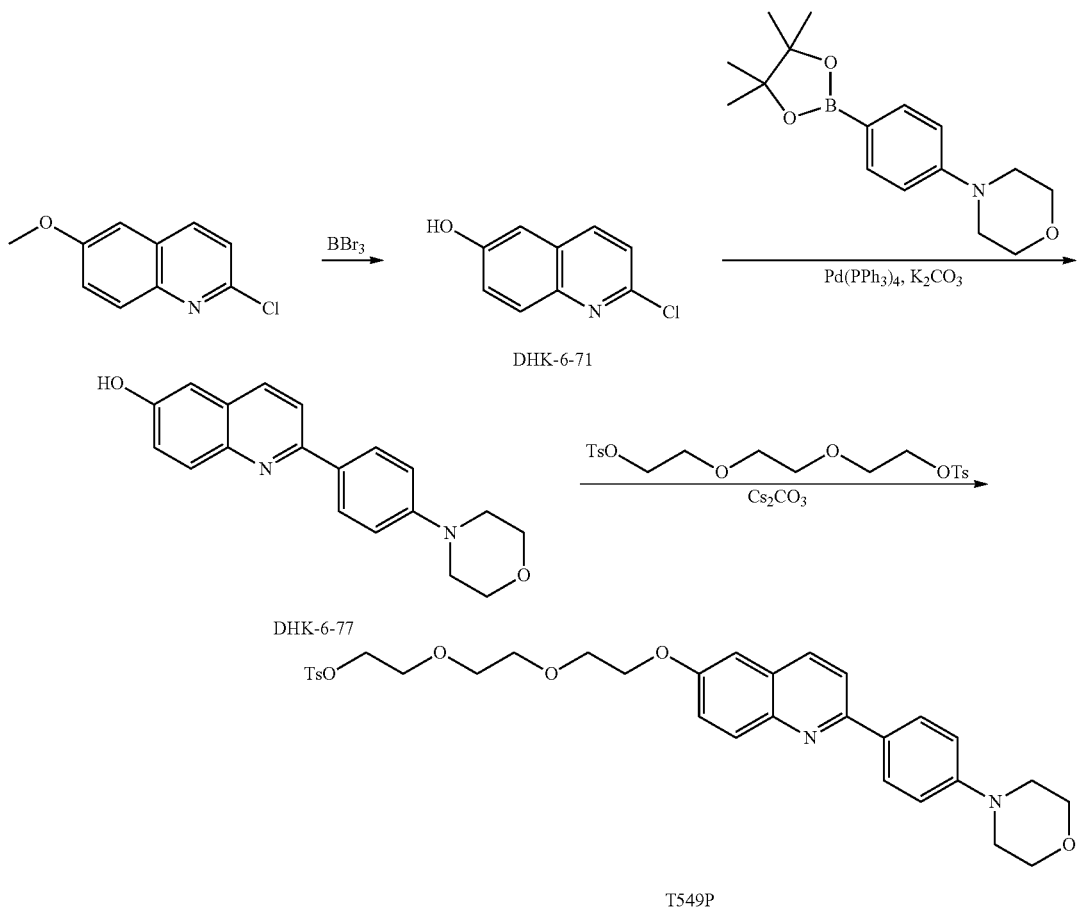

2-chloroquinolin-6-ol: DHK-6-71 was prepared using general procedure G. Reaction was performed on a 2 g scale. DHK-6-71 was isolated as yellow solid (1.72 g, 93%). MS (ESI): 180.0 (M+H$^+$).

2-(4-morpholinophenyl)quinolin-6-ol: DHK-6-77 was prepared using general procedure A. Reaction was performed on a 0.2 g scale. DHK-6-77 was isolated as yellow solid (0.31 g, 91%). MS (ESI): 307.1 (M+H$^+$).

2-(2-(2-((2-(4-morpholinophenyl)quinolin-6-yl)oxy)ethoxy)ethoxy)ethyl 4-methylbenzenesulfonate:T549P was prepared using general procedure C. Reaction was performed on a 0.19 g scale. T549P was isolated as white solid (0.1 g, 27%). NMR (400 MHz, CDCl$_3$): δ 8.07 (d, J=8.8 Hz, 2H), 8.03 (d, J=8.8 Hz, 1H), 8.00 (d, J=9.2 Hz, 1H), 7.78 (d, J=8.0 Hz, 3H), 7.35 (dd, J=9.2, 2.8 Hz, 1H), 7.30 (d, J=8.0 Hz, 2H), 7.07 (d, J=3.2 Hz, 1H), 7.01 (d, J=8.8 Hz, 2H), 4.23 (t, J=4.8 Hz, 2H), 4.15 (t, J=4.4 Hz, H), 3.89 (t, J=4.8 Hz, 3H), 3.88 (t, J=4.8 Hz, 3H), 3.71-3.62 (m, 4H), 3.64-3.62 (m, 2H), 3.25 (t, J=4.8 Hz, 4H), 2.40 (s, 3H); MS (ESI): 593.1 (M+H$^+$).

Preparation of

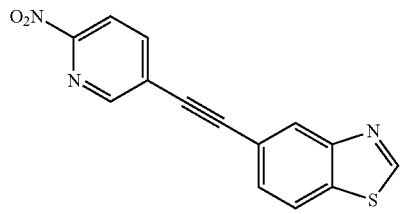 [SMILES: O=[N+]([O-])c1ccc(C#Cc2ccc3scnc3c2)cn1]

5-((6-Nitropyridin-3-yl)ethynyl)benzo[d]thiazole: T114P was prepared using general procedure A. Reaction was performed on a 0.04 g scale. T114P was isolated as yellow solid (0.070 g, 99%). $^1$H NMR (400 MHz, DMSO-d$_6$): δ 9.53 (s, 1H), 8.91 (d, J=1.6 Hz, 1H), 8.46-8.39 (m, 3H), 8.32 (d, J=8.0 Hz, 1H), 7.68 (dd, J=8.4, 1.2 Hz, 1H); MS (ESI): 282.0 (M+H$^+$).

Preparation of

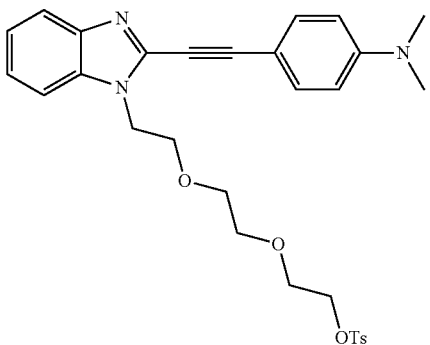 [SMILES: Cc1ccc(S(=O)(=O)OCCOCCOCCn2c(C#Cc3ccc(N(C)C)cc3)nc3ccccc32)cc1]

T508P was prepared using general procedure D. The reaction was performed on a 0.2 g scale. T508P was isolated as a solid (0.18 g, 42.9%). $^1$H NMR (400 MHz, CD$_3$CN): δ 7.74-7.72 (m, 2H), 7.63-7.61 (m, 1H), 7.51-7.48 (m, 3H), 7.41-7.38 (m, 2H), 7.29-7.24 (m, 2H), 6.77-6.75 (m, 2H), 4.52-4.49 (m, 2H), 3.94-3.92 (m, 2H), 3.86-3.83 (m, 2H), 3.46-3.36 (m, 6H), 3.01 (s, 6H), 2.42 (s, 3H); MS (ESI): 548.1 (M+H$^+$).

Preparation of

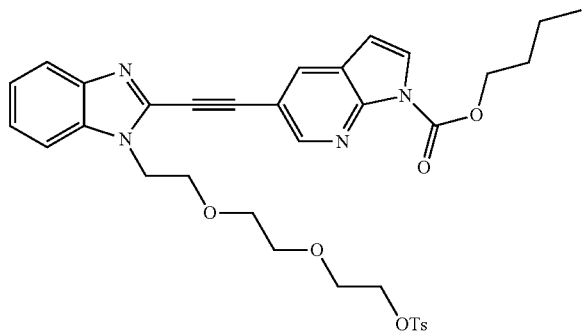 [SMILES: CCCCOC(=O)n1ccc2cc(C#Cc3nc4ccccc4n3CCOCCOCCOS(=O)(=O)c3ccc(C)cc3)cnc21]

T527P was prepared using general procedure D from butyl 5-((1H-benzo[d]imidazol-2-yl)ethynyl)-1H-pyrrolo[2,3-b]pyridine-1-carboxylate and 2,2'-(ethane-1,2-diylbis(oxy))bis(ethane-2,1-diyl) bis(4-methylbenzenesulfonate). The reaction was performed on a 0.21 g scale of butyl 5-((1H-benzo[d]imidazol-2-yl)ethynyl)-1H-pyrrolo[2,3-b]pyridine-1-carboxylate. T527P was isolated as a colorless oil (0.07 g, 18.53%). $^1$H NMR (400 MHz, CD$_3$CN) δ 8.69 (m, 1H), 8.27-8.26 (m, 1H), 7.88-7.87 (m, 1H), 7.72-7.66 (m, 3H), 7.55-7.53 (m, 1H), 7.38-7.28 (m, 4H), 6.71-6.70 (m, 1H), 4.59-4.56 (m, 2H), 4.48-4.44 (m, 2H), 3.93-3.86 (m, 4H), 3.47-3.45 (m, 2H), 3.41-3.36 (m, 4H), 2.40 (s, 3H), 1.83-1.79 (m, 2H), 1.57-1.51 (m, 2H), 1.02-1.00 (m, 3H); MS (ESI): 645.0 (M+H$^+$).

Preparation of

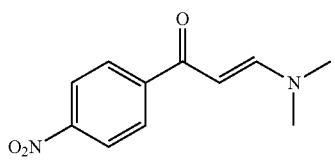 [SMILES: CN(C)/C=C/C(=O)c1ccc([N+](=O)[O-])cc1]

(E)-3-(Dimethylamino)-1-(4-nitrophenyl)prop-2-en-1-one: A solution of 1-(4-nitrophenyl)ethanone (2.2 g, 13 mmol) and N,N-dimethylformamide dimethyl acetal (25 ml) was heated to 120° C. in a sealed tube overnight. The volatiles were removed. The residue was dissolved in DCM and washed twice with H$_2$O. The DCM layer was dried with MgSO$_4$. The crude product was purified by flash chromatography (silica gel, 100% EtOAc) to isolate (E)-3-(dimethylamino)-1-(4-nitrophenyl)prop-2-en-1-one (2.2 g,) as a yellow solid. $^1$H NMR (400 MHz, CDCl$_3$) δ 2.99 (s, 3H), 3.23 (s, 3H), 5.70 (d, J=12.4 Hz, 1H), 7.94 (d, J=12.4 Hz, 1H), 8.03 (m, 2H), 8.26 (m, 2H). MS (ESI): 221 (M+H$^+$)

Preparation of

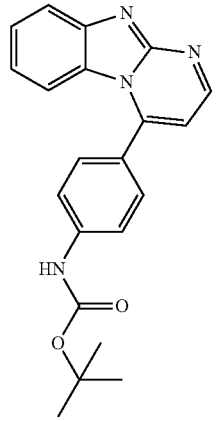 [SMILES: CC(C)(C)OC(=O)Nc1ccc(-c2ccnc3nc4ccccc4n23)cc1]

tert-Butyl(4-(benzo[4,5]imidazo[1,2-a]pyrimidin-4-yl)phenyl)carbamate: A solution of 4-(benzo[4,5]imidazo[1,2-a]pyrimidin-4-yl)aniline (350 mg, 1.3 mmol) in di-tert-butyl dicarbonate (4 mL) was heated in a sealed tube at 120° C. for 15 minutes. The reaction mixture was diluted with DCM and purified directly by flash chromatography (silica gel, 100% EtOAc) to give tert-butyl (4-(benzo[4,5]imidazo[1,2-a]pyrimidin-4-yl)phenyl)carbamate (249 mg, 53%) as an orange solid. $^1$H NMR (400 MHz, CDCl$_3$): δ 1.59 (s, 9H), 6.89 (m, 2H), 6.97 (m, 1H), 7.16 (m, 1H), 7.54-7.58 (m, 3H), 8.11 (m, 1H), 8.88 (d, J=4.4 Hz, 1H). MS (ESI): 361 (M+H$^+$).

Preparation of

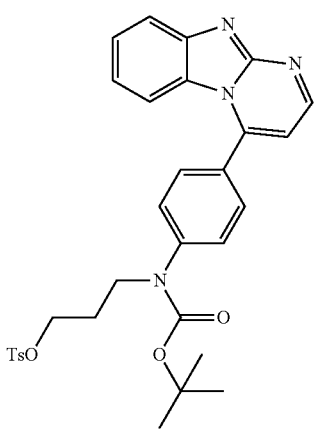 [SMILES: Cc1ccc(S(=O)(=O)OCCCN(C(=O)OC(C)(C)C)c2ccc(-c3ccnc4nc5ccccc5n34)cc2)cc1]

3-((4-(Benzo[4,5]imidazo[1,2-a]pyrimidin-4-yl)phenyl)(tert-butoxycarbonyl)amino)propyl 4-methylbenzenesulfonate T544P The title compound was prepared using general procedure D from 4-(benzo[4,5]imidazo[1,2-a]pyrimidin-4-yl)aniline and propane-1,3-diyl bis(4-methylbenzenesulfonate). T554P was isolated as a solid (130 mg, 21%). $^1$H NMR (400 MHz, CDCl$_3$): δ 1.51 (s, 9H), 2.09 (m, 2H), 2.46 (s, 3H), 3.87-3.90 (m, 2H), 4.12-4.15 (m, 2H), 6.94 (m, 1H), 7.04 (bs, 1H), 7.19 (m, 1H), 7.35 (m, 1H), 7.52-7.65 (m, 5H), 7.77-7.79 (m, 2H), 8.18 (m, 1H), 8.97 (d, J=4.4 Hz, 1H). MS (ESI): 573.1 (M+H$^+$).

Preparation of

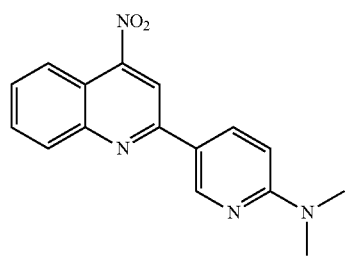 [SMILES: CN(C)c1ccc(-c2cc([N+](=O)[O-])c3ccccc3n2)cn1]

N,N-Dimethyl-5-(4-nitroquinolin-2-yl)pyridin-2-amine T480P was prepared using general procedure A from 2-Bromo-4-nitroquinoline (50 mg, 0.2 mmol) and (6-(dimethylamino)pyridin-3-yl)boronic acid (34 mg, 0.2 mmol). The product was obtained as a yellow solid (40 mg, 68%). $^1$H NMR (400 MHz, CDCl$_3$): δ 8.99 (d, J=2.4 Hz, 1H), 8.36-8.34 (m, 2H), 8.30 (s, 1H), 8.19 (m, 1H), 7.81 (m, 1H), 7.65 (m, 1H), 6.66 (d, J=9.0 Hz, 1H), 3.21 (s, 6H); MS (ESI): 295 (M+H$^+$).

Preparation of

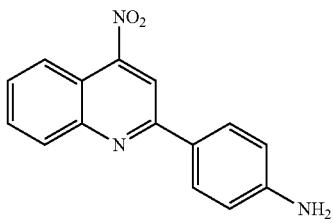 [SMILES: Nc1ccc(-c2cc([N+](=O)[O-])c3ccccc3n2)cc1]

4-(4-Nitroquinolin-2-yl)aniline T492P was prepared by using general procedure A from 2-Bromo-4-nitroquinoline (50 mg, 0.2 mmol) and 4-(4,4,5,5-tetramethyl-1,3,2-dioxaborolan-2-yl)aniline (44 mg, 0.2 mmol). The product was obtained as a dark brown solid (31 mg, 58%). NMR (400 MHz, CDCl$_3$): δ 8.36 (m, 1H), 8.32 (s, 1H), 8.20 (m, 1H), 8.06 (m, 2H), 7.80 (m, 1H), 7.65 (m, 1H), 6.81 (m, 2H), 3.99 (br s, 2H); MS (ESI): 266 (M+H$^+$).

Preparation of

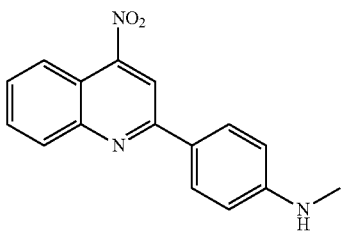 [SMILES: CNc1ccc(-c2cc([N+](=O)[O-])c3ccccc3n2)cc1]

N-Methyl-4-(4-nitroquinolin-2-yl)aniline T466P was prepared using general procedure A from 2-bromo-4-nitroquinoline (50 mg, 0.2 mmol) and N-methyl-4-(4,4,5,5-tetramethyl-1,3,2-dioxaborolan-2-yl)aniline (46 mg, 0.2 mmol). The product T466P was obtained as a brown solid (37 mg, 66%). $^1$H NMR (400 MHz, CDCl$_3$): δ 8.34 (m, 1H), 8.32 (s, 1H), 8.19 (m, 1H), 8.09 (m, 2H), 7.79 (m, 1H), 7.63 (m, 1H), 6.72 (m, 2H), 2.93 (s, 3H); MS (ESI): 280 (M+H$^+$).

Preparation of

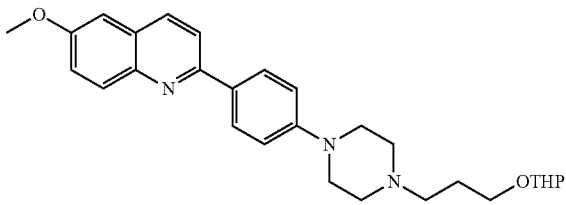

6-Methoxy-2-(4-(4-(3-((tetrahydro-2H-pyran-2-yl)oxy)propyl)piperazin-1-yl)-phenyl)quinoline AS-5332-79 was prepared using general procedure E. Reaction performed on a 0.032 g. AS-5332-79 was isolated as a off white solid (0.025 g, 54%). $^1$H NMR (400 MHz, CDCl$_3$): δ 8.05 (dt, J=8.8, 2.8 Hz, 2H), 8.00 (d, J=10.4 Hz, 2H), 7.76 (d, J=8.8 Hz, 1H), 7.32 (dd, J=9.2, 2.8 Hz, 1H), 7.04 (d, J=2.8 Hz, 1H), 7.01 (dt, J=9.2, 2.8 Hz, 2H), 4.58 (t, J=4.4 Hz, 1H), 3.92 (s, 3H), 3.86-3.77 (m, 1H), 3.51-3.45 (m, 2H), 3.30 (t, J=4.8 Hz, 4H), 2.63 (t, J=4.8 Hz, 4H), 2.53-2.49 (m, 2H), 1.88-1.80 (m, 4H), 1.73-1.68 (m, 1H), 1.59-1.49 (m, 4H); MS (ESI): 462.4 (M+H$^+$).

Preparation of

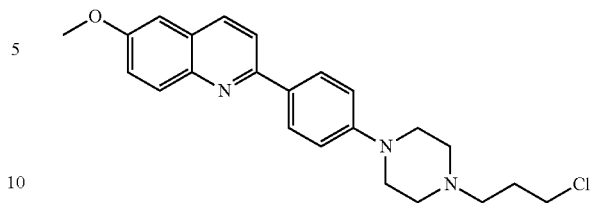

2-(4-(4-(3-Chloropropyl)piperazin-1-yl)phenyl)-6-methoxyquinoline AS-5332-94, T499P (CI) was prepared using general procedure E. Reaction performed on a 0.025 g. T-99P (CI) was isolated as a off white solid (0.010 g, 32%). $^1$H-NMR (400 MHz, CDCl$_3$): δ 8.6-7.99 (m, 4H), 7.77 (d, J=8.8 Hz, 1H), 7.33 (dd, J=9.2, 2.8 Hz, 1H), 7.06-7.00 (m, 3H), 3.92 (s, 3H), 3.66 (t, J=6.4 Hz, 2H), 3.29 (t, J=5.2 Hz, 4H), 2.62 (t, J=4.8 Hz, 4H), 2.55 (t, J=7.6 Hz, 2H), 1.99 (m, 2H); MS (ESI): 396.1 (M+H$^+$).

4. General Procedures for Radiochemistry

Description of Radiolabeling Manufacturing Process and Process Controls

General Process for the production of [F-18] fluoride ion 18F-Radiolabeling:

Aqueous [F-18]Fluoride ion produced in the cyclotron target, is passed through an anion exchange resin cartridge. The [O-18]H20 readily passes through the anion exchange resin while [F-18]fluoride is retained. The [F-18]fluoride is eluted from the column using a solution of potassium carbonate (3 mg) in water (0.4 mL) and is collected in a reaction vessel. Kryptofix® 222 (20 mg) dissolved in acetonitrile (1 mL) is added to the aqueous [F-18]fluoride mixture in the reaction vessel. The Kryptofix sequesters the potassium ions preventing the formation of strong K+/F on-pairs. This increases the chemical reactivity of the [F-18]fluoride ions. The mixture is dried by heating between 70-115° C. under a stream of inert gas and/or reduced pressure (250 mbar) and additional aliquots of acetonitrile may added to insure the fluoride mixture is completely dry. This evaporation step removes the water and converts the [F-18] to an anhydrous form, which is much more reactive than aqueous [F-18]fluoride.

Fluorine-18 [F-18] is produced by proton bombardment of the stable isotope, oxygen-18 (O-18) in water. For bombardment, the chemical form of the enriched O-18 is [O-18]H$_2$O. The [F-18]Fluorine produced is aqueous [F-18]fluoride ion. The target water is loaded into an approximately 1-2 mL target and pressurized to approximately 350 psi. The tantalum target body is outfitted with a high strength, durable metal foil. The foil is an alloy referred to as, "Havar®". The major components of Havar® are cobalt, nickel, chromium, and iron. This thin Havar® foil window permits entry of the protons, yet is sufficiently durable to withstand the pressurized water and proton irradiation. The facility utilizes two Siemens RDS-111 Eclipse cyclotron that produces 11 MeV protons with a 40-60 microamp beam current. Both targets are made of tantalum metal and are used exclusively for the production of F-18. After proton bombardment, the [O-18] H$_2$O containing the [F-18]fluoride ion is transferred to a shielded enclosure ("hot cell"). The aqueous [F-18]Fluoride is then separated from the [O-18]H$_2$O.

Extraction of [F-18]-Fluoride and Conversion to Anhydrous Form

Aqueous [F-18]Fluoride ion produced in the cyclotron target, as described in the preceding Section, is passed through an anion exchange resin cartridge. The [O-18]H$_2$O readily passes through the anion exchange resin while [F-18]fluoride is retained. The [F-18]fluoride is eluted from the column using a solution of potassium carbonate (3 mg) in water (0.4 mL) and is collected in a reaction vessel. Kryptofix® 222 (20 mg) dissolved in acetonitrile (1 mL) is added to the aqueous [F-18]fluoride mixture in the reaction vessel. The Kryptofix sequesters the potassium ions preventing the formation of strong $K^+/F$ ion-pairs. This increases the chemical reactivity of the [F-18]fluoride ions.

The mixture is dried by heating between 70-115° C. under a stream of inert gas and/or reduced pressure (250 mbar) and additional aliquots of acetonitrile may added to insure the fluoride mixture is completely dry. This evaporation step removes the water and converts the [F-18] to an anhydrous form, which is much more reactive than aqueous [F-18]fluoride.

Reaction of Anhydrous [F-18]Fluoride with W366 Precursor

A solution of the nitro precursor, (1 to 20 mg), dissolved in anhydrous DMSO (0.5-2.5 mL) is added to the reaction vessel containing the anhydrous [F-18]Fluoride. The vessel is heated to approximately 150±10° C. for 15±5 minutes to induce displacement of the aromatic nitro leaving group by [F-18]fluoride as illustrated in the scheme below. The reaction mixture is then treated with 2N HCl (1 mL) and refluxed at 105° C. for 10 min.

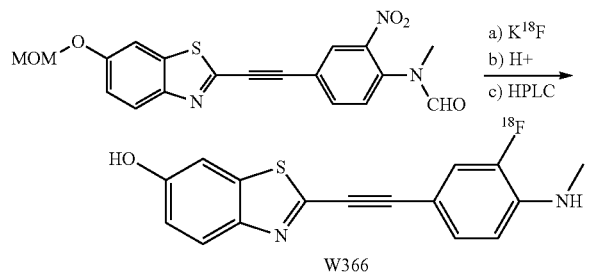

HPLC Purification of [F-18]W366

The reaction mixture containing crude [F-18]W366 is cooled and first passes through an $Al_2O_3$ cartridge followed by a mixture of MeCN (1±0.5 mL) and $H_2O$ (2±1.0 mL). The final solution is then transferred to the HPLC sample loop and is purified via chromatographic separation using a semi-preparative HPLC column (Either ACE C18 Pyramid, 7μ, 250×10 mm, Phenomenex Luna, C18, 5μ, 10×250 mm or Phenomenex Synergi Hydro-RP C18, 250×10 mm, using a gradient system, up to 5.5 mL/min, however lower flow rates may be used if there is a high backpressure, or the system may start at a lower flow rate and then increase to the maximum flow rate). The first column uses a linear gradient starting at 5% MeCN (0.1% formic acid):95% H20 (0.1% formic acid) containing 100 mg/L of ascorbic acid and to a 95:5 mix of the solvents at 30 minutes. The column effluent is monitored using UV (220, 254 or 280 nm) and radiometric detectors connected in series. The purified [F-18]W366 is collected from the column at the retention time window determined for the W366 reference standard which coincides with the time that the radiometric detectors begin showing the main peak. After the product elutes, it is collected, loaded onto the HPLC load loop and purified again. (Either ACE C18 Pyramid, 7μ, 250×10 mm, Phenomenex Luna, C18, 5μ, 10×250 mm or Phenomenex Synergi Hydro-RP C18, 250×10 mm, using a isocratic solvent system suitable to purify W366, such as 40% MeCN: water with 0.1% formic acid and 100 mg/L of ascorbic acid, up to 5.5 ml/min, however lower flow rates may be used if there is a high backpressure, or the system may start at a lower flow rate and then increase to the maximum flow rate).

Formulation, Sterile Filtration and Aseptic Filling of Purified [F-18]W366

The purified [F-18]W366 fraction elutes from the second HPLC purification column, is diluted with water (40 100 mL) containing 5±5 mg/mL of ascorbic acid, and is captured onto a C18 SepPak cartridge. The C18 SepPak cartridge is washed with water (10 mL) containing 5±5 mg/mL ascorbic acid followed by eluting the product with 0.5-0.9 mL of EtOH. The sample is then diluted with sterile water (4.5-9.0 mL of water) containing 25±25 mg/mL of ascorbic acid affording a final formulation of [F-18]W366 in a maximum of 10% EtOH:water. The solution is then processed through a 0.45 sterile filter into the preloaded collection vial.

Biological Data

The disclosed compounds compete favorably for binding against 18F-PiB, as shown below. Briefly, 5 micron thick human brain slices from regions of the brain bearing high amyloid plaque and fibril burden were incubated with approximately 20 uCi of a radiolabeled tracer in 2.5%:2.5%: 95% DMSO:EtOH:PBS in the presence of blocker (2.5 and 0.25 uM total concentration) or absence of blocker (control). The slices were incubated at rt for 90 min. The slices were then quickly washed in PBS, followed by 70% EtOH:PBS for 2 min, then 30% EtOH:PBS for 2 min and then quickly washed with PBS. The slices were dried for 30 min and then exposed on autoradiographic film for 20 min. The brain slices were then removed from the slide and the radioactivity counted in a gamma counter. The counts are normalized and the percent blocking is determined in order to determine $IC_{50}$ values. The lower the number, the more effective the compounds displaced the tracer.

Reaction of Anhydrous [F-18] Fluoride with T114 Precursor

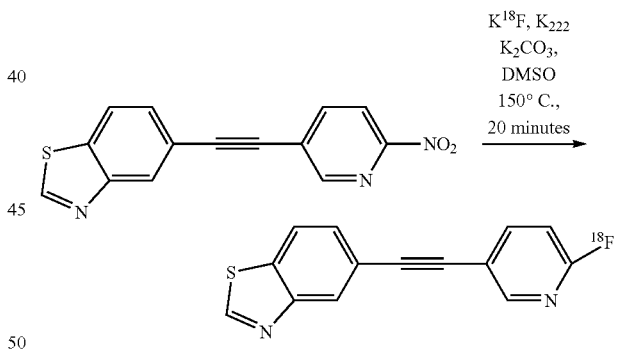

[F-18] Fluoride was prepared using $K_2CO_3$ and Kryptofix-2.2.2 according to the general procedure described above. A solution of T114P (10 mg) dissolved in anhydrous DMSO (1.0 mL) is added to the reaction vessel containing the anhydrous [F-18] Fluoride. The vessel is heated to approximately to 150° C. for 20 minutes. Reaction was loaded to a vial containing water (4 mL) and the resultant solution is then transferred to the HPLC sample loop (5 mL) and purified via chromatographic separation using a semi-preparative HPLC column (Phenomenex Gemini C18, 250×10 mm). This column uses a flow rate of 5 mL/min and an isocratic solvent system of 40% MeCN: 60% $H_2O$ containing 0.85 mL of 12N HCl per 1000 mL of water. The column effluent is monitored using UV (254 nM) and radiometric detectors connected in series. The purified [F-18] T114 is collected from the column at the retention time window determined for the T114 reference standard which coincides with the time that the radiometric detectors begin showing the main peak. The retention time of the [F-18] T114 in this system is approximately 39 minutes.

Formulation of Purified [F-18] T114

The purified [F-18] T114 fraction eluted from the HPLC purification column is diluted with water (50 mL) and filtered thru a C18 SepPak cartridge. The C18 SepPak cartridge is washed with water (10 mL) followed by elution of the product with 0.5 mL of ethyl alcohol. The sample is then diluted with 4.5 mL of water to afford a final formulation of [F-18] T114 in a maximum of 10% ethyl alcohol in water.

General Procedure for [F-18] Labeling of Aliphatic Tosylates

[F-18] Fluoride was prepared using $K_2CO_3$ and Kryptofix-2.2.2 according to the general procedure described above. After cooling, a solution of the tosylate precursor (5 mgs to 20 mgs) in anhydrous DMSO or MeCN (1 mL) was added to the residue of "dry" reactive [F-18] fluoride ion in the reaction vessel of the Explora RN synthesis module and the reaction was heated (80° C. to 110° C.) for 10 to 15 mins. The reaction was cooled to 70° C.

If the precursor contains an acid labile protecting group, 1N HCl (1 mL) was added to the reaction mixture and heated to 100° C. After 5 minutes, the reaction was cooled to room temperature and 2M NaOAc (0.5 mL) was added. The resulting mixture was added to a separate vial containing water (1.5 mL) and loaded to the HPLC sample loop to initiate purification.

If the precursor contains a basic labile protecting group, 1:1 MeOH: 1N NaOH (1 mL) was added to the reaction mixture and heated to 100° C. After 5 minutes, the reaction was added to a separate vial containing water (2 mL) and loaded to the HPLC sample loop to initiate purification.

If the precursor contains no protecting groups, the resulting reaction mixture is added to a separate vial containing water (3 mL) and loaded to the HPLC sample loop to initiate purification.

Purification was performed by semi-preparative HPLC (Phenomenex Gemini C18, 250×10 mm, flow rate 5 mL/min). The elution of the final product is initiated at 5% MeCN (0.05% TFA) in $H_2O$ (0.05% TFA) until the final concentration of MeCN (0.05% TFA) is reached within 15 to 20 minutes. Once the final concentration of the MeCN (0.05% TFA) is reached then the elution is allowed to run isocratic until the [F-18] product is collected. Once collected, the final formulation described above is followed.

TABLE 4

Radiolabeling results of aliphatic tosylates

| Cmpd # | Precursor | [F-18] Product | Yield (mCi) | Radio-chem. Purity | HPLC conditions |
|---|---|---|---|---|---|
| T114 | 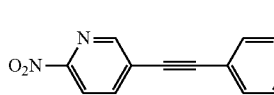 | 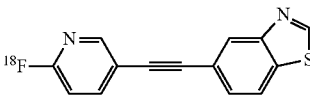 | 48 | >98% | as described above |
| T442 | 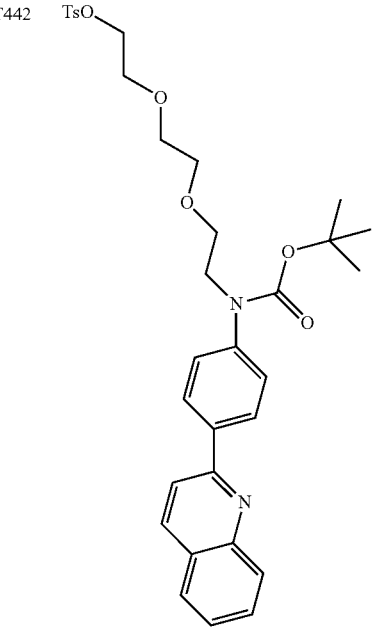 | 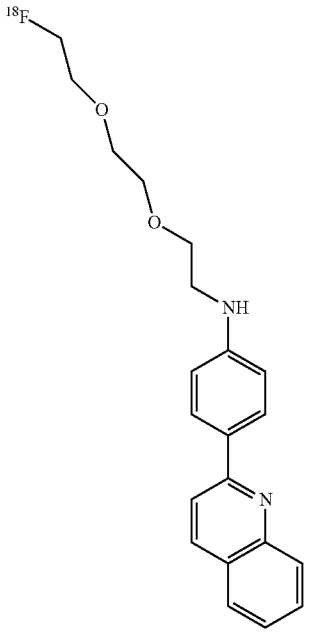 [SMILES: [18F]CCOCCOCCNc1ccc(-c2ccc3ccccc3n2)cc1] | 40 | >98% | Final conc: 25% MeCN (0.05% TFA) in water 0.05% TFA) |
| T482 | 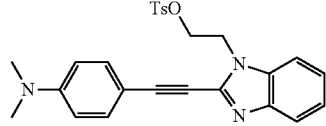 [SMILES: Cc1ccc(S(=O)(=O)OCCn2c(C#Cc3ccc(N(C)C)cc3)nc3ccccc32)cc1] | 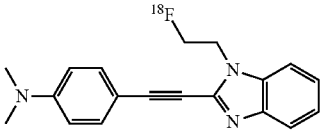 [SMILES: CN(C)c1ccc(C#Cc2nc3ccccc3n2CC[18F])cc1] | 28 | >98% | Final conc: 30% MeCN (0.05% TFA) in water (0.05% TFA) |

TABLE 4-continued

Radiolabeling results of aliphatic tosylates

| Cmpd # | Precursor | [F-18] Product | Yield (mCi) | Radio-chem. Purity | HPLC conditions |
|---|---|---|---|---|---|
| T510 | (structure) | (structure) | 30 | >98% | Final conc: 30% MeCN (0.05% TFA) in water (0.05% TFA) |
| T525 | (structure) | (structure) | 258 | >98% | Final conc: 20% MeCN (0.05% TFA) in water (0.05% TFA) |

TABLE 4-continued

Radiolabeling results of aliphatic tosylates

| Cmpd # | Precursor | [F-18] Product | Yield (mCi) | Radio-chem. Purity | HPLC conditions |
|---|---|---|---|---|---|
| T527 | | | 15 | >98% | Final conc: 25% MeCN in water (0.08% HCl) |
| T549 | | | 78 | >98% | Final conc: 25% MeCN (0.05% TFA) in water (0.05% TFA) |

General Experimental Procedures for the Preparation of Disclosed Compounds:

General Experimental Procedure A: Suzuki Coupling

To a microwave vial equipped with a magnetic stir bar was placed aryl/heterocyclic halide (1 equiv), boronic acid or boronate ester (1.1 equiv), $K_2CO_3$ (3 equiv), $P[PPh_3]_4$ (0.05 equiv) and DMF (30 vol). The suspension was irradiated in a Biotage Emrys Initiator microwave reactor (250 W) at 100° C. for 30 min. After cooling to room temperature, the solvent was removed in vacuo. The residue was purified over silica gel using Hexanes:EtOAc or DCM:EtOAc or DCM:MeOH as the eluent to afford the biaryl.

General Experimental Procedure B: Sonogashira Coupling

To a microwave vial equipped with a magnetic stir bar was placed aryl/heterocyclic halide (1 equiv), acetylene (1.1-1.5 equiv), CuI (0.05 equiv), $P[PPh_3]_4$ or $PdCl_2(PPh_3)_2$ (0.01-0.05 equiv), DIPEA (3 equiv) and ACN (30 vol). The suspension was irradiated in a Biotage Emrys Initiator microwave reactor (250 W) at 120° C. for 30 min. After cooling to room temperature, the solvent was removed in vacuo. The residue was purified over silica gel using Hexanes:EtOAc or DCM:EtOAc or DCM:MeOH as the eluent to afford the disubstituted acetylene.

General Experimental Procedure C: Alkylation of Phenols

To a round bottomed flask equipped with a magnetic stir bar, rubber septum, and argon inlet containing DMF (10 vol) was placed phenol (1 equiv). To this solution was added alkylating agent (1.1 equiv), $Cs_2CO_3$ (3 equiv) and the reaction was allowed to stir at 60° C. for 1-3 h. After the reaction was complete, the solvents were removed in vacuo. The residue was purified over silica gel using Hexanes:EtOAc or DCM:EtOAc or DCM:MeOH as the eluent to afford the alkylated product.

General Experimental Procedure D: N-Alkylation Using NaH

To a round bottomed flask equipped with a magnetic stir bar, rubber septum, and argon inlet containing DMF (10 vol) was placed amine (1 equiv). To this solution was added NaH (1.5-6 equiv), alkylating agent (1.1-2 equiv) and the reaction was allowed to stir at room temperature for 1-15 h. The reaction was then poured into water (50 vol) and extracted into EtOAc (4×40 vol). The combined organic extracts were washed with $H_2O$ (3×40 vol) brine (50 vol), dried ($Na_2SO_4$) and concentrated in vacuo. The residue was purified over silica gel using Hexanes:EtOAc or DCM:EtOAc or DCM:MeOH as the eluent to afford the N-alkylated product.

General Experimental Procedure E: N-Alkylation Using $Cs_2CO_3$

To a round bottomed flask equipped with a magnetic stir bar DMF (10 vol) was placed amine (1 equiv). To this solution was added alkylating agent (1.1-2 equiv), $Cs_2CO_3$ (2-3 equiv) and the reaction was allowed to stir at 60° C. for 1-15 h. After the reaction was complete, the solvents were removed in vacuo. The reaction mixture was then poured into water (50 vol). If the product is a solid, filtered, washed with water and dried.

If the product is soluble in water extracted into EtOAc (4×40 vol). The combined organic extracts were washed with $H_2O$ (3×40 vol), brine (50 vol), dried ($Na_2SO_4$) and concentrated in vacuo. The residue was purified over silica gel using Hexanes:EtOAc DCM:EtOAc or DCM:MeOH as the eluent to afford the N-alkylated product.

General Experimental Procedure F: Tosylation of Alcohols

To a round bottomed flask equipped with a magnetic stir bar containing DCM (17 vol) was placed alcohol (1 equiv) cooled to 0° C. To this solution was added $Ts_2O$ (1.5 equiv), $Et_3N$ (3 equiv) and the reaction was allowed to stir at room temperature for 1 h. After the reaction was complete, DCM was removed in vacuo. The residue was purified over silica gel using Hexanes:EtOAC as the eluent to afford the final tosylate.

General Experimental Procedure G: Demethylation of Aryl Methyl Ether

To a round bottomed flask equipped with a magnetic stir bar, rubber septum, and argon inlet containing DCM (5 vol) was placed methyl ether (1 equiv) cooled to 0° C. To this solution was added $BBr_3$ (5 equiv) slowly and the reaction was allowed to stir at room temperature for 15 h. After the reaction was complete, the reaction was quenched with $NaHCO_3$ solution (50 vol) and extracted into DCM (4×10 vol). The combined organic extracts were washed with $H_2O$ (3×10 vol), dried ($Na_2SO_4$) and concentrated in vacuo to afford the phenol.

General Experimental Procedure H: "Click" Reaction Between Azides and Acetylenes Using CuI and DIPEA To a round bottomed flask equipped with a magnetic stir bar, rubber septum, and argon inlet containing THF (29 vol) was placed azide (1 equiv). To this solution was added acetylene (1 equiv), CuI (0.2 equiv), DIPEA (0.4 equiv) and the reaction was allowed to stir at room temperature for until deemed complete by LCMS. After the reaction was complete, the solvents were removed in vacuo. The residue was purified over silica gel using Hexanes:EtOAC as the eluent to afford the final triazole.

General Experimental Procedure I: Silyl Deprotection Using $K_2CO_3$

To a round bottomed flask equipped with a magnetic stir bar was placed silyl protected compound (1 equiv) in MeOH (20 vol). To this compound was added $K_2CO_3$ (1.2 equiv) and the reaction was allowed to stir at room temperature for 1 h. After the reaction was complete, the solvents were removed in vacuo. The residue was purified over silica gel using Hexanes:EtOAC as the eluent to afford the deprotected product.

General Experimental Procedure J: Silyl Deprotection with TBAF

To a round bottomed flask equipped with a magnetic stir bar was placed silyl protected compound (1 equiv). To this compound was added TBAF (1M solution in THF) (1 equiv) and the reaction was allowed to stir at room temperature for 10 min. After the reaction was complete, the solvents were removed in vacuo. The residue was purified over silica gel using Hexanes:EtOAC as the eluent to afford the deprotected product.

General Experimental Procedure K: Boc, THP and Ketal Deprotections

To a round bottomed flask equipped with a magnetic stir bar was placed protected material (1 equiv). To this compound was added HCl (4M solution in dioxane, 3.8 vol) and the reaction was allowed to stir at room temperature for 2 h. To this solution was added conc. HCl (0.08 vol) in MeOH (3.8 vol) and the reaction was allowed to stir at room temperature for 2 h. After the reaction was complete, the solvents were removed in vacuo to afford the final compound.

General Experimental Procedure L: Conversion of Nitropyridyl to Fluoropyridyl Compound To a round bottomed flask equipped with a magnetic stir bar DMSO (10 vol) was placed nitro compound (1 equiv). To this solution was added KF (5 equiv) and the reaction was allowed to stir at 140° C. for 1.5 h. After the reaction was complete, the reaction was quenched with water (10 vol) and extracted into DCM (4×10 vol). The combined organic extracts were washed with $H_2O$ (3×10 vol), dried ($Na_2SO_4$) and concentrated in vacuo. The residue was purified over silica gel using Hexanes:EtOAc or DCM:EtOAc or DCM:MeOH as the eluent to afford the F-pyridyl compound.

General Experimental Procedure M: Conversion of Fluoropyridyl to Aminopyridyl Compound To a microwave vial equipped with a magnetic stir bar was placed fluoropyridyl derivative (1 equiv), amine (excess). The suspension was irradiated in a Biotage Emrys Initiator microwave reactor (250 W) at 120° C. for 10 min. After the reaction was complete, the reaction was quenched with water (10 vol) and extracted into DCM (4×10 vol). The combined organic extracts were washed with $H_2O$ (3×10 vol), dried ($Na_2SO_4$) and concentrated in vacuo. The residue was purified over silica gel using EtOAC:DCM as the eluent to afford the aminopyridyl compound.

General Experimental Procedure N: "Click" Reaction Between Azides and Acetylenes Using $CuSO_4.H_2O$ and Sodium Ascorbate To a round bottomed flask equipped with a magnetic stir bar, rubber septum, and argon inlet containing t-BuOH: $H_2O$ (1:1, 100 vol) was placed azide (1 equiv). To this solution was added acetylene (0.9 —1.2 equiv), $CuSO_4.5H_2O$ (0.2 equiv), sodium L-ascorbate (0.4 equiv) and the reaction was allowed to stir at room temperature for until deemed complete by LCMS. After the reaction was complete, the solvents were removed in vacuo. The residue was washed with water (100 vol), cooled at 0° C., filtered, washed with ether (50 vol) dried in vacuo to afford the final triazole.

General Experimental Procedure O: Fluorination with TBAF

To a round bottomed flask or vial equipped with a magnetic stir bar, was placed the precursor (1 equiv). To this compound was added Bu$_4$NF (4M solution in THF, 20 vol) and the reaction was allowed to stir at 90° C. for 30 min. To this reaction was added HCl (1N, 40 vol) and the reaction was allowed to stir at 65° C. for 30 min. The reaction mixture was diluted with water/acetonitrile (1 mL), filtered through 0.45 µm filter prior to purification by HPLC using ACN:Water both containing 0.05% TFA to afford the fluorinated product.

General Experimental Procedure P: Boc and Ketal Deprotections Using TFA

To a round bottomed flask equipped with a magnetic stir bar was placed protected material (1 equiv) in DCM (200 vol). To this compound was added TFA (10 vol) and the reaction was allowed to stir at room temperature for 15 h. The reaction was then poured into water (200 vol) and extracted into DCM (2×100 vol). The combined organic extracts were washed with brine (50 vol), NaHCO$_3$ solution (50 vol), dried (Na$_2$SO$_4$) and concentrated in vacuo. The residue was purified over silica gel using Hexanes:EtOAc as the eluent to afford the deprotected material.

General Experimental Procedure Q: Preparation of 2- and 4-Aryl benzo[4,5]imidazo[1,2-a]pyrimidine A solution of 2-bromo-1-arylethanone (20 mmol) in 30 mL of 1,1-dimethoxy-N,N-dimethylmethanamine was heated at 110° C. for 15 h and cooled to rt. The volatiles were removed under reduced pressure and the residue was purified by silica gel chromatography to afford 3-(dimethylamino)-1-aryl-prop-2-en-1-one.

A mixture of 3-(dimethylamino)-1-arylprop-2-en-1-one (10 mmol) and 1H-benzo[d]imidazol-2-amine (10 mmol) in 40 mL of acetic acid was heated at reflux for 15 h and cooled to rt. The volatiles were removed under reduced pressure. The residue was suspended in EtOAc (50 mL) and washed with saturated Na$_2$CO$_3$ (2×50 mL). The crude product was purified by silica gel chromatography or reversed phase HPLC to afford linear shaped 2-aryl benzo[4,5]imidazo[1,2-a]pyrimidine and "L" shaped 4-aryl benzo[4,5]imidazo[1,2-a]pyrimidine.

General Experimental Procedure R: Reduction of Nitrobenzene to Aniline with SnCl$_2$ A suspension of nitrobenzene (1 mmol) and SnCl$_2$.2H$_2$O (5 mmol) in 30 mL EtOH was heated at reflux for 2 h and cooled to rt. The volatiles were removed under reduced pressure and the residue was taken up to 1 M NaOH (30 mL). The mixture was extracted with DCM (3×30 mL) and the organic phase was dried over MgSO4 and concentrated. The crude product was purified by silica chromatography or reversed phase HPLC.

General Experimental Procedure S: Alkylation of Aniline Via Reductive Amination

To a stirred solution of alcohol (1 mmol) in 3 mL o DCM at rt was added Dess-Martin reagent (1.5 mmol). The mixture was stirred for 1 h at rt and 3 mL of DCE was added. It was filtered through a cotton pad directly into a stirred mixture of aniline (0.5 mmol) and NaBH(AcO)$_3$ (1.5 mmol) in 3 mL of DCE. The reaction was vigorously stirred for 5 min and quenched by adding Na$_2$CO$_3$ (30 mL, saturated). The mixture was extracted with EtOAc (3×30 mL) and the combined organic phase was washed with water (2×50 mL) and dried over MgSO$_4$ and concentrated under reduced pressure. The crude product was purified by silica chromatography or reversed phase HPLC.

The Preparation of Disclosed Compounds According to the General Procedures Described Above:
Synthesis of T698:

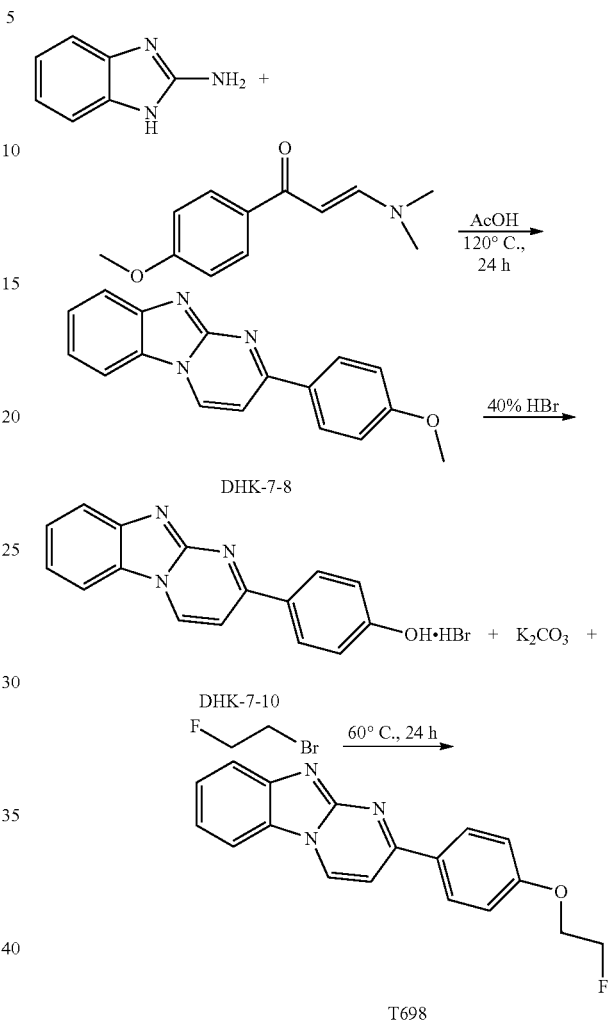

Preparation of 2-(4-methoxyphenyl)benzo[4,5]imidazo[1,2-a]pyrimidine: DHK-7-8:

To a round bottomed flask equipped with a magnetic stir bar, containing AcOH (2 mL) was placed 1H-benzoimidazol-2-amine (0.13 g, 0.974 mmol, 1.0 equiv). To this solution was added (E)-3-(dimethylamino)-1-(4-methoxyphenyl)prop-2-en-1-one (0.2 g, 0.974 mmol, 1 equiv) and the reaction was allowed to stir at 120° C. for 24 h. After the reaction was complete by LCMS, the solvent was completely evaporated and the reaction mixture was neutralized with NaHCO$_3$ solution, extracted with DCM (3×), washed with water, dried (Na$_2$SO$_4$), concentrated. The crude product was purified by Combiflash purification system using 60% EtOAc:Hexanes mixture in a gradient elution gave 0.05 g (20%) of the methoxy compound DHK-7-8 as an yellow solid. MS (ESI, Pos.) m/z: 276.1 [M+H]$^+$.

Preparation of 4-(benzo[4,5]imidazo[1,2-a]pyrimidin-2-yl)phenol hydrobromide: DHK-7-10:

To a round bottomed flask equipped with a magnetic stir bar, containing HBr (40% in H$_2$O (10 mL) was placed DHK-7-8 (0.02 g, 0.0727 mmol, 1.0 equiv). The reaction was allowed to stir at 135° C. for 15 h. After the reaction was complete by LCMS, the solvent was completely evaporated to yield 0.023 g (82%) of DHK-7-10 as a brown solid. MS (ESI, Pos.) m/z: 262.0 [M+H]+ was performed on a 0.02 g scale. Isolated 0.015 g (83%) of DHK-7-10. MS (ESI, Pos.) m/z 261.0 (M+H)+

Preparation of 2-(4-(2-fluoroethoxy)phenyl)benzo[4,5]imidazo[1,2-a]pyrimidine: T698:

General experimental procedure for Phenolic alkylation (C) was followed. Reaction was performed on a 0.01 g scale. Isolated 6 mg (55%) of T698 as an yellow solid. MS (ESI, Pos.) m/z 308.1 (M+H)+

Synthesis of T705:

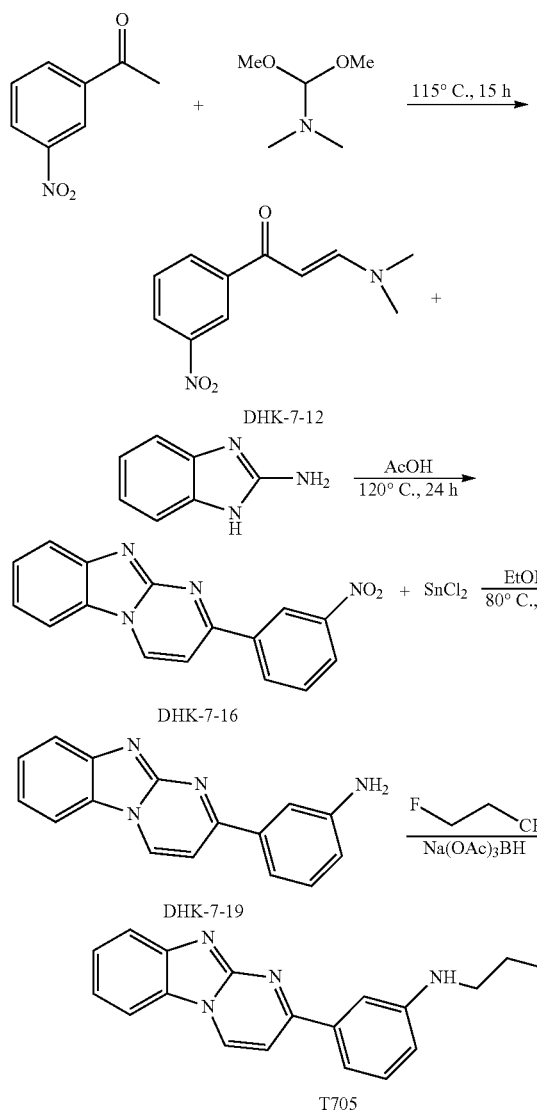

Preparation of (E)-3-(dimethylamino)-1-(3-nitrophenyl)prop-2-en-1-one: DHK-7-12:

To a sealed tube equipped with a magnetic stir bar, containing 1,1-dimethoxy-N,N-dimethylmethanamine (50 mL) was placed 1-(3-nitrophenyl)ethanone (5 g, 30 mmol, 1.0 equiv). The reaction was allowed to stir at 115° C. for 15 h. After the reaction was complete by LCMS, the solid product was filtered and washed with ether to yield 5.3 g (80%) of DHK-7-12 as an yellow solid. MS (ESI, Pos.) m/z: 221.1 [M+H]+.

Preparation of 2-(3-nitrophenyl)benzo[4,5]imidazo[1,2-a]pyrimidine: DHK-7-16:

To a round bottomed flask equipped with a magnetic stir bar, containing AcOH (20 mL) was placed 1H-benzoimidazol-2-amine (1 g, 7.5 mmol, 1.0 equiv). To this solution was added (E)-3-(dimethylamino)-1-(3-nitrophenyl)prop-2-en-1-one (1.7 g, 7.5 mmol, 1 equiv) and the reaction was allowed to stir at 120° C. for 24 h. After the reaction was complete by LCMS, the solvent was completely evaporated and the reaction mixture was neutralized with NaHCO₃ solution. Yellow solid was filtered and washed with DCM to give the nitro compound DHK-7-16 0.83 g (39%). MS (ESI, Pos.) m/z: 291.1 M+H]+.

Preparation of 3-(benzo[4,5]imidazo[1,2-a]pyrimidin-2-yl)aniline: T711:

To a round bottomed flask equipped with a magnetic stir bar, containing EtOH (50 mL) was placed DHK-7-16 (0.825 g, 2.8 mmol, 1.0 equiv). To this solution was added SnCl₂.2H₂O (0.87 g, 17 mmol, 6 equiv) and the reaction was allowed to stir at 80° C. for 2 h. After the reaction was complete by LCMS, the solvent was completely evaporated and 1N NaOH was added. Yellow solid was filtered and washed with water to give the amino compound T711 0.74 g (100%). MS (ESI, Pos.) m/z: 261.1 [M+H]+.

Preparation of 3-(benzo[4,5]imidazo[1,2-a]pyrimidin-2-yl)-N-(3-fluoropropyl)aniline: T705:

General experimental procedure for Reductive amination (Q) was followed. Reaction was performed on a 0.023 g scale. Isolated 18 mg (64%) of T705 as an yellow solid. MS (ESI, Pos.) m/z: 321.1 (M+H)+.

Synthesis of T721:

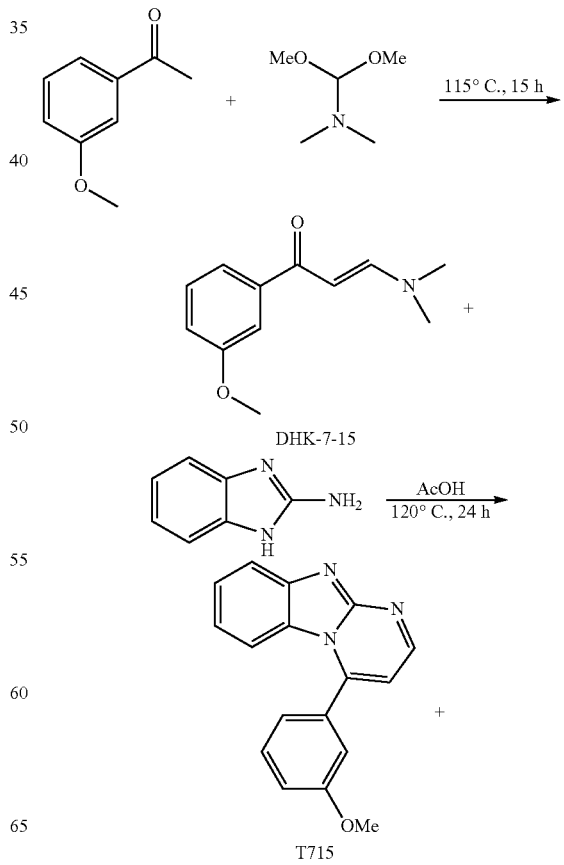

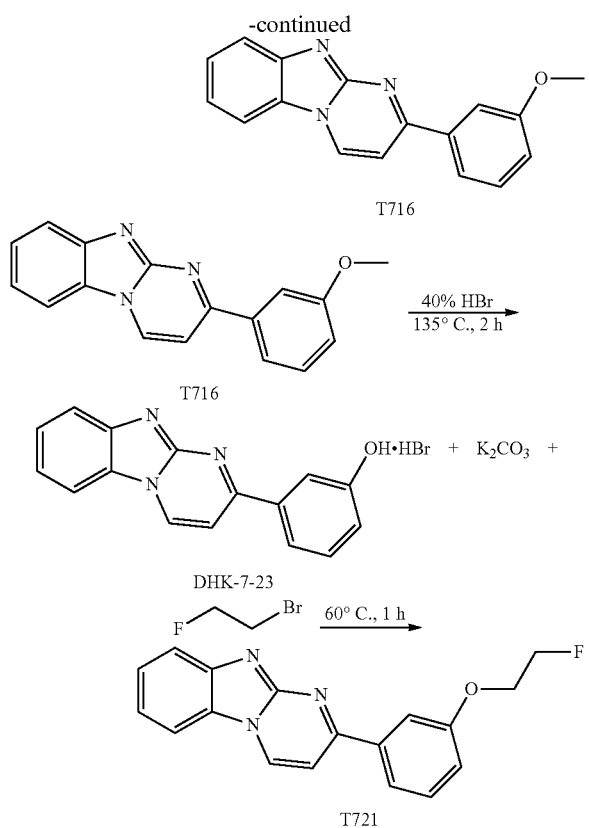

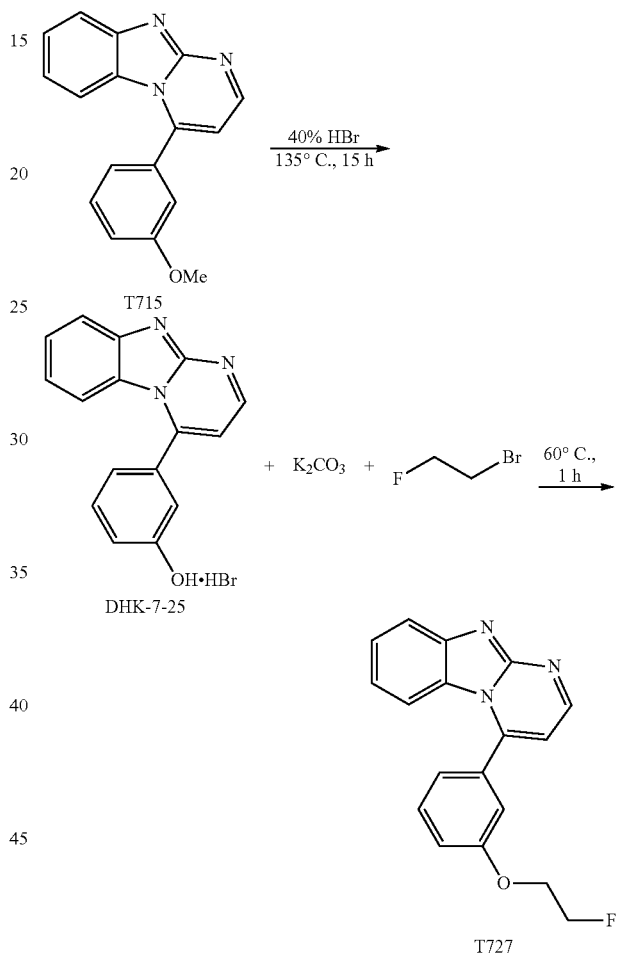

Preparation of (E)-3-(dimethylamino)-1-(3-methoxyphenyl)prop-2-en-1-one: DHK-7-15:

To a sealed tube equipped with a magnetic stir bar, containing 1,1dimethoxy-N,N-dimethylmethanamine (50 mL) was placed 1-(3-methodyphenyl)ethanone (5 g, 30 mmol, 1.0 equiv). The reaction was allowed to stir at 115° C. for 15 h. After the reaction was complete by LCMS, the solvent was evaporated. The crude product was purified by Combiflash purification system using 70% EtOAc:Hexanes mixture in a gradient elution gave 5.5 g (81%) of the methoxy compound DHK-7-15 as an yellow solid. MS (ESI, Pos.) m/z: 206.1 (M+H)+

Preparation of 4-(3-methoxyphenyl)benzo[4,5]imidazo[1,2-a]pyrimidine T715 and 2-(3-methoxyphenyl)benzo[4,5]imidazo[1,2-a]pyrimidine: T716:

To a round bottomed flask equipped with a magnetic stir bar, containing AcOH (20 mL) was placed 1H-benzoimidazol-2-amine (1 g, 7.5 mmol, 1.0 equiv). To this solution was added DHK-7-15 (1.5 g, 7.5 mmol, 1 equiv) and the reaction was allowed to stir at 135° C. for 24 h. After the reaction was complete by LCMS, the solvent was completely evaporated and the reaction mixture was neutralized with NaHCO3 solution, extracted with DCM, organic layer was washed with water, dried and evaporated. The crude product was purified by Combiflash purification system using 60-70% EtOAc:Hexanes mixture in a gradient elution gave 0.42 g (81%) of T716 as an yellow solid. MS: [M+H]+: 276.1. Eluting the column with 100% EtOAc gave 0.58 g (81%) of T715 as an yellow solid. MS (ESI, Pos.) m/z: 276.1 [M+H]+.

Preparation of 4-(benzo[4,5]imidazo[1,2-a]pyrimidin-2-yl)phenol hydrobromide: DHK-7-23:

To a round bottomed flask equipped with a magnetic stir bar, containing HBr (40% in H2O (10 mL) was placed T716 (0.34 g, 1.2 mmol, 1.0 equiv). The reaction was allowed to stir at 135° C. for 2 h. After the reaction was complete by LCMS, the solvent was completely evaporated to yield 0.35 g (83%) of DHK-7-23 as a brown solid. MS: [M+H]+: 262.0.

Preparation of 2-(3-(2-fluoroethoxy)phenyl)benzo[4,5]imidazo[1,2-a]pyrimidine: T721:

General experimental procedure for Phenolic alkylation (C) was followed. Reaction was performed on a 0.023 g scale. Isolated 15 mg (75%) of T721 as an yellow solid. MS (ESI, Pos.) m/z 308.1 (M+H)+

Synthesis of T727:

Preparation of 3-(benzo[4,5]imidazo[1,2-a]pyrimidin-4-yl)phenol hydrobromide: DHK-7-25:

To a round bottomed flask equipped with a magnetic stir bar, containing HBr (40% in H2O (10 mL) was placed T715 (0.55 g, 2.0 mmol, 1.0 equiv). The reaction was allowed to stir at 135° C. for 15 h. After the reaction was complete by LCMS, the solvent was completely evaporated to yield 0.58 g (85%) of DHK-7-25 as a brown solid. MS (ESI, Pos.) m/z 262.0 (M+H)+

Preparation of 4-(3-(2-fluoroethoxy)phenyl)benzo[4,5]imidazo[1,2-a]pyrimidine: T727:

General experimental procedure for Phenolic alkylation (C) was followed. Reaction was performed on a 0.03 g scale. Isolated 0.02 mg (74%) of T727 as an yellow solid. MS (ESI, Pos.) m/z 308.1 (M+H)+

Synthesis of T745:

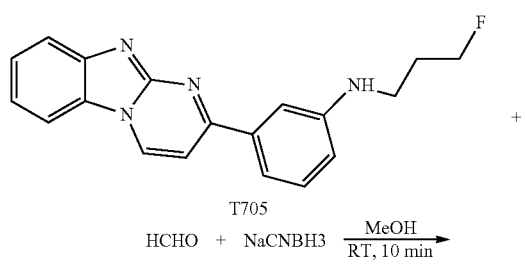

Preparation of 3-(benzo[4,5]imidazo[1,2-a]pyrimidin-2-yl)-N-(3-fluoropropyl)-N-methylaniline T745:

To a round bottomed flask equipped with a magnetic stir bar, MeOH (2 mL) was placed T705 (0.003 g, 0.012 mmol, 1.0 equiv). To this solution was added HCHO in water (0.007 g, 0.23 mmol, 20 equiv) and NaCNBH$_3$ (0.002 mg, 0.035 mmol, 3 equi) and the reaction was allowed to stir at RT for 10 min. After the reaction was complete by LCMS, the solvent was completely evaporated and purified by HPLC to yield 1.5 mg (50%) of T745 as an yellow solid. MS (ESI, Pos.) m/z 335.0 (M+H)$^+$ Synthesis of T746:

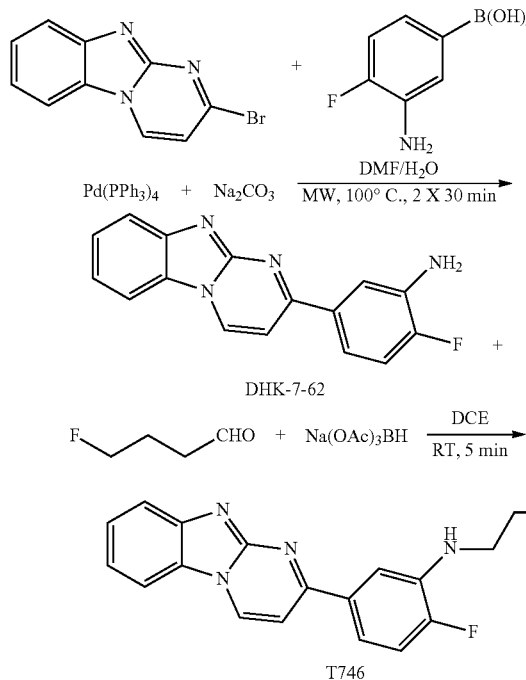

Preparation of 5-(benzo[4,5]imidazo[1,2-a]pyrimidin-2-yl)-2-fluoroaniline: DHK-7-62:

General experimental procedure for Suzuki coupling (A) was followed. Reaction was performed on a 0.05 g scale. Isolated 0.015 g (27%) of DHK-7-62 as an yellow solid. MS (ESI, Pos.) m/z 279.1 (M+H)$^+$ Preparation of 5-(benzo[4,5]imidazo[1,2-a]pyrimidin-2-yl)-2-fluoro-N-(3-fluoropropyl)aniline: T746:

General experimental procedure for Reductive amination (Q) was followed. Reaction was performed on a 0.014 g scale. Isolated 8 mg (47%) of T746 as an yellow solid. MS (ESI, Pos.) m/z: 339.1 (M+H)$^+$.

Synthesis of T752:

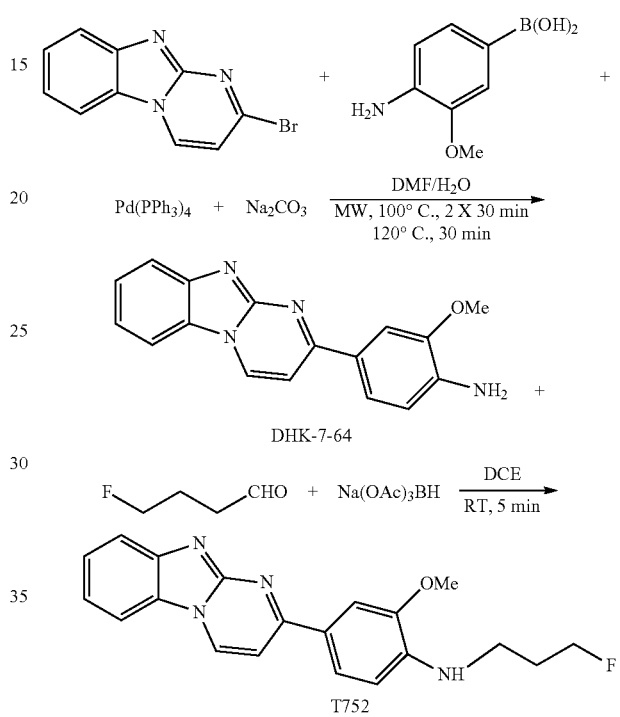

Preparation of 4-(benzo[4,5]imidazo[1,2-a]pyrimidin-2-yl)-2-methoxyaniline: DHK-7-64:

General experimental procedure for Suzuki coupling (A) was followed. Reaction was performed on a 0.078 g scale. Isolated 0.09 g (99%) of DHK-7-64 as an yellow solid. MS (ESI, Pos.) m/z 291.3 (M+H)$^+$ Preparation of 5-(benzo[4,5]imidazo[1,2-a]pyrimidin-2-yl)-2-fluoro-N-(3-fluoropropyl)aniline: T752:

General experimental procedure for Reductive amination (Q) was followed. Reaction was performed on a 0.036 g scale. Isolated 2 mg (4%) of T752 as an yellow solid. MS (ESI, Pos.) m/z: 351.1 (M+H)$^+$.

Synthesis of T756:

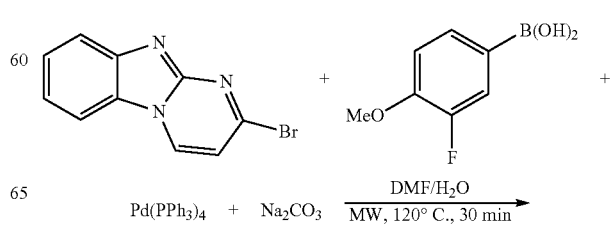

-continued

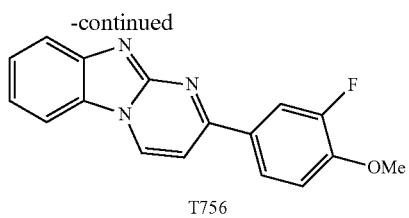
T756

Preparation of 2-(3-fluoro-4-methoxyphenyl)benzo[4,5]imidazo[1,2-a]pyrimidine: T756:

General experimental procedure for Suzuki coupling (A) was followed. Reaction was performed on a 0.078 g scale. Isolated 0.09 g (95%) of T756 as an yellow solid. MS (ESI, Pos.) m/z 294.1 (M+H)$^+$ Synthesis of T760:

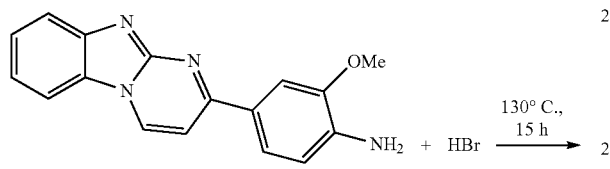

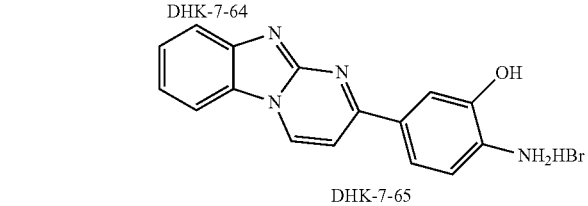

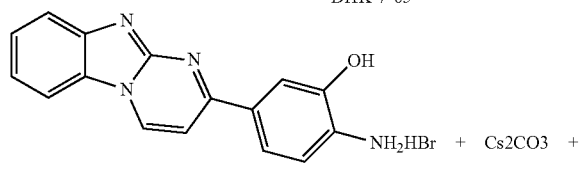
T760

Preparation of 2-amino-5-(benzo[4,5]imidazo[1,2-a]pyrimidin-2-yl)phenol hydrobromide: DHK-7-65:

To a round bottomed flask equipped with a magnetic stir bar, containing HBr (40% in H$_2$O (10 mL) was placed DHK-7-64 (0.05 g, 0.17 mmol, 1.0 equiv). The reaction was allowed to stir at 130° C. for 15 h. After the reaction was complete by LCMS, the solvent was completely evaporated to yield 0.06 g (98%) of DHK-7-65 as a brown solid. MS (ESI, Pos.) m/z 277.1 (M+H)$^+$ Preparation of 4-(benzo[4,5]imidazo[1,2-a]pyrimidin-2-yl)-2-(2-fluoroethoxy)aniline: T760:

General experimental procedure for Phenolic alkylation (C) was followed. Reaction was performed on a 0.06 g scale. Isolated 0.004 mg (7%) of T760 as an yellow solid. MS (ESI, Pos.) m/z 323.1 (M+H)$^+$ Synthesis of T770:

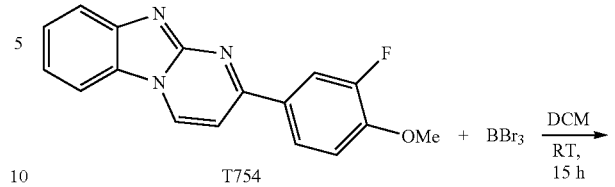

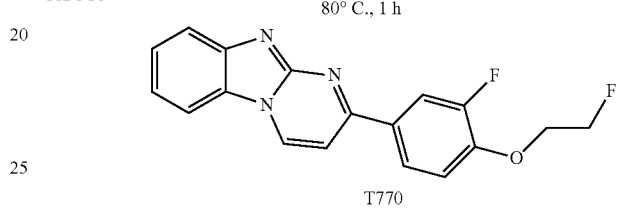
T770

Preparation of 4-(benzo[4,5]imidazo[1,2-a]pyrimidin-2-yl)-2-fluorophenol: DHK-7-90:

General experimental procedure for demethylation reaction (G) was followed. Reaction was performed on a 0.03 g scale. Isolated 0.028 g (98%) of DHK-7-90. MS (ESI, Pos.) m/z, 280.1 (M+H)$^+$.

Preparation of 2-(3-fluoro-4-(2-fluoroethoxy)phenyl)benzo[4,5]imidazo[1,2-a]pyrimidine: T770:

General experimental procedure for Phenolic alkylation (C) was followed. Reaction was performed on a 0.04 g scale. Isolated 0.010 mg (28%) of T770 as an yellow solid. MS (ESI, Pos.) m/z: 326.1 (M+H)$^+$.

Synthesis of T777:

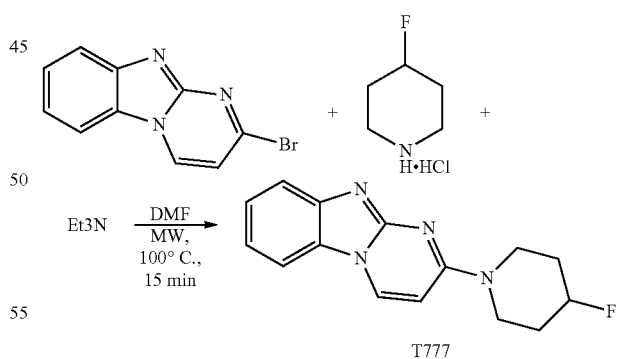
T777

Preparation of 2-(4-fluoropiperidin-1-yl)benzo[4,5]imidazo[1,2-a]pyrimidine: T777:

To a microwave vial equipped with a magnetic stir bar, containing DMF (1 mL) was placed 2-bromobenzo[4,5]imidazo[1,2-a]pyrimidine (0.02 g, 0.089 mmol, 1.0 equiv), 4-fluoropiperidine hydrochloride (0.019 g, 0.133 mmol, 1.5 equiv) and triethylamine (0.037 ml, 0.266 mmol, 3.0 equiv). The suspension was irradiated in a Biotage Initiator microwave reactor (250 W) at 100° C. for 15 min. After cooling to room temperature, the crude product was purified by HPLC to afford 0.015 g (63%) of T777 as an off-white solid. MS (ESI, Pos.) m/z: 271.1 (M+H)⁺.

Synthesis of T780:

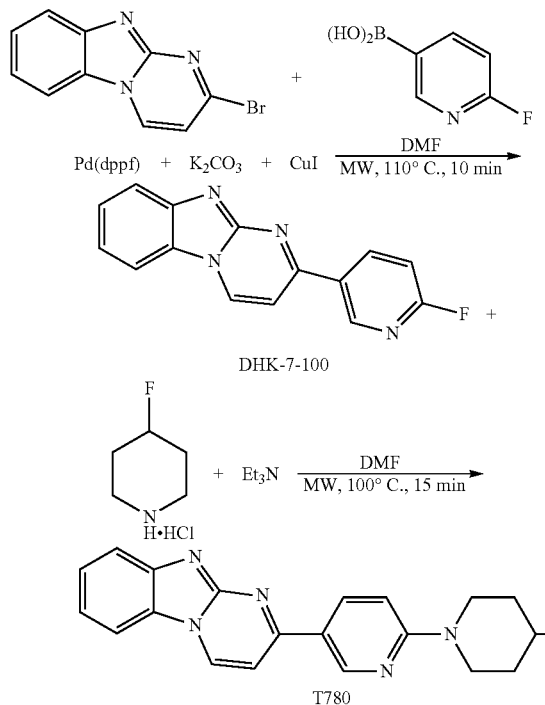

Preparation of 2-(6-fluoropyridin-3-yl)benzo[4,5]imidazo [1,2-a]pyrimidine: DHK-7-100:

General experimental procedure for Suzuki coupling (A) was followed. Reaction was performed on a 0.058 g scale. Isolated 0.06 g (97%) of DHK-7-100 as an yellow solid. MS (ESI, Pos.) m/z 265.1 (M+H)⁺.

Preparation of 2-(6-(4-fluoropiperidin-1-yl)pyridin-3-yl) benzo[4,5]imidazo[1,2-a]pyrimidine: T780:

To a microwave vial equipped with a magnetic stir bar, containing DMF (1 mL) was DHK-7-100 (0.025 g, 0.095 mmol, 1.0 equiv), 4-fluoropiperidine hydrochloride (0.020 g, 0.142 mmol, 1.5 equiv) and triethylamine (0.040 ml, 0.284 mmol, 3.0 equiv). The suspension was irradiated in a Biotage Initiator microwave reactor (250 W) at 100° C. for 15 min. After cooling to room temperature, the crude product was purified by HPLC to afford 0.025 g (76%) of T780 as an yellow solid. MS (ESI, Pos.) m/z 348.1 (M+H)⁺.

Synthesis of T802:

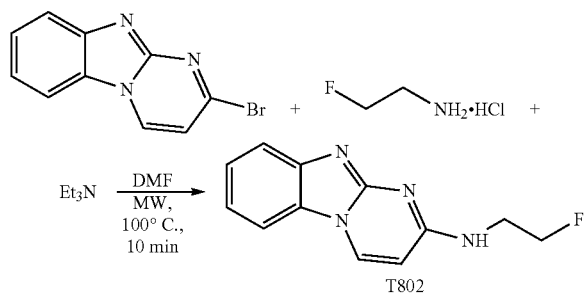

Preparation of N-(2-fluoroethyl)benzo[4,5]imidazo[1,2-a] pyrimidin-2-amine: T802:

To a microwave vial equipped with a magnetic stir bar, containing DMF (1 mL) was 2-bromobenzo[4,5]imidazo[1, 2-a]pyrimidine (0.02 g, 0.081 mmol, 1.0 equiv), 2-fluoroethylamine hydrochloride (0.012 g, 0.121 mmol, 1.5 equiv) and triethylamine (0.034 ml, 0.242 mmol, 3.0 equiv). The suspension was irradiated in a Biotage Initiator microwave reactor (250 W) at 100° C. for 10 min. After cooling to room temperature, the crude product was purified by HPLC to afford 0.015 g (81%) of T802 as an off-white solid. MS (ESI, Pos.) m/z 331.1 (M+H)⁺.

Synthesis of T808:

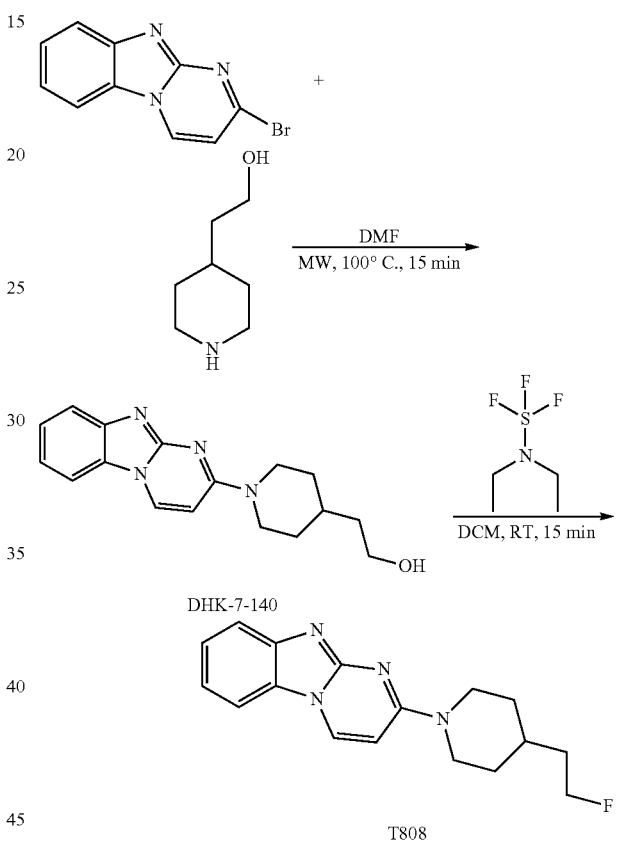

Preparation of 2-(1-(benzo[4,5]imidazo[1,2-a]pyrimidin-2-yl)piperidin-4-yl)ethanol: DHK-7-140:

To a microwave vial equipped with a magnetic stir bar, containing DMF (1 mL) was 2-bromobenzo[4,5]imidazo[1, 2-a]pyrimidine (0.108 g, 0.435 mmol, 1.0 equiv) and 2-(piperidin-4-yl)ethanol) (0.067 g, 0.522 mmol, 1.2 equiv). The suspension was irradiated in a Biotage Initiator microwave reactor (250 W) at 100° C. for 10 min. After cooling to room temperature, water was added and the product was collected by filtration to afford 0.07 g (54%) of DHK-7-140 as brown solid. MS (ESI, Pos.) m/z 297.1 (M+H)⁺.

Preparation of: 2-(4-(2-fluoroethyl)piperidin-1-yl)benzo [4,5]imidazo[1,2-a]pyrimidine: T808:

To a round bottomed flask equipped with a magnetic stir bar, DCM (1 mL) was placed DHK-7-140 (0.01 g, 0.034 mmol, 1.0 equiv) and the mixture was cooled to 0° C. To this solution was added DAST (0.041 mL, 0.34 mmol, 10 equiv) and the reaction was allowed to stir at RT for 10 min. After the reaction was complete by LCMS, the solvent was completely evaporated and purified by HPLC to yield 5 mg (50%) of T808 as a white solid. MS (ESI, Pos.) m/z 299.0 (M+H)⁺.

Synthesis of T809:

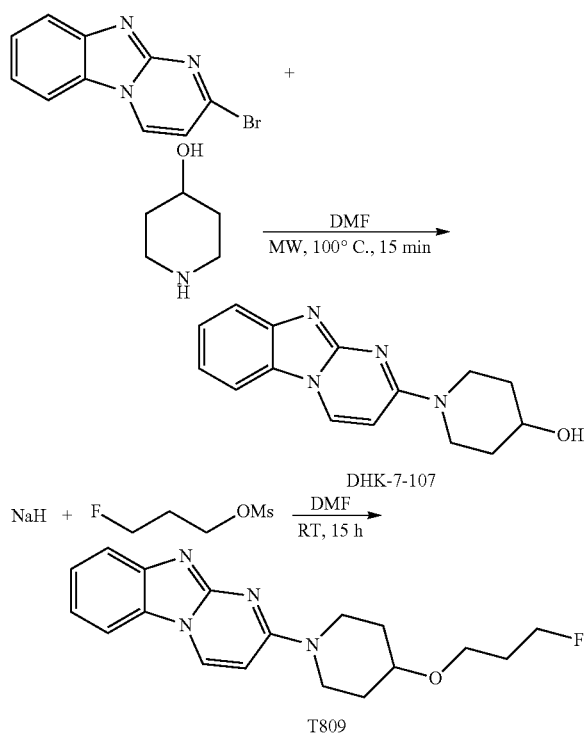

Preparation of 1-(benzo[4,5]imidazo[1,2-a]pyrimidin-2-yl)piperidin-4-ol: DHK-7-107:

To a microwave vial equipped with a magnetic stir bar, containing DMF (1 mL) was 2-bromobenzo[4,5]imidazo[1,2-a]pyrimidine (0.15 g, 0.604 mmol, 1.0 equiv) and piperidin-4-ol (0.092 g, 0.906 mmol, 1.5 equiv). The suspension was irradiated in a Biotage Initiator microwave reactor (250 W) at 100° C. for 15 min. After cooling to room temperature, water was added and the product was collected by filtration to afford 0.095 g (59%) of DHK-7-107 as brown solid. MS (ESI, Pos.) m/z: 269.1 (M+H)$^+$.

Preparation of 2-(4-(3-fluoropropoxy)piperidin-1-yl)benzo[4,5]imidazo[1,2-a]pyrimidine: T809:

To a round bottomed flask equipped with a magnetic stir bar, DMF (1 mL) under argon was placed DHK-7-107 (0.017 g, 0.063 mmol, 1.0 equiv) and the mixture was cooled to 0° C. To this solution was added NaH (60%) (0.003 g, 0.127 mmol, 2 equiv) and 3-fluoropropyl methanesulfonate (0.02 g, 0.127 mmol, 2 equiv) and the reaction was allowed to stir at RT for 15 h. After the reaction was complete by LCMS, the solvent was completely evaporated and purified by HPLC to yield 5 mg (24%) of T809 as a white solid. MS (ESI, Pos.) m/z: 329.1 (M+H)$^+$.

Synthesis of T819:

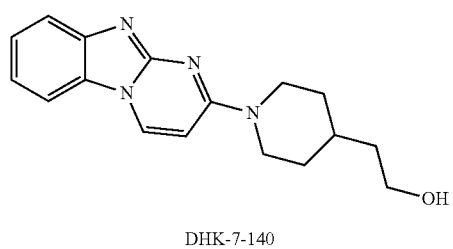

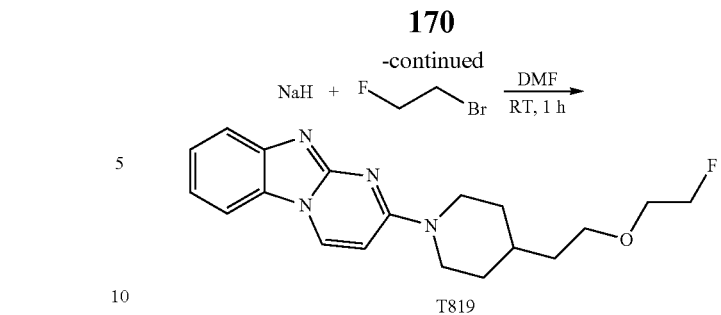

Preparation 2-(4-(2-(2-fluoroethoxy)ethyl)piperidin-1-yl)benzo[4,5]imidazo[1,2-a]pyrimidine: T819:

To a round bottomed flask equipped with a magnetic stir bar, DMF (1 mL) under argon was placed DHK-7-140 (0.02 g, 0.066 mmol, 1.0 equiv) and the mixture was cooled to 0° C. To this solution was added NaH (60%) (0.016 g, 0.675 mmol, 10 equiv) and 1-bromo-2-fluoroethane (0.086 g, 0.675 mmol, 10 equiv) and the reaction was allowed to stir at RT for 1 h. After the reaction was complete by LCMS, the solvent was completely evaporated and purified by HPLC to yield 3 mg (13%) of T819 as a white solid. MS (ESI, Pos.) m/z 343.1 (M+H)$^+$ Synthesis of Precursors:

Synthesis of T698 Precursor:

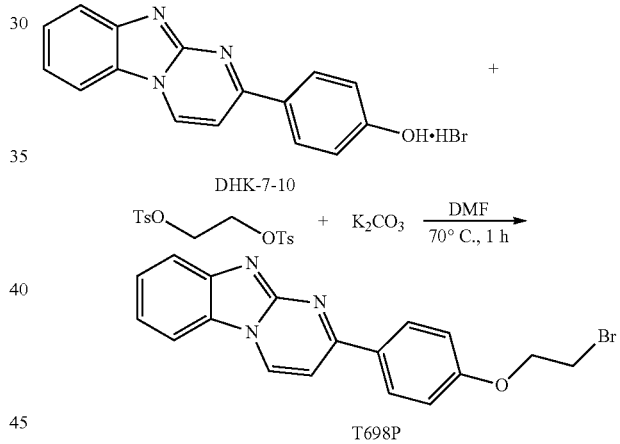

Preparation of 2-(4-(2-bromoethoxy)phenyl)benzo[4,5]imidazo[1,2-a]pyrimidine: T698P:

General experimental procedure for Phenolic alkylation (C) was followed. Reaction was performed on a 0.2 g scale. Isolated 0.030 mg (14%) of T698P as an yellow solid. MS (ESI, Pos.) m/z: 368.1 (M+H)$^+$.

Synthesis of T705 Precursor:

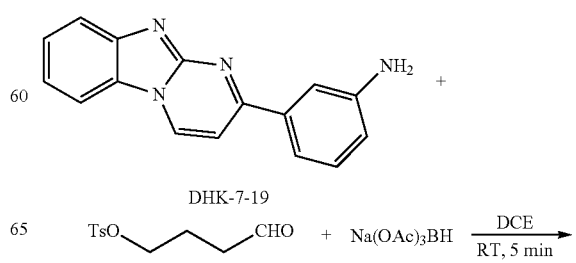

-continued

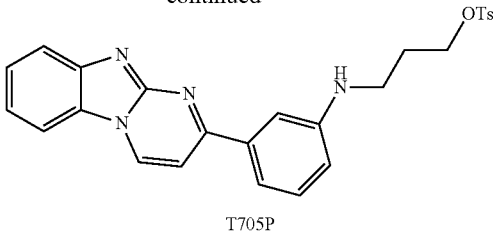

T705P

Preparation of 3-((3-(benzo[4,5]imidazo[1,2-a]pyrimidin-2-yl)phenyl)amino)propyl 4-methylbenzenesulfonate: T705P:

General experimental procedure for Reductive amination (Q) was followed. Reaction was performed on a 0.12 g scale. Isolated 30 mg (14%) of T705P as an yellow solid. MS (ESI, Pos.) m/z: 473.1 (M+H)$^+$.

Synthesis of T777 Precursor 1:

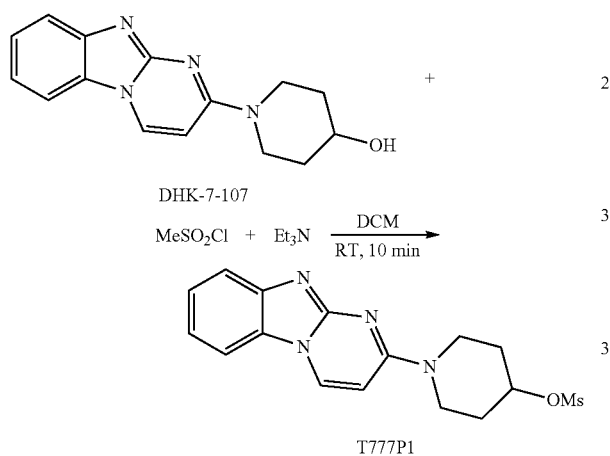

Preparation of 1-(benzo[4,5]imidazo[1,2-a]pyrimidin-2-yl)piperidin-4-yl methanesulfonate: T777P1:

To a round bottomed flask equipped with a magnetic stir bar, DCM (1 mL) was placed DHK-7-107 (0.03 g, 0.112 mmol, 1.0 equiv). To this solution was added methane sulfonylchloride (0.064 g, 0.559 mmol, 5 equiv) and Et$_3$N (0.113 g, 1.11 mmol, 10 equiv) and the reaction was allowed to stir at RT for 10 min. After the reaction was complete by LCMS, the solvent was completely evaporated and purified by HPLC to yield 30 mg (77%) of T777P1 as a white solid. MS (ESI, Pos.) m/z: 347.1 (M+H)$^+$ Synthesis of T777 Precursor 2:

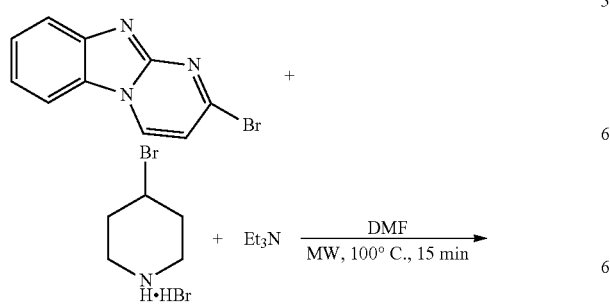

-continued

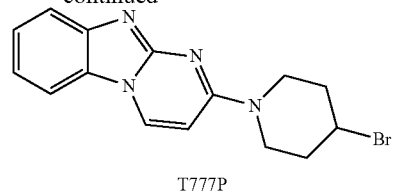

T777P

Preparation of 2-(1-(benzo[4,5]imidazo[1,2-a]pyrimidin-2-yl)piperidin-4-yl)ethanol: T777P2:

To a microwave vial equipped with a magnetic stir bar, containing DMF (1 mL) was 2-bromobenzo[4,5]imidazo[1,2-a]pyrimidine (0.067 g, 0.27 mmol, 1.0 equiv), 4-bromopiperidine hydrochloride (0.099 g, 0.405 mmol, 1.5 equiv) and triethylamine (0.113 ml, 0.810 mmol, 3.0 equiv). The suspension was irradiated in a Biotage Initiator microwave reactor (250 W) at 100° C. for 10 min. After cooling to room temperature, the crude product was purified by HPLC to afford 0.06 g (67%) of T777P2 as a white solid. MS (ESI, Pos.) m/z: 332.1 (M+H)$^+$ Synthesis of T808 Precursor:

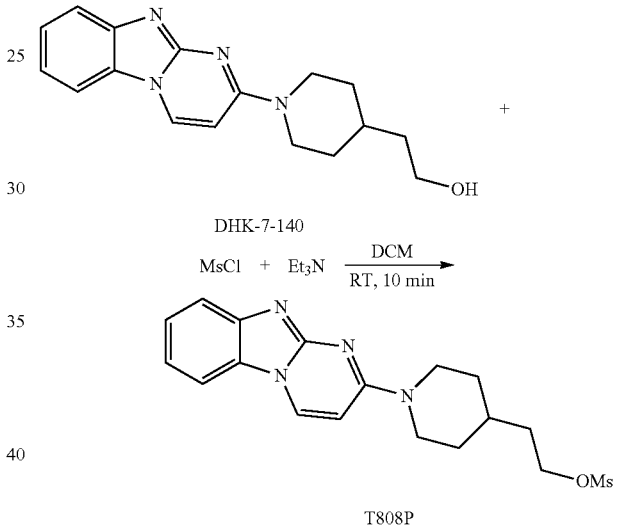

Preparation of 2-(1-(benzo[4,5]imidazo[1,2-a]pyrimidin-2-yl)piperidin-4-yl)ethyl methanesulfonate: T808P:

To a round bottomed flask equipped with a magnetic stir bar, DCM (1 mL) was placed DHK-7-140 (0.06 g, 0.202 mmol, 1.0 equiv). To this solution was added methane sulfonylchloride (0.158 mL, 2.02 mmol, 10 equiv) and Et$_3$N (0.564 mL, 4.05 mmol, 20 equiv) and the reaction was allowed to stir at RT for 10 min. After the reaction was complete by LCMS, the solvent was completely evaporated and purified by HPLC to yield 35 mg (46%) of T808P as a white solid. MS (ESI, Pos.) m/z: 375.1 (M+H)$^+$ 5-(2-Fluoroethyl)-3-(4-Methoxyphenyl)-1-oxo-1H,5H-pyrido[1,2-a]benzimidazole: T626

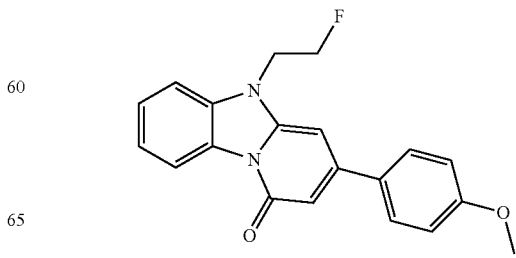

General experimental procedure (E) for N-alkylation reaction with 1-bromo-2-fluoroethane was followed. Reaction was performed on a 10.0 mg scale of 3-(4-methoxyphenyl)-1-oxo-1H,5H-pyrido[1,2-a]benzimidazole. Isolated 3.8 mg (33%) of T626 as a white solid. $^1$H NMR (CDCl$_3$): δ 8.84 (1H, d, J=8.0 Hz), 7.62 (2H, m), 7.45 (1H, m), 7.31 (2H, m), 6.97 (2H, m), 6.54 (1H, s), 6.28 (1H, s), 4.90 (1H, t, J=4.8 Hz), 4.79 (1H, t, J=4.8 Hz), 4.52 (1H, t, J=4.8 Hz), 4.46 (1H, t, J=4.8 Hz), 3.84 (3H, s); MS: 337 (M+H$^+$).

1-Chloro-3-(4-methoxyphenyl)-pyrido[1,2-a]benzimidazole: T639

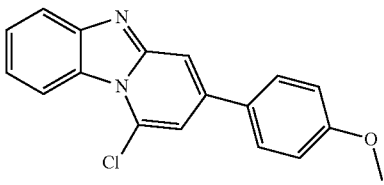 [SMILES: COc1ccc(-c2cc(Cl)n3c(c2)nc2ccccc23)cc1]

A suspension of T628 (108 mg, 0.37 mmol) in POCl$_3$ (1 ml) was heated at 100° C. for 3 hours. The mixture was poured into water and basified with sodium bicarbonate solid to pH ~8. The mixture was extracted with DCM for 3 times. The combined DCM layers was concentrated and the residue was purified by flush chromatography (EtOAc/DCM, 0 to 20%) to give 37.0 mg (32%) of T639 as an orange solid. $^1$H NMR (CDCl$_3$): δ 8.57 (1H, d, J=8.4 Hz), 7.92 (1H, d, J=8.4 Hz), 7.79 (1H, s), 7.63 (2H, m), 7.55 (1H, m), 7.35 (1H, m), 7.15 (1H, s), 7.01 (2H, m), 3.86 (3H, s); MS: 309 (M+H$^+$).

2-(1H-benzimidazol-2-yl)-pyrido[1,2-a]benzimidazole: T640

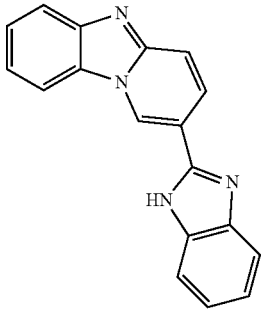 [SMILES: c1ccc2[nH]c(-c3ccc4nc5ccccc5n4c3)nc2c1]

To a microwave vial was added 2-ethynyl-1H-benzimidazole (10 mg, 0.070 mmol), and acetic acid (2 mL). The mixture was heated at 120° C. for 10 minutes in a microwave synthesizer. The acetic acid was removed the residue was neutralized with NaHCO$_3$ solution. The mixture was concentrated and purified flush chromatography (MeOH/DCM, 0 to 10%) to give 5.0 mg (50%) of T640 as a white solid. $^1$H NMR (CD$_3$OD): δ 9.56 (1H, s), 8.20 (2H, m), 7.83 (1H, d, J=8.4 Hz), 7.77 (1H, d, J=9.6 Hz), 7.56-7.63 (3H, m, overlapped), 7.27 (2H, m); MS: 285 (M+H$^+$).

2-[1-(2-Fluoroethyl)-1H-benzimidazol-2-yl]-pyrido[1,2-a]benzimidazole: T644

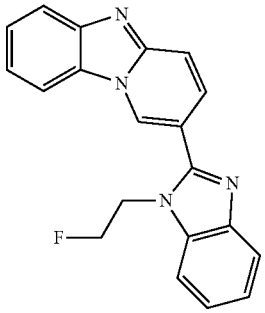 [SMILES: FCCn1c(-c2ccc3nc4ccccc4n3c2)nc2ccccc21]

General experimental procedure (E) for N-alkylation reaction with 1-bromo-2-fluoroethane was followed. Reaction was performed on a 3.2 mg scale of T640. Isolated 2.5 mg (68%) of T644 as a white solid. $^1$H NMR (CDCl$_3$): δ 9.10 (1H, s), 7.98 (2H, m), 7.86-7.92 (3H, m, overlapped), 7.60 (1H, m), 7.36-7.47 (4H, m, overlapped), 5.00 (1H, t, J=4.0 Hz), 4.89 (1H, t, J=4.0 Hz), 4.64 (1H, t, J=4.0 Hz), 4.58 (1H, t, J=4.0 Hz); MS: 331 (M+H$^+$).

1-Amino-3-(4-Methoxyphenyl)-pyrido[1,2-a]benzimidazole: T662

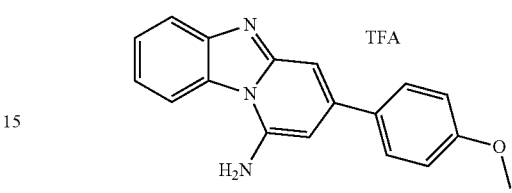

To a solution of 1-azido-3-(4-Methoxyphenyl)-pyrido[1,2-a]benzimidazole (12.0 mg, 0.038 mmol) in benzene (2 mL) was added triphenylphosphine (15.0 mg, 0.057 mmol). The mixture was stirred at room temperature for 3 hours and concentrated to a residue. Methanol (2 mL) was added to above residue followed by HCl (conc., 1 mL). Reaction mixture was heated at 60° C. for 2 hours and concentrated. The residue was purified by HPLC (acetonitrile/water) to give 4.6 mg (42%) of T662 as a light yellow solid. $^1$H NMR (CD$_3$OD): δ 8.50 (1H, d, J=8.8 Hz), 7.80 (2H, m), 7.72 (2H, m), 7.54 (1H, m), 7.27 (1H, s), 7.10 (2H, m), 6.99 (1H, s); MS: 290 (M+H$^+$).

1-Hydroxyl-3-(4-hydroxyphenyl)-pyrido[1,2-a]benzimidazole*HBr: T664

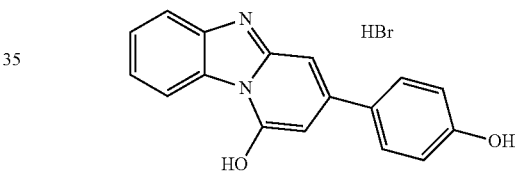

A suspension of T628 (60 mg, 0.21 mmol) in 48% HBr/H$_2$O (1.0 mL) and 48% HBr/HOAc (1.0 mL) was heated at 140° C. for 1 hour in a sealed tube. The mixture was cooled and the resulting solid precipitate was collected by filtration. The solid was washed with ether and dried under high vacuum to give 35 mg (47%) of T664 as a grey solid. $^1$H NMR (CD$_3$OD): δ 8.59 (1H, d, J=8.4 Hz), 7.70-7.74 (4H, m, overlapped), 7.53 (1H, m), 7.40 (1H, s), 6.95 (2H, m), 6.88 (1H, s); MS: 277 (M+H$^+$).

1-Hydroxyl-3-(4-(2-fluoroethyl)phenyl)-pyrido[1,2-a]benzimidazole*TFA: T665

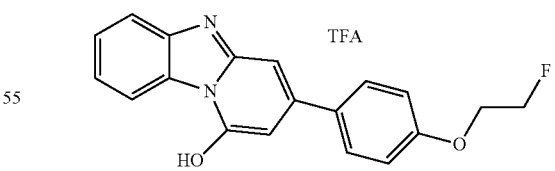

General experimental procedure (C) for phenolic alkylation with 1-bromo-2-fluoroethane was followed. Reaction was performed on a 40 mg scale of T664. Isolated 10.8 mg (22%) of T665 as a light yellow solid. $^1$H NMR (DMSO-d$_6$): δ 12.53 (1H, s), 8.63 (1H, d, J=8.4 Hz), 7.70 (2H, d, J=8.0 Hz), 7.44 (2H, m), 7.24 (1H, m), 7.05 (2H, d, J=8.0 Hz), 6.40 (1H, s), 6.13 (1H, s), 4.80 (1H, t, J=3.4 Hz), 4.68 (1H, t, J=3.4 Hz), 4.31 (1H, t, J=3.4 Hz), 4.24 (1H, t, J=3.4 Hz); MS: 323 (M+H$^+$).

3-(4-(2-Fluoroethyl)phenyl)-pyrido[1,2-a]benzimidazole*TFA: T666

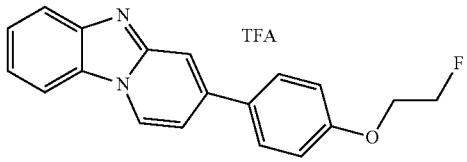 [SMILES: FCCOc1ccc(-c2ccn3c(c2)nc2ccccc23)cc1]

A suspension of 3-(4-methoxyphenyl)-pyrido[1,2-a]benzimidazole*TFA (4.6 mg, 0.012 mmol) in 48% HBr/H₂O (1.0 mL) and 48% HBr/HOAc (1.0 mL) was heated at 140° C. for 1 hour in a sealed tube. The mixture was concentrated to dryness to give the intermediate phenol. General experimental procedure (C) for phenolic alkylation with 1-bromo-2-fluoroethane was then followed. The residue was purified by HPLC (acetonitrile/water) to give 1.5 mg (30%) of T666 as a white solid. ¹H NMR (CD₃OD): δ 9.23 (1H, d, J=7.2 Hz), 8.35 (1H, d, J=8.4 Hz), 8.06 (1H, s), 7.86-7.90 (3H, m, overlapped), 7.80 (1H, m), 7.74 (1H, m), 7.61 (1H, m), 7.11 (2H, m), 4.74 (1H, t, J=3.4 Hz), 4.62 (1H, t, J=3.4 Hz), 4.28 (1H, t, J=3.4 Hz), 4.21 (1H, t, J=3.4 Hz); MS: 307 (M+H⁺).

1-(4-Aminophenyl)-3-methylpyrido[1,2-a]benzimidazole-4-carbonitrile*TFA: T672

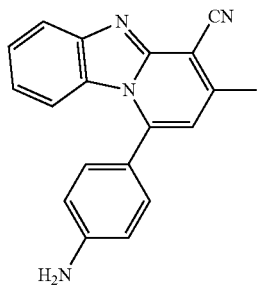 [SMILES: Cc1cc(-c2ccc(N)cc2)n2c(nc3ccccc32)c1C#N]

General experimental procedure (A) for Suzuki coupling reaction with 4-aminophenyl boronic acid was followed. Reaction was performed on a 241 mg scale of 1-chloro-3-methylpyrido[1,2-a]benzimidazole-4-carbonitrile. Isolated 100 mg (34%) of T672 as a yellow solid. NMR (CD₃OD): δ 7.85 (1H, d, J=8.4 Hz), 7.66 (1H, m), 7.43 (2H, m), 7.26-7.30 (2H, m, overlapped), 7.07 (1H, d, J=8.4 Hz), 7.38 (1H, dd, J=9.0, 2.6 Hz), 6.97 (2H, m), 2.80 (3H, s); MS: 299 (M+H⁺).

1-(4-(3-Fluoropropylamino)phenyl)-3-methylpyrido[1,2-a]benzimidazole-4-carbonitrile*TFA: T679

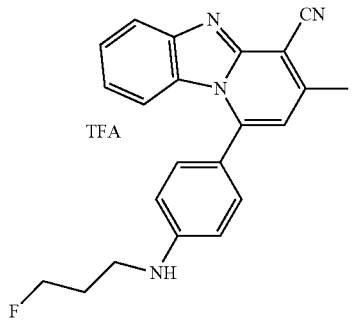 [SMILES: Cc1cc(-c2ccc(NCCCF)cc2)n2c(nc3ccccc32)c1C#N]

General experimental procedure (Q) for one-pot reductive amination with 3-fluoropropanol was followed. Reaction was performed on a 3.2 mg scale of T672. Isolated 2.4 mg (65%) of T679 as a yellow solid. ¹H NMR (CD₃OD): δ 7.85 (1H, d, J=8.0 Hz), 7.63 (1H, m), 7.41 (2H, m), 7.26 (1H, m), 7.20 (1H, s), 7.13 (1H, d, J=8.8 Hz), 6.85 (2H, m), 4.64 (1H, t, J=6.6 Hz), 4.53 (1H, t, J=6.6 Hz), 3.36 (2H, m), 2.78 (3H, s) 2.08 (1H, m), 2.01 (1H, m); MS: 359 (M+H⁺).

1-(4-(3-(4-Methylphenylsulfonyloxy)propylamino)phenyl)-3-methylpyrido[1,2-a]benzimidazole-4-carbonitrile: T679-precursor

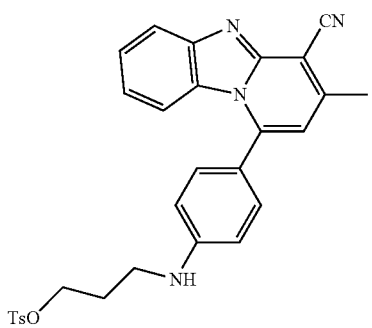 [SMILES: Cc1ccc(S(=O)(=O)OCCCNc2ccc(-c3cc(C)c(C#N)c4nc5ccccc5n34)cc2)cc1]

General experimental procedure (Q) for one-pot reductive amination with 3-hydroxypropyl 4-methylbenzenesulfonate was followed. Reaction was performed on a 100 mg scale of T672. Isolated 40 mg (23%) of T679-precursor as a yellow solid. ¹H NMR (CD₂Cl₂): δ 7.90 (1H, d, J=8.4 Hz), 7.80 (2H, m), 7.45 (1H, m), 7.38 (2H, m), 7.33 (2H, m), 7.05 (1H, m), 6.94 (1H, d, J=8.4 Hz), 6.72 (2H, m), 6.57 (1H, s), 4.19 (2H, t, J=6.0 Hz), 3.33 (2H, m), 2.67 (3H, s), 2.43 (3H, s), 2.01 (2H, m); MS: 511 (M+H⁺).

5-((2-(2-(2-Fluoroethoxy)ethoxy)ethyl))-3-(4-hydroxyphenyl)-1-oxo-1H,5H-pyrido[1,2-a]benzimidazole *TFA: T682

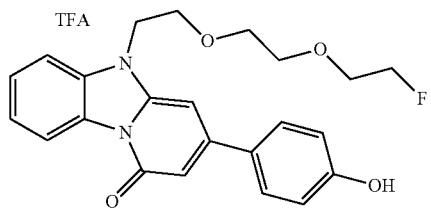 [SMILES: O=c1cc(-c2ccc(O)cc2)cc2n(CCOCCOCCF)c3ccccc3n12]

General experimental procedure (E) for N-alkylation with 2-(2-(2-fluoroethoxy)ethoxy)ethyl tosylate was followed. Reaction was performed on a 40 mg scale of T664. Isolated 7.9 mg (13%) of T682 as a white solid. ¹H NMR (CD₃OD): 8.70 (1H, d, J=8.0 Hz), 7.62-7.66 (3H, m, overlapped), 7.55 (1H, m), 7.36 (1H, m), 6.88-6.91 (3H, m, overlapped), 6.43 (1H, s), 4.57 (2H, t, J=4.8 Hz), 4.30 (1H, m), 4.18 (1H, m), 3.93 (2H, t, J=4.8 Hz), 3.53 (2H, m), 3.43-3.46 (3H, m, overlapped), 3.35-3.38 (1H, m); MS: 411 (M+H⁺).

7-Amino-2-(4-methoxyphenyl)pyrimido[1,2-a]benzimidazole: T696

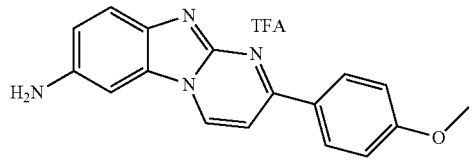 [SMILES: COc1ccc(-c2ccn3c(n2)nc2ccc(N)cc23)cc1]

To a suspension of 2-(4-methoxyphenyl)-7/8-nitro-pyrimido[1,2-a]benzimidazole (40 mg, 0.125 mmol) in EtOH (6 mL) was added SnCl₂2H₂O (169 mg, 0.75 mmol). The mixture was heated at 95° C. for 2 hours and concentrated. The residue was treated with 3N NaOH solution, and then extracted with DCM (3×10 mL). The DCM layers were combined and evaporated to a residue, which is purified by HPLC (acetonitrile/water) to give 18.0 mg (36%) of T696 as an orange solid. ¹H NMR (CD₃OD): δ 9.30 (1H, d, J=7.2 Hz), 8.35 (2H, m), 8.07 (1H, d, J=7.2 Hz), 7.57 (1H, d, J=8.8 Hz), 7.47 (1H, s), 7.20 (1H, m), 7.10 (2H, m), 3.89 (3H, s); MS: 291 (M+H⁺).

8-Amino-2-(4-methoxyphenyl)pyrimido[1,2-a]benzimidazole: T697

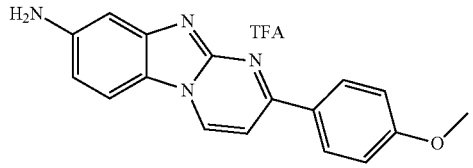 [SMILES: COc1ccc(-c2ccn3c(n2)nc2cc(N)ccc23)cc1]

To a suspension of 2-(4-methoxyphenyl)-7/8-nitro-pyrimido[1,2-a]benzimidazole (40 mg, 0.125 mmol) in EtOH (6 mL) was added SnCl₂2H₂O (169 mg, 0.75 mmol). The mixture was heated at 95° C. for 2 hours and concentrated. The residue was treated with 3N NaOH solution, and then extracted with DCM (3×10 mL). The DCM layers were combined and evaporated to a residue, which is purified by HPLC (acetonitrile/water) to give 10.0 mg (20%) of T697 as a yellow solid. ¹H NMR (CD₃OD): δ 9.30 (1H, d, J=7.2 Hz), 8.35 (2H, m), 8.07 (1H, d, J=7.2 Hz), 7.57 (1H, d, J=8.8 Hz), 7.47 (1H, s), 7.20 (1H, m), 7.10 (2H, m), 3.89 (3H, s); MS: 291 (M+H⁺).

7-(3-Fluoropropylamino)-2-(4-methoxyphenyl)pyrimido[1,2-a]benzimidazole: T699

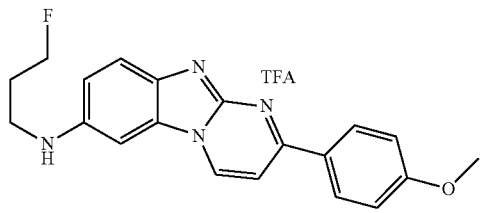 [SMILES: COc1ccc(-c2ccn3c(n2)nc2ccc(NCCCF)cc23)cc1]

General experimental procedure (Q) for one-pot reductive amidation with 3-fluoropropanol was followed. Reaction was performed on a 5.5 mg scale of T696 with adding 1N HCl prior to HPLC purification. Isolated 1.3 mg (22%) of T699 as a yellow solid. ¹H NMR (CD₃OD): δ 9.41 (1H, d, J=7.8 Hz), 8.38 (2H, m), 8.10 (1H, d, J=7.8 Hz), 7.55 (1H, d, J=8.8 Hz), 7.35 (1H, s), 7.13-7.16 (3H, m overlapped), 4.65 (1H, t, J=5.6 Hz), 4.54 (1H, t, J=5.6 Hz), 3.91 (3H, s), 3.36 (2H, t, J=6.8 Hz), 2.01-2.12 (2H, m); MS: 351 (M+H⁺).

6-Chloro-7-(3-fluoropropylamino)-2-(4-methoxyphenyl)pyrimido[1,2-a] benzimidazole: T700

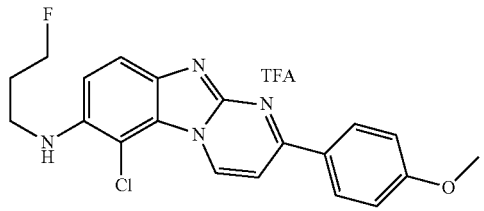 [SMILES: COc1ccc(-c2ccn3c(n2)nc2ccc(NCCCF)c(Cl)c23)cc1]

General experimental procedure (Q) for one-pot reductive amidation with 3-fluoropropanol was followed. Reaction was performed on a 5.5 mg scale of T696 with adding 1N HCl prior to HPLC purification. Isolated 2.0 mg (33%) of T699 as a yellow solid. ¹H NMR (CD₃OD): δ 9.81 (1H, d, J=7.8 Hz), 8.33 (2H, m), 7.96 (1H, d, J=7.8 Hz), 7.63 (1H, d, J=8.8 Hz), 7.25 (1H, d, J=8.8 Hz), 7.11 (2H, m), 4.64 (1H, t, J=5.6 Hz), 4.52 (1H, t, J=5.6 Hz), 3.90 (3H, s), 3.47 (2H, t, J=6.8 Hz), 1.99-2.12 (2H, m); MS: 385 (M+H⁺).

2-(4-Cyanophenyl)pyrimido[1,2-a]benzimidazole: T709

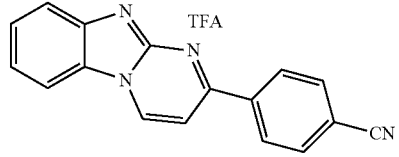 [SMILES: N#Cc1ccc(-c2ccn3c(n2)nc2ccccc23)cc1]

To a solution of (E)-4-(3-(dimethylamino)acryloyl)benzonitrile (2.0 g, 10.0 mmol) and 2-aminobenzimidazole (1.33 g, 10 mmol) in acetic acid (15 mL) was heated at 120° C. for 16 hours. The mixture was concentrated to a residue and treated with sodium bicarbonate solution to neutralize the residual acetic acid. The resulting suspension was added EtOAc, sonicated, and filtered. The solid collected was washed with water, ether, and dried under high vacuum to give 630 mg (23%) of T709 as yellow solid. A small amount was purified by HPLC (acetonitrile/H2O) for NMR and bioassay. ¹H NMR (CD₃OD): δ 9.83 (1H, d, J=8.4 Hz), 8.59 (2H, m), 8.46 (1H, d, J=8.4 Hz), 8.36 (1H, d, J=6.8 Hz), 8.01 (2H, m), 7.93 (1H, m), 7.87 (1H, m), 7.74 (1H, m); MS: 271 (M+H⁺).

8-(3-Fluoropropylamino)-2-(4-methoxyphenyl)pyrimido[1,2-a]benzimidazole: T723

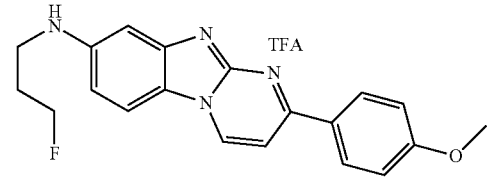 [SMILES: COc1ccc(-c2ccn3c(n2)nc2cc(NCCCF)ccc23)cc1]

General experimental procedure (Q) for one-pot reductive amidation with 3-fluoropropanol was followed. Reaction was performed on a 2.0 mg scale of T697. Isolated 0.6 mg (25%) of T699 as a yellow solid. ¹H NMR (CD₃OD): δ 9.35 (1H, d, J=7.2 Hz), 8.36 (2H, m), 8.09 (1H, d, J=7.2 Hz), 8.00 (1H, d, J=9.2 Hz), 7.14 (2H, m), 6.96 (1H, dd, J=9.2, 2.0 Hz), 6.75 (1H, d, J=2.0 Hz), 4.63 (1H, t, J=5.6 Hz), 4.52 (1H, t, J=5.6 Hz), 3.91 (3H, s), 3.35 (2H, t, J=7.0 Hz), 2.00-2.09 (2H, m); MS: 351 (M+H⁺).

7-Amino-2-(4-(2-fluoroethoxy)phenyl)pyrimido[1,2-a]benzimidazole: T729

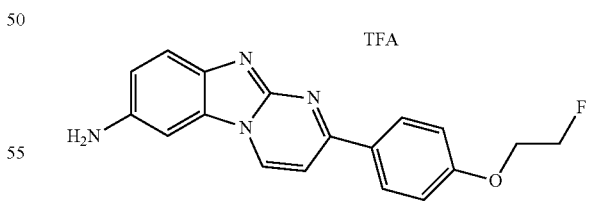

A suspension of T696 (10.0 mg, 0.034 mmol) in 48% HBr/H₂O (1.0 mL) and 48% HBr/HOAc (1.0 mL) was heated at 140° C. for 1 hour in a sealed tube. The mixture was concentrated to dryness to give the intermediate phenol. General experimental procedure (C) for phenolic alkylation with 1-bromo-2-fluoroethane was then followed. The residue was purified by HPLC (acetonitrile/water) to give 2.8 mg (25%) of T729 as a yellow solid. ¹H NMR (CD₃OD): δ 9.33 (1H, d, J=7.2 Hz), 8.39 (2H, m), 8.10 (1H, d, J=7.2 Hz), 7.58 (1H, d, J=8.8 Hz), 7.47 (1H, d, J=2.0 Hz), 7.16-7.22 (3H, m, overlapped), 4.82 (1H, t, J=4.0 Hz), 4.70 (1H, t, J=4.0 Hz), 4.38 (1H, t, J=4.0 Hz), 4.31 (1H, t, J=4.0 Hz); MS: 323 (M+H$^+$).

8-Amino-2-(4-(2-fluoroethoxy)phenyl)pyrimido[1,2-a]benzimidazole: T730

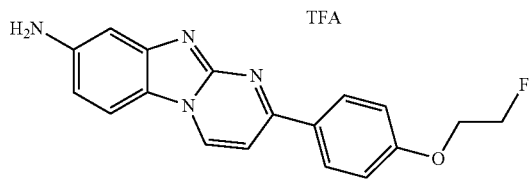 [SMILES: Nc1ccc2c(c1)nc1nc(-c3ccc(OCCF)cc3)ccn12]

A suspension of T697 (6.1 mg, 0.021 mmol) in 48% HBr/H$_2$O (1.0 mL) and 48% HBr/HOAc (1.0 mL) was heated at 140° C. for 1 hour in a sealed tube. The mixture was concentrated to dryness to give the intermediate phenol. General experimental procedure (C) for phenolic alkylation with 1-bromo-2-fluoroethane was then followed. The residue was purified by HPLC (acetonitrile/water) to give 1.9 mg (28%) of T730 as a yellow solid. $^1$H NMR (CD$_3$OD): δ 9.36 (1H, d, J=7.2 Hz), 8.36 (2H, m), 8.09 (1H, d, J=7.2 Hz), 7.98 (1H, d, J=8.8 Hz), 7.16 (2H, m), 6.96 (1H, dd, J=8.8, 2.0 Hz), 6.87 (1H, d, J=2.0 Hz), 4.82 (1H, t, J=4.0 Hz), 4.70 (1H, t, J=4.0 Hz), 4.37 (1H, t, J=4.0 Hz), 4.30 (1H, t, J=4.0 Hz); MS: 323 (M+H$^+$).

8-Boc-amino-2-(4-(2-(4-methylsulfonyloxy)ethoxy)phenyl)pyrimido[1,2-a]benzimidazole: T730-precursor

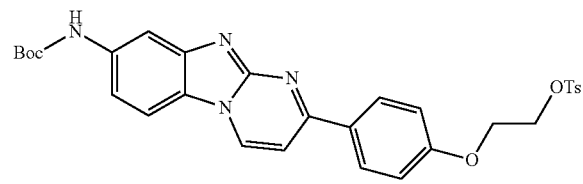 [SMILES: Cc1ccc(S(=O)(=O)OCCOc2ccc(-c3ccn4c(n3)nc3cc(NC(=O)OC(C)(C)C)ccc34)cc2)cc1]

A suspension of 8-amino-2-(4-(2-(4-methylsulfonyloxy)ethoxy)phenyl)pyrimido[1,2-a]benzimidazole*3TFA (80 mg, 0.098 mmol) in THF (10 mL) was added Boc$_2$O (367 mg, 1.68 mmol) and TEA (85 mg, 0.841 mmol). The mixture was heated at 60° C. for 6 hours. The residue was purified by flush chromatography (EtOAc/DCM, 0 to 40%) to give 21.2 mg (38%) of T730-precursor as a yellow solid. $^1$H NMR (DMSO-d$_6$): δ 9.52 (1H, s), 9.39 (1H, d, J=7.2 Hz), 8.24 (2H, m), 8.11 (1H, d, J=8.8 Hz), 7.93 (1H, s), 7.79 (2H, m), 7.70 (1H, d, J=7.2 Hz), 7.46 (2H, m), 7.41 (1H, d, J=8.8 Hz), 7.00 (2H, m), 4.36 (2H, t, J=4.0 Hz), 4.26 (2H, t, J=4.0 Hz), 2.38 (3H, s); MS: 575 (M+H$^+$).

2-(4-Aminomethylphenyl)pyrimido[1,2-a]benzimidazole: T732

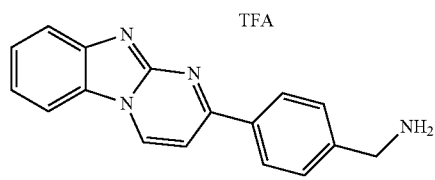 [SMILES: NCc1ccc(-c2ccn3c(n2)nc2ccccc23)cc1]

General experimental procedure (A) for Suzuki coupling with 4-(tert-butoxycarbonylamino)phenylboronic acid was followed. Reaction was performed on a 40 mg scale of 2-chloropyrimido[1,2-a]benzimidazole. After Suzuki reaction, the mixture was treated with 4 N HCl in dioxane/DCM to remove the Boc group. The residue was purified by HPLC (acetonitrile/water) to give 8.7 mg (16%) of T732 as a white solid. $^1$H NMR (CD$_3$OD): δ 9.72 (1H, d, J=7.2 Hz), 8.51 (2H, m), 8.41 (1H, d, J=8.4 Hz), 8.28 (1H, d, J=7.2 Hz), 7.90 (1H, d, J=8.0 Hz), 7.82 (1H, m), 7.67-7.74 (3H, m), 4.26 (2H, s); MS: 275 (M+H$^+$).

2-(2-Fluoropyridin-4-yl)pyrimido[1,2-a]benzimidazole: T737

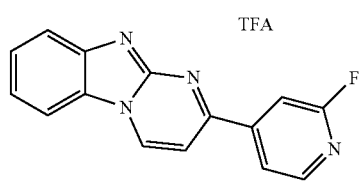 [SMILES: Fc1cc(-c2ccn3c(n2)nc2ccccc23)ccn1]

General experimental procedure (A) for Suzuki coupling with 2-fluoropyridin-4-ylboronic acid was followed. Reaction was performed on a 40 mg scale of 2-chloropyrimido[1,2-a]benzimidazole. The residue was purified by HPLC (acetonitrile/water) to give 6.2 mg (12%) of T732 as a white solid. $^1$H NMR (CD$_3$OD): δ 9.91 (1H, d, J=7.2 Hz), 8.47-8.53 (2H, m, overlapped), 8.39 (PH, d, J=7.2 Hz), 8.25 (1H, m), 8.04 (1H, m), 7.95 (1H, d, J=8.4 Hz), 7.89 (1H, m), 7.76 (1H, m); MS: 265 (M+H$^+$).

7-N,N-dimethylamino-2-(4-hydroxyphenyl)pyrimido[1,2-a]benzimidazole: T767

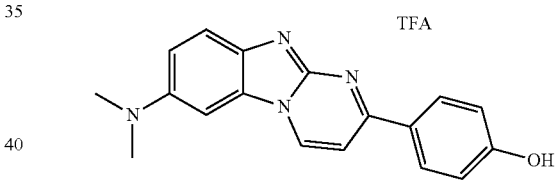

A suspension of T696 (54.0 mg, 0.186 mmol) in 48% HBr/H$_2$O (1.0 mL) and 48% HBr/HOAc (1.0 mL) was heated at 140° C. for 1 hour in a sealed tube. The mixture was concentrated to dryness to give the phenol-amine. The residue was dissolved in methanol (10 mL) and formaldehyde solution (37% in water, 1 mL) was added. The mixture was added NaBH$_3$CN (60 mg, 0.955 mmol) and stirred at room temperature for 10 min. The residue was purified by HPLC (acetonitrile/water) to give 36 mg (64%) of T767 as a red solid. $^1$H NMR (CD$_3$OD): δ 9.43 (1H, d, J=7.2 Hz), 8.31 (2H, m), 8.08 (1H, d, J=8.8 Hz), 7.64 (1H, d, J=9.2 Hz), 7.52 (1H, d, J=2.4 Hz), 7.30 (1H, dd, J=9.2, 2.4 Hz), 6.97 (2H, m), 3.11 (6H, s); MS: 305 (M+H$^+$).

7-N,N-dimethylamino-2-(4-(2-fluoroethoxy)phenyl)pyrimido[1,2-a]benzimidazole: T769

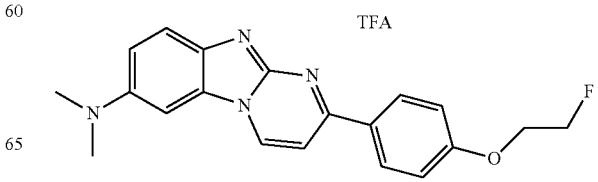

General experimental procedure (C) for phenolic alkylation with 1-bromo-2-fluoroethane was followed. Reaction was performed on a 6.8 mg scale of T767. The residue was purified by HPLC (acetonitrile/water) to give 4.9 mg (63%) of T769 as a red solid. $^1$H NMR (CD$_3$OD): δ 9.48 (1H, d, J=7.2 Hz), 8.40 (2H, m), 8.11 (1H, d, J=7.2 Hz), 7.66 (1H, d, J=9.2 Hz), 7.52 (1H, d, J=2.4 Hz), 7.31 (1H, dd, J=9.2, 2.4 Hz), 7.18 (2H, m), 4.82 (1H, t, J=4.0 Hz), 4.70 (1H, t, J=4.0 Hz), 4.38 (1H, t, J=4.0 Hz), 4.31 (1H, t, J=4.0 Hz), 3.11 (6H, s); MS: 351 (M+H$^+$).

8-N,N-dimethylamino-2-(4-(2-fluoroethoxy)phenyl)pyrimido[1,2-a]benzimidazole: T772

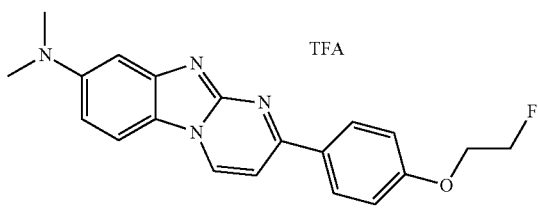 [SMILES: CN(C)c1ccc2c(c1)nc1nc(-c3ccc(OCCF)cc3)ccn12]

A solution of T730 (6.0 mg, 0.0186 mmol) in methanol (2 mL) was added formaldehyde solution (37% in water, 0.1 mL) and NaBH$_3$CN (6.0 mg, 0.0952 mmol). The mixture was stirred at room temperature for 10 min. The residue was purified by HPLC (acetonitrile/water) to give 1.0 mg (15%) of T772 as a red solid. $^1$H NMR (CD$_3$OD): δ 9.40 (1H, d, J=7.2 Hz), 8.38 (2H, m), 8.12 (1H, d, J=7.2 Hz), 8.11 (1H, d, J=9.2 Hz), 7.18 (2H, m), 7.12 (1H, dd, J=9.2, 2.4 Hz), 6.84 (1H, d, J=2.4 Hz), 4.82 (1H, t, J=4.0 Hz), 4.70 (1H, t, J=4.0 Hz), 4.39 (1H, t, J=4.0 Hz), 4.31 (1H, t, J=4.0 Hz), 3.13 (6H, s); MS: 351 (M+H$^+$).

(8-Methoxypyrido[1,2-a]benzimidazol-3-yl)piperidin-4-yl methanesulfonate: T798-precursor 1

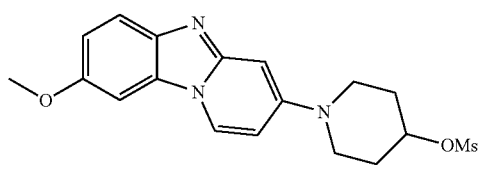 [SMILES: COc1ccc2nc3cc(N4CCC(OS(C)(=O)=O)CC4)ccn3c2c1]

To a solution of (8-methoxypyrido[1,2-a]benzimidazol-3-yl)piperidin-4-ol (66.3 mg, 0.223 mmol) in DCM (6.0 mL) was added methanesulfonyl chloride (51 mg, 0.445 mmol) and TEA (45 mg, 0.446 mmol). The mixture was stirred for 10 min before sodium bicarbonate solution (saturated, 6 mL) was added. The mixture was stirred at room temperature for another 30 minutes. The DCM layer was separated and concentrated. The residue purified by HPLC (acetonitrile/water), and then neutralized with NaHCO$_3$ to give 65.6 mg (52%) of T798-precursor 1 as a white solid. $^1$H NMR (CDCl$_3$): δ 8.09 (1H, d, J=7.6 Hz), 7.65 (1H, d, J=8.8 Hz), 7.18 (1H, d, J=2.4 Hz), 7.06 (1H, dd, J=8.8, 2.4 Hz), 6.72 (1H, d, J=2.0 Hz), 6.56 (1H, dd, J=7.6, 2.4 Hz), 4.96 (1H, m), 3.88 (3H, s), 3.57 (2H, m), 3.27 (2H, m), 3.05 (3H, s), 2.14 (2H, m), 2.02 (2H, m); MS: 303 (M+H$^+$).

2-(4-Bromopiperidin-1-yl)-8-methoxypyrido[1,2-a]benzimidazole: T798-precursor 2

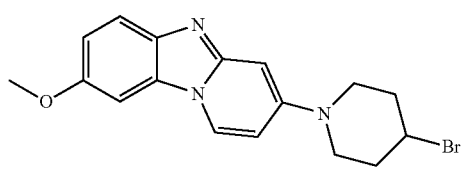 [SMILES: COc1ccc2nc3cc(N4CCC(Br)CC4)ccn3c2c1]

To a solution of T798-precursor 1 (3.0 mg, 0.008 mmol) in DMF (1.0 mL) was added LiBr (14 mg, 0.163 mmol). The mixture was heated at 80° C. for 24 hours. The residue purified by HPLC (acetonitrile/water), and then neutralized with NaHCO$_3$ to give 1.4 mg (48%) of T798-precursor 2 as a white solid. $^1$H NMR (CDCl$_3$): δ 8.09 (1H, d, J=7.6 Hz), 7.66 (1H, d, J=8.8 Hz), 7.18 (1H, d, J=2.4 Hz), 7.06 (1H, dd, J=8.8, 2.4 Hz), 6.72 (1H, d, J=2.0 Hz), 6.57 (1H, dd, J=7.6, 2.4 Hz), 4.41 (1H, m), 3.89 (3H, s), 3.61 (2H, m), 3.28 (2H, m), 2.27 (2H, m), 2.14 (2H, m); MS: 362 (M+H$^+$).

Synthesis of T704:

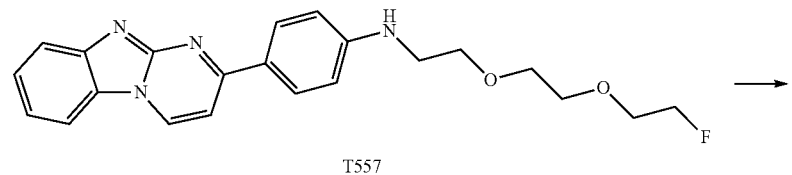

T557

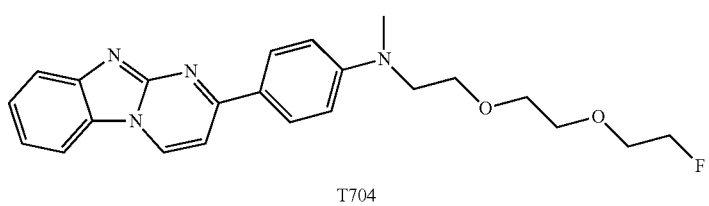

T704

Sodium cyanoborohydride (15.93 mg, 0.254 mmol) was added to a solution containing T557 (10 mg, 0.025 mmol) and Formaldehyde solution (0.041 ml, 0.507 mmol) in MeOH (2 ml). Stirred for 20 mins. Purified by prep HPLC to afford T704 (2 mg, 4.90 µmol 19.31% yield). MS (ESI, Pos.) m/z: 409.1 [M+H]$^+$.

Synthesis of T717 and T718

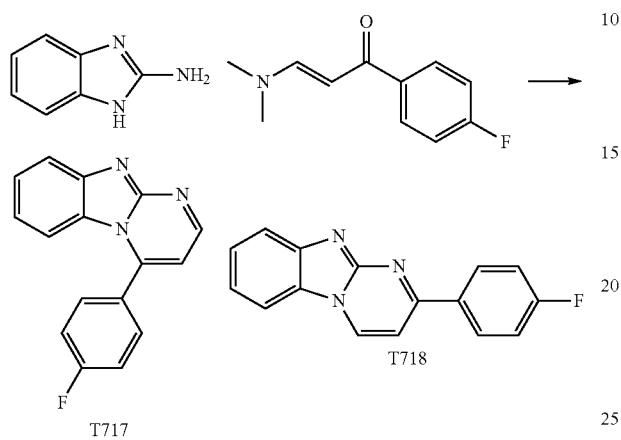

Combined 2-aminobenzimidazole (0.345 g, 2.59 mmol) and (E)-1-(4-bromophenyl)-3-(dimethylamino)prop-2-en-1-one (0.5 g, 2.59 mmol) in Acetic Acid (Volume: 12 ml). Heated the reaction for 2 hours. Let the reaction cool to room temperature. Concentrated and diluted with water. Filtered and dried solid. Diluted and purified by prepHPLC to afford T717 (0.1 g, 0.380 mmol, 14.68% yield) MS (ESI, Pos.) m/z: 264.0 [M+H]$^+$. and T718 (0.1 g, 0.380 mmol, 14.68% yield) MS (ESI, Pos.) m/z: 264.0 [M+H]$^+$.

Synthesis of T720

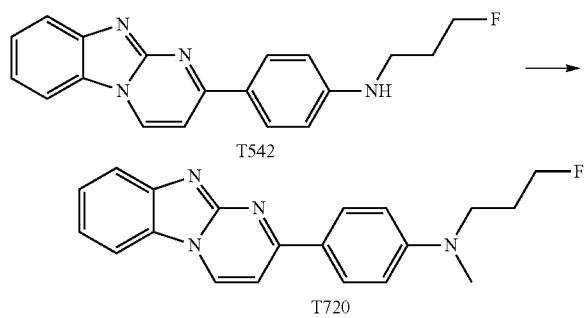

Sodium cyanoborohydride (19.62 mg, 0.312 mmol) was added to a solution containing T542 (10 mg, 0.031 mmol) and Formaldehyde solution (0.019 ml, 0.624 mmol) in MeOH (1 ml). After 20 mins, purified by prep HPLC to afford T720 (1.4 mg, 4.19 µmol, 13.41% yield). MS (ESI, Pos.) m/z: 335.1 [M+H]$^+$.

Synthesis of T768:

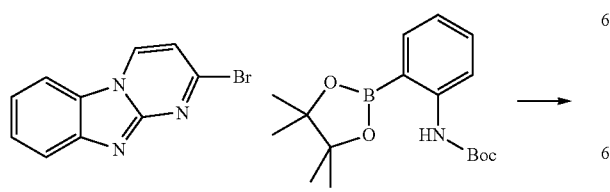

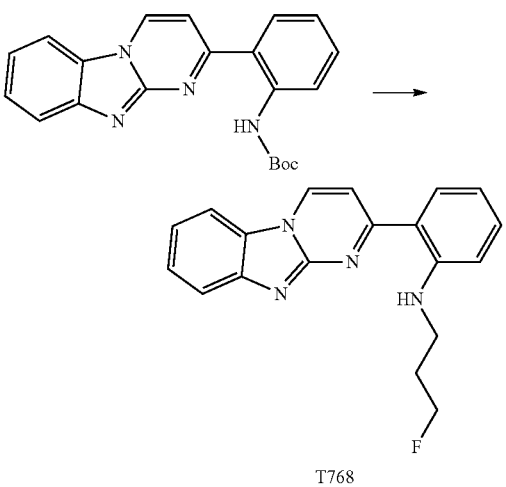

Preparation of tert-butyl (2-(benzo[4,5]imidazo[1,2-a]pyrimidin-2-yl)phenyl)carbamate.

1,1' Bis(diphenylphosphino)ferrocnee]dichloropalladium (II),w/DCM (0.033 g, 0.040 mmol) was added to a solution containing 2-bromobenzo[4,5]imidazo[1,2-a]pyrimidine (0.2 g, 0.806 mmol), tert-butyl (2-(4,4,5,5-tetramethyl-1,3,2-dioxaborolan-2-yl)phenyl)carbamate (0.386 g, 1.209 mmol), Copper(I) iodide (0.015 g, 0.081 mmol), and Potassium carbonate (0.806 ml, 1.612 mmol) in DMF. The solution was heated in the microwave for 15 minutes at 120° C. The reaction was cooled to room temperature. Diluted with water, extracted with ethyl acetate, combined organics, dried, filtered and concentrated. Purified by Combiflash column using 0% to 80% ethyl acetate in hexanes to afford tert-butyl (2-(benzo[4,5]imidazo[1,2-a]pyrimidin-2-yl)phenyl)carbamate (0.13 g, 0.361 mmol, 44.7% yield).

Preparation of T768. Sodium hydride 60% (0.028 g, 0.721 mmol) was added to a solution containing tert-butyl (2-(benzo[4,5]imidazo[1,2-a]pyrimidin-2-yl)phenyl)carbamate (0.13 g, 0.361 mmol) in DMF (Volume: 2 ml). After 5 minutes, 1-bromo-3-fluoropropane (0.102 g, 0.721 mmol) was added to the mixture and stirred for 4 hours. Diluted the reaction with water, extracted with ethyl acetate, combined organics, dried, filtered and concentrated. TFA (Trifluoroacetic acid) (1 ml, 12.98 mmol) was added to the resulting residue. After 5 minutes, the solution was concentrated and the product purified by PREP HPLC to afford T768 (0.007 g, 0.022 mmol, 6.06% yield) MS (ESI, Pos.) m/z: 321.0 [M+H]$^+$.

Synthesis of T776 and T778:

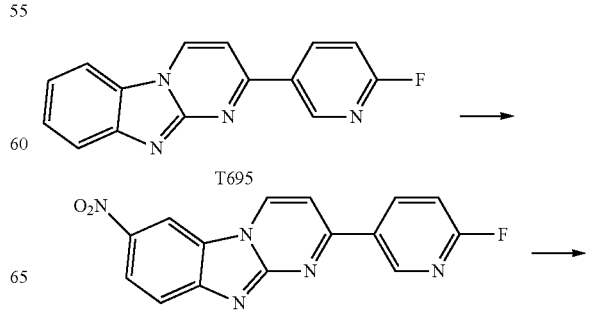

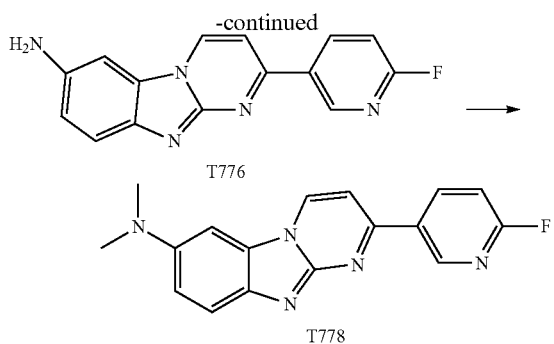

Preparation of 2-(6-fluoropyridin-3-yl)-7-nitrobenzo[4,5]imidazo[1,2-a]pyrimidine. Nitric acid red fuming 90% (0.076 ml, 1.514 mmol) was added dropwise to a precooled solution of T695 (0.2 g, 0.757 mmol) in Sulfuric acid (0.5 ml, 9.38 mmol) at 0° C. The reaction was stirred for 15 minutes. Diluted reaction with water and vacuum filtrated the resulting precipitate to afford 2-(6-fluoropyridin-3-yl)-7-nitrobenzo[4,5]imidazo[1,2-a]pyrimidine (0.234 g, 0.757 mmol, 100% yield).

Preparation of T776. Sodium cyanoborohydride (0.041 g, 0.647 mmol) was added to a solution containing 2-(6-fluoropyridin-3-yl)-7-nitrobenzo[4,5]imidazo[1,2-a]pyrimidine (0.1 g, 0.323 mmol) in THF (Ratio: 10.00, Volume: 1 ml) and MeOH (Ratio: 1.000, Volume: 0.1 ml). The reaction was stirred for 30 minutes. Diluted with methanol, filtered and purified by PREP HPLC to afford T776 (0.007 g, 0.025 mmol, 7.75% yield) MS (ESI, Pos.) m/z: 280.0 [M+H]+.

Preparation of T778. Sodium cyanoborohydride (0.023 g, 0.358 mmol) was added to a solution containing Formaldehyde solution (0.029 ml, 0.358 mmol) and T776 (0.01 g, 0.036 mmol) in MeOH (Volume: 2 ml). The reaction was stirred for 10 minutes. Purified by PREP HPLC to afford T778 (0.002 g, 6.51 µmol, 18.17% yield) MS (ESI, Pos.) m/z: 308.0 [M+H]+.

Synthesis of T812

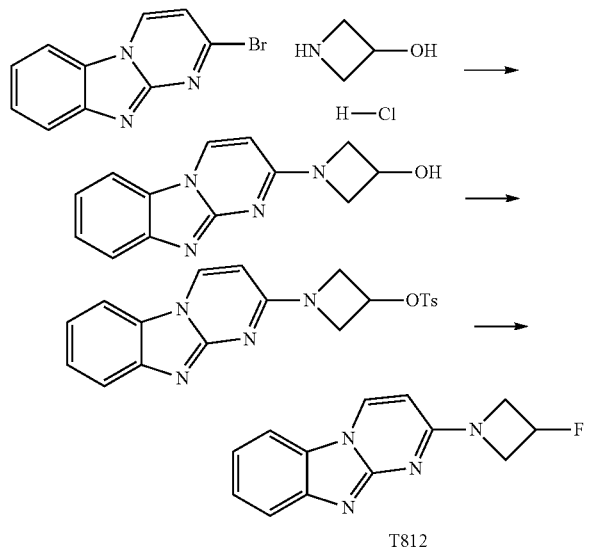

Preparation of 1-(benzo[4,5]imidazo[1,2-a]pyrimidin-2-yl)azetidin-3-ol. Azetidin-3-ol hydrochloride (0.022 g, 0.202 mmol), 2-bromobenzo[4,5]imidazo[1,2-a]pyrimidine (0.05 g, 0.202 mmol) and Triethylamine (0.028 ml, 0.202 mmol) were heated to 100° C. for 10 minutes in a microwave. Let the reaction cool to room temperature. Diluted with water and vacuum filtered ppt. Washed with water to afford 1-(benzo[4,5]imidazo[1,2-a]pyrimidin-2-yl)azetidin-3-ol (0.048 g, 0.200 mmol, 99% yield).

Preparation of 1-(benzo[4,5]imidazo[1,2-a]pyrimidin-2-yl)azetidin-3-yl 4-methylbenzenesulfonate. p-Toluenesulfonic anhydride (0.098 g, 0.300 mmol) was added to a solution containing 1-(benzo[4,5]imidazo[1,2-a]pyrimidin-2-yl)azetidin-3-yl 4-methylbenzenesulfonate (0.079 g, 0.200 mmol, 100% yield) and N,N-Diisopropylethylamine (0.070 ml, 0.400 mmol) in DCM (Volume: 0.666 ml). Let the reaction stir for 30 minutes. Diluted reaction with water, extracted with ethyl acetate, combined organics, dried, filtered and concentrated to afford crude 1-(benzo[4,5]imidazo[1,2-a]pyrimidin-2-yl)azetidin-3-yl-4-methylbenzenesulfonate (0.079 g, 0.200 mmol, 100% yield).

Preparation of T812. TBAF (Tetrabutyl ammonium fluoride 1M THF) (1 ml, 1.000 mmol) and 1-(benzo[4,5]imidazo[1,2-a]pyrimidin-2-yl)azetidin-3-yl 4-methylbenzenesulfonate (0.035 g, 0.089 mmol) were stirred at room temperature overnight. Concentrated and purified by PREP HPLC to afford T812 (0.002 g, 8.26 µmol, 9.30% yield) MS (ESI, Pos.) m/z: 243.0 [M+H]+.

Synthesis of T814

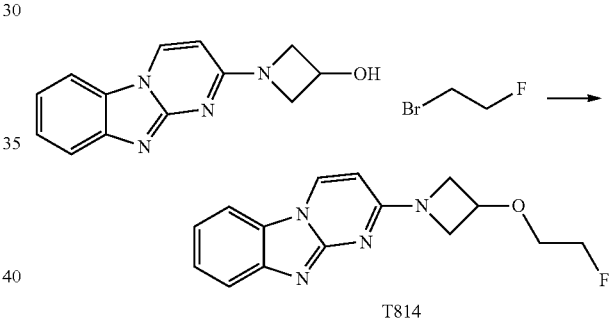

Preparation of T814. Sodium hydride 60% (6.70 mg, 0.291 mmol) was added to a solution containing 1-(benzo[4,5]imidazo[1,2-a]pyrimidin-2-yl)azetidin-3-ol (0.035 g, 0.146 mmol) and 1-bromo-2-fluoroethane (0.037 g, 0.291 mmol) in DMF (Volume: 0.486 ml). Let the reaction stir overnight. Purified by PREP HPLC to afford T814 (0.002 g, 6.99 µmol, 4.80% yield) MS (ESI, Pos.) m/z: 287.0 [M+H]+.

Synthesis of T815

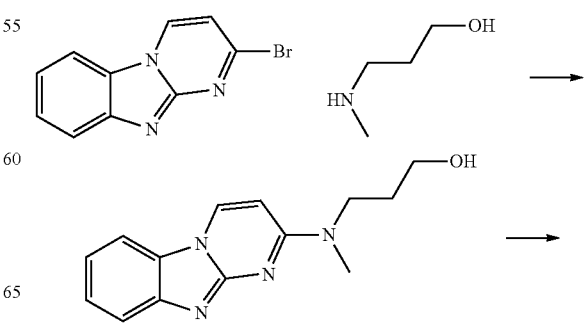

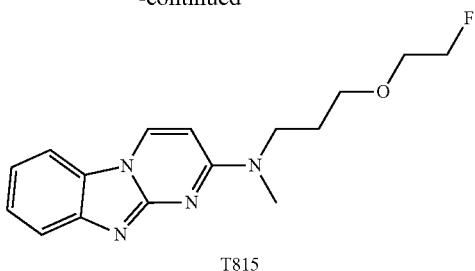

T815

Preparation of 3-(benzo[4,5]imidazo[1,2-a]pyrimidin-2-ylmethyl)amino)propan-1-ol. 2-Bromobenzo[4,5]imidazo[1,2-a]pyrimidine (0.2 g, 0.806 mmol), 3-(methylamino)propan-1-ol (0.072 g, 0.806 mmol) and N,N-Diisopropylethylamine (0.141 ml, 0.806 mmol) were heated to 100° C. for 10 minutes in a microwave. Let the reaction cool to room temperature. Diluted reaction with water, extracted with ethyl acetate, combined organics, dried, filtered and concentrated to afford crude 3-(benzo[4,5]imidazo[1,2-a]pyrimidin-2-ylmethyl)amino)propan-1-ol (0.207 g, 0.808 mmol, 100% yield).

Preparation of T815. Sodium hydride 60% (3.59 mg, 0.156 mmol) was added to a solution containing 3-(benzo[4,5]imidazo[1,2-a]pyrimidin-2-yl(methyl)amino)propan-1-ol (0.02 g, 0.078 mmol) and 1-bromo-2-fluoroethane (0.020 g, 0.156 mmol) in DMF (Volume: 0.390 ml). Let the reaction stir overnight. Concentrated and purified by PREP HPLC to afford T815 (0.002 g, 6.61 µmol, 8.48% yield) MS (ESI, Pos.) m/z: 303.0 [M+H]$^+$.

Synthesis of T816

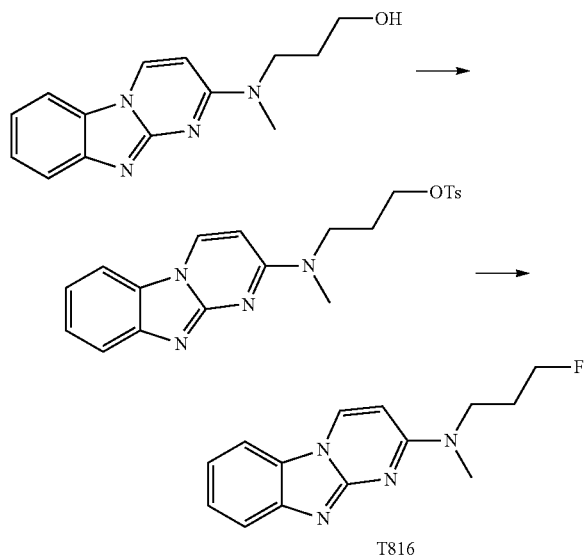

T816

Preparation of 3-(benzo[4,5]imidazo[1,2-a]pyrimidin-2-yl(methyl)amino)propyl 4-methylbenzenesulfonate. p-Toluenesulfonic anhydride (0.382 g, 1.170 mmol) was added to a solution containing 3-(benzo[4,5]imidazo[1,2-a]pyrimidin-2-yl(methyl)amino)propan-1-ol (0.2 g, 0.780 mmol) and N,N-Diisopropylethylamine (0.273 ml, 1.561 mmol) in DCM (Volume: 1.951 ml). The reaction was stirred for 30 minutes. Concentrated and purified by PREP HPLC to afford 3-(benzo[4,5]imidazo[1,2-a]pyrimidin-2-yl(methyl)amino)propyl 4-methylbenzenesulfonate (0.02 g, 0.049 mmol, 6.24% yield).

Preparation of T816. DAST (0.206 ml, 1.561 mmol) was added to a solution 3-(benzo[4,5]imidazo[1,2-a]pyrimidin-2-yl(methyl)amino)propan-1-ol (0.1 g, 0.390 mmol) in DCM (Volume: 1.951 ml) at 0° C. The reaction was stirred for 30 minutes. Let the reaction warm to room temperature. Diluted with sat'd NaHCO$_3$, extracted with DCM, combined organics, dried, filtered, concentrated and purified by PREP HPLC to afford T816 (0.003 g, 0.012 mmol, 2.98% yield) MS (ESI, Pos.) m/z: 259.0 [M+H]$^+$.

Synthesis of T818

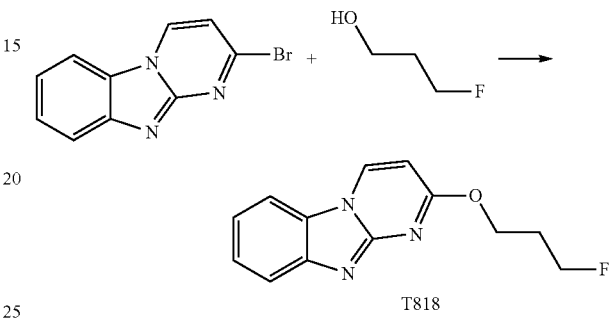

T818

Preparation of T818. Sodium hydride 60% (9.27 mg, 0.403 mmol) was added to a solution containing 2-bromobenzo[4,5]imidazo[1,2-a]pyrimidine (0.05 g, 0.202 mmol), 3-fluoropropan-1-ol (0.031 g, 0.403 mmol) in DMF (Volume: 1.008 ml). Let the reaction stir for 1 hour. Purified by PREP HPLC to afford T818 (0.003 g, 0.012 mmol, 6.07% yield) MS (ESI, Pos.) m/z: 246.0 [M+H]$^+$.

Synthesis of 2-bromobenzo[4,5]imidazo[1,2-a]pyrimidine

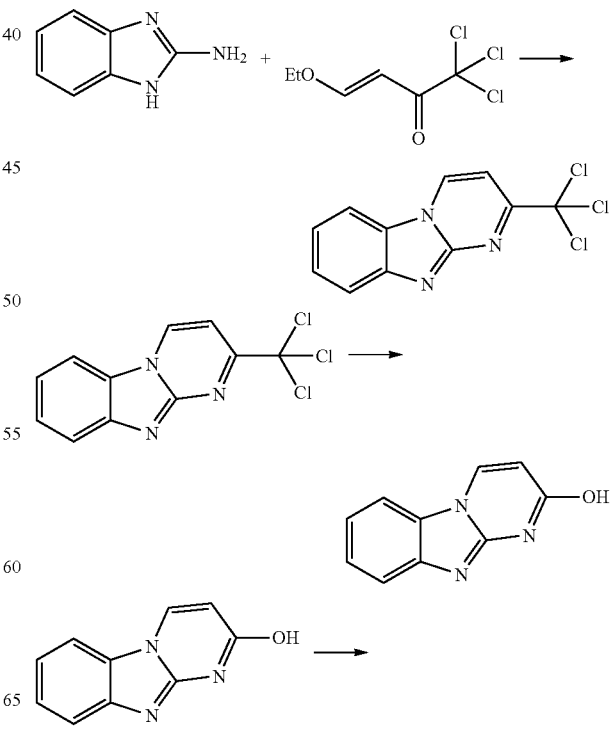

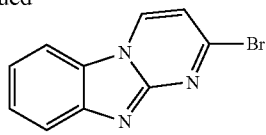

Preparation of 2-(trichloromethyl)benzo[4,5]imidazo[1,2-a]pyrimidine. (E)-1,1,1-trichloro-4-ethoxybut-3-en-2-one (6.1 g, 28.0 mmol) was added to a solution containing 1H-benzo[d]imidazol-2-amine (3.73 g, 28.0 mmol) and Triethylamine (3.91 mL, 28.0 mmol) in Toluene (Volume: 100 mL). Heated the reaction to 120° C. for 2 hours. Let the reaction cool to room temperature and concentrated under vacuum. Diluted with water and filtered. Collected solid and dried under vacuum to afford crude 2-(trichloromethyl)benzo[4,5]imidazo[1,2-a]pyrimidine (8.04 g, 28.1 mmol, 100% yield).

Preparation of benzo[4,5]imidazo[1,2-a]pyrimidin-2-ol. Sodium hydroxide (36.5 ml, 36.5 mmol) was added to a solution containing 2-(trichloromethyl)-benzo[4,5]imidazo[1,2-a]pyrimidine (8.04 g, 28.1 mmol) in Acetonitrile (Volume: 122 ml). Heated the reaction to 90 C for 30 minutes. Cooled the reaction to room temperature and concentrated. Added ice to the resulting residue, followed by 35 mL of 1M HCl. Filtered the solid and dried under vacuum to afford crude benzo[4,5]imidazo[1,2-a]pyrimidin-2-ol (5.2 g, 28.1 mmol, 100% yield).

Preparation of 2-bromobenzo[4,5]imidazo[1,2-a]pyrimidine. Phosphorus oxybromide (25 g, 87 mmol) was added to a suspension of benzo[4,5]imidazo[1,2-a]pyrimidin-2-ol (5.2 g, 28.1 mmol) in DCE (Ratio: 1.000, Volume: 93 ml) and DMF (Ratio: 0.01, Volume: 0.927 ml). Heated the reaction mixture to 100° C. for 3 hours. Cooled the reaction to room temperature and concentrated. Diluted with ice water and quenched to pH ~8 with concentrated ammonium hydroxide. The resulting residue was filtered and washed with water followed by ethyl ether. Dried under vacuum to afford crude 2-bromobenzo[4,5]imidazo[1,2-a]pyrimidine (6.97 g, 28.1 mmol, 100% yield).

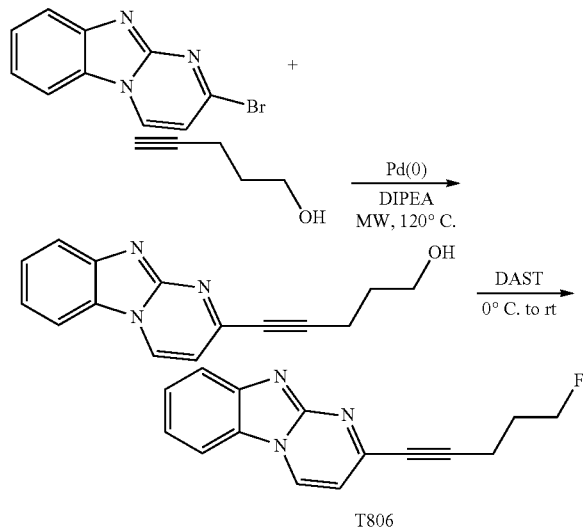

T806

5-(Benzo[4,5]imidazo[1,2-a]pyrimidin-2-yl)pent-4-yn-1-ol. A mixture of 2-bromobenzo[4,5]imidazo[1,2-a]pyrimidine (40 mg, 0.2 mmol), pent-4-yn-1-ol (22 mg, 0.26 mmol), tetrakis(triphenylphosphine)palladium (23 mg, 0.02 mmol), DIPEA (50 mg, 0.4 mmol) in 2 mL dioxane was heated at 120° C. for 20 min in a microwave reactor and then cooled to rt. It was diluted with EtOAc (20 mL) and washed with brine (30 mL) and water (2×30 mL) and concentrated. The residue was purified by silica chromatography (EtOAc in DCM, 10% to 100%) to afford 5-(benzo[4,5]imidazo[1,2-a]pyrimidin-2-yl)pent-4-yn-1-ol as a yellow solid (28 mg, 56%). $^1$H NMR (400 MHz, CDCl$_3$): δ 8.68 (d, J=6.8, 1H), 8.03 (d, J=8.4 Hz, 1H), 7.86 (d, J=8.4 Hz, 1H), 7.57 (m, 1H), 7.42 (m, 1H), 6.95 (d, J=6.8 Hz, 1H), 3.85 (t, J=6 Hz, 2H), 2.82 (t, J=6.8 Hz, 2H), 1.93 (m, 2H); MS (ESI) m/z [M+H]$^+$252.

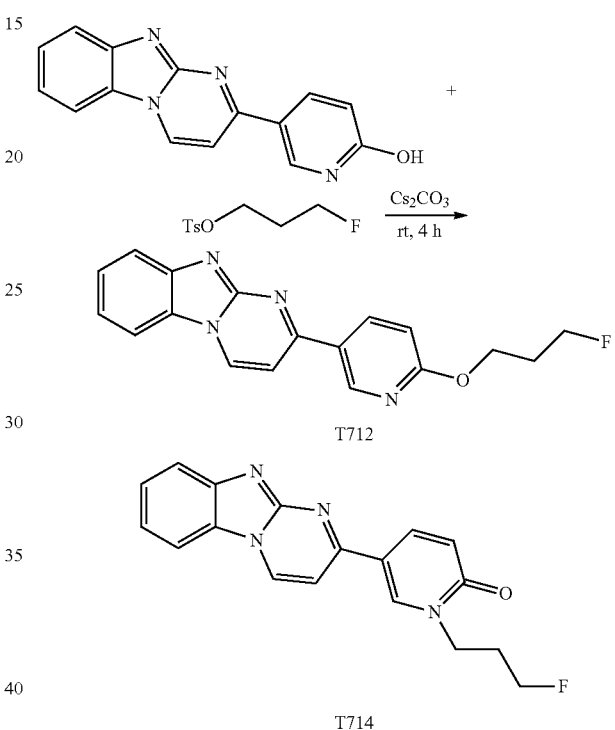

2-(6-(3-Fluoropropoxy)pyridin-3-yl)benzo[4,5]imidazo[1,2-a]pyrimidine. To 5-(benzo[4,5]imidazo[1,2-a]pyrimidin-2-yl)pyridin-2-ol (8 mg, 0.03 mmol), and 3-fluoropropyl 4-methylbenzenesulfonate (21 mg, 0.09 mmol) in 0.3 mL of NMP was added Cs$_2$CO$_3$ (15 mg, 0.045 mmol). The reaction was stirred at rt for 4 h and diluted with EtOAc (10 mL). The mixture was washed with water (3×10 mL) and dried over MgSO$_4$ and concentrated under reduced pressure. The residue was purified by reversed phase HPLC (water/MeCN with TFA buffer) to afford 2-(6-(3-fluoropropoxy)pyridin-3-yl)benzo[4,5]imidazo[1,2-a]pyrimidine as a off-white solid (3 mg, 31%). $^1$H NMR (400 MHz, methanol-d4): δ 9.79 (d, J=7.2 Hz, 1H), 8.66 (d, J=2.8 Hz, 1H), 8.69 (dd, J=8.8, 2.8 Hz, 1H), 8.40 (d, J=8.8 Hz, 1H), 8.29 (d, J=7.2 Hz, 1H), 7.90-7.82 (m, 2H), 7.72 (m, 1H), 7.04 (d, J=8.8 Hz, 1H), 4.68 (t, J=5.6 Hz, 1H), 4.57 (t, J=6.4 Hz, 2H), 4.56 (t, J=5.6 Hz, 1H), 2.30-2.16 (m, 2H); MS (ESI) m/z [M+H]$^+$323.

5-(Benzo[4,5]imidazo[1,2-a]pyrimidin-2-yl)-1-(3-fluoropropyl)pyridin-2(1H)-one (T567). The title compound was isolated as a by-product from above purification as a white solid (2 mg, 20%). $^1$H NMR (400 MHz, methanol-d4): δ 9.61 (d, J=7.2 Hz, 1H), 9.01 (d, J=2.8 Hz, 1H), 8.50 (dd, J=9.2, 2.4 Hz, 1H), 8.35 (m, 1H), 8.12 (d, J=7.2 Hz, 1H), 7.88-7.78 (m, 2H), 7.69 (t, J=7.6 Hz, 1H), 6.72 (d, J=9.6 Hz, 1H), 4.62 (t, J=5.6 Hz, 1H), 4.50 (t, J=5.6 Hz, 1H), 4.30 (t, J=6.8 Hz, 2H), 2.30-2.16 (m, 2H); MS (ESI) m/z [M+H]⁺323.

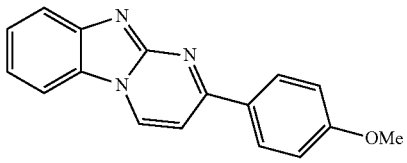
T567

2-(4-Methoxyphenyl)benzo[4,5]imidazo[1,2-a]pyrimidine. The title compound was prepared using General Procedure Q from 2-bromo-1-(4-methoxyphenyl)ethanone on 1 mmol scale. After neutralized with Na₂CO₃, the solid was collected via filtration and washed with EtOAc (3×10 mL) to afford 2-(4-methoxyphenyl)benzo[4,5]imidazo[1,2-a]pyrimidine as a yellow solid (55 mg, 20%). ¹H NMR (400 MHz, DMSO-d6): δ 9.51 (d, J=7.2, 1H), 8.34 (m, 2H), 8.29 (d, J=8.0 Hz, 1H), 7.81 (d, J=8.0 Hz, 1H), 7.78 (d, J=7.2 Hz, 1H), 7.52 (m, 1H), 7.39 (m, 1H), 7.15 (m, 2H), 3.88 (s, 3H); MS (ESI) m/z [M+H]⁺276.

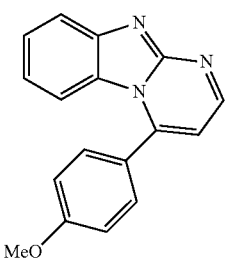
T572

4-(4-Methoxyphenyl)benzo[4,5]imidazo[1,2-a]pyrimidine (T572). The title compound was prepared using General Procedure Q from 2-bromo-1-(4-methoxyphenyl)ethanone on a 1 mmol scale. After neutralized with Na₂CO₃, the suspension was filtered and the filtrate was concentrated and purified by silica chromatography (EtOAc in DCM, 5% to 80%) to afford 4-(4-methoxyphenyl)benzo[4,5]imidazo[1,2-a]pyrimidine as a yellow solid (42 mg, 15%). ¹H NMR (400 MHz, methanol-d4): δ 9.15 (d, J=4.4, 1H), 7.91-7.88 (m, 1H), 7.76 (m, 1H), 7.72 (m, 2H), 7.54 (d, J=4.4 Hz, 1H), 7.38 (m, 1H), 7.28 (m, 2H), 7.09 (d, J=8.8 Hz, 1H), 3.97 (s, 3H); MS (ESI) m/z [M+H]⁺ 276.

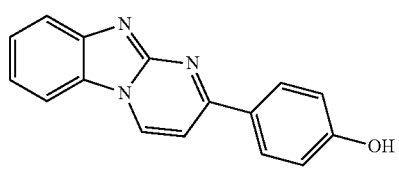
T582

4-(Benzo[4,5]imidazo[1,2-a]pyrimidin-2-yl)phenol (T582). To 4-(4-methoxyphenyl)benzo[4,5]imidazo[1,2-a]pyrimidine (12 mg, 0.043 mmol) in 0.5 mL DCM was added 1 mL of BBr₃ solution (1 M in DCM). The reaction was stirred at rt for 15 h and quenched on ice (10 g). The mixture was neutralized with saturated Na2PO4 and extracted with EtOAc (3×10 mL). The organic phase was dried over MgSO4 and concentrated. The crude product was purified by reversed phase HPLC (TFA buffered water/MeCN) to afford 4-(benzo[4,5]imidazo[1,2-a]pyrimidin-2-yl)phenol as a pale yellow solid. ¹H NMR (400 MHz, MeCN-d3): δ 9.15 (d, J=7.2, 1H), 8.29 (d, J=9.2 Hz, 2H), 8.21 (d, J=8.8 Hz, 1H), 8.02 (d, J=7.2 Hz, 1H), 7.98 (d, J=8.4 Hz, 1H), 7.79 (t, J=7.2 Hz, 1H), 7.67 (t, J=7.2 Hz, 1H), 7.06 (d, J=8.8 Hz, 2H); MS (ESI) m/z [M+H]⁺262.

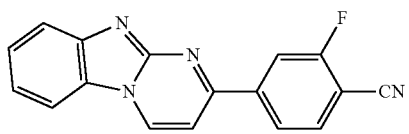
T747

4-(Benzo[4,5]imidazo[1,2-a]pyrimidin-2-yl)-2-fluorobenzonitrile (T747). The title compound was prepared using General Experimental Procedure A (Suzuki coupling reaction) from 2-bromobenzo[4,5]imidazo[1,2-a]pyrimidine and (4-cyano-3-fluorophenyl)boronic acid on a 0.1 mmol scale. The residue was washed with water (3×5 mL), EtOAc (3×2 mL), and DCM (3×2 mL) and dried under high vacuum to afford 4-(Benzo[4,5]imidazo[1,2-a]pyrimidin-2-yl)-2-fluorobenzonitrile (T747) as a orange solid (10 mg, 35%). ¹H NMR (400 MHz, DMSO-d6): δ 9.74 (d, J=6.8 Hz, 1H), 8.46 (d, J=10.8 Hz, 1H), 8.41-8.38 (m, 2H), 8.19 (t, J=7.6 Hz, 1H), 7.98 (d, J=6.8 Hz, 1H), 7.90 (d, J=8.4 Hz, 1H), 7.60 (t, J=7.2 Hz, 1H), 7.45 (t, J=7.2 Hz, 1H); MS (ESI) m/z [M+H]⁺289.

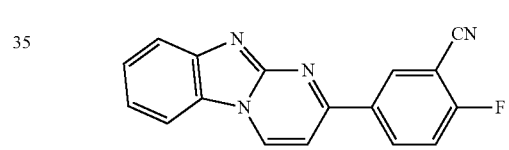
T748

5-(Benzo[4,5]imidazo[1,2-a]pyrimidin-2-yl)-2-fluorobenzonitrile (T748). The title compound was prepared using General Experimental Procedure A (Suzuki coupling reaction) from 2-bromobenzo[4,5]imidazo[1,2-a]pyrimidine and (4-cyano-3-fluorophenyl)boronic acid on a 0.1 mmol scale. The residue was washed with water (3×5 mL), EtOAc (3×2 mL), and DCM (3×2 mL) and dried under high vacuum to afford 4-(Benzo[4,5]imidazo[1,2-a]pyrimidin-2-yl)-2-fluorobenzonitrile (T747) as a orange solid (12 mg, 41%). ¹H NMR (400 MHz, DMSO-d6): δ 9.67 (d, J=7.2 Hz, 1H), 8.86 (dd, J=5.6, 2.0 Hz, 1H), 8.74 (m, 1H), 8.33 (d, J=7.6 Hz, 1H), 7.91 (d, J=7.2 Hz, 1H), 7.84 (d, J=9.2 Hz, 1H), 7.760 (t, J=8.8 Hz, 1H), 7.54 (t, J=7.2 Hz, 1H), 7.42 (t, J=7.6 Hz, 1H); MS (ESI) m/z [M+H]⁺289.

I. Preparation of 3-aryl substituted pyrimido[1,2-a]benzimidazole series compounds (T590, T591, T592, T600, T601, T602, T621, T622)

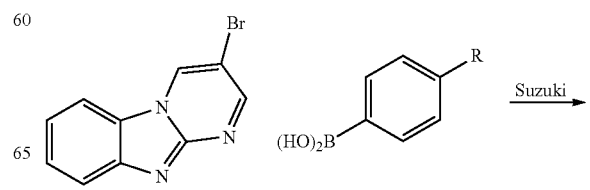

-continued

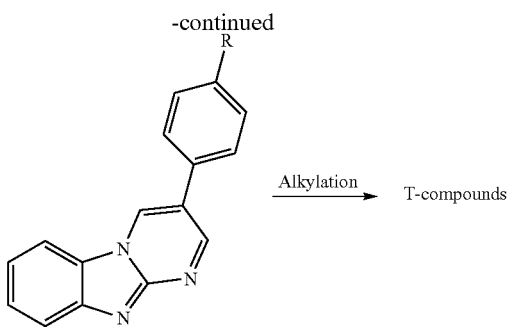

The compounds were generally prepared via the above scheme using standard Suzuki and alkylation (or reductive amination) procedures.

3-(4-fluoroethyloxyphenyl)pyrimido[1,2-a]benzimidazole; T590

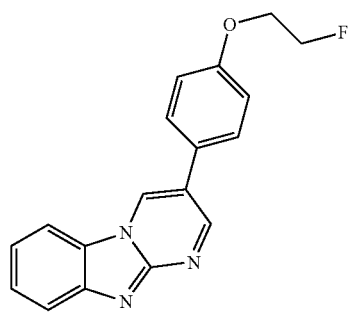 [SMILES: FCCOc1ccc(-c2cnc3nc4ccccc4n3c2)cc1]

¹H-NMR (400 MHz, CD₃CN) δ: 9.50 (s, 1H), 9.36 (s, 1H), 8.36-8.34 (m, 1H), 8.10-8.08 (m, 1H), 7.80-7.77 (m, 3H), 7.69 (m, 1H); 7.20-7.17 (m, 1H); LRMS for $C_{18}H_{14}FN_3O+H^+$, calc'd: 308.1. found: 308.1 (M+H⁺).

3-(4-aminophenyl)pyrimido[1,2-a]benzimidazole, TFA salt; T591

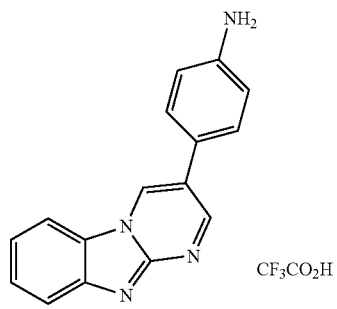

¹H-NMR (400 MHz, CD₃CN) δ: 9.49 (s, 1H), 9.40 (s, 1H), 8.38-8.36 (m, 1H), 8.02-8.00 (m, 1H), 7.88-7.72 (m, 2H), 7.60-7.58 (m, 2H), 6.88-6.85 (m, 2H); LRMS for $C_{18}H_{13}F_3N_4O_2+H^+$, calc'd: 375.1. found: 261.1 (M+H⁺-TFA).

3-(4-2-(2-(2-fluoroethoxy)ethoxy)ethoxy)phenyl)pyrimido[1,2-a]benzimidazole, TFA salt; T592

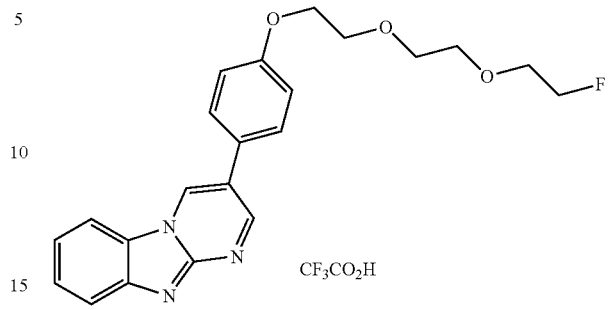

¹H-NMR (400 MHz, CD₃CN) δ: 9.38 (s, 1H), 9.25 (s, 1H), 8.29-8.27 (m, 1H), 8.04-8.02 (m, 2H), 7.76-7.58 (m, 4H), 7.16-7.14 (m, 2H); 4.60-4.46 (m, 2H), 4.21-4.19 (m, 2H) 3.80-3.63 (8H); LRMS for $C_{24}H_{23}F_4N_3O_5+H^+$, calc'd: 509.2. found: 396.2 (M+H⁺-TFA).

3-(4-hydroxyphenyl)pyrimido[1,2-a]benzimidazole, TFA salt; T600

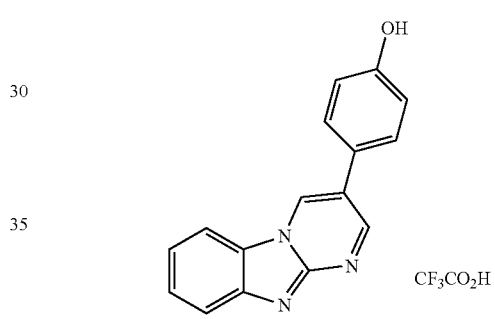

¹H-NMR (400 MHz, CD₃CN) δ: 9.45 (s, 1H), 9.32 (s, 1H), 8.34-8.32 (m, 1H), 8.07-8.05 (m, 1H), 7.79-7.77 (m, 1H), 7.69-7.66 (m, 3H), 7.05-7.03 (m, 2H); LRMS for $C_{18}H_{12}F_3N_3O_3+H^+$, calc'd: 376.1. found: 262.1 (M+H⁺-TFA).

3-(4(2-(2-fluoroethoxy)ethoxy)phenyl)pyrimido[1,2-a]benzimidazole, TFA salt; T601

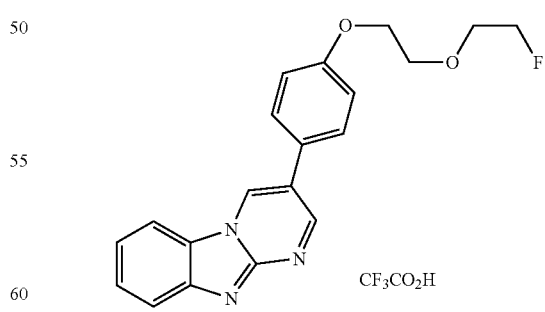

¹H-NMR (400 MHz, CD₃CN) δ: 9.45 (s, 1H), 9.31 (m, 1H), 8.30-8.30 (m, 1H), 8.07-8.05 (m, 1H), 7.77-7.17 (m, 4H), 7.17-7.14 (m, 2H), 4.64-4.51 (m, 2H), 4.23-4.20 (m, 2H), 3.83-3.73 (m, 4h); LRMS for $C_{22}H_{19}F_4N_3O_4+H^+$, calc'd: 466.1. found: 352.1 (M+H⁺-TFA).

3-(3-(2-fluoropyridyl)pyrimido[1,2-a]benzimidazole, TFA salt; T602

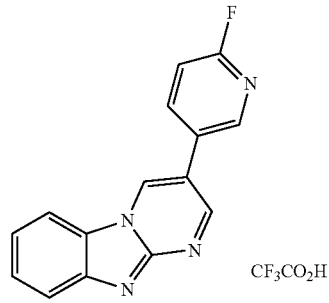

$^1$H-NMR (400 MHz, CD$_3$CN) δ: 9.68 (s, 1H), 9.40 (s, 1H), 8.68 (s, 1H), 8.38-8.32 (m, 2H), 8.13 (m, 1H), 7.88-7.72 (m, 2H), 7.31-7.29 (m, 1H); LRMS for C$_{15}$H$_9$F$_4$N$_4$O$_2$+H$^+$, calc'd: 379.1. found: 265.1 (M+H$^+$-TFA).

3-(4-Fluoroethylaminophenyl)pyrimido[1,2-a]benzimidazole, TFA salt T621

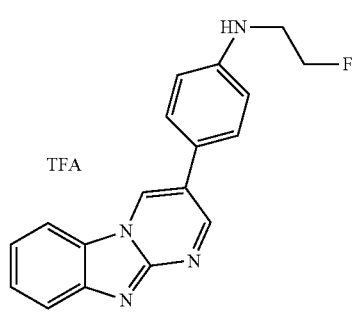 [SMILES: FCCNc1ccc(-c2cnc3nc4ccccc4n3c2)cc1]

$^1$H-NMR (400 MHz, CD$_3$CN) δ: δ: 9.44 (s, 1H), 9.37 (s, 1H), 8.36-8.33 (m, 1H), 8.04-8.02 (m, 1H), 7.81-7.63 (m, 4H), 6.88 (m, 2H); LRMS for C$_{20}$H$_{15}$F$_4$N$_4$O+H$^+$, calc'd: 404.1. found: 307.1 (M+H$^+$-TFA).

3-(4-N-(2-(2-(2-fluoroethoxy)ethoxy)ethyl)aminophenyl pyrimido[1,2-a]benzimidazole, TFA salt; T622

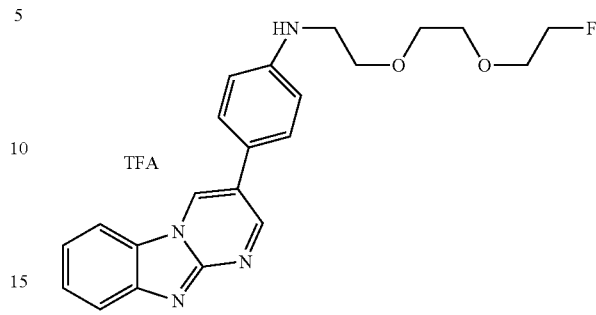

$^1$H-NMR (400 MHz, CD$_3$CN) δ: 9:35 (s, 1H), 9.28 (s, 1H), 8.30-8.28 (m, 1H), 7.74-7.60 (m, 4H), 6.84-6.82 (m, 2H), 4.61-4.46 (m, 2H), 3.74-3.64 (m, 8H), 3.35-3.32 (m, 2H); LRMS for C$_{24}$H$_{23}$F$_4$N$_4$O$_3$+H$^+$, calc'd: 491.2. found: 395.2 (M+H$^+$-TFA).

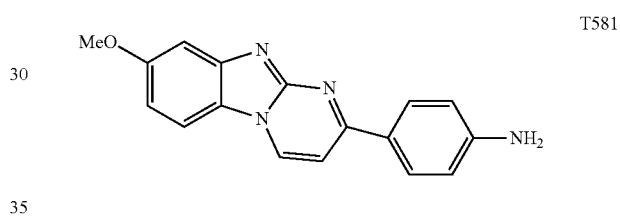

4-(8-Methoxybenzo[4,5]imidazo[1,2-a]pyrimidin-2-yl) aniline. The title compound was prepared using General Procedure Q and R from 2-bromo-1-(4-nitrophenyl)ethanone and 5-methoxy-1H-benzo[d]imidazol-2-amine on a 0.1 mmol scale 4-(8-methoxybenzo[4,5]imidazo[1,2-a]pyrimidin-2-yl)aniline (T581) obtained as a yellow solid (1.2 mg, 0.4%). $^1$H NMR (400 MHz, DMSO-d6): δ 9.56 (d, J=7.6, 1H), 8.33 (d, J=10.0 Hz, 1H), 8.19-8.12 (m, 3H), 7.22 (m, 2H), 6.74 (d, J=8.8 Hz, 2H), 3.92 (s, 3H); MS (ESI) m/z [M+H]$^+$ 291.

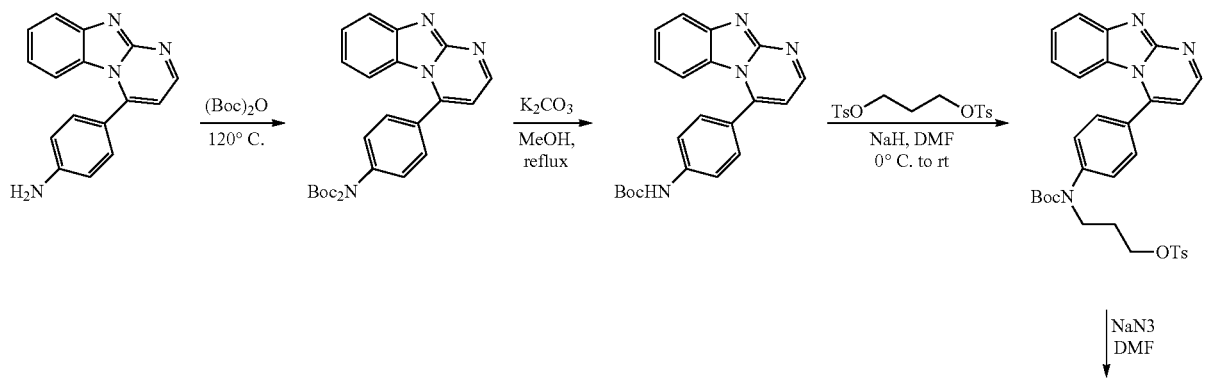

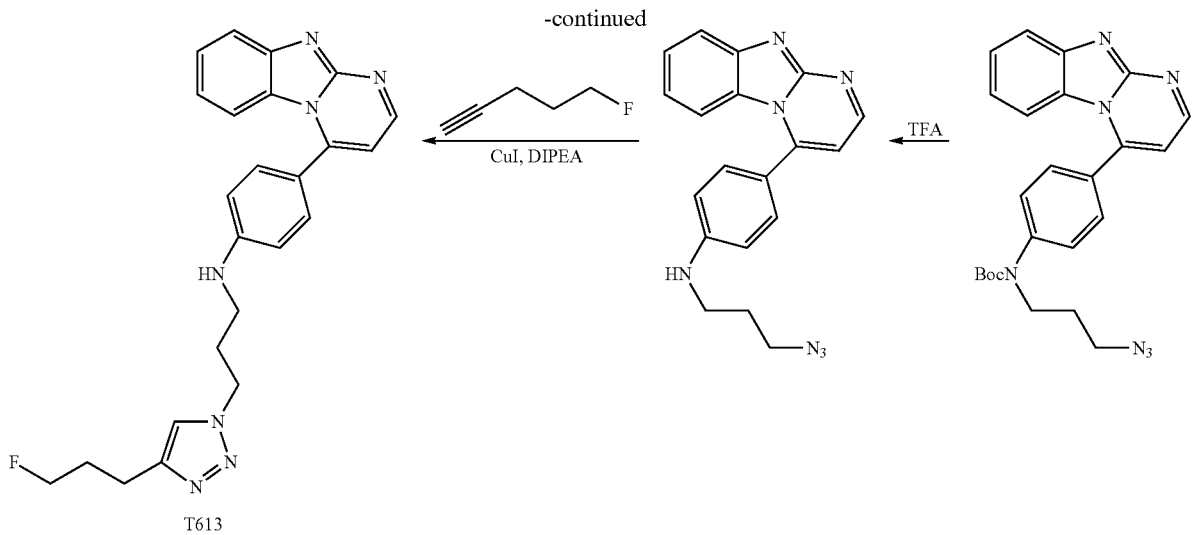

N-DiBoc 4-(benzo[4,5]imidazo[1,2-a]pyrimidin-4-yl)aniline. A suspension of 4-(benzo[4,5]imidazo[1,2-a]pyrimidin-4-yl)aniline (521 mg, 2 mmol) in 5 mL of di-tert-butyl dicarbonate was heated at 120° C. for 2 h and cooled to rt. The mixture was subjected to silica chromatography to afford the title compound as a yellow wax (550 mg, 60%). MS (ESI) m/z [M+H]$^+$461.

tert-butyl (4-(benzo[4,5]imidazo[1,2-a]pyrimidin-4-yl)phenyl)carbamate. A mixture of N-DiBoc 4-(benzo[4,5]imidazo[1,2-a]pyrimidin-4-yl)aniline (532 mg, 1.15 mmol) and $K_2CO_3$ (828 mg, 6 mmol) in 6 mL of MeOH was at reflux for 1 h and cooled to rt. Volatiles were removed under reduced pressure and the residue was partitioned between DCM and water. The organic phase was dried over $MgSO_4$ and concentrated under reduced pressure. The crude product was purified by silica chromatography to afford the title compound as a yellow solid (300 mg, 72%). MS (ESI) m/z [M+H]$^+$361.

3-((4-(Benzo[4,5]imidazo[1,2-a]pyrimidin-4-yl)phenyl)(tert-butoxycarbonyl)amino)propyl 4-methylbenzenesulfonate. To a solution of tert-butyl (4-(benzo[4,5]imidazo[1,2-a]pyrimidin-4-yl)phenyl)carbamate (300 mg, 0.83 mmol) in DMF (9 mL) at 0° C. was added NaH (38 mg, 0.91 mmol, 60% dispersed in oil). After stirring for 5 min at 0° C. for 5 min, ice bath was removed and reaction was stirred at rt for 20 min. The reaction was cooled again at 0° C. and propane-1,3-diyl bis(4-methylbenzenesulfonate) (653 mg, 1.7 mmol) was added in 6 portions. After stirring at 0° C. for 5 min, the reaction was let stir at rt for 2 h and quenched with saturated $NH_4Cl$ solution (40 mL). The mixture was extracted with DCM (3×30 mL). The combined organic phase was washed with water (2×50 mL) and dried over $MgSO_4$ and concentrated. The residue was first purified by silica chromatography (THF in DCM, 0% to 18%) and then reversed phase HPLC (TFA buffered water/MeCN) to afford the title compound as an orange solid (160 mg, 34%). MS (ESI) m/z [M+H]$^+$573.

tert-Butyl (3-azidopropyl)(4-(benzo[4,5]imidazo[1,2-a]pyrimidin-4-yl)phenyl)carbamate. To a solution of 3-((4-(benzo[4,5]imidazo[1,2-a]pyrimidin-4-yl)phenyl)(tert-butoxycarbonyl)amino)propyl 4-methylbenzenesulfonate (130 mg, 0.23 mmol) in DMF (2 mL) was added $NaN_3$ (83 mg, 1.3 mmol). The mixture as stirred at rt for 2 h and concentrated under reduced pressure to remove volatiles. The residue was taken up to DCM (50 mL) and washed with water (2×50 mL) and dried over $MgSO_4$ and concentrated to afford the title compound as a yellow solid. The product was used directly for the next reaction without further purification. MS (ESI) m/z [M+H]$^+$444.

N-(3-Azidopropyl)-4-(benzo[4,5]imidazo[1,2-a]pyrimidin-4-yl)aniline. To a solution of tert-butyl (3-azidopropyl)(4-(benzo[4,5]imidazo[1,2-a]pyrimidin-4-yl)phenyl)carbamate (above mentioned material) in 3 mL of DCM was added TFA (1 mL). The mixture was stirred at rt for 1.5 h and concentrated under reduced pressure. The residue was purified by reversed phase HPLC (TFA buffered water/MeCN) to afford the title compound as a orange-colored oil (61 mg, TFA salt). MS (ESI) m/z [M-1-H]$^+$344.

4-(Benzo[4,5]imidazo[1,2-a]pyrimidin-4-yl)-N-(3-(4-(3-fluoropropyl)-1H-1,2,3-triazol-1-yl)propyl)aniline. To a solution of N-(3-azidopropyl)-4-(benzo[4,5]imidazo[1,2-a]pyrimidin-4-yl)aniline (9 mg, 0.026 mmol), in THF (0.25 mL) at rt was added 5-fluoropent-1-yne (2 drops), CuI (1 mg, 0.005 mmol), and DIPEA (10 mg, 0.08 mmol). The mixture was stirred at rt for 5 h and concentrated under reduced pressure. The residue was purified by reversed phase HPLC (TFA buffered water/MeCN) to afford the title compound as an orange solid (5 mg, 44%). MS (ESI) m/z [M+H]$^+$430.

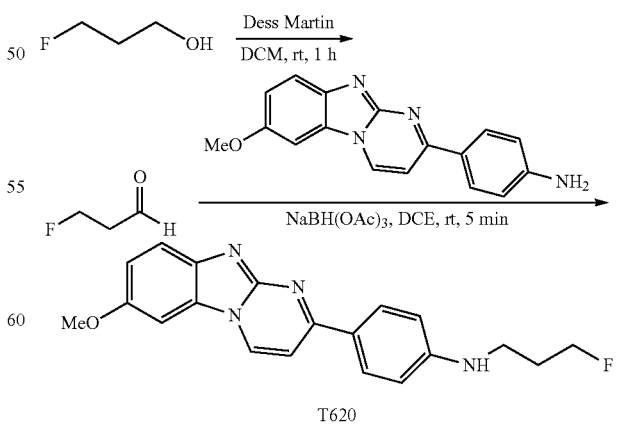

N-(3-Fluoropropyl)-4-(7-methoxybenzo[4,5]imidazo[1,2-a]pyrimidin-2-yl)aniline (T620). To a stirred solution of 3-fluoropropan-1-ol (5 mg, 0.05 mmol) in 0.3 mL o DCM at rt was added Dess-Martin reagent (42 mg, 0.1 mmol). The mixture was stirred for 1 h at rt and 0.3 mL of DCE was added. It was filtered through a cotton pad into a stirred mixture of 4-(7-methoxybenzo[4,5]imidazo[1,2-a]pyrimidin-2-yl) aniline (5 mg, 0.017 mmol, prepared following General Experiment Procedures Q and R) and NaBH(AcO)$_3$ (42 mg, 0.2 mmol) in 0.3 mL of DCE. The reaction was vigorously stirred for 5 min and quenched by adding Na$_2$CO$_3$ (2 mL, saturated). The mixture was extracted with EtOAc (3×5 mL) and the combined organic phase was washed with water (2×10 mL) and dried over MgSO$_4$ and concentrated under reduced pressure. The crude product was purified by reversed phase HPLC (TFA buffered water/MeCN) to afford the title compound as an orange solid (5 mg, 53%, TFA salt). MS (ESI) m/z [M+H]$^+$351.

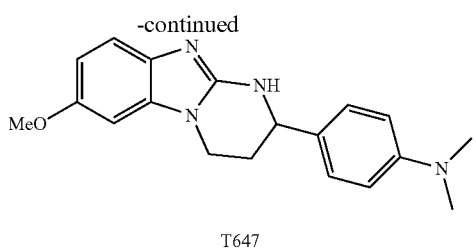

T647

4-(7-Methoxybenzo[4,5]imidazo[1,2-a]pyrimidin-2-yl)-N,N-dimethylaniline (T646) and 4-(7-methoxy-1,2,3,4-tetrahydrobenzo[4,5]imidazo[1,2-a]pyrimidin-2-yl)-N,N-dimethylaniline (T647). To a suspension of 4-(7-methoxybenzo[4,5]imidazo[1,2-a]pyrimidin-2-yl)aniline (20 mg, 0.069 mmol) in 1 mL DCE was added paraformaldehyde (11 mg, 0.35 mmol), followed by NaBH(AcO)$_3$ (102 mg, 0.48 mmol). The reaction was stirred at rt for 60 h and quenched by adding Na$_2$CO$_3$ (5 mL, saturated). The mixture was extracted with EtOAc (2×10 mL) and the combined organic phase was washed with water (2×20 mL) and dried over MgSO$_4$ and concentrated under reduced pressure. The residue was subjected to reversed phase HPLC (TFA buffered water/MeCN) to afford the title compounds as TFA salts: 4-(7-methoxybenzo[4,5]imidazo[1,2-a]pyrimidin-2-yl)-N,N-dimethylaniline (T646, 1.5 mg, 7%), orange solid. $^1$H NMR (400 MHz, DMSO-d6): δ 9.53 (d, J=7.6, 1H), 8.26 (d, J=9.2 Hz, 2H), 8.15 (m, 1H), 8.07 (s, 1H), 7.66 (d, J=8.4 Hz, 1H), 7.27 (d, J=8.8 Hz, 1H), 6.87 (d, J=8.8 Hz, 2H), 3.88 (s; 3H), 3.08 (s, 6H); MS (ESI) m/z [M+H]$^+$319. 4-(7-methoxy-1,2,3,4-tetrahydrobenzo[4,5]imidazo[1,2-a]pyrimidin-2-yl)-N,N-dimethylaniline (T647, 7 mg, 27%), yellow solid. MS (ESI) m/z [M+H]$^+$323.

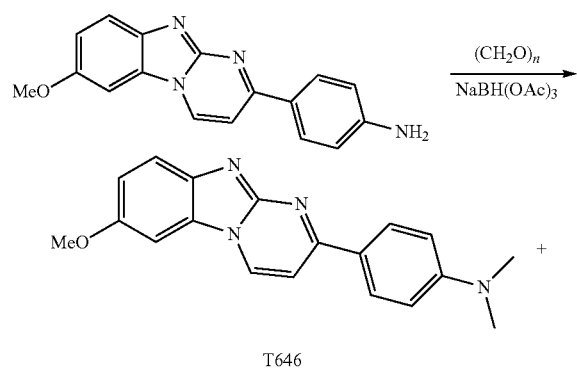

T646

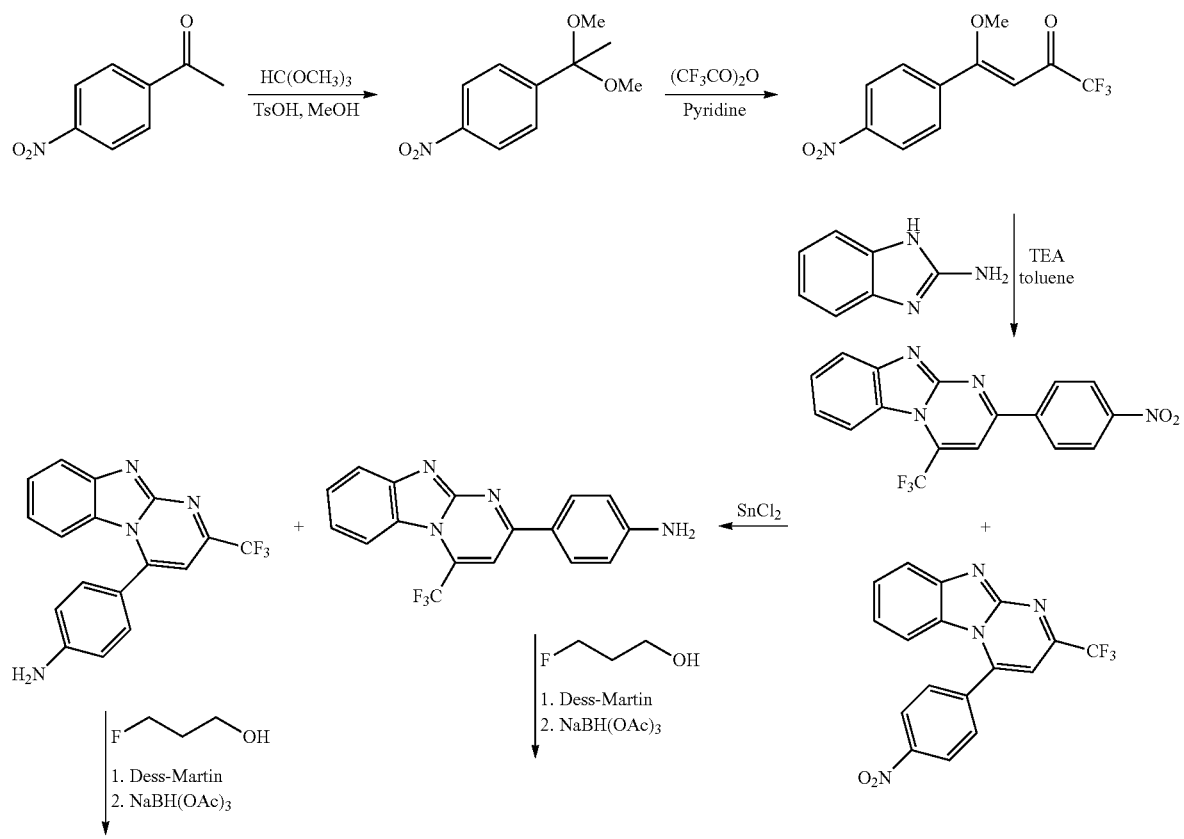

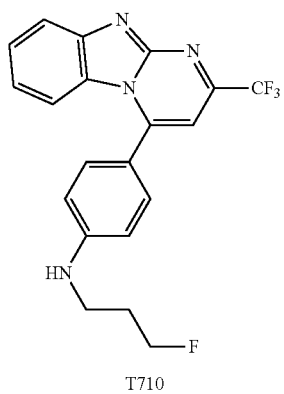

T710

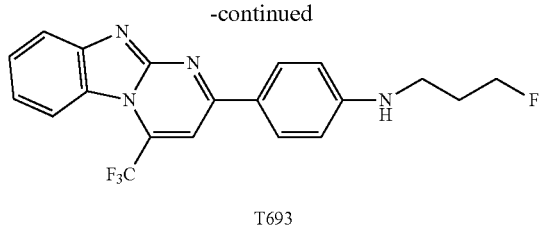

T693

1-(1,1-Dimethoxyethyl)-4-nitrobenzene. To a solution of 1-(4-nitrophenyl)ethanone (5 g, 30 mmol) in MeOH was added trimethoxymethane (3.2 g, 30 mmol) followed by 4-methylbenzenesulfonic acid (29 mg, 0.15 mmol). The mixture was stirred for 72 h and quenched by adding solid Na2CO3 (16 mg, 0.15 mmol). Stirring was continued for 30 min and the mixture was filtered through a neutral alumina pad. The filtrate was concentrated and the crude product was re-crystallized with MeOH to afford the title compound as a white solid (6.4 g, 100%). MS (ESI) m/z [M+H]$^+$212.

1,1,1-Trifluoro-4-methoxy-4-(4-nitrophenyl)but-3-en-2-one. To a solution of 1-(1,1-mimethoxyethyl)-4-nitrobenzene (2.9 g, 14 mmol) in CHCl$_3$ (70 mL) was added pyridine (2.2 g, 28 mmol) at 0° C. followed by dropwise addition of 2,2,2-trifluoroacetic anhydride (5.9 g, 28 mmol). The solution was then transferred to a sealed tube and heated to 90° C. for 4 h. After cooling to rt, it was washed with 0.1 N HCl (3×70 mL) and water (70 mL) dried over MgSO$_4$ and concentrated under reduced pressure. The crude product was purified by silica chromatography (EtOAc in hexane, 5% to 20%) to afford the title compound (1.7 g, 44%). MS (ESI) m/z [M+H]$^+$276.

2-(4-Nitrophenyl)-4-(trifluoromethyl)benzo[4,5]imidazo[1,2-a]pyrimidine and 4-(4-nitrophenyl)-2-(trifluoromethyl)benzo[4,5]imidazo[1,2-a]pyrimidine. To a solution of 1H-benzo[d]imidazol-2-amine (479 mg, 3.6 mmol) in toluene (36 mL) was added TEA. It was stirred for 15 min at rt followed by addition of 1,1,1-trifluoro-4-methoxy-4-(4-nitrophenyl)but-3-en-2-one (1 g, 3.6 mmol). The mixture was then heated at reflux for 15 h and cooled to rt. Volatiles were removed under reduced pressure and the residue was partitioned between DCM and water. The organic layer was dried over MgSO$_4$ and concentrated under reduced pressure. The crude product containing two isomers was used directly for the next reaction without further purification. MS (ESI) m/z [M+H]$^+$359.

4-(4-(Trifluoromethyl)benzo[4,5]imidazo[1,2-a]pyrimidin-2-yl)aniline and 4-(2-(trifluoromethyl)benzo[4,5]imidazo[1,2-a]pyrimidin-4-yl)aniline. The above material was treated with SnCl$_2$ using General Experimental Procedure R. The crude material was subjected to silica chromatography (EtOAc in DCM, 5% to 60%) to afford the separated title compounds as orange-colored solids: 4-(4-(trifluoromethyl)benzo[4,5]imidazo[1,2-a]pyrimidin-2-yl)aniline (236 mg, 20%), MS (ESI) m/z [M+H]$^+$329; 4-(2-(trifluoromethyl)benzo[4,5]imidazo[1,2-a]pyrimidin-4-yl)aniline (940 mg, 80%), MS (ESI) m/z [M+H]$^+$329.

N-(3-Fluoropropyl)-4-(4-(trifluoromethyl)benzo[4,5]imidazo[1,2-a]pyrimidin-2-yl)aniline (T693). The title compound was prepared using General Procedure S from 4-(4-(trifluoromethyl)benzo[4,5]imidazo[1,2-a]pyrimidin-2-yl)aniline and 3-fluoropropan-1-ol on a 0.03 mmol scale. N-(3-Fluoropropyl)-4-(4-(trifluoromethyl)benzo[4,5]imidazo[1, 2-a]pyrimidin-2-yl)aniline (T693) was obtained as a orange solid (3.9 mg, 33%). $^1$H NMR (400 MHz, DMSO-d6): δ 8.25 (d, J=8.8, 2H), 8.07 (s, 1H), 7.94 (d, J=8.4 Hz, 1H), 7.88 (d, J=8.0 Hz, 1H), 7.57 (t, J=7.6 Hz, 1H), 7.46 (t, J=7.6 Hz, 1H), 6.81 (t, J=5.2 Hz, 1H), 6.76 (d, J=8.8 Hz, 2H), 4.64 (t, J=5.6 Hz, 1H), 4.53 (t, J=5.6 Hz, 1H), 3.28 (m, 2H), 1.97 (m, 2H); MS (ESI) m/z [M+H]$^+$389.

N-(3-Fluoropropyl)-4-(2-(trifluoromethyl)benzo[4,5]imidazo[1,2-a]pyrimidin-4-yl)aniline. The title compound was prepared using General Procedure S from -(trifluoromethyl)benzo[4,5]imidazo[1,2-a]pyrimidin-4-yl)aniline and 3-fluoropropan-1-ol on a 0.03 mmol scale. N-(3-Fluoropropyl)-4-(4-(trifluoromethyl)benzo[4,5]imidazo[1,2-a]pyrimidin-2-yl)aniline (T693) was obtained as a orange solid (5 mg, 43%). $^1$H NMR (400 MHz, DMSO-d6): δ 7.95 (d, J=8.4 Hz, 1H), 7.59-7.54 (m, 3H), 7.30 (d, J=0.8 Hz, 1H), 7.25 (d, J=4.0 Hz, 2H), 6.83 (t, J=8.4 Hz, 2H), 6.61 (t, J=5.2 Hz, 1H), 4.67 (t, J=5.6 Hz, 1H), 4.55 (t, J=5.6 Hz, 1H), 3.28 (m, 2H), 2.00 (m, 2H); MS (ESI) m/z [M+H]$^+$389.

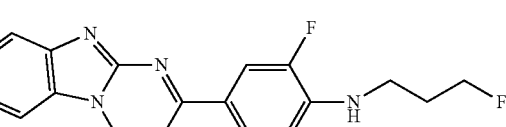

T713

4-(Benzo[4,5]imidazo[1,2-a]pyrimidin-2-yl)-2-fluoroaniline (T713). The title compound was synthesized using General Experimental Procedure A (Suzuki coupling reaction) from 2-bromobenzo[4,5]imidazo[1,2-a]pyrimidine and (4-amino-3-fluorophenyl)boronic acid on a 0.059 mmol scale. 4-(Benzo[4,5]imidazo[1,2-a]pyrimidin-2-yl)-2-fluoroaniline was obtained as a orange solid (10 mg, 61%). $^1$H NMR (400 MHz, DMSO-d6): δ 9.63 (d, J=7.2 Hz, 1H), 8.45 (d, J=8.0 Hz, 1H), 8.20 (d, J=7.2 Hz, 1H), 8.12 (dd, J=23.2, 2.0 Hz, 1H), 8.11 (s, 1H), 7.82 (d, J=8.4 Hz, 1H), 7.72 (t, J=7.2 Hz, 1H), 7.62 (d, J=7.6 Hz, 1H), 6.94 (t, J=8.8 Hz, 1H); MS (ESI) m/z [M+H]$^+$279.

T725

4-(Benzo[4,5]imidazo[1,2-a]pyrimidin-2-yl)-2-fluoro-N-(3-fluoropropyl)aniline (T725). The title compound was prepared first using General Experimental Procedure A (Suzuki coupling reaction) from 2-bromobenzo[4,5]imidazo[1,2-a]pyrimidine and (4-amino-3-fluorophenyl)boronic acid and then using General Experimental Procedure S for alkylation.

4-(Benzo[4,5]imidazo[1,2-a]pyrimidin-2-yl)-2-fluoro-N-(3-fluoropropyl)aniline was obtained as a orange solid. ¹H NMR (400 MHz, methanol-d4): δ 9.12 (d, J=7.6, 1H), 8.06 (d, J=8.0 Hz, 1H), 8.04-7.98 (m, 2H), 7.76 (d, J=8.0 Hz, 1H), 7.57 (d, J=7.6 Hz, 1H), 7.52 (t, J=8.0 Hz, 1H), 7.38 (t, J=7.6 Hz, 1H), 6.86 (t, J=8.4 Hz, 1H), 4.62 (t, J=5.6 Hz, 1H), 4.50 (t, J=5.6 Hz, 1H), 3.41 (t, J=6.8 Hz, 1H), 2.03 (m, 2H); MS (ESI) m/z [M+H]⁺ 339.

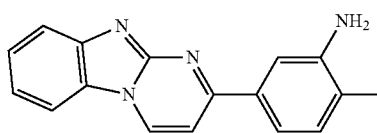

T736

5-(Benzo[4,5]imidazo[1,2-a]pyrimidin-2-yl)-2-fluoroaniline (T736). The title compound was prepared using General Experimental Procedure A (Suzuki coupling reaction) from 2-bromobenzo[4,5]imidazo[1,2-a]pyrimidine and (3-amino-4-fluorophenyl)boronic acid. 5-(Benzo[4,5]imidazo[1,2-a]pyrimidin-2-yl)-2-fluoroaniline was obtained as a orange solid. ¹H NMR (400 MHz, methanol-d4): δ 9.63 (d, J=7.2 Hz, 1H), 8.38 (d, J=8.4 Hz, 1H), 8.17 (d, J=7.2 Hz, 1H), 7.92 (dd, J=8.8, 2.8 Hz, 1H), 7.88-7.80 (m, 2H), 7.73-7.68 (m, 2H), 7.19 (dd, J=10.8, 8.4 Hz, 1H); MS (ESI) m/z [M+H]⁺ 318.

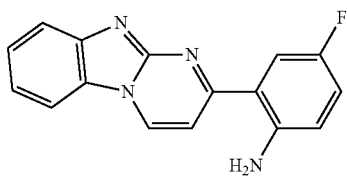

T739

2-(Benzo[4,5]imidazo[1,2-a]pyrimidin-2-yl)-4-fluoroaniline (T739). The title compound was prepared using General Experimental Procedure A (Suzuki coupling reaction) from 2-bromobenzo[4,5]imidazo[1,2-a]pyrimidine and (2-amino-5-fluorophenyl)boronic acid. 2-(Benzo[4,5]imidazo[1,2-a]pyrimidin-2-yl)-4-fluoroaniline was obtained as a orange solid. ¹H NMR (400 MHz, DMSO-d6): δ 9.75 (d, J=7.6 Hz, 1H), 8.49 (d, J=8.0 Hz, 1H), 8.26 (d, J=7.6 Hz, 1H), 7.99 (dd, J=11.2, 3.2 Hz, 1H), 7.92 (d, J=8.0 Hz, 1H), 7.74 (d, J=7.2 Hz, 1H), 7.64 (d, J=8.4 Hz, 1H), 7.29 (m, 1H), 6.95 (dd, J=9.2, 5.2 Hz, 1H); MS (ESI) m/z [M+H]⁺ 279.

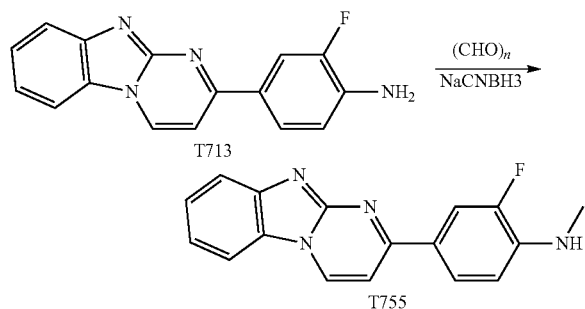

T713

T755

4-(Benzo[4,5]imidazo[1,2-a]pyrimidin-2-yl)-2-fluoro-N-methylaniline. To a suspension of 4-(Benzo[4,5]imidazo[1,2-a]pyrimidin-2-yl)-2-fluoroaniline (20 mg, 0.072 mmol) in 1 mL DCE was added paraformaldehyde (4.5 mg, 0.14 mmol), followed by NaBH(AcO)₃ (51 mg, 0.24 mmol). The reaction was stirred at rt for 6 h and quenched by adding Na₂CO₃ (5 mL, saturated). The mixture was extracted with EtOAc (2×10 mL) and the combined organic phase was washed with water (2×20 mL) and concentrated under reduced pressure. The residue was subjected to reversed phase HPLC (TFA buffered water/MeCN) to afford 4-(Benzo[4,5]imidazo[1,2-a]pyrimidin-2-yl)-2-fluoro-N-methylaniline as orange solid (4.5 mg, 21%). ¹H NMR (400 MHz, methanol-d4): δ 9.10 (d, J=7.2 Hz, 1H), 8.05 (d, J=8.0 Hz, 1H), 8.01 (d, J=11.2 Hz, 2H), 7.75 (d, J=8.4 Hz, 1H), 7.56 (d, J=7.6 Hz, 1H), 7.51 (t, J=7.2 Hz, 1H), 7.38 (d, J=7.2 Hz, 1H), 6.94 (t, J=8.8 Hz, 1H), 2.90 (s, 3H); MS (ESI) m/z [M+H]⁺ 293.

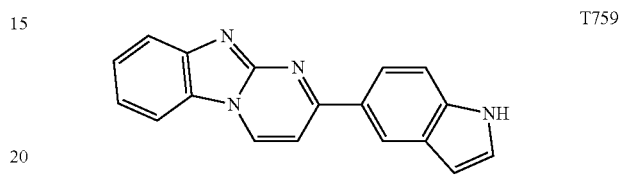

T759

2-(1H-Indol-5-yl)benzo[4,5]imidazo[1,2-a]pyrimidine (T759). The title compound was prepared using General Experimental Procedure A (Suzuki coupling reaction) from 2-bromobenzo[4,5]imidazo[1,2-a]pyrimidine and (1H-indol-5-yl)boronic acid on a 0.12 mmol scale. The crude product was subjected to reversed phase HPLC (TFA buffered water/MeCN) to afford 2-(1H-indol-5-yl)benzo[4,5]imidazo[1,2-a]pyrimidine (T759) as a orange solid (20 mg, 50%). ¹H NMR (400 MHz, DMSO-d6): 9.85 (d, J=7.2 Hz, 1H), 8.80 (s, 1H), 8.52 (d, J=8.0 Hz, 1H), 8.46 (d, J=7.2 Hz, 1H), 8.26 (dd, J=8.8, 1.2 Hz, 1H), 7.87 (d, J=7.6 Hz, 1H), 7.77 (t, J=7.2 Hz, 1H), 7.68-7.64 (m, 2H), 7.55 (t, J=2.4 Hz, 1H), 6.70 (m, 1H); MS (ESI) m/z [M+H]⁺ 285.

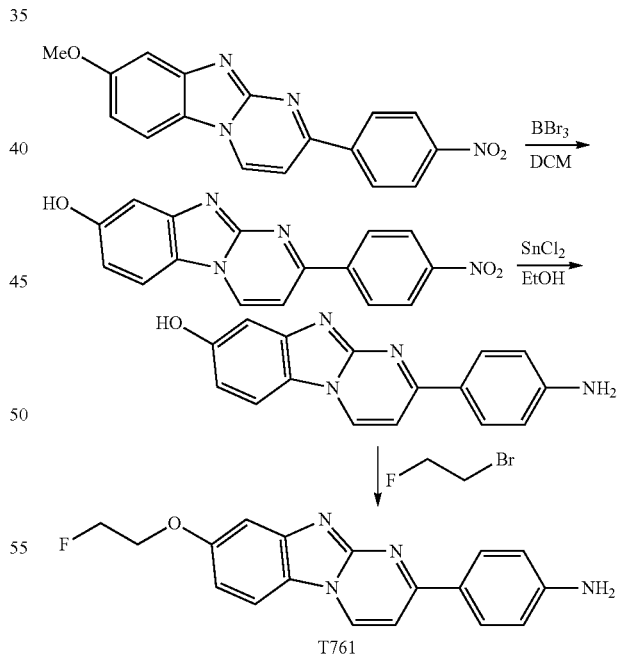

T761

8-Methoxy-2-(4-nitrophenyl)benzo[4,5]imidazo[1,2-a]pyrimidine. The title compound was prepared using General Experimental Procedure Q from 2-bromo-1-(4-nitrophenyl)ethanone and 5-methoxy-1H-benzo[d]imidazol-2-amine on a 6 mmol scale. 8-Methoxy-2-(4-nitrophenyl)benzo[4,5]imidazo[1,2-a]pyrimidine was obtained as a orange solid (50 mg, 2.6%). ¹H NMR (400 MHz, DMSO-d6): δ 9.64 (d, J=7.6, 1H), 8.59 (m, 2H), 8.42 (d, J=9.2 Hz, 2H), 8.26 (d, J=8.8 Hz, 1H), 7.93 (d, J=7.2 Hz, 1H), 7.35 (d, J=2.4 Hz, 1H), 7.08 (dd, J=8.8, 2.4 Hz, 1H), 3.90 (s, 3H); MS (ESI) m/z [M+H]$^+$ 321.

4-(8-(2-Fluoroethoxy)benzo[4,5]imidazo[1,2-a]pyrimidin-2-yl)aniline (T761). To 8-methoxy-2-(4-nitrophenyl)benzo[4,5]imidazo[1,2-a]pyrimidine (20 mg, 0.062 mmol) in 0.5 mL DCM at 0° C. was added BBr$_3$ (0.31 mL, 0.31 mmol, 1.0 M DCM solution). The mixture was stirred at 0° C. for 1 h and concentrated under reduced pressure. The crude product was subjected to reversed phase HPLC (TFA buffered water/MeCN) to afford 2-(4-nitrophenyl)benzo[4,5]imidazo[1,2-a]pyrimidin-8-ol as a orange solid (5 mg, 21%, TFA salt). MS (ESI) m/z [M+H]$^+$307.

A suspension of 2-(4-nitrophenyl)benzo[4,5]imidazo[1,2-a]pyrimidin-8-ol (2 mg, 0.007 mmol) and SnCl$_2$.2H$_2$O (6 mg, 0.026 mmol) in 0.1 mL EtOH was heated at reflux for 2.5 h. General Experimental Procedure R was followed. The crude product, 2-(4-aminophenyl)benzo[4,5]imidazo[1,2-a]pyrimidin-8-ol, was used directly for the next reaction without further purification.

To a solution of 2-(4-aminophenyl)benzo[4,5]imidazo[1, 2-a]pyrimidin-8-ol (0.5 mg, 0.002 mmol) in DMF (0.1 mL) was added 1-bromo-2-fluoroethane (5 mg, 0.04 mmol) and Cs$_2$CO$_3$ (3.5 mg, 0.01 mmol). The mixture was stirred at rt for 30 min. General Experimental Procedure C was followed. The crude product was subjected to reversed phase HPLC (TFA buffered water/MeCN) to afford 44842-fluoroethoxy)benzo[4,5]imidazo[1,2-a]pyrimidin-2-yl)aniline (T761) as a orange solid (0.6 mg, 100%). $^1$H NMR (400 MHz, MeCN-d6): δ 9.00 (d, J=7.6, 1H), 8.15 (m, 2H), 8.04 (d, J=9.2 Hz, 1H), 7.85 (d, J=7.2 Hz, 1H), 7.51 (d, J=2.4 Hz, 1H), 7.20 (dd, J=9.2, 2.4 Hz, 1H), 6.81 (d, J=8.8 Hz, 2H), 4.88 (t, J=4.0 Hz, 1H), 4.75 (t, J=4.0 Hz, 1H), 4.41 (t, J=4.0 Hz, 1H), 4.34 (t, J=4.0 Hz, 1H); MS (ESI) m/z [M+H]$^+$323.

3-(4-(2-Fluoroethyl)piperidin-1-yl)-8-methoxybenzo[4,5]imidazo[1,2-a]pyridine (AS-5357-59, T-821)

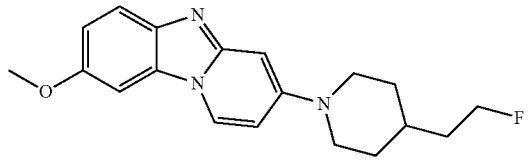 [SMILES: COc1ccc2nc3cc(N4CCC(CCF)CC4)ccn3c2c1]

General experimental process for Buchwald reaction (Method) was followed. Reaction was carried out in 0.060 g scale and reaction mixture was heated for 2½ hrs. The product T-821 was purified by Combifash purification system (DCM-MeOH) followed by HPLC (Acetonitrile: H$_2$O: 0.05 TFA) afforded solid 0.008 g (11%) as a light yellow solid; $^1$H NMR (400 MHz, CDCl$_3$): δ 8.15 (dd, J=8.0 and 4.41 Hz, 1H), 7.66 (d, J=8.8 Hz, 1H). 7.24 (m, 1H), 7.06 (d, J=6.8 Hz, 1H), 6.91 (br s, 1H), 6.73 (d, J=7.2 Hz, 1H), 4.56 (tt, J=7.6 and 2.0 Hz, 1H), 4.48 (t, J=7.6 Hz, 1H), 3.95 (br d, J=13.0 Hz, 1H), 3.90 (s, 3H), 2.99 (t, J=12.0 Hz, 2H), 1.90 (br m, 2H), 1.74-1.62 (m, 2H), 1.40-1.30 (m, 2H); MS (ESI): 328.1 [M+H$^+$, Free base].

3-(4-Fluoropiperidin-1-yl)-8-methoxybenzo[4,5]imidazo[1,2-a]pyridine TFA salt (AS-5357-11, T-798)

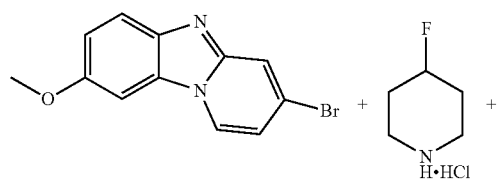

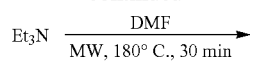

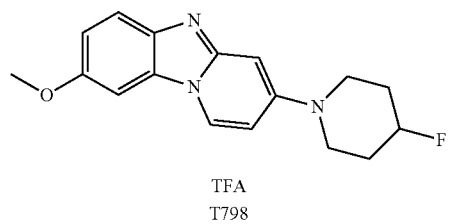

TFA
T798

General experimental procedure for N-alkylation using Et$_3$N as the base and MW heating was used (Method D). Reaction was performed on a 0.035 g scale. Product T-798 was purified by HPLC using ACN and H$_2$O with 0.05% TFA as a white solid 0.006 g (12%); $^1$H NMR (400 MHz, CD$_3$OD): δ 8.80 (d, J=8.0 Hz, 1H), 7.32 (d, J=2.4 Hz, 1H), 7.50 (d, J=8.8 Hz, 1H), 7.28 (dd, J=8.0 and 2.8 Hz, 1H), 7.19 (dd, J=9.2 and 2.4 Hz, 1H), 6.82 (d, J=2.8 Hz, 1H), 4.86-4.84 (m, 1H), 3.92 (s, 3H), 3.77-3.74 (m, 4H), 2.14-1.92 (m, 4H); MS (ESI): 300.10 [M+H$^+$, Free base].

3-(6-(4-Fluoropiperidin-1-yl)pyridine-3-yl)-8-methoxybenzo[4,5]imidazo[1,2-a]pyridine TFA salt (AS-5357-6, T-797)

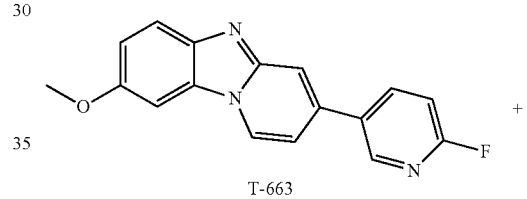

T-663

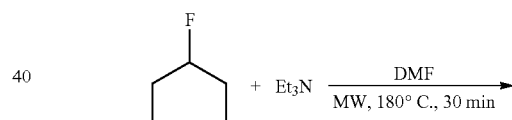

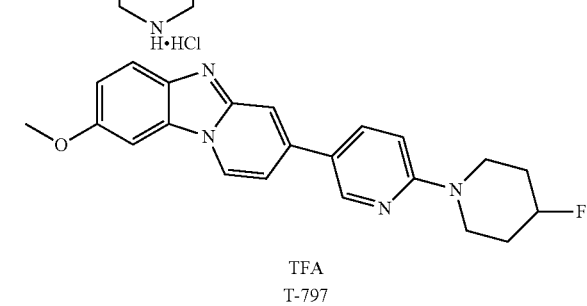

TFA
T-797

General experimental procedure (Method D) for N-alkylation using Et$_3$N as a base and MW heating afforded T-797. Reaction was performed on a 0.127 g scale, and product T-797 was purified by HPLC using ACN and H$_2$O with 0.05% TFA as a white solid 0.006 mg ( ); $^1$H NMR (400 MHz, CD$_3$OD): δ 9.21 (dd, J=7.2 and 0.81 Hz, 1H), 8.71 (d, J=2.0 Hz, 1H), 8.16 (dd, J=9.2 and 2.8 Hz, 1H), 8.06 (dd, J=1.6 and 0.8 Hz, 1H), 7.97 (d, J=2.0 Hz, 1H), 7.89 (dd, J=7.6 and 2.0 Hz, 1H), 7.58 (d, J=8.8 Hz, 1H), 7.40 (dd, J=9.2 and 2.4 Hz, 1H), 7.07 (d, J=9.2 Hz, 1H), 4.98-4.93 (m, 1H), 3.98 (s, 3H), 3.91-3.74 (m, 4H), 2.07-1.81 (m, 4H); LC-MS (ESI): 377.2 [M+H$^+$, Free base].

8-(2-Fluoroethoxy)3-(2-methoxypyridin-3-yl)benzo[4,5]imidazo[1,2-a]pyridine (AS-5332-187, T-774)

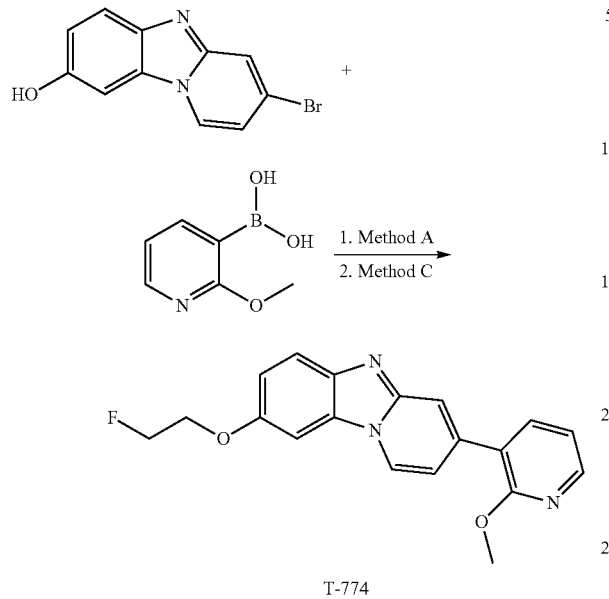

T-774

General experimental procedure for Suzuki coupling (Method A) followed by phenolic-alkylation (Method C) was used to prepare T-774. Reaction was performed on a 0.036 g scale. Product eluted out in 35% EtOAc:DCM mixture in a gradient elution on a Combiflash purification system. Isolated 0.005 g (10%, in two steps) of T-774 as off white solid; $^1$H NMR (400 MHz, CDCl$_3$): δ 8.36 (dd, J=7.6 and 0.8 Hz, 1H), 8.24 (dd, J=5.2 and 2.0 Hz, 1H), 7.94 (br s, 1H), 7.86 (d, J=9.2 Hz, 1H), 7.76 (dd, J=7.2 and 1.6 Hz, 1H), 7.38 (d, J=2.0 Hz, 1H), 7.26-7.23 (m, 1H), 7.20 (br d, J=8.0 Hz, 1H), 7.03 (dd, J=8.0 and 5.2 Hz, 1H), 4.89-4.87 (m, 1H), 4.77-4.75 (m, 1H), 4.39-4.37 (m, 1H), 4.32-4.30 (m, 1H), 4.01 (s, 3H); LC-MS (ESI): 338.1 [M+H$^+$].

3-(2-Fluoropyridin-4-yl)-8-methoxybenzo[4,5]imidazo[1,2-a]pyridine (AS-5332-183, T-771)

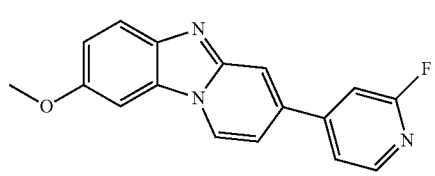 [SMILES: COc1ccc2nc3cc(-c4ccnc(F)c4)ccn3c2c1]

General experimental procedure for Suzuki coupling (Method A) was followed to prepare T-771. Reaction was performed on a 0.126 g scale. Product eluted out in 40% EtOAc:DCM mixture in a gradient elution on a Combiflash purification system. Isolated 0.0.25 g (19%) of T-771 as a yellow solid; $^1$H NMR (400 MHz, DMSO-d$_6$): δ 9.13 (dd, J=7.6 and 0.8 Hz, 1H), 8.34 (d, J=5.2 Hz, 1H), 8.24 (q, J=2.8 Hz, 1H), 7.95 (d, J=2.4 Hz, 1H), 7.92 (dt, J=5.2 and 0.8 Hz, 1H), 7.78 (br s, 1H), 7.72 (d, J=8.0 Hz, 1H), 7.47 (dd, J=7.6 and 2.0 Hz, 1H), 7.14 (dd, J=8.8 and 2.4 Hz, 1H), 3.87 (s, 3H); LC-MS (ESI): 294.1 [M+H$^+$].

4-(8-(2-Fluoroethoxy)benzo[4,5]imidazo[1,2-a]pyridine-3-yl)-N-methylaniline (AS-5332-181, T-766)

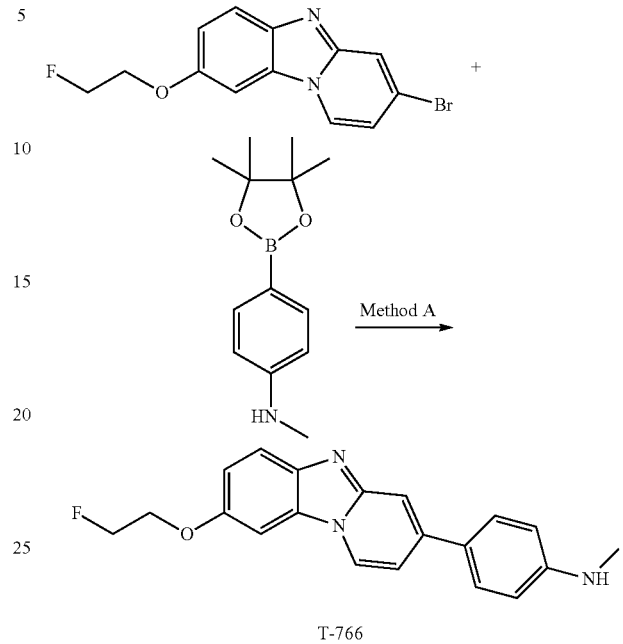

T-766

General experimental procedure for Suzuki coupling (Method A) was used to synthesize T-766. Reaction was performed on a 0.040 g scale. Product eluted out in 45% EtOAc:DCM mixture in a gradient elution on a Combiflash purification system. Isolated 0.0.25 g (19%) of T-766 as a yellow color solid; $^1$H NMR (400 MHz, DMSO-d$_6$): δ 8.88 (dd, J=7.6 and 0.8 Hz, 1H), 8.90 (d, J=2.0 Hz, 1H), 7.67-7.65 (m, 3H), 7.61 (d, J=8.8 Hz, 1H), 7.27 (dd, J=7.2, and 2.0 Hz, 1H), 7.09 (dd, J=8.8 and 2.4 Hz, 1H), 6.62 (d, J=8.8 Hz, 2H), 7.08 (q, J=4.8 Hz, 2H), 4.86-4.84 (m, 1H), 4.75-4.72 (m, 1H), 4.36-4.34 (m, 1H), 4.28-4.26 (m, 1H), 2.71 (d, J=3H); LC-MS (ESI): 336.2 [M+H]$^+$.

3(6-Fluoropyridine-2-yl)-8-methoxybenzo[4,5]imidazo[1,2-a]pyridine (AS-5332-176, T-765

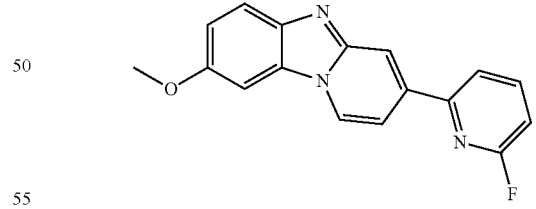

General experimental procedure for Suzuki coupling (method A) was followed to synthesize T-765. Reaction was performed on a 0.076 g scale. Product eluted out in 30% EtOAc:DCM mixture in a gradient elution on a Combiflash purification system. Isolated 0.025 g (19%) of T-765 as a yellow solid; $^1$H NMR (400 MHz, CDCl$_3$): δ 8.45 (d, J=7.2 Hz, 1H), 8.36 (br s, 1H), 7.94 (q, J=8.0 Hz, 1H), 7.87 (d, J=8.8 Hz, 1H), 7.83 (br d, J=6.4 Hz, 1H), 7.74 (br s, 1H), 7.26-7.22 (m, 1H), 6.97 (dd, J=8.0 and 2.8 Hz, 1H), 3.96 (s, 3H); LC-MS (ESI): 294.1 [M+H].

4-(8-(2-Fluoroethoxy)benzo[4,5]imidazo[1,2-a]pyridine-3-yl)aniline (AS-5332-175, T-764)

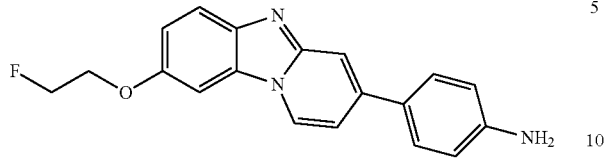

General experimental procedure for Suzuki coupling (Method A) was followed to synthesize T-764. Reaction was performed on a 0.042 g scale. Product eluted out in 10% MeOH:DCM mixture in a gradient elution on a Combiflash purification system. Isolated 0.032 g (74%) of T-764 as a yellow solid; $^1$H NMR (400 MHz, CDCl$_3$): δ 8.72 (dd, J=7.2 and 0.8 Hz, 1H), 7.69 (d, J=2.4 Hz, 1H), 6.76-7.65 (m, 2H), 7.59 (dq J=8.8 and 2.0 Hz, 2H), 7.27 (dd, J=7.2 and 1.6 Hz, 1H), 7.20 (dd, J=8.8 and 2.0 Hz, 1H), 6.81 (dq, J=8.8 and 2.0 Hz, 2H), 4.87-4.84 (m, 1H), 4.75-4.73 (m, 1H), 4.40-4.38 (m, 1H), 4.33-4.31 (m, 1H); LC-MS (ESI): 293.1 [M+H$^+$].

2-Fluoro-4-(8-methoxybenzo[4,5]imidazo[1,2-a]pyridine-3-yl)aniline (AS-5332-174, T-763)

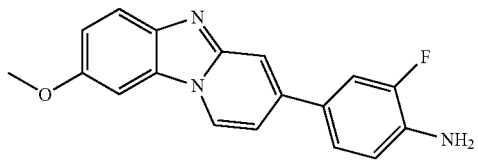 [SMILES: COc1ccc2nc3cc(-c4ccc(N)c(F)c4)ccn3c2c1]

General experimental procedure for Suzuki coupling (Method A) was followed to synthesize T-763. Reaction was performed on a 0.100 g scale. Product eluted out in 10% MeOH:DCM mixture in a gradient elution on a Combiflash purification system. Isolated 0.006 g (5.4%) of T-763 as a light yellow solid; $^1$H NMR (400 MHz, DMSO-d$_6$): δ 8.94 (d, J=6.8 Hz, 1H), 7.86 (d, J=2.4 Hz, 1H), 7.73 (br s, 1H), 7.61 (dq, J=9.2 and 2.0 Hz, 2H), 7.47 (dd, J=8.4 and 2.6 Hz, 1H), 7.27 (dd, J=7.2 and 1.6 Hz, 1H), 7.06 (dd, J=8.8 and 2.4 Hz, 1H), 6.83 (t, J=8.8 Hz, 1H), 3.85 (s, 3H); LC-MS (ESI): 308.0 [M+H$^+$].

N-(3-Fluoropropyl)-3-(8-methoxybenzo[4,5]imidazo[1,2-a]pyridine-3-yl)aniline TFA salt (AS-5332-171, T-761)

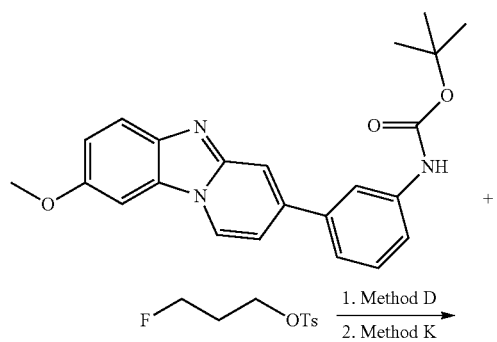

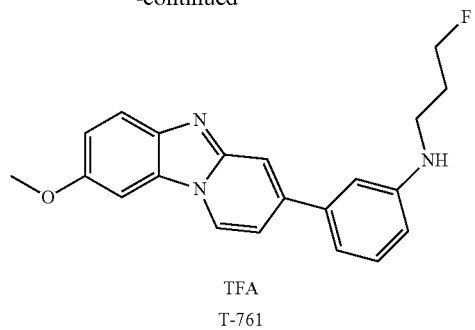

TFA
T-761

General experimental procedure for N-alkylation using NaH as a base (Method D) followed by deprotection of Boc (Method K) afforded T-761. Reaction performed on a 0.039 g scale. After work-up product T-761 was purified by HPLC using ACN and H$_2$O with 0.05% TFA as a white solid 0.022 mg (49%); $^1$H NMR (400 MHz, CD$_3$OD): δ 9.28 (d, J=8.4 Hz, 1H), 8.09 (br s, 1H), 8.02 (d, J=4.0 Hz, 1H), 7.88 (dd, J=7.2 and 1.6 Hz, 1H), 7.79 (d, J=8.8 Hz, 1H), 7.43 (dd, J=8.8 and 2.4 Hz, 1H), 7.34 (t, J=8.0 Hz, 1H), 7.16-7.12 (m, 2H), 6.85 (dd, J=7.6 and 1.6 Hz, 1H), 4.65 (t, J=5.6 Hz, 1H), 4.53 (t, J=5.6 Hz, 1H), 4.01 (s, 3H), 3.35 (t, J=5.6 Hz, 2H), 2.05 (m, 2H); LC-MS (ESI): 350.0 [M+H$^+$, Free base].

2-Fluoro-4-(8-methoxybenzo[4,5]imidazo[1,2-a]pyridine-3-yl)benzonitrile (AS-5332-167, T-751)

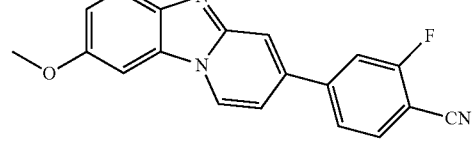

General experimental procedure for Suzuki coupling (Method A) was followed to synthesize T-751. Reaction was performed on a 0.080 g scale. Product eluted out in 24% EtOAc:DCM mixture in a gradient elution on a Combiflash purification system. Isolated 0.018 g (20%) of T-749 as a light yellow solid; $^1$H NMR (400 MHz, CDCl$_3$): δ 8.51 (br d, J=7.2 Hz, 1H), 8.08 (br s, 1H), 7.90 (d, J=8.8 Hz, 1H), 7.77 (t, J=8.0 Hz, 1H), 7.62 (d, J=8.0 Hz, 1H), 7.56 (d, J=8.0 Hz, 1H), 7.34 (br s, 1H), 7.28 (dt, J=8.8 and 1.2 Hz, 1H), 7.17 (d, J=7.2 Hz, 1H), 3.95 (s, 3H); LC-MS (ESI): 318.0 [M+H$^+$].

3-(3-Fluoro-4-methoxyphenyl)-8-methoxybenzo[4,5]imidazo[1,2-a]pyridine (AS-5332-166, T-749)

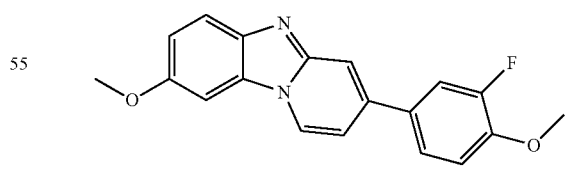

General experimental procedure for Suzuki coupling (Method A) was followed to synthesize T-749. Reaction was performed on a 0.085 g scale. Product eluted out in 25% EtOAc:DCM mixture in a gradient elution on a Combiflash purification system. Isolated 0.018 g (18%) of T-749 as a light yellow solid; $^1$H NMR (400 MHz, CDCl$_3$): δ 8.39 (br d, J=7.2 Hz, 1H), 7.84 (br s, 1H), 7.83 (d, J=8.0 Hz, 1H), 7.47-7.42 (m, 2H), 7.30 (t, J=2.0 Hz, 1H), 7.19 (dt, J=9.2 and 2.0 Hz, 1H), 7.10-7.05 (m, 2H), 3.95 and 3.94 (s, 3H each); LC-MS (ESI): 323.0 [M+H⁺].

2-Fluoro-4-(8-methoxybenzo[4,5]imidazo[1,2-a]pyridine-3-yl)N-methylaniline (AS-5332-159, T-708)

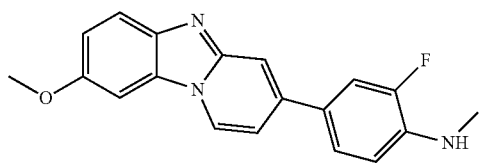

General experimental procedure for N-alkylation using NaH as a base (Method D) followed by Boc deprotection (Method K) of T-707 afforded T-708. Reaction was performed on a 0.031 g scale. After usual work-up product was triturated with MeOH and filtered the solid 0.003 g (12%); ¹H NMR (400 MHz, CDCl₃): δ 9.09 (d, J=7.2 Hz, 1H), 7.95 (br s, 1H), 7.91 (d, J=2.4 Hz, 1H), 7.80 (dd, J=7.6 and 1.6 Hz, 1H), 7.71 (d, J=9.2 Hz, 1H), 7.70-7.61 (m, 2H), 7.34 (dd, J=9.2 and 2.4 Hz, 1H), 6.83 (t, J=8.4 Hz, 1H), 3.97 and 2.90 (s, 3H each); LC-MS (ESI): 322.1 [M+H⁺].

Tert-butyl(2-fluoro-4-(8-methoxybenzo[4,5]imidazo[1,2-a]pyridine-3-yl)-phenyl)-carbamate (AS-5332-158, T-707)

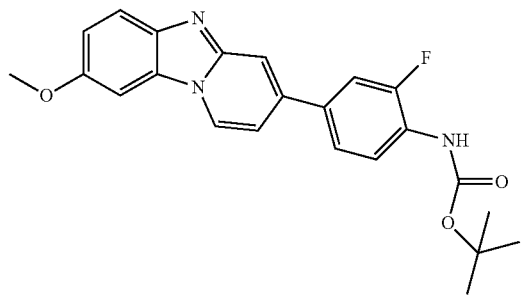 [SMILES: COc1ccc2nc3cc(-c4ccc(NC(=O)OC(C)(C)C)c(F)c4)ccn3c2c1]

General experimental procedure for Suzuki coupling (Method A) was followed. Reaction was performed on a 0.167 g scale. Product eluted out in 8%

MeOH:DCM mixture in a gradient elution on a Combiflash purification system. Isolated 0.040 g (16%) of T-707 as light yellow solid; ¹H NMR (400 MHz, CDCl₃): δ 8.42 (br d, J=7.2 Hz, 1H), 8.24 (t, J=7.2 Hz, 1H), 7.94 (br s, 1H), 7.85 (d, J=8.8 Hz, 1H), 7.46 (tt, J=11.6 and 2.0 Hz, 2H), 7.32 (br s, J=8.8 Hz, 2H), 7.24-7.17 (m, 2H), 6.92 (br s, 1H), 3.95 (s, 3H), 1.54 (s, 9H); LC-MS (ESI): 408.0 [M+H⁺].

3-(6-Fluoropyridin-3-yl)benzo[4,5]imidazo[1,2-a]pyridineFluoroprpyl (AS-5332-137, T-671)

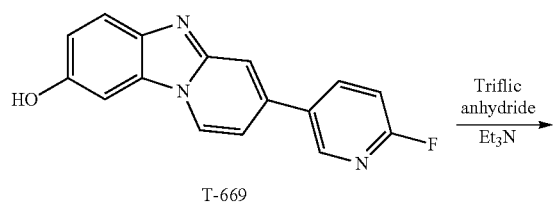

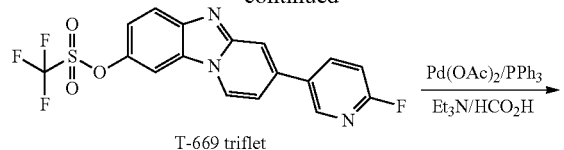

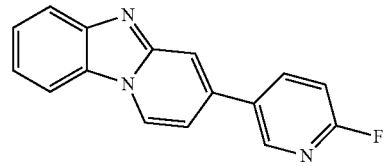

T-669 was O-alkylated using general experimental procedure (Method C). Reaction performed on a 0.090 g scale. T-669-triflet eluted out in 30% EtOAc:DCM mixture in a gradient elution on a Combiflash purification system. Isolated 0.016 g (12%); ¹H NMR (400 MHz, CDCl₃): δ 8.57 (br s, 1H), 8.53 (dd, J=7.2 and 1.2 Hz, 1H), 8.11 (tt, J=8.4 and 1.2 Hz, 1H), 7.98 (dd, J=9.2 and 2.0 Hz, 1H), 7.88 (s, 2H), 7.45 (dt, J=9.2 and 2.0 Hz, 1H), 7.23 (d, J=2.4 Hz, 1H), 7.16 (dt, J=6.8 and 2.0 Hz, 1H), 7.10 (dt, J=8.4 and 2.0 Hz, 1H); LC-MS (ESI): 412.2 [M+H⁺]. To a solution of T-669 triflet (0.016 g, 0.039 mmol) in DMF (1 mL), PPh₃ (0.005 g, 0.019 mmol, 0.5 eq), Et₃N (0.016 mL, 0.117 mmol, 3.0 eq), Pd (OAc)₂ (0.005 g, 0.019 mmol, 0.5 eq) was added followed by formic acid (0.0005 mL, 0.117 mmol, 3.0 eq). The reaction mixture was stir at 60° C. for 1 h. After the reaction is complete the residue was diluted with MeOH and purified by HPLC using ACN-water with 0.05% TFA system afforded T-671 solid 0.005 g (49%); ¹H NMR (400 MHz, CD₃OD): δ 9.43 (d, J=7.2 Hz, 1H), 8.81 (d, J=2.0 Hz, 1H), 8.50 (td, J=9.2 and 2.0 Hz, 1H), 8.47 (d, J=8.4 Hz, 1H), 8.29 (s, 1H), 7.97 (d, J=7.2 Hz, 1H), 7.92 (d, J=8.4 Hz, 1H), 7.85 (t, J=6.8 Hz, 1H), 7.72 (t, J=7.2 Hz, 1H), 7.32 (dd, J=9.2 and 2.8 Hz, 1H); LC-MS (ESI): 264.1 [M+H⁺, Free base].

3-(6-Fluoropyridin-3-yl)benzo[4,5]imidazo[1,2-a]pyridine-8-ol TFA salt (AS-5332-131, T-669)

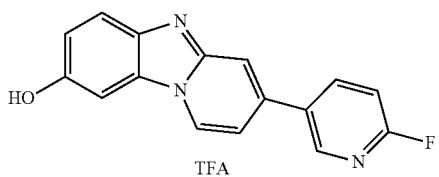 [SMILES: Oc1ccc2nc3cc(-c4ccc(F)nc4)ccn3c2c1]

General experimental procedure for Suzuki coupling (Method A) was used. Reaction was performed on a 0.048 g scale. Product T-669 was purified by HPLC using ACN and H₂O with 0.05% TFA as a white solid 0.005 mg (7%); ¹H NMR (400 MHz, CDCl₃): δ 8.22 (d, J=7.2 Hz, 1H), 8.78 (d, J=2.4 Hz, 1H), 8.48 (td, J=7.2 and 2.4 Hz, 1H), 8.20 (s, 1H), 7.86 (d, J=6.8 Hz, 1H), 7.74 (dd, J=4.0 and 3.6 Hz, 1H), 7.32 (td, J=8.8 and 1.2 Hz, 1H); LC-MS (ESI): 280.1 [M+H⁺, Free base].

3-(6-Fluoropyridin-3-yl)-8-methoxybenzo[4,5]imidazo[1,2-a]pyridine (AS-5332-125, T-663)

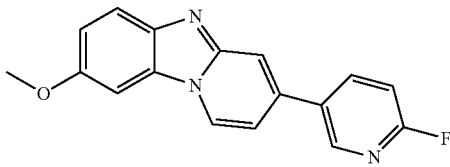 [SMILES: COc1ccc2nc3cc(-c4ccc(F)nc4)ccn3c2c1]

General experimental procedure for Suzuki coupling (Method A) was used. Reaction was performed on a 0.339 g scale. Product eluted out in 10% MeOH:DCM mixture in a gradient elution on a Combiflash purification system. Isolated 0.035 g (9%) of T-663 as off yellow solid; $^1$H NMR (400 MHz, CDCl$_3$): δ 8.57 (br s, 1H), 8.51 (br d, J=6.8 Hz, 1H), 8.14 (t, J=8.0 Hz, 1H), 8.03 (br s, 1H), 7.87 (dd, J=8.8 and 1.2 Hz, 1H), 7.35 (br s, 1H), 7.26-7.18 (m, 2H), 7.09 (dt, J=8.4 and 2.8 Hz, 1H), 3.95 (s, 3H); LC-MS (ESI): 294.1 [M+H$^+$].

8-Methoxy-3-(6-nitropyridin-3-yl)benzo[4,5]imidazo[1,2-a]pyridine (AS-5332-149, T-663P)

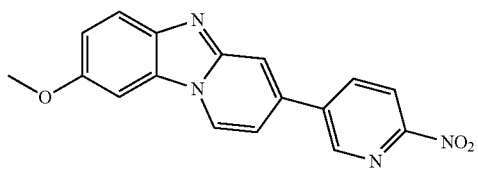 [SMILES: COc1ccc2nc3cc(-c4ccc([N+](=O)[O-])nc4)ccn3c2c1]

General experimental procedure for Suzuki coupling (Method A) was used. Reaction was performed on a 0.155 g scale. Product eluted out in 10% MeOH:DCM mixture in a gradient elution on a Combiflash purification system. Isolated 0.015 g (9%) of T-663P as a yellow color solid; $^1$H NMR (400 MHz, DMSO-d$_6$): δ 9.21 (d, J=2.0 Hz, 1H), 9.15 (d, J=7.2 Hz, 1H), 8.72 (dd, J=8.4 and 2.0 Hz, 1H), 8.39 (d, J=8.4 Hz, 1H), 8.24 (br s, 1H), 7.95 (d, J=2.0 Hz, 1H), 7.72 (d, J=8.8 Hz, 1H), 7.49 (d, J=7.2 Hz, 1H), 7.14 (dd, J=8.8 and 2.4 Hz, 1H), 3.88 (s, 3H); LC-MS (ESI): 321.1 [M+H$^+$].

8-Methoxy-3-(4-(4-methylpiperazine-1-yl)phenyl)benzo[4,5]imidazo[1,2-a]pyridine (AS-5332-124, T-657)

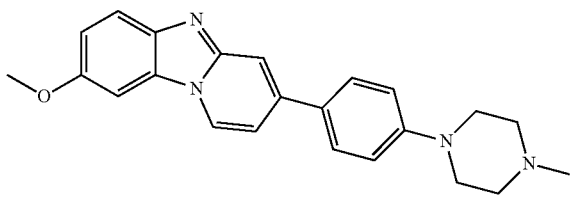

General experimental procedure for O-alkylation of T-656 using Cs$_2$CO$_3$ as a base (Method A) was used. Reaction performed on a 0.070 g scale of. Product eluted out in 12% MeOH:DCM mixture in a gradient elution on a Combiflash purification system. Isolated 0.005 g (7%) of T-657 as a off white solid; $^1$H NMR (400 MHz, CDCl$_3$): δ 8.32 (d, J=7.6 Hz, 1H), 7.79 (dd, J=8.8 and 1.2 Hz, 1H), 7.76 (d, J=0.8 Hz, 1H), 7.62 (dd, J=8.8 and 1.2 Hz, 2H), 7.28 (t, J=2.0 Hz, 1H), 7.16 (dt, J=8.0 and 4.0 Hz, 1H), 7.06 (dt, J=7.2 and 4.0 Hz, 1H), 7.01 (dd, J=8.0 and 1.2 Hz, 2H), 3.93 (s, 3H), 3.36 (br s, 4H), 2.69 (br s, 4H), 2.43 (s, 3H); LC-MS (ESI): 373.2 [M+H$^+$].

3-(4-(4-Methylpiperizine-1-yl)phenyl)benzo[4,5]imidazo[1,2-a]pyridine-8-ol TFA salt (AS-5332-121, T-656)

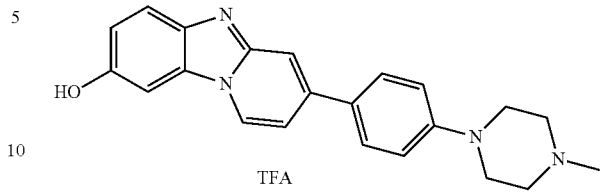

General experimental procedure for Suzuki coupling (Method A) was used. Reaction was performed on a 0.130 g scale. Product T-656 was purified by HPLC using ACN and H$_2$O with 0.05% TFA as a white solid 0.012 mg (14%); $^1$H NMR (400 MHz, CD$_3$OD): δ 8.07 (d, J=7.2 Hz, 1H), 8.02 (br s, 1H), 7.91 (d, J=7.2 Hz, 2H), 7.82 (d, J=7.2 Hz, 1H), 7.678-7.66 (m, 2H), 7.27 (dt, J=8.8 and 1.2 Hz, 1H), 7.21 (d, J=8.4 Hz, 2H), 3.29-3.27 (m, 4H), 2.97 (s, 3H); LC-MS (ESI): 359.1 [M+H$^+$, Free base].

8-(2-Fluoroethoxy)-3-(4-(4-methoxypiperizin-1-yl)phenyl)benzo[4,5]imidazo[1,2-a]pyridine (AS-5332-118, T-643)

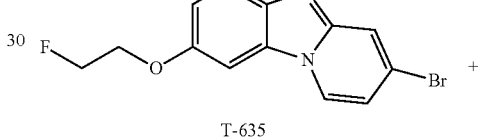

T-635

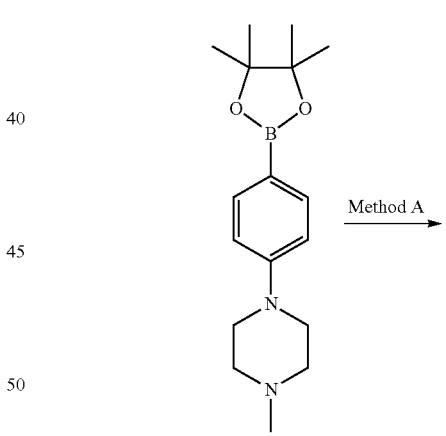

Method A

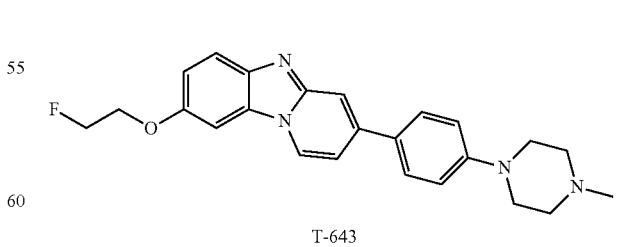

T-643

General experimental procedure for Suzuki coupling (Method A) was used. Reaction was performed on a 0.013 g scale. Product was purified by Combiflash purification system using 11% MeOH:DCM mixture in a gradient elution gave 0.006 g (35%) of T-643 as a off white solid; ¹H NMR (400 MHz, CDCl₃): δ 8.26 (d, J=7.6 Hz, 1H), 7.75 (dd, J=8.8 and 0.8 Hz, 1H), 7.72 (br s, 1H), 7.58 (d, J=8.0 Hz, 2H), 7.30 (t, J=0.8 Hz, 1H), 7.15 (dq, J=9.2 and 4.0 Hz, 1H), 7.04 (dq, J=9.2 and 4.0 Hz, 1H), 6.96 (d, J=7.6 Hz, 2H), 4.83-4.81 (m, 1H), 4.71-4.69 (m, 1H), 4.33-4.31 (m, 1H), 4.26-4.24 (m, 1H), 3.34 (br s, 4H), 2.69 (br s, 4H), 2.41 (s, 3H); LC-MS (ESI): 405.2 [M+H⁺].

3-Bromo-8-(2-fluoroethoxy)benzo[4,5]imidazo[1,2-a]pyridine (AS-5332-117, T-635)

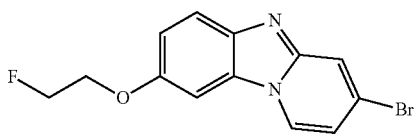 [SMILES: FCCOc1ccc2nc3cc(Br)ccn3c2c1]

General experimental procedure for phenolic alkylation using Cs₂CO₃ as the base (Method C) was followed. Reaction was performed on a 0.104 g scale. The product was purified by Combiflash purification system, using 17% EtOAc:Hexanes mixture in a gradient elution gave 0.015 g (12%) of T-635 as a light yellow color solid; ¹H NMR (400 MHz, CDCl₃): δ 8.21 (d, J=7.2 Hz, 1H), 7.93 (br s, 1H), 7.83 (d, J=9.2 Hz, 1H), 7.33 (d, J=2.4 Hz, 1H), 7.26-7.23 (m, 1H), 6.97 (dd, J=7.2 and 2.0 Hz, 1H), 4.88-4.86 (m, 1H), 4.76-4.74 (m, 1H), 4.37-4.35 (m, 1H), 4.30-4.28 (m, 1H); LC-MS (ESI): 309.1 and 310.9 [M⁺ and M+2H⁺].

1-(4-(2-Fluoroethoxy)phenyl)-3-methylbenzo[4,5]imidazo[1,2-a]pyridine-4-carbonitrile (AS-5332-168, T-750)

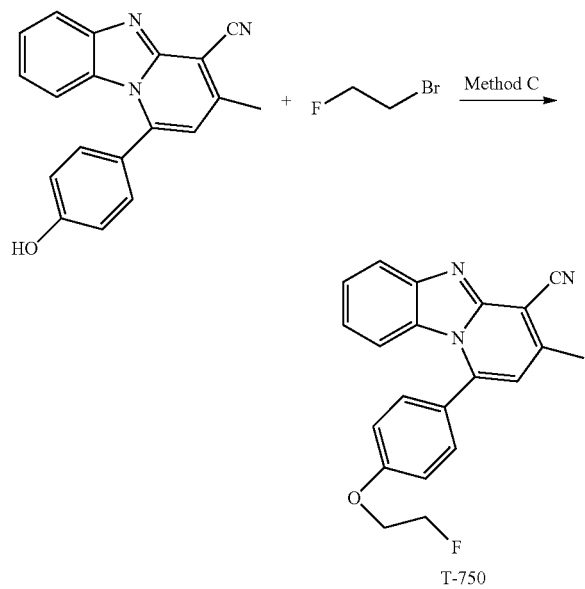

General experimental procedure for N-alkylation with NaH as a base was followed to prepare T-750. Reaction performed on a 0.010 g scale. Product eluted out in 15% EtOAc: DCM mixture in a gradient elution on a Combiflash purification system. Isolated 0.002 g (17%) of T-750 as a off white solid; ¹H NMR (400 MHz, CDCl₃): δ 7.98 (d, J=8.4 Hz, 1H), 7.48-7.42 (m, 3H), 7.15-7.13 (m, 2H), 7.03 (tt, J=8.0 and 0.8 Hz, 1H), 6.67 (d, J=8.4 Hz, 1H), 6.58 (s, 1H), 4.91-4.89 (m, 1H), 4.80-4.78 (m, 1H), 4.40-4.38 (m, 1H), 4.33-4.31 (m, 1H), 2.70 (s, 3H); LC-MS (ESI): 346.1 [M+H⁺].

1-(Dimethylamino)-3-methylbenzo[4,5]imidazo[1,2-a]pyridine-4-carbonitrile (AS-5332-141, T-677)

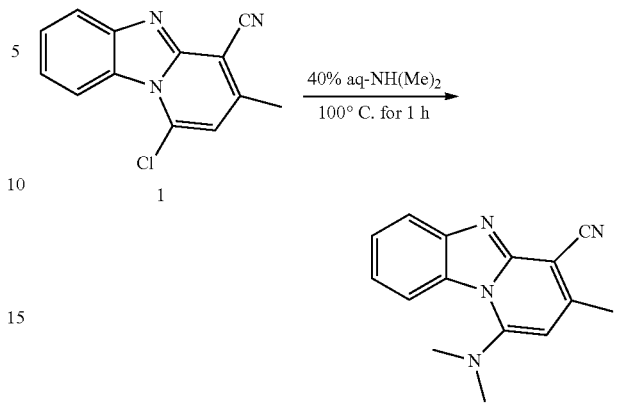

A 5 mL microwave vial was charged with 1 chloro-3-methylbenzo[4,5]imidazo[1,2-a]pyridine-4-carbonitrile (1, 0.048 g, 0.200 mmol) and 40% N(Me)₂ in water (1 ml) and heated at 100° C. for 1 h. The reaction mixture was cooled and filtered the solid of T-677 0.030 g (60%); ¹H NMR (400 MHz, DMSO-d₆): δ 8.11 (d, J=8.4 Hz, 1H), 7.30 (d, J=8.0 Hz, 1H), 7.50 (t, J=6.8 Hz, 1H), 7.34 (t, J=6.8 Hz, 1H), 6.58 (s, 1H), 2.89 (s, 6H), 2.57 (s, 3H); LC-MS (ESI): 223.1 [M+H⁺].

1-Amino-3-methylbenzo[4,5]imidazo[1,2-a]pyridine-4-carbonitrile (AS-5332-140, T-676)

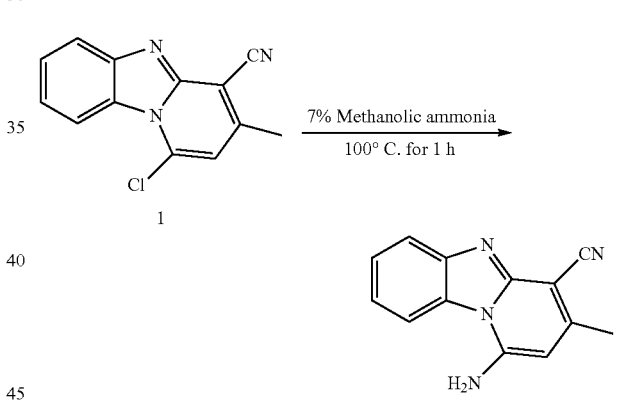

A 5 mL microwave vial was charged with 1 chloro-3-methylbenzo[4,5]imidazo[1,2-a]pyridine-4-carbonitrile (1, 0.048 g, 0.200 mmol) and 7% NH₃ in MeOH (1 ml) and heated at 100° C. for 1 h. The reaction mixture was cooled and filtered the solid of T-676 0.022 g (49%); ¹H NMR (400 MHz, DMSO-d₆): δ 8.37 (d, J=8.8 Hz, 1H), 7.78 (s, 2H), 7.71 (d, J=7.6 Hz, 1H), 7.47 (t, J=5.6 Hz, 1H), 7.25 (t, J=5.6 Hz, 1H), 6.02 (s, 1H), 2.45 (s, 3H); LC-MS (ESI): 223.1 [M+H⁺].

3-Methyl-1-(methylamino)benzo[4,5]imidazo[1,2-a]pyridine-4-carbonitrile (AS-5332-139, T-675)

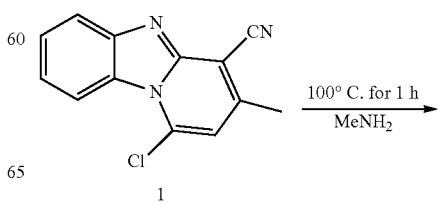

-continued

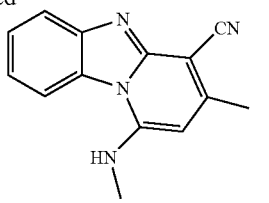

A 5 mL microwave vial was charged with 1 chloro-3-methylbenzo[4,5]imidazo[1,2-a]pyridine-4-carbonitrile (1, 0.048 g, 0.200 mmol) and 40% methyl amine in water (1 ml) and heated at 100° C. for 1 h. The residue was diluted with MeOH afforded T-675 as a off white solid 0.022 g (47%) collected by filtration; $^1$H NMR (400 MHz, CDCl$_3$): δ 8.46 (d, J=8.0 Hz, 1H), 7.77 (d, J=8.0 Hz, 1H), 7.52 (t, J=7.6 Hz, 1H), 7.46 (br m, 1H), 7.32 (d, J=7.6 Hz, 1H), 6.09 (s, 1H), 3.08 (s, 3H), 2.54 (s, 3H); LC-MS (ESI): 237.1 [M+H$^+$].

3-Methyl-1-morpholinobenzo[4,5]imidazo[1,2-a]pyridine-4-carbonitrile (AS-5332-138, T-674)

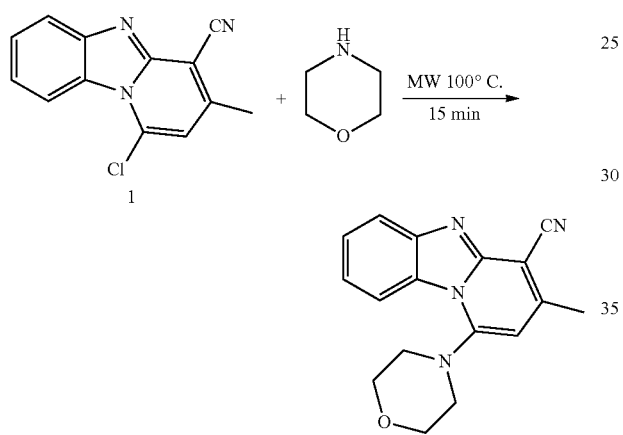

A 5 mL microwave vial was charged with 1 chloro-3-methylbenzo[4,5]imidazo[1,2-a]pyridine-4-carbonitrile (1, 0.048 g, 0.200 mmol) and morpholine (0.100 mL, 0.600 mmol, 3 eq) in DMF (3 mL). The suspension was irradiated in a Biotage Emrys Optimizer microwave reactor (250 W) at 100° C. for 15 min. The residue was diluted with MeOH afforded T-674 as a off white solid 0.040 g (69%) collected by filtration; $^1$H NMR (400 MHz, DMSO-d$_6$): δ 8.29 (d, J=8.8 Hz, 1H), 7.86 (d, J=8.4 Hz, 1H), 7.56 (t, J=7.2 Hz, 1H), 7.42 (t, J=7.2 Hz, 1H), 6.71 (s, 1H), 3.97 (br s, 4H), 3.37 (m, 1H), 3.17 (d, J=5.2 Hz, 1H), 3.01 (br m, 2H), 2.62 (s, 3H); LC-MS (ESI): 293.1 [M+H$^+$].

1-(4-(2-(2-Hydroxyethoxy)ethyl)piperizine-1-yl-3-methylbenzo[4,5]imidazo[1,2-a]pyridine-4-carbonitrile (AS-5332-133, T-670)

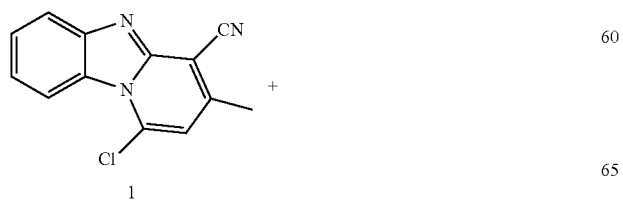

-continued

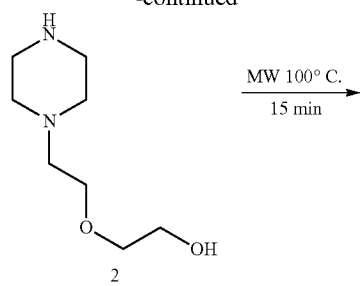

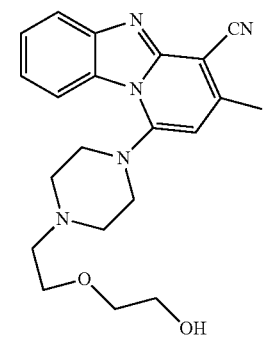

A 5 mL microwave tube was charged with 1 chloro-3-methylbenzo[4,5]imidazo[1,2-a]pyridine-4-carbonitrile (1, 0.120 g, 0.5 mmol) and 2(2-piperizin-1-yl)ethoxy)ethanol (2, 0.260 g, 1.5 mmol) in DMF (3 mL). The suspension was irradiated in a Biotage Emrys Optimizer microwave reactor (250 W) at 100° C. for 15 min. The residue was diluted with MeOH afforded T-670 as a brown solid 0.145 g (77%) collected by filtration; $^1$H NMR (400 MHz, CDCl$_3$): δ 8.18 (br d, J=8.4 Hz, 1H), 7.98 (d, J=8.4, 1H), 7.52 (tt, J=8.0 and 1.2 Hz, 1H), 7.36-7.32 (m, 3H), 7.06 (d, J=2.4 Hz, 1H), 7.00 (t, J=8.8 Hz, 1H), 7.34 (t, J=8.8 Hz, 1H), 3.78 (br s, 4H), 3.72 (m, 1H), 3.66 (m, 1H), 3.46 (br d, J=11.6 Hz, 2H), 3.21 (br, 3H), 2.86 (br, 3H), 2.63 (s, 3H); LC-MS (ESI): 380.3 [M+H$^+$].

Synthesis of T815

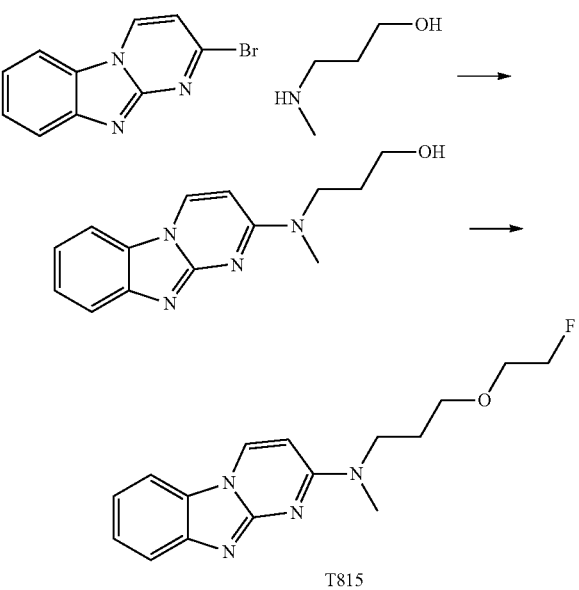

Preparation of 3-(benzo[4,5]imidazo[1,2-a]pyrimidin-2-yl (methyl)amino)propan-1-ol. 2-Bromobenzo[4,5]imidazo[1,2-a]pyrimidine (0.2 g, 0.806 mmol), 3-(methylamino)propan-1-ol (0.072 g, 0.806 mmol) and N,N-Diisopropylethylamine (0.141 ml, 0.806 mmol) were heated to 100° C. for 10 minutes in a microwave. Let the reaction cool to room temperature. Diluted reaction with water, extracted with ethyl acetate, combined organics, dried, filtered and concentrated to afford crude 3-(benzo[4,5]imidazo[1,2-a]pyrimidin-2-yl(methyl)amino)propan-1-ol (0.207 g, 0.808 mmol, 100% yield).

Preparation of T815. Sodium hydride 60% (3.59 mg, 0.156 mmol) was added to a solution containing 3-(benzo[4,5]imidazo[1,2-a]pyrimidin-2-yl(methyl)amino)propan-1-ol (0.02 g, 0.078 mmol) and 1-bromo-2-fluoroethane (0.020 g, 0.156 mmol) in DMF (Volume: 0.390 ml). Let the reaction stir overnight. Concentrated and purified by PREP HPLC to afford T815 (0.002 g, 6.61 μmol, 8.48% yield) MS (ESI, Pos.) m/z: 303.0 [M+H]$^+$.

Human AD Brain Section Autoradiography 5 micron thick human AD brain slices were first examined using antibodies for Aβ and Tau to determine whether the tested human brain contains Aβ and Tau. Thus, three types of human brain slices were selected for autoradiography: Aβ+/Tau+; Aβ+/Tau−; and Aβ−/Tau−(control).

The experimental protocol is as follows:
Pick one brain section for each type and air-dry in hood. A solution of diluted F-18 labeled tracer (40 μCi/mL, 500 μL) which was obtained from the dilution of F-18 tracer with 1×PBS containing 2.5% EtOH and 2.5% DMSO was applied onto each slides to cover the whole tissue section. The resulting slides were incubated at room temperature for 90 minutes, drained, and placed onto a slide holder. The slides were then washed sequentially with 1×PBS for 1 min; 70% EtOH in 1×PBS for 2 min; 30% EtOH in 1×PBS for 2 min; and 1×PBS for 1 min. The slides were dried in the hood for 30 min, and then placed on Fuji imaging plates and exposed overnight. The imaging plates were then scanned and the signal was measured using Fuji software to produce an autoradiography image of the brain section. (PBS—Phosphate Buffer Saline)

Protocol for Synthetic Beta-amyloid and Tau Kds

Various concentrations solution of F-18 labeled and its parent cold compound in 1×PBS containing 5% Ethanol and 5% DMSO (pH 7.4) were incubated with synthetic beta-Amyloid or synthetic tau at room temperature in glass tubes for 90 min. The reaction mixture in each tube was filtered under vacuum through a microfiber filter. Each tube was washed with a solution of 20% EtOH in PBS. The PBS wash solution was filtered under vacuum through the filters. Each filter was then washed with a solution of 20% EtOH in PBS and then placed into a gamma counter vial for CPM counting. The data obtained was plotted for Kd determination.

Tau fluorescent compounds staining on human brain sections (Double or triple labeled with tau and β-amyloid Immunohistochemistry (IHC))

Serial sections (6 μm thick) from OCT-embedded frozen blocks of front lobe were used for staining (OCT—optimal cutting temperature). After fixation and quenching of autofluorescence, tissue sections were incubated with in 100 μM of tau compound in 50% ethanol PBS for 60 min. Then sections were dipped briefly into water, rinsed in PBS, blocked with 5% normal horse serum in PBS for 1 hour at room temperature. After blocking, the tissue was incubated with tau or β-amyloid primary antibody at 4° C. overnight in a humid chamber. Next day, the sections were washed with PBS and then incubated with secondary antibody for 1 hour. The sections were washed and covered, and they were observed with a Nikon (Tokyo, Japan) Eclipse microscope equipped with violet, blue, and green filters.

Mouse and Rat Brain microPET Imaging

Wild type mice and rats were injected intravenously with the candidate tracers. Mice (weight range 25-45 g) were injected with doses between 180 and 300 μCi in 200 uL of saline solution. Rats (weight range 300-400 g) were injected with doses between 300 and 500 μCi of tracer in 400 μL of saline solution. Anesthesia was induced and maintained with Isoflurane. CT and PET scans were performed with a MM INVEON scanner (SIEMENS™). Acquisition for CT images preceded PET scanning and lasted 5 minutes. Only several minutes after the beginning of the PET acquisition, the radioactive dose was injected into the animal through the tail vein. Images were generated as dynamic scans that typically lasted 30 minutes. The initial image analysis consisted of determining whether there was uptake of the tracer in the brain which would establish its ability to cross the blood-brain barrier. All measurements were performed at the time point of 5 minutes following the injection of the tracer. The degree of uptake in the brain was estimated relative to the uptake of the traces in the region of neck muscles. The ratio between the percentage of injected dose per gram in the brain and that of the muscular neck region was provided as an estimate of brain uptake. Brain images of the representative tracers of formula (I) are shown in FIGS. 17-22.

Having thus descried in detail advantageous embodiments of the present invention, it is to be understood that the invention defined by the above paragraphs is not to be limited to particular details set forth in the above description as many apparent variations thereof are possible without departing from the spirit or scope of the present invention.

We claim:

1. A compound of Formula Vb':

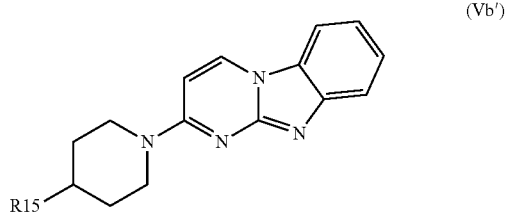

(Vb')

wherein, $R_{15}$ is selected from the group consisting of H, nitro, cyano, amino, alkyl, alkylaryl, alkylamino, cycloalkylamino, alkylamine, arylamine, arylamino, alkoxy, $NR_{10}$COOalkyl, $NR_{10}$COOaryl, $NR_{10}$COalkyl, $NR_{10}$CO aryl, COOalkyl, COOaryl, COalkyl, COaryl, aryl, and cycloalkyl, wherein at least one H is replaced by halo or a radioactive isotope.

2. The compound of claim 1, wherein $R_{15}$ is $C_1$-$C_6$ alkyl wherein at least one H is replaced by halo.

3. The compound of claim 1, wherein $R_{15}$ is $C_1$-$C_6$ alkyl wherein at least one H is replaced by a radioactive isotope.

4. The compound of claim 1, wherein $R_{15}$ is $C_2$-$C_6$ alkyl-$^{18}$F.

5. The compound of claim 1, wherein $R_{15}$ is $^{18}$F or $^{11C}$.

6. A compound of claim 1, which is:

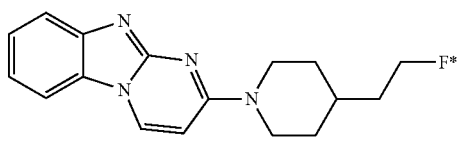

or a pharmaceutically acceptable salt thereof, wherein F* is F or $^{18}$F.

7. A compound of claim 1, which is

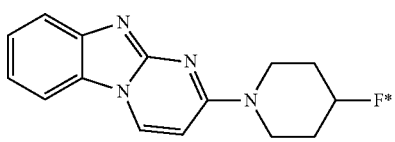

or a pharmaceutically acceptable salt thereof, wherein F* is F or $^{18}$F.

8. A process for the preparation of the compound of claim 6 wherein F* is $^{18}$F, comprising reacting 2-(1-(benzo[4,5]imidazo[1,2-a]pyrimidin-2-yl)piperidin-4-yl)ethyl methanesulfonate with anhydrous [F-18] fluoride ion.

9. The compound of claim 1, wherein at least one H is replaced by a radioactive isotope.

10. A method for in vivo detection of neurofibrillary tangles in a patient comprising administering an effective amount of a radiolabeled compound of claim 9 to the patient, and measuring the radioactive signal of the compound.

11. The method of claim 10, wherein the detection is by gamma imaging and is PET or SPECT or fluorescence.

12. A compound selected from the group consisting of:
2-(1-(benzo[4,5]imidazo[1,2-a]pyrimidin-2-yl)piperidin-4-yl)ethanol:

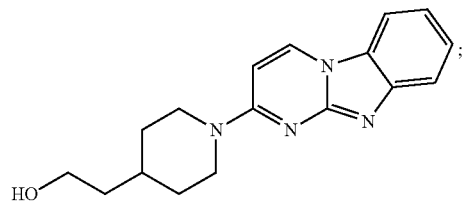 [SMILES: OCCC1CCN(c2ccn3c(n2)nc2ccccc23)CC1]

2-(1-(benzo[4,5]imidazo[1,2-a]pyrimidin-2-yl)piperidin-4-yl)ethyl methanesulfonate:

1-(benzo[4,5]imidazo[1,2-a]pyrimidin-2-yl)piperidin-4-ol:

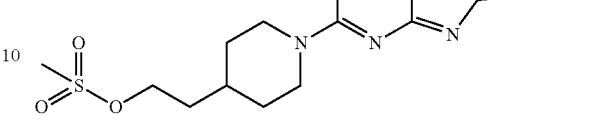

1-(benzo[4,5]imidazo[1,2-a]pyrimidin-2-yl)piperidin-4-yl methanesulfonate:

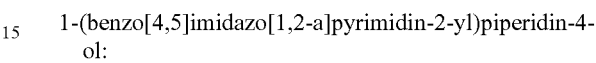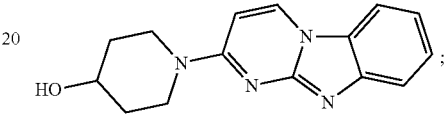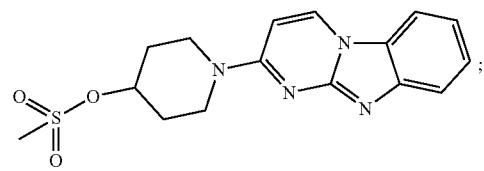 [SMILES: CS(=O)(=O)OC1CCN(c2ccn3c(n2)nc2ccccc23)CC1]

and 2-(4-bromo-1-piperidyl)pyrimido[1,2-a]benzimidazole:

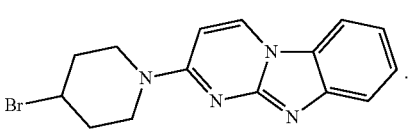 [SMILES: BrC1CCN(c2ccn3c(n2)nc2ccccc23)CC1]

* * * * *

UNITED STATES PATENT AND TRADEMARK OFFICE
CERTIFICATE OF CORRECTION

| | | |
|---|---|---|
| PATENT NO. | : 8,691,187 B2 | Page 1 of 1 |
| APPLICATION NO. | : 13/035405 | |
| DATED | : April 8, 2014 | |
| INVENTOR(S) | : Anna Katrin Szardenings et al. | |

It is certified that error appears in the above-identified patent and that said Letters Patent is hereby corrected as shown below:

On the Title Page, Item (56)

Page 2 Col. 1 (Other Publications), Line 10, Delete "benzimidaloses" and insert -- benzimidazoles --

Page 2 Col. 1 (Other Publications), Line 22, Delete "Benzemediamines," and insert
-- Benzenediamines, --

Page 2 Col. 2 (Other Publications), Line 13, Delete "Phamacotherapy," and insert
-- Pharmacotherapy, --

Page 2 Col. 2 (Other Publications), Line 62, Delete "meth ylchromene" and insert
-- methylchromene --

Page 3 Col. 1 (Other Publications), Line 8, Delete "[418F]" and insert -- [18F] --

Page 3 Col. 1 (Other Publications), Line 14, Delete "Tetrahenron" and insert -- Tetrahedron --

Page 3 Col. 1 (Other Publications), Line 19, Delete "biodistrubtion" and insert -- biodistribution --

Page 3 Col. 2 (Other Publications), Line 14, Delete "Fluoralkyl-2Initroimidazoles" and insert
-- Fluoroalkyl-2-Nitroimidazoles --

Page 3 Col. 2 (Other Publications), Line 18, Delete "Radiophaarmaceuticlas," and insert
-- Radiopharmaceuticals, --

In the Claims

Column 22, Line 55 (approx.), In Claim 1, delete "NR10 CO aryl," and insert -- NR10 COaryl, --

Column 22, Line 66 (approx.), In Claim 5, delete "11C." and insert -- $^{11}$C. --

Signed and Sealed this
First Day of July, 2014

Michelle K. Lee
*Deputy Director of the United States Patent and Trademark Office*